(12) United States Patent
Jolly et al.

(10) Patent No.: US 11,279,949 B2
(45) Date of Patent: Mar. 22, 2022

(54) RECOMBINANT VECTORS COMPRISING 2A PEPTIDE

(71) Applicant: DENOVO BIOPHARMA LLC, San Diego, CA (US)

(72) Inventors: Douglas J. Jolly, Encinitas, CA (US); Amy H. Lin, San Diego, CA (US); Andrew Hofacre, Laguna Niguel, CA (US); Daniel J. Hogan, San Diego, CA (US); Derek G. Ostertag, San Diego, CA (US)

(73) Assignee: DENOVO BIOPHARMA LLC, San Diego, CA (US)

(*) Notice: Subject to any disclaimer, the term of this patent is extended or adjusted under 35 U.S.C. 154(b) by 198 days.

(21) Appl. No.: 15/757,292

(22) PCT Filed: Sep. 1, 2016

(86) PCT No.: PCT/US2016/049947
§ 371 (c)(1),
(2) Date: Mar. 2, 2018

(87) PCT Pub. No.: WO2017/040815
PCT Pub. Date: Mar. 9, 2017

(65) Prior Publication Data
US 2018/0251786 A1  Sep. 6, 2018

Related U.S. Application Data

(60) Provisional application No. 62/214,884, filed on Sep. 4, 2015.

(51) Int. Cl.
| | | |
|---|---|---|
| *C12N 15/86* | (2006.01) | |
| *A61K 48/00* | (2006.01) | |
| *C07K 16/28* | (2006.01) | |
| *A61P 35/00* | (2006.01) | |
| *C07K 14/535* | (2006.01) | |
| *C07K 14/705* | (2006.01) | |
| *C12N 15/113* | (2010.01) | |

(52) U.S. Cl.
CPC ............ *C12N 15/86* (2013.01); *A61K 48/005* (2013.01); *A61P 35/00* (2018.01); *C07K 14/535* (2013.01); *C07K 14/70507* (2013.01); *C07K 16/2827* (2013.01); *A61K 48/00* (2013.01); *C07K 2317/76* (2013.01); *C07K 2319/30* (2013.01); *C07K 2319/50* (2013.01); *C07K 2319/60* (2013.01); *C07K 2319/75* (2013.01); *C12N 15/1138* (2013.01); *C12N 2310/141* (2013.01); *C12N 2740/13021* (2013.01); *C12N 2740/13022* (2013.01); *C12N 2740/13043* (2013.01); *C12N 2840/20* (2013.01); *C12N 2840/203* (2013.01)

(58) Field of Classification Search
None
See application file for complete search history.

(56) References Cited

U.S. PATENT DOCUMENTS

| | | |
|---|---|---|
| 6,033,905 A | 3/2000 | Eiden et al. |
| 6,117,681 A | 9/2000 | Salmons et al. |
| 6,303,380 B1 | 10/2001 | Lin et al. |
| 6,410,313 B1 | 6/2002 | Kasahara et al. |
| 6,448,390 B1 | 9/2002 | Albritton et al. |
| 6,451,304 B1 | 9/2002 | Friedmann |
| 6,576,463 B1 | 6/2003 | Kasahara et al. |
| 6,806,080 B2 | 10/2004 | Kasahara et al. |
| 6,899,871 B2 | 5/2005 | Kasahara et al. |
| 6,953,688 B2 | 10/2005 | Ferrick |
| 7,056,730 B2 | 6/2006 | Pedersen et al. |
| 2002/0068362 A1 | 6/2002 | Murray et al. |
| 2002/0137889 A1 | 9/2002 | Soong et al. |
| 2003/0003565 A1 | 1/2003 | Dubensky |
| 2003/0157070 A1 | 8/2003 | Jolly |
| 2003/0157718 A1 | 8/2003 | Pedersen et al. |
| 2003/0165466 A1 | 9/2003 | Gromeier et al. |
| 2003/0219410 A1 | 11/2003 | Calatrava |
| 2004/0068762 A1 | 4/2004 | Attar |
| 2004/0096972 A1 | 5/2004 | Audit et al. |
| 2004/0142449 A1 | 7/2004 | Tonjes et al. |
| 2004/0146489 A1 | 7/2004 | Yu et al. |
| 2004/0197308 A1 | 10/2004 | Takahashi et al. |
| 2004/0248827 A1 | 12/2004 | Zheng et al. |
| 2005/0002903 A1 | 1/2005 | Kasahara et al. |
| 2005/0059004 A1 | 3/2005 | Atabekov et al. |

(Continued)

FOREIGN PATENT DOCUMENTS

| | | |
|---|---|---|
| JP | 2013523754 A | 8/2020 |
| WO | 1999020742 A2 | 4/1999 |

(Continued)

OTHER PUBLICATIONS

Neogi (J. Int. AIDS Soc., 16(1): 18472, pp. 1-8, 2013 ). (Year: 2013).*
Minskaia (BioMed Research International, 2013; 1-12, 2013). (Year: 2013).*
Whisstock (Quarterly Reviews of Biophysics, 36(3): 307-340, 2003, (Year: 2003).*
Rathore, (J. Mol. Biol. 425, 4442-4454 (2013) (Year: 2013).*
Yan (2000, Science 290:523-527) (Year: 2000).*
Donnelly (Journal of General Virology (2001), 82, 1027-1041, (Year: 2001).*
Hiraoka et al., "Tumor-Selective Gene Expression in a Hepatic Metastasis Model after Locoregional Delivery of a Replication-Competent Retrovirus Vector," Clin. Cancer Res. 12(23):7108-7116 (2006).

(Continued)

*Primary Examiner* — Anoop K Singh
*Assistant Examiner* — Magdalene K Sgagias
(74) *Attorney, Agent, or Firm* — Rimon, P.C.

(57) ABSTRACT

This disclosure provides modified recombinant retroviruses comprisings containing a 2A-peptide or peptide-like coding sequence operably linked to a heterologous polynucleotide. The disclosure further relates to cells and vector expressing or comprising such vectors and methods of using such modified vectors in the treatment of disease and disorders.

22 Claims, 18 Drawing Sheets

Specification includes a Sequence Listing.

(56) References Cited

U.S. PATENT DOCUMENTS

| | | |
|---|---|---|
| 2007/0003522 A1 | 1/2007 | Albritton |
| 2007/0254357 A1 | 11/2007 | Gregory et al. |
| 2008/0008685 A1 | 1/2008 | Kasahara |
| 2008/0227736 A1 | 9/2008 | Chen et al. |
| 2009/0169580 A1 | 7/2009 | Whelan et al. |
| 2012/0028821 A1 | 2/2012 | Jaenisch et al. |
| 2012/0052554 A1 | 3/2012 | Kasahara et al. |

FOREIGN PATENT DOCUMENTS

| | | |
|---|---|---|
| WO | 1999036561 A1 | 7/1999 |
| WO | 200104266 A1 | 1/2001 |
| WO | 03/022052 A1 | 3/2003 |
| WO | 03/060101 A2 | 7/2003 |
| WO | 2005/086922 A1 | 9/2005 |
| WO | 2006/048749 A1 | 5/2006 |
| WO | 2006127980 A2 | 11/2006 |
| WO | 2007/041350 A2 | 4/2007 |
| WO | 2007/065690 A1 | 6/2007 |
| WO | 2007095201 A2 | 8/2007 |
| WO | 2007107156 A2 | 9/2007 |
| WO | 2008151633 A2 | 12/2008 |
| WO | 2010002937 A1 | 1/2010 |
| WO | 2010036986 A2 | 4/2010 |
| WO | 2010045002 A2 | 4/2010 |
| WO | 2011126864 A2 | 10/2011 |
| WO | 2012021794 A1 | 2/2012 |
| WO | 2014/066700 A1 | 5/2014 |
| WO | 2014066700 A1 | 5/2014 |

OTHER PUBLICATIONS

Hiraoka et al., "Therapeutic Efficacy of Replication-Competent Retrovirus Vector-Mediated Suicide Gene Therapy in a Multifocal Colorectal Cancer Metastasis Model," Cancer Research 67(11):5345-5353 (2007).

Hirschowitz et al., "In vivo adenovirus-mediated gene transfer of the *Escherichia coli* cytosine deaminase gene to human colon carcinoma-derived tumors induces chemosensitivity to 5-fluorocytosine," Hum. Gene Ther. 6(8):1055-63 (1995).

Horn et al., "Highly efficient gene transfer into baboon marrow repopulating cells using GALV-pseudotype oncoretroviral vectors produced by human packaging cells," Blood 100:3960-3967 (2002).

Huber et al., "Metabolism of 5-fluorocytosine to 5-fluorouracil in human colorectal tumor cells transduced with the cytosine deaminase gene: significant antitumor effects when only a small percentage of tumor cells express cytosine deaminase," PNAS 91(17):8302-8306 (1994).

Hughes, Stephen H., "The RCAS Vector System," Folia Biologica (Praha) 50(3-4):107019 (2004).

Jespersen et al., "Epression of hterologous genes from an IRES translational cassette in replication competent murine leukemia virus vectors," Gene 239(2):227-235 (1999).

Johann et al., "Definition of a domain of GLVR1 which is necessary for infection by gibbon ape leukemia virus and which is highly polymorphic between species," J. Virol. 67:6733-6736 (1993).

Kaliberov et al., "Mutation of *Escherichia coli* cytosine deaminase significantly enhances molecular chemotherapy of human glioma," Gene Ther. 14(14):1111-9; Epub May 10, 2007.

Kaliberova et al., "Molecular chemotherapy of pancreatic cancer using novel mutant bacterial cytosine deaminase gene," 7(9):2845-54 (2008).

Kawasaki et al., "Replication-competent retrovirus vector-mediated prodrug activator gene therapy in experimental models of human malignant mesothelioma," Cancer Gene Therapy 18:571-578 (2011).

Kikuchi et al., "Highly Efficient Gene Delivery for Bladder Cancers by Intravesically Administered Replication-Competent Retroviral Vectors," Clin. Cancer Res. 13:4511-4518 (2007).

Klein et al., "Rapid identification of viable retrovirus-transduced cells using the green fluorescent protein as a marker," Gene Ther. 4:1256-1260 (1997).

Korean Application No. 10-2011-7008744, Office Action dated Aug. 25, 2015.

Kornblihtt et al., "Multiple links between transcription and splicing," RNA 10:1489-1498 (2004).

Kurozumi et al., "Apotosis Induction With 5-Fluorocytosine/Cytosine Deaminase gene therapy for Human Malignant Glioma Cells Mediated by Adenovirus," Journal of Neuro-Oncology 66(1-2):117-127 (2004).

Lazo et al., "Splice acceptor site for the env message of Moloney murine leukemia virus," J. Virol. 61:2038-2041 (1987).

Lipinski et al., "Optimization of a synthetic beta-catenin-dependent promoter for tumor-specific cancer gene therapy," Mol. Ther. 10:150-161 (2004).

Liu et al., "Tumor-specific therapeutic effect induced by an oncolytic adenoviral vector containing heat shock protein 70 and prodrug activation genes," Gene Therapy, 13(16):1235-43; Epub Apr. 13, 2006.

Liu et al. "Engineering conditionally replication-competent adenoviral vectors carrying the cytosine deaminase gene increase the infectivity and therapeutic effect for breast cancer gene therapy," Cancer Gene Therapy, 13(4):346-56 (2006).

Liu et al., "The receptors for gibbon ape leukemia virus and amphotropic murine leukemia virus are not downregulated in productively infected cells," Retrovirology 8:53 (2011).

Logg et al., "A Uniquely Stable Replication-Competent Retrovirus Vector Achieves Efficient Gene Delivery in Vitro and in Solid Tumors," Human Gene Therapy 12:921-932 (2001).

Logg et al., "Genomic Stability of Murine Leukemia Viruses Containing Insertions at the Env-3' Untranslated Region Boundary," Journal of Virology 75(15):6989-6998 (2001).

Logg et al., "Tissue-Specific Transcriptional Targeting of a Replication-Competent Retroviral Vector," Journal of Virology 76(24):12783-12791 (2002).

Logg et al., "Retrovirus-Mediated Gene Transfer to Tumors," Methods in Molecular Biology 246:499-525 (2004).

Logg et al., "Adaptive Evolution of a Tagged Chimeric Gammaretrovirus: Identification of Novel cis-Acting Elements that Modulate Splicing," J. Mol. Biol., 2007, 369, pp. 1214-1229.

Lu et al., "Highly efficient gene transfer to solid tumors in vivo by tumor-selective replicating retrovirus vectors," Int. J. Mol. Med. 25(5):769-75 (2010).

Maguire, Simon. Examination Report. New Zealand Application No. 592070, dated May 24, 2011.

Malim et al., "The HIV-1 rev trans-activator acts through a structured target sequence to activate nuclear export of unspliced viral mRNA," Nature 338:254-257 (1989).

Maria Gabriela Cabrera Valladares, Office Action, Mexican Patent Application No. MX/2014/059693, dated Dec. 1, 2014.

Marzio et al., "In vitro evolution of a highly replicating, doxycycline-dependent HIV for applications in vaccine studies," Proc. Natl Acad. Sci. USA 98:6342-6347 (2001).

Metzl et al., "Tissue- and Tumor-Specific Targeting of Murine Leukemia Virus-Based Replication-Competent Retroviral Vectors," Journal of Virology 80(14):7070-7078 (2006).

Mild et al., "Frequent intrapatient recombination between human immunodeficiency virus type 1 R5 and X4 envelopes: implications for coreceptor switch," J. Virol. 81:3369-3376 (2007).

Miller et al., "Gene transfer by retrovirus vectors occurs only in cells that are actively replicating at the time of infection," Mol. Cell. Biol. 10:4239-4242 (1990).

Miller et al., "Construction and properties of retrovirus packaging cells based on gibbon ape leukemia virus," J. Virol. 65:2220-2224 (1991).

Miller et al., "Intratumurol 5-Fluorouracil Produced by Cytosine Deaminase/5-Fluorocytosine Gene Therapy Is Effective for Experimental Human Glioblastomas," Cancer Res. 62:773 (2002).

Morgan et al., "Retroviral vectors containing putative internal ribosome entry sites: development of a polycistronic gene transfer system and applications to human gene therapy," Nucleic Acids Research 20(6):1293-1299 (1992).

Mullen et al., "Transfer of the bacterial gene for cytosine deaminase to mammalian cells confers lethal sensitivity to 5-fluorocytosine: a negative selection system," PNAS 89(1):33-37 (1992).

(56) References Cited

OTHER PUBLICATIONS

Murakami et al., "High-level expression of exogenous genes by replication-competent retrovirus vectors with an internal ribosomal entry site," Gene 202:23-29 (1997).
Nack et al., "Replacement of the murine leukemia virus (MLV) envelope gene with a truncated HIV envelope gene in MLV generates a virus with impaired replication capacity," Virology 315:209-216 (2003).
Nakamura et al., "Multimodality Therapy with a Replication-conditional Herpes Simplex Virus 1 Mutant that Expresses Yeast Cytosine Deaminase for intratumoral Conversion of 5-Fluorocytosine to 5-Fluorouracil," Cancer Res. 61:5447-5452 (2001); Epub Jul. 1, 2001.
Naldini et al., "Efficient transfer, integration, and sustained long-term expression of the transgene in adult rat brains injected with a lentiviral vector," Proc. Natl. Acad. Sci. USA 93:11382-11388 (1996).
Negroni et al., "Treatment of colon cancer cells using the cytosine deaminase/5-fluorocytosine suicide system induces apotosis, modulation of the proteome, and Hsp90B phsophorylation," Molecular Cancer Therapeutics 6:2747-2756 (2007).
Nogues et al., "Transcriptional activators differ in their abilities to control alternative splicing," J. Biol. Chem. 277:43110-43114 (2002).
Nyati et al., "High and Selective Expression of Yeast Cytosine Deaminase Under a Carcinoembryonic Antigen Promoter-Enhancer," Cancer Res. 62:2337-2342 (2002).
O'Reilly et al., "Second-site changes affect viability of amphotropic/ecotropic chimeric enveloped murine leukemia viruses," J. Virol. 74:899-913 (2000).
Overbaugh et al., "Receptors and entry cofactors for retroviruses include single and multiple transmembrane-spanning proteins as well as newly described glycophosphatidylinositol-anchored and secreted proteins," Microbiol. Mol. Biol. Rev. 65:371-389 (2001).
Owens et al., "Human and simian immunodeficiency virus capsid proteins are major viral determinants of early, postentry replication blocks in simian cells," J. Virol. 77:726-731 (2003).
Paar et al., "Effects of Viral Strain, Transgene Position, and Target Cell Type on Replication Kinetics, Genomic Stability and Transgene Expression of Replication-Competent Murine Leukemia Virus-Based Vectors," Journal of Virology 81(13):6973-6983 (2007).
Paar et al., "Influence of vector design and host cell on the mechanism of recombination and emergence of mutant subpopulations of replicating retroviral vectors," BMC Molecular Biology 10(8) (2009).
Fu, Yilong, Search Report and Written Opinion, Application No. 11201801731S, Intellectual Property Office of Singapore, dated Apr. 30, 2019.
Ibrahimi et al., "Highly Efficient Multicistronic Lentiviral Vectors with Peptide 2A Sequences", Human Gene Therapy 20:845-860 (Aug. 2009).
Browne, Edward P., "An Interleukin-1 Beta-Encoding Retrovirus Exhibits Enhanced Replication In Vivo", Journal of Virology, Jan. 2015, vol. 89, No. 1, pp. 155-164.
Young, Lee W. International Search Report and Written Opinion. International Application No. PCT/US2009/049322, dated Sep. 2, 2009.
Bieniasz, "Intrinsic Immunity: a front-line defense against viral attack," Nat. Immunol., 5(11):1109-1115, 2004.
Chavanne, Franz, Extended European Search Report, European Patent Office, Application No. 16842998.3, dated Dec. 14, 2018.
Kim et al., "High Cleavage Efficiency of a 2A Peptide Derived from Porcine Teschovirus-1 in Human Cell Lines, Zebrafish and Mice", PLOS One, vol. 6, No. 4, Apr. 29, 2011, e18556, pp. 1-8.
Perez et al., "Design and Selection of Toca 511 for Clinical Use: Modified Retroviral Replicating Vector with Improved Stability and Gene Expression," Molecular Therapy, vol. 20, No. 9, May 1, 2012, pp. 1689-1698.

Yang et al., "Development of optimal bicistronic lentiviral vectors facilitates high-level TCR gene expression and robust tumor cell recognition", Gene Therapy, vol. 15, No. 21, May 22, 2008, pp. 1-20.
Wittmann-Regis, Agnes, International Preliminary Report on Patentability and Written Opinion, PCT/US2016/044947, The International Bureau of WIPO, dated Mar. 15, 2018.
Young, Lee W., International Search Report and Written Opinion, PCT/US16/49947, United States Patent and Trademark Office, dated Feb. 3, 2017.
Aagaard et al., "Fv1-like restriction of N-tropic replication-competent murine leukaemia viruses in mCAT-1-expressing human cells," Journal of General Virology 83:439-442 (2002).
Addison et al., "Comparison of the human versus murine cytomegalovirus immediate early gene promoters for transgene expression by adenoviral vectors," J. Gen. Virol. 78:1653-1661 (1997).
Akbulut et al., "Cytotoxic effect of replication-competent adenoviral vectors carrying L-plastin promoter regulated E1A and cytosine deaminase genes in cancers of the breast, ovary, and colon," Cancer Gene Therapy 10:388-395 (2003.
Akbulut et al., "Vector targeting makes 5-fluorouracil chemotherapy less toxic and more effective in animal models of epithelial neoplasms," 10(22):7738-46 (2004).
Amar et al., "Control of small inhibitory RNA levels and RNA interference by doxycycline induced activation of a minimal RNA polymerase III promoter", Nucleic Acids Research, 2006, vol. 34, No. 5, pp. 1-7.
Ambrose et al., "In vitro characterization of a simian immunodeficiency virus human immunodeficiency virus (HIV) chimera expressing HIV type 1 reverse transcriptase to study antiviral resistance in pigtail macaques," J. Virol. 78:13553-13561 (2004).
Anello et al., "Adenovirus Mediated Cytosine Deaminase Gene Transduction and 5-fluorocytosine Therapy Sensitizes Mouse Prostate Cancer to Irradiation," The Journal of Urology 164(6):2173-2177 (2005).
Arrigo et al., "Regulation of Rous sarcoma virus RNA splicing and stability," Mol. Cell Biol. 8:4858-4867 (1988).
Bachrach et al., "Efficient Gene Transfer into Spleen Cells of Newborn Mice by a Replication-Competent Retroviral Vector," 293(2):328-334 (2002).
Bachrach et al., "In Vivo Infection of Mice by Replication-Competent MLV-Based Retrovirus Vectors," Methods in Molecular Medicine 76:343-352 (2003).
Baranick et al., "Splicing mediates the activity of four putative cellular internal ribosome entry sites," PNAS 105(12):4733-4738 (2008).
Barsov et al., "Adaptation of chimeric retroviruses in vitro and in vivo: isolation of avian retroviral vectors with extended host range," J. Virol. 75:4973-4983 (2001).
Beijer, Gijsbertus. International Preliminary Report on Patentability. International Application No. PCT/US2009/058510, dated Apr. 7, 2011.
Beijer, Gijsbertus. International Preliminary Report on Patentability. International Application No. PCT/US2009/058512, dated Apr. 7, 2011.
Blackburn et al., "Adenovrial transduction of a cytosine deaminase/thymidine kinase fusion gene into prostate carcinoma cells enhances prodrug and radiation sensitivity," International Journal of Cancer 82(2):293-297 (1999).
Bourbeau et al., "Suicide gene therapy with an adenovirus expressing the fusion gene CD::UPRT in human glioblastomas: different sensitivities correlate with p53 status," The Journal of Gene Medicine 6:1320-1332 (2004).
Bourbeau et al., "Improvement of antitumor activity by gene amplification with a replicating but nondisseminating adenovirus," 67(7):3387-95 (2007).
Bunnell et al., "Transplantation of transduced nonhuman primate CD34+ cells using a gibbon ape leukemia virus vector: restricted expression of the gibbon ape leukemia virus receptor to a subset of CD34+ cells," Gene Ther. 6:48-56 (1999).
Chang et al., "A Replication-Competent Feline Leukemia Virus, Subgroup A (FELV-A), Tagged with Green Fluorescent Protein

(56) References Cited

OTHER PUBLICATIONS

Reporter Exhibits In Vitro Biological Properties Similar to Those of the Parental FeIV-A," Journal of Virology 75(18):8837-8841 (2001).
Chen et al., "Inhibition of Marek's disease virus replication by retroviral vector-based RNA interference," Virology, 2008, vol. 377, No. 2, 265-272.
Cherry et al., "Retroviral Expression in Embryonic Stem Cells and Hematopoietic Stem Cells," Molecular and Cellular Biology 20(20):7419-7426 (2000).
Chio, Jun Ho. International Search Report and Written Opinion. International Application No. PCT/US2009/058510, dated Jul. 6, 2010.
Cho, Jeong Han. International Search Report and Written Opinion. International Application No. PCT/US2009/058512, dated May 11, 2011.
Coulombe et al., "A replication-competent promoter-trap retrovirus," J. Virol. 70:6810-6815 (1996).
Cupelli et al., "Transcriptional initiation and postinitiation effects of murine leukemia virus long terminal repeat R-region sequences," J. Virol. 65:6961-6968 (1991).
Cupelli et al., "The secondary structure of the R region of a murine leukemia virus is important for stimulation of long terminal repeat-driven gene expression," J. Virol. 72:7807-7814 (1998).
Delassus et al., "Genetic organization of gibbon ape leukemia virus," Virology 173:205-213 (1989).
Delviks, Krista Anda., "Development of murine leukemia virus-based vectors for more effective gene therapy: genetic analysis of direct repeat deletions," Dissertation, West Virginia (1999).
Dias et al., "Targeted chemotherapy for head and neck cancer with a chimeric oncolytic adenovirus coding for bifunctional suicide protein FCU1," Clin. Cancer Res. 16(9):2540-9; Epub Apr. 13, 2010.
Diaz et al., "Exchange of viral promoter/enhancer elements with heterologous regulatory sequences generates targeted hybrid long terminal repeat vectors for gene therapy of melanoma," J. Virol. 72:789-795 (1998).
Dillon et al., "Construction of a replication competent murine retrovirus vector expressing the human immunodeficiency virus type 1 Tat transactivator protein," J. Virol. 65:4490-4493 (1991).
Donahue et al., "Helper virus induced T cell lymphoma in nonhuman primates after retroviral mediated gene transfer," J. Expt. Med. 176:1125-1135 (1992).
Duch et al., "Transgene stability for three replication-competent murine leukemia virus vectors," Gene 329:61-69 (2004).
Edelstein et al., "Gene therapy clinical trials worldwide 1989-2004—an overview," J. Gene Med. 6:597-602 (2004).
Erbs et al., "In Vivo Cancer Gene Therapy by Adenovirus-mediated Transfer of a Bifunctional Yeast Cystosine Deaminase/Uracil Phosphoribosyltransferase Fusion Gene," Cancer Research 60(14):3813-3822 (2000).
Erbs et al. "Modified vaccinia virus Ankara as a vector for suicide gene therapy," Cancer Gene Ther. 15(1):18-28 (2008); Epub Nov. 9, 2007.
Erlwein et al., "The proline-rich region of the ecotropic Moloney murine leukaemia virus envelope protein tolerates the insertion of the green fluorescent protein and allows the generation of replication-competent virus," J. Gen. Virol. 84:369-373 (2003).
Ernst et al., "A structured retroviral RNA element that mediates nucleocytoplasmic export of intron containing RNA," Mol. Cell Biol. 17:135-144. (1997).
Evans et al., "A neutralizable epitope common to the envelope glycoproteins of ecotropic, polytropic, xenotropic, and amphotropic murine leukemia viruses," J. Virol. 64: 6176-6183 (1990).
Finger et al., "Replicating retroviral vectors mediating continuous production and secretion of therapeutic gene products from cancer cells," Cancer Gene Ther. 12:464-474 (2005).
Fischer et al., "Mechanisms of thymidine kinase/ganciclovir and cytosine deaminase/5-fluorocytosine suicide gene therapy-induced cell death in glioma cells," Oncogene 24:1231-1243 (2005).
Foloppe et al., "Targeted delivery of a suicide gene to human colorectal tumors by a conditionally replicating vaccinia virus," Gene Ther. 15(20):1361-71 (2008); Epub May 15, 2008.
Freytag et al., "Phase I Study of Replication-competent Adenovirus-mediated Double Suicide Gene Therapy for the Treatment of Locally Recurrent Prostate Cancer," Cancer Res. 62:4968 (2002).
Fuji, Miho, Final Office Action, Application No. 2016-159893, Japanese Patent Office, dated May 29, 2018.
Garton et al., "Efficient Expression of Exogenous Genes in Primary Vascular Cells Using IRES-Based Retroviral Vectors," Biotechniques 32:830-843 (2002).
Giffo-Schmitt, Beate. International Preliminary Report on Patentability. International Application No. PCT/US2009/049322, dated Jan. 5, 2011.
Guffey et al., "Engineered herpes simplex virus expressing bacterial cytosine deaminase for experimental therapy for brain tumors," Cancer Gene Therapy 14(1):45-56 (2007); Epub Sep. 22, 2006.
Hacein-Bey-Abina et al., "LMO2-associated clonal T cell proliferation intwo patients after gene therapy for SCID-X1," Science 302:415-419 (2003).
Heo, Joo Hyung, International Search Report and Written Opinion, PCT/US2013/066709, Korean Intellectual Property Office, dated Jan. 28, 2014.
Hiavaty et al., "Effects of sequences of prokaryotic origin on titer and transgene expression in retroviral vectors," Virology 330:351-360 (2004).
Pao et al., "Use of avian retroviral vectors to introduce transcriptional regulators into mammalian cells for analyses of tumor maintenance," PNAS, Jul. 22, 2003 100(15):8764-8769.
Paola et al., "Suicide Gene Therapy With the Yeast Fusion Gene Cytosine Deaminase/Uracil Phosphoribosyltransferase is Not Enough For Pancreatic Cancer," Pancreas 35(3):224-231 (2007).
Pluta et al., "Use of HIV as a gene transfer vector", Acta Biochimica Polonica, vol. 56, No. 4, 2009, pp. 531-595.
Poon et al. "Nucleocapsid and matrix protein contributions to selective human immunodeficiency virus type 1 genomic RNA packaging," J. Virol. 72:1983-1993 (1998).
Qiao et al. "VSV-G pseudotyped, MuLV-based, semi-replication-competent retrovirus for cancer treatment", Gene Ther., 13:1457-1470 (2006).
Rainov et al., "Clinical trials with retrovirus mediated gene therapy—what have we learned?," J. Neurooncol. 65:227-236 (2003).
Reik et al., Replication-competent Moloney murine leukemia virus carrying a bacterial suppressor tRNA gene: selective cloning of proviral and flanking host sequences. Proc. Natl. Acad. Sci. USA 82:1141-1145 (1985).
Robson et al., "Selection of optimal polypurine tract region sequences during Moloney murine leukemia virus replication," J. Virol. 74:10293-10303 (2000).
Roscigno et al., "A mutational analysis of the polypyrimidine tract of introns. Effects of sequence differences in pyrimidine tracts on splicing," J. Biol. Chem. 268:11222-11229 (1993).
Saavedra et al., "The simian retrovirus-1 constitutive transport element, unlike the HIV-1 RRE, uses factors required for cellular mRNA export," Curr. Biol. 7:619-628 (1997).
Sanders, D. A. "No false start for novel pseudotyped vectors," Curr. Opin. Biotechnol. 13, 437-442 (2002).
Schulz, Regine, Communication Pursuant to Article 94(3) EPC, European Patent Application No. 09816967.5, dated Oct. 17, 2014.
Schulz, Regine, Communication Pursuant to Article 94(3) EPC, European Patent Office, Application No. 09820986.9, dated Apr. 19, 2017.
Segall et al., "Characterization and Detection of Artificial Replication-Competent Lentivirus of Altered Host Range," Molecular Therapy 8:118-129 (2003).
Shikova-Lekova et al. "Replication-competent hybrids between murine leukemia virus and foamy virus," J. Virol. 77, 7677-7681 (2003).
Shin et al., "Replication of lengthened Moloney murine leukemia virus genomes is impaired at multiple stages," J. Virol. 74:2694-2702 (2000).

(56) References Cited

OTHER PUBLICATIONS

Short et al., "Correlation of leukemogenic potential of murine retroviruses with transcriptional tissue preference of the viral long terminal repeats," J. Virol. 61:1067-1072 (1987).
Sliva et al., "Stable integration of a functional shRNA expression cassette into the murine leukemia virus genome," Virology 351(1):218-225 (2006).
Sodroski et al., "Repetitive structure in the long-terminal-repeat element of a type II human T-cell leukemia virus," Proc. Natl. Acad. Sci. USA 81:4617-4621. 1984.
Soifer et al., "A Novel, Helper-Dependent, Adenovirus-Retrovirus Hybrid Vector: Stable Transduction by a Two-Stage Mechanism," Molecular Therapy 5(5):599-608 (2002).
Solly et al., "Replicative retroviral vectors for cancer gene therapy," Cancer Gene Ther. 10:30-39 (2003).
Staffa et al., Identification of positive and negative splicing regulatory elements within the terminal tat-rev exon of human immunodeficiency virus type 1. Mol. Cell Biol. 15:4597-4605 (1995).
Stewart et al., "Lentivirus-delivered gene stable gene silencing by RNAi in primary cells", RNA, 2003, vol. 9, No. 4, 493-501.
Stuhlmann et al., "Construction and properties of replication-competent murine retroviral vectors encoding methotrexate resistance," Mol. Cell. Biol. 9:100-108 (1989).
Subramanian et al., "Temperature-sensitive replication-competent adenovirus shRNA vectors to study cellular genes in virus-induced apoptosis," Methods in Molecular Medicine 130:125-134 (2007).
Sun et al., "Chronic gene delivery of interferon-inducible protein 10 through replication competent retrovirus vectors suppresses tumor growth," Cancer Gene Ther. 12:900-912 (2005).
Svarovskaia et al., Retroviral mutation rates and reverse transcriptase fidelity, Front. Biosci. 8:d117-d134 (2003).
Swanstrom et al., "Synthesis, assembly, and processing of viral proteins," In Retroviruses (Coffin, J. M., Hughes, S. H. & Varmus, H., eds), pp. 263-334, (1997). Cold Spring Harbor Laboratory Press, Plainview, NY.
Tai et al., "Antibody-Mediated Targeting of Replication-Competent Retroviral Vectors," Human Gene Therapy 14:789-802 (2003).
Tai et al., "Single-Shot, Multicycle Suicide Gene Therapy by Replication-Competent Retrovirus Vectors Achieves Long-Term Survival Benefit in Experimental Glioma," Molecular Therapy 12(5):842-851 (2005).
Tai et al., "Replication-competent retrovirus vectors for cancer gene therapy," Frontiers in Bioscience 13:3083-95 (2008).
Takeuchi et al., "Type C retrovirus inactivation by human complement is determined by both the viral genome and the producer cell," J. Virol. 68: 8001-8007 (1994).
Ter Brake, Olivier, "Lentiviral Vector Design for Multiple shRNA Expression and Durable HIV-1 Inhibition", Molecular Therapy, vol. 16, No. 3, pp. 557-564, Mar. 2008.
Trubetskoy et al., "R region sequences in the long terminal repeat of a murine retrovirus specifically increase expression of unspliced RNAs," J. Virol. 73:3477-3483 (1999).
Valsamakis et al., The human immunodeficiency virus type 1 polyadenylylation signal: a 3' long terminal repeat element upstream of the AAUAAA necessary for efficient polyadenylylation, Proc. Natl. Acad. Sci. USA 88:2108-2112 (1991).
Van Santen et al., "mRNA precursor splicing in vivo: sequence requirements determined by deletion analysis of an intervening sequence," Proc. Natl Acad. Sci. USA 82:2885-2889 (1985).
Vermes et al., "An accelerated stability study of 5-flucytosine in intravenous solution", Pharmacy World & Science, vol. 21, No. 1, 1999, pp. 35-39.

Vermes et al., "Prediction of Flucytosine-Induced Thrombocytopenia Using Creatinine Clearance", Chemotherapy, 2000, 46:335-341.
Vermes et al., "Flucytosine: Correlation between Toxicity and Pharmacokinetic Parameters", Chemotherapy, 2000, 46:86-94.
Vermes et al., "An in vitro Study on the Active Conversion of Flucytosine to Fluorouracil by Microorganisms in the Human Intestinal Microflora", Chemotherapy, 2003, 49:17-23.
Wang et al., "Highly Efficient and Tumor-Restricted Gene Transfer to Malignant Gliomas by Replication-Competent Retroviral Vectors," Human Gene Therapy 14:117-127 (2003).
Wang et al., "A murine leukemia virus with Cre-LoxP excisible coding sequences allowing superinfection, transgene delivery, and generation of host genomic deletions," Retrovirology 1(5) (2004).
Warmann et al., "Adenovirus-mediated cytosine deaminase/5-fluorocytosine suicide gene therapy of human hepatoblastoma in vitro," Pediatric Blood & Cancer, 53: 145-151 (2009).
Xie et al., "Adenovirus-mediated tissue-targeted expression of a caspase-9-based artificial death switch for the treatment of prostate cancer," Cancer Res. 61:6795-6804 (2001).
Xie et al., "Enhanced Retinal Ganglion Cell Differentiation by ath5 and NSCL1 Coexpression," IOVS 45(9):2922-2928 (2004).
Yamashita et al., "The cell cycle independence of HIV infections is not determined by known karyophilic viral elements," PLoS Pathog. 1:e18 (2005).
Yap et al., "Trim5alpha protein restricts both HIV-1 and murine leukemia virus," Proc. Natl. Acad. Sci. USA 101:10786-10791 (2004).
Yi, et al., "Retroviral gene therapy: safety issues and possible solutions," Curr. Gene Ther. 5:25-35 (2005).
Yoon, Laurent, "Genomic Stability of Transcriptionally Targeted Replication Competent Retroviral Vectors", Dissertation, University of Southern California, May 2008.
Young et al., "Chimeric Retroviral Helper Virus and Picornavirus IRES Sequence To Eliminate DNA Methylation for Improved Retroviral Packaging Cells," J. Virol. 74(11):5242-5249 (2000).
Notice of Reasons for Rejection for Japanese patent application JP2018-511704, dated Jul. 7, 2020, 9 pages with extra 8 pages of English language equivalent or summary.
Response to Office Action for Japanese patent application JP2018-511704, dated Jan. 7, 2021, 15 pages.
Amendment Claims as filed for Japanese patent application JP2018-511704, dated Jan. 7, 2021, 6 pages.
International Search Report for international patent application PCT/US2016/049947, dated Feb. 3, 2017, 6 pages.
Written Opinion of the International Searching Authority for international patent application PCT/US2016/049947, dated Feb. 3, 2017, 10 pages.
International Preliminary Report on Patentability for international patent application PCT/US2016/049947, dated Mar. 6, 2018, 11 pages.
Armitage et al., "APOBEC3G-Induced Hypermutation of Human Immunodeficiency Virus Type-1 Is Typically a Discrete "All or Nothing" Phenomenon," PLoS Genet., 2012, vol. 8; e1002550, pp. 1-12.
Kim et al., "High Cleavage Efficiency of a 2A Peptide Derived from Porcine Teschovirus-1 in Human Cell Lines, Zebrafish and Mice," PLoS One, 2011, vol. 6; e18556, pp. 1-8.
Kodama et al., "II. Mechanism of HIV infection and proliferation, Focusing on the action points of antiviral agents," The Journal of the Japanese Society of Internal Medicine, 2009, vol. 98, pp. 2754-2761.
Neogi et al., "Human APOBEC3G-mediated hypermutation is associated with antiretroviral therapy failure in HIV-1 subtype C-infected individuals," J. Int. AIDS Soc., 2013, vol. 16; 18472, pp. 1-8.

* cited by examiner

Equine rhinitis A virus (ERAV)     E2A - - - - QCTNYALLKLAGDVESNPG P-
Foot-and-mouth disease (FMDV)      F2A - PVKQLLNFDLLKLAGDVESNPG P-
Porcine teschovirus-1 (PTV1)       P2A - - - - - ATNFSLLKQAGDVEENPG P-
Thosea asigna virus (TaV)          T2A - - - - - - EGRGSLLTCGDVEENPG P-

FIG. 1

*Picornaviruses*

| | | |
|---|---|---|
| EMC-B | GIFNAHYAGYFADLLIHDIETNPG P | (SEQ ID NO:59) |
| EMC-D | GYFADLLIHDIETNPG P | (SEQ ID NO:60) |
| EMC-PV21 | RIFNAHYAGYFADLLIHDIETNPG P | (SEQ ID NO:61) |
| MENGO | HVFETHYAGYFSDLLIHDVETNPG P | (SEQ ID NO:62) |
| TME-GD7 | KAVRGYHADYYKQRLIHDVEMNPG P | (SEQ ID NO:63) |
| TME-DA | RAVRAYHADYYKQRLIHDVEMNPG P | (SEQ ID NO:64) |
| TME-BEAN | KAVRGYHADYYRQRLIHDVETNPG P | (SEQ ID NO:65) |
| Theiler's-Like Virus | KHVREYHAAYYKQRLMHDVETNPG P | (SEQ ID NO:66) |
| Ljungan virus (174F) | MHSDEMDFAGGKFLNQCGDVETNPG P | (SEQ ID NO:67) |
| Ljungan virus (145SL) | MHNDEMDYSGGKFLNQCGDVESNPG P | (SEQ ID NO:68) |
| Ljungan virus (87-012) | MHSDEMDFAGGKFLNQCGDVETNPG P | (SEQ ID NO:69) |
| Ljungan virus (M1146) | YHDKDMDYAGGKFLNQCGDVETNPG P | (SEQ ID NO:70) |
| FMD-A10 | APAKQ LLNFDLLKLAGDVESNPG P | (SEQ ID NO:71) |
| FMD-A12 | APGKQ LLNFDLLKLAGDVESNPG P | (SEQ ID NO:72) |
| FMD-C1 | APAKQ LLNFDLLKLAGDVESNPG P | (SEQ ID NO:73) |
| FMD-O1G | APVKQ LLNFDLLKLAGDMESNPG P | (SEQ ID NO:74) |
| FMD-O1K | APVKQ LTNFDLLKLAGDVESNPG P | (SEQ ID NO:75) |
| FMD-O (Taiwan) | APAKQ LLNFDLLKLAGDVESNPG P | (SEQ ID NO:76) |
| FMD-O/SK | APVKQ LLSFDLLKLAGDVESNPG P | (SEQ ID NO:77) |
| FMD-SAT3 | KPDKQ MCNFDLLKLAGDVESNPG P | (SEQ ID NO:78) |
| FMD-SAT2 | GVAKQ LLNFDLLKLAGDVESNPG P | (SEQ ID NO:79) |
| ERAV | NINKQ CTNYSLLKLAGDVESNPG P | (SEQ ID NO:80) |
| ERBV | TILSE GATNFSLLKLAGDVELNPG P | (SEQ ID NO:81) |
| ERV-3 | NLLSQ GATNFDLLKLAGDVESNPG P | (SEQ ID NO:82) |
| PTV-1 | VMAFQ GPGATNFSLLKQAGDVEENPG P | (SEQ ID NO:83) |
| PTV-2 | TMMLQ GPGATNFSLLKQAGDVEENPG P | (SEQ ID NO:84) |
| PTV-3 | TMSFQ GPGASSFSLLKQAGDVEENPG P | (SEQ ID NO:85) |
| PTV-4 | TMMLQ GPGASNFSLLKQAGDVEENPG P | (SEQ ID NO:86) |
| PTV-5 | TMLFQ GPGAANFSLLRQAGDVEENPG P | (SEQ ID NO:87) |
| PTV-6 | TMSFQ GPGATNFSLLKQAGDVEENPG P | (SEQ ID NO:88) |
| PTV-7 | VVSFQ GPGATNFSLLKQAGDVEENPG P | (SEQ ID NO:89) |
| PTV-8 | TMSLQ GPGATNFSLLKQAGDIEENPG P | (SEQ ID NO:90) |
| PTV-9 | TMAFQ GPGATNFSLLKQAGDVEENPG P | (SEQ ID NO:91) |
| PTV-10 | TLSFQ GPGATNFSLLKQAGDVEENPG P | (SEQ ID NO:92) |
| PTV-11 | RMSFQ GPGATNFSLLKRAGDVEENPG P | (SEQ ID NO:93) |

*Insect Viruses*

| | | |
|---|---|---|
| CrPV | FLRKRTQLLMSGDVESNPG P | (SEQ ID NO:94) |
| DCV | EAARQMLLLLSGDVETNPG P | (SEQ ID NO:95) |
| ABPV | GSWTDILLLLSGDVETNPG P | (SEQ ID NO:96) |
| ABPV isolate Poland 1 | GSWTDILLLLSGDVETNPG P | (SEQ ID NO:97) |
| ABPV isolate Hungary 1 | GSWTDILLLWSGDVETNPG P | (SEQ ID NO:98) |
| IFV | TRAEIEDELIRAGIESNPG P | (SEQ ID NO:99) |
| TaV | RAEGRGSLLTCGDVEENPG P | (SEQ ID NO:100) |
| EEV | QGAGRGSLVTCGDVEENPG P | (SEQ ID NO:101) |
| APV | NYPMPEALQKIIDLESNPP P | (SEQ ID NO:102) |
| KBV | GTWESVLNLLAGDIELNPG P | (SEQ ID NO:103) |
| PnPV (a) | AQGWVPDLTVDGDVESNPG P | (SEQ ID NO:104) |
| PnPV (b) | IGGGQKDLTQDGDIESNPG P | (SEQ ID NO:105) |
| Ectropis obliqua picorna-like virus | (a) AQGWAPDLTQDGDVESNPG P | (SEQ ID NO:106) |
| | (b) IGGGQRDLTQDGDIESNPG P | (SEQ ID NO:107) |
| Providence virus | (a) VGDRGSLLTCGDVESNPG P | (SEQ ID NO:108) |
| | (c) SGGRGSLLTAGDVEKNPG P | (SEQ ID NO:110) |
| | (b) GDPIEDLTDDGDIEKNPG P | (SEQ ID NO:109) |

FIG. 2

*Type C Rotaviruses*

Bovine Rotavirus         SKFQIDRILISGDIELNPG P  (SEQ ID NO:111)
    Porcine Rotavirus        AKFQIDKILISGDVELNPG P  (SEQ ID NO:112)
    Human Rotavirus          SKFQIDKILISGDIELNPG P  (SEQ ID NO:113)

*Reovirus (cypovirus 1)*

Bombyx mori              FRSNYDLLKLCGDIESNPG P  (SEQ ID NO:114)
    Lymantria dispar         FRSNYDLLKLCGDVESNPG P  (SEQ ID NO:115)
    Dendrolimus punctatus    FRSNYDLLKLCGDVESNPG P  (SEQ ID NO:116)

*Trypansoma spp. Repeated Sequences*

T. brucei TSR1           SSIIRTKMLVSGDVEENPG P  (SEQ ID NO:117)
    (CAB95325.1)             SSIIRTKMLLSGDVEENPG P  (SEQ ID NO:118)
    (CAB95559.1)             SSIIRTKILLSGDVEENPG P  (SEQ ID NO:119)
    T. cruzi AP
     Endonuclease            CDAQRQKLLLSGDIEQNPG P  (SEQ ID NO:120)

*Prokaryotic Sequences*

T. maritima aguA         YIPDFGGFLVKADSEFNPG  P  (SEQ ID NO:121)
    B. bronchiseptica        VHCAGRGGPVRLLDKEGNPG P  (SEQ ID NO:122)

*Eukaryotic (cellular) Sequences*

Mouse mor-1F             DLELETVGSHQADAETNPG P  (SEQ ID NO:123)
    D. melanogaster
     mod(mdg4)               TAADKIQGSWKMDTEGNPG P  (SEQ ID NO:124)
    A. nidulans Ca
     channel MID1            PITNRPRNSGLIDTEINPG P  (SEQ ID NO:125)

FIG. 2 (continued)

RECOMBINANT VECTORS COMPRISING 2A PEPTIDE

CROSS REFERENCE TO RELATED APPLICATIONS

This application is a U.S. National Stage Application filed under 35 U.S.C § 371 and claims priority to International Application No. PCT/US2016/049947, filed Sep. 1, 2016, which application claims priority to U.S. Provisional Application Ser. No. 62/214,884, filed Sep. 4, 2015, the disclosures of which are incorporated herein by reference.

REFERENCE TO SEQUENCE LISTING

The present application is being filed along with a Sequence Listing in electronic format. The Sequence Listing is provided as a file entitled Sequence-Listing_ST25.txt, created Sep. 1, 2016, which is 245,703 bytes (239 Kb) in size. The information in the electronic format of the Sequence Listing is incorporated herein by reference in its entirety.

TECHNICAL FIELD

This disclosure relates to replication competent retroviral vectors. The disclosure further relates to the use of such replication competent retroviral vectors for delivery and expression of heterologous nucleic acids in cells.

BACKGROUND

Effective methods of delivering genes and heterologous nucleic acids to cells and subjects has been a goal of researchers for scientific development and for possible treatments of diseases and disorders.

SUMMARY

The disclosure provides a recombinant replication competent retrovirus comprising a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a cassette comprising a 2A peptide or peptide-like coding sequence operably linked to a heterologous polynucleotide, wherein the cassette is positioned 5' to the 3' LTR and is operably linked and 3' to the env nucleic acid domain encoding the retroviral envelope; and cis-acting sequences necessary for reverse transcription, packaging and integration in a target cell. In one embodiment, the envelope is chosen from one of amphotropic, polytropic, xenotropic, 10A1, GALV, Baboon endogenous virus, RD114, rhabdovirus, alphavirus, measles or influenza virus envelopes. In another embodiment, the retroviral polynucleotide sequence is derived from a virus selected from the group consisting of murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus (XMRV), avian reticuloendotheliosis virus (REV), or Gibbon ape leukemia virus (GALV). In yet another embodiment, the retrovirus is a gammaretrovirus. In another embodiment, the target cell is a mammalian cell. In yet another embodiment, the 2A peptide or peptide like coding sequence encodes a peptide containing the sequence of SEQ ID NO:1. In still another embodiment, the 2A peptide or peptide-like coding sequence encodes a peptide set forth in any one of SEQ ID Nos:55-125. In another embodiment, the 2A peptide or peptide-like coding sequence comprises a sequence as set forth in SEQ ID Nos: 8-19. In still another embodiment of any of the foregoing embodiments, the heterologous polynucleotide is >500 bp, >1000 bp, >1100 bp, >1200 bp >1300 bp, >1403 bp or >1500 bp in length. In another embodiment, the heterologous polynucleotide comprises at least 2 coding sequences. In yet another embodiment, the retrovirus further comprises a second cassette comprising a 2A peptide or peptide-like coding sequence downstream of the cassette. In yet another embodiment, the retrovirus further comprises a second cassette downstream of the cassette, wherein the second cassette comprises an internal ribosome entry site (IRES) or a minipromoter or a polIII promoter operably linked to a second heterologous polynucleotide.

The disclosure also provides a recombinant replication competent retrovirus comprising: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a cassette comprising a regulatory domain operably linked to a first heterologous polynucleotide operably linked to at least one 2A cassette comprising a 2A peptide or pep-ide-like coding sequence operably linked to a second heterologous polynucleotide, wherein the cassette is positioned 5' to the 3' LTR and 3' to the env nucleic acid domain encoding the retroviral envelope and wherein the 2A cassette is downstream and operably linked to first heterologous polynucleotide; and cis-acting sequences necessary for reverse transcription, packaging and integration in a target cell. In one embodiment, the envelope is chosen from one of amphotropic, polytropic, xenotropic, 10A1, GALV, Baboon endogenous virus, RD114, rhabdovirus, alphavirus, measles or influenza virus envelopes. In another embodiment, the retroviral polynucleotide sequence is derived from a virus selected from the group consisting of murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus (XMRV), avian reticuloendotheliosis virus (REV), or Gibbon ape leukemia virus (GALV). In yet another embodiment, the retrovirus is a gammaretrovirus. In yet another embodiment, the target cell is a mammalian cell. In another embodiment, the 2A peptide or peptide like coding sequence encodes a peptide containing the sequence of SEQ ID NO:1. In another embodiment, the 2A peptide or peptide-like coding sequence encodes a peptide set forth in any one of SEQ ID Nos: 55-125. In still another embodiment, the 2A peptide or peptide-like coding sequence comprises a sequence as set forth in any one of SEQ ID Nos:8-19. In any of the foregoing embodiments, the target cell is selected from the group consisting of lung cancer cell, colon-rectum cancer cell, breast cancer cell, prostate cancer cell, urinary tract cancer cell, uterine cancer cell, brain cancer cell, head and neck cancer cell, pancreatic cancer cell, melanoma cell, stomach cancer and ovarian cancer cell. In still any of the foregoing embodiments, the promoter sequence is associated with a growth regulatory gene. In yet a further embodiment of any of the foregoing embodiments, the promoter sequence comprises a tissue-specific promoter sequence. In a further embodiment, the tissue-specific promoter sequence comprises at least one androgen response element (ARE). In a further embodiment of any of the foregoing, the promoter comprises a CMV promoter having a sequence as set forth in SEQ ID NO:2 from nucleotide 1 to about nucleotide 582 and may include modification to one or more nucleic acid bases and which is capable of directing and initiating transcription. In a further embodiment of any of the foregoing, the promoter comprises a CMV-R-U5 domain polynucleotide. In further embodiment, the CMV-R-U5 domain comprises the immediately early promoter from human cytomegalovirus linked to an MLV R-U5 region. In still a further embodiment, the CMV-R-U5 domain polynucleotide comprises a sequence as set forth in SEQ ID NO:2 from about nucleotide 1 to about nucleotide 1202 or sequences that are at least 95% identical to a sequence as set forth in SEQ ID NO:2 from nucleotide 1 to about 1202, wherein the polynucleotide promotes transcription of a nucleic acid molecule operably linked thereto. In a further embodiment of any of the foregoing, the gag polynucleotide is derived from a gammaretrovirus. In a further embodiment, the gag nucleic acid domain comprises a sequence from about nucleotide number 1203 to about nucleotide 2819 of SEQ ID NO: 2 or a sequence having at least 95%, 98%, 99% or 99.8% identity thereto. In a further embodiment of any of the foregoing, the pol domain of the polynucleotide is derived from a gammaretrovirus. In a further embodiment, the pol domain comprises a sequence from about nucleotide number 2820 to about nucleotide 6358 of SEQ ID NO:2 or a sequence having at least 95%, 98%, 99% or 99.9% identity thereto. In a further embodiment of any of the foregoing, the env domain comprises a sequence from about nucleotide number 6359 to about nucleotide 8323 of SEQ ID NO:2 or a sequence having at least 95%, 98%, 99% or 99.8% identity thereto. In a further embodiment of any of the foregoing, the 3' LTR is derived from a gammaretrovirus. In a further embodiment, the 3' LTR comprises a U3-R-U5 domain. In still a further embodiment, the 3' LTR comprises a sequence as set forth in SEQ ID NO:2 from about nucleotide 9111 to about 11654 or a sequence that is at least 95%, 98% or 99.5% identical thereto. In a further embodiment of any of the foregoing, the heterologous nucleic acid sequence encodes a biological response modifier or an immunopotentiating cytokine. In a further embodiment, the immunopotentiating cytokine is selected from the group consisting of interleukins 1 through 38, interferon, tumor necrosis factor (TNF), and granulocyte-macrophage-colony stimulating factor (GM-CSF). In a further embodiment, the immunopotentiating cytokine is interferon gamma. In a further embodiment of any of the foregoing, the heterologous nucleic acid encodes a polypeptide that converts a nontoxic prodrug in to a toxic drug. In a further embodiment, the polypeptide that converts a nontoxic prodrug in to a toxic drug is thymidine kinase, purine nucleoside phosphorylase (PNP), or cytosine deaminase. In a further embodiment of any of the foregoing, the heterologous nucleic acid sequence encodes a receptor domain, an antibody, or antibody fragment. In one embodiment, the second cassette comprises an inhibitory polynucleotide. In a further embodiment, the inhibitory polynucleotide comprises an miRNA, RNAi or siRNA sequence.

The disclosure also provides a recombinant retroviral polynucleotide genome for producing a retrovirus as describe in any of the embodiments above. In one embodiment, the polynucleotide comprises an MLV 4070A envelope protein gene in-frame with 2A peptide or peptide-like coding sequence with or without a GSG linker coding sequence, and a second gene in-frame with the 2A peptide or 2A-like coding sequence. In another embodiment, the polynucleotide comprises an MLV 10A1 envelope protein gene in-frame with 2A peptide or peptide-like coding sequence with or without a GSG linker coding sequence, and a second gene in-frame with the 2A peptide or 2A-like coding sequence. In another embodiment, the polynucleotide comprises an XMRV envelope protein gene in-frame with 2A peptide or peptide-like coding sequence with or without a GSG linker coding sequence, and a second gene in-frame with the 2A peptide or 2A-like coding sequence. In another embodiment, the polynucleotide comprises a non-Friend MLV envelope protein gene in-frame with 2A peptide or peptide-like coding sequence with or without a GSG linker coding sequence, and a second gene in-frame with the 2A peptide or 2A-like coding sequence. In another embodiment of any of the foregoing, the heterologous polynucleotide is a secretory, membrane, cytoplasmic, nuclear, or cellular-compartment-specific proteins.

In any of the foregoing embodiments, the recombinant retrovirus and/or the heterologous polynucleotide are engineered to remove tryptophan codons susceptible to human APOBEC hypermutations. In one embodiment, the heterologous polynucleotide encodes a polypeptide having cytosine deaminase activity. In a further embodiment, the polypeptide having cytosine deaminase activity encodes a polypeptide of SEQ ID NO:29, wherein X is any amino acid except tryptophan.

The disclosure also provides a recombinant replication competent retrovirus that is resistant to inactivation by human APOBEC by engineering codons in a retroviral polynucleotide susceptible to APOBEC hypermutation to a non-susceptible codon. In one embodiment, a codon susceptible to APOBEC hypermutation encodes a tryptophan amino acid. In yet another embodiment, the recombinant retrovirus comprises an IRES cassette, promoter cassette and/or 2A peptide cassette downstream of the env gene.

The disclosure also provides a method of treating a cell proliferative disorder comprising contacting the subject with a retrovirus as described in any of the foregoing embodiments, under conditions such that the heterologous polynucleotide is expressed and wherein the heterologous polynucleotide encodes a protein the converts a prodrug to a cytotoxic drug.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 1 shows a sequence alignment of amino acid sequence of the 2A regions of foot-and-mouth disease virus (F2A), equine rhinitis A virus (E2A), *Thosea asigna* virus (T2A) and porcine teschovirus-1 (P2A) (SEQ ID Nos: 55 to 58).

FIG. 2 shows a sequence alignment of 2A peptide sequences present in different classes of viruses (SEQ ID Nos: 59 to 125).

DETAILED DESCRIPTION

Figure 3:
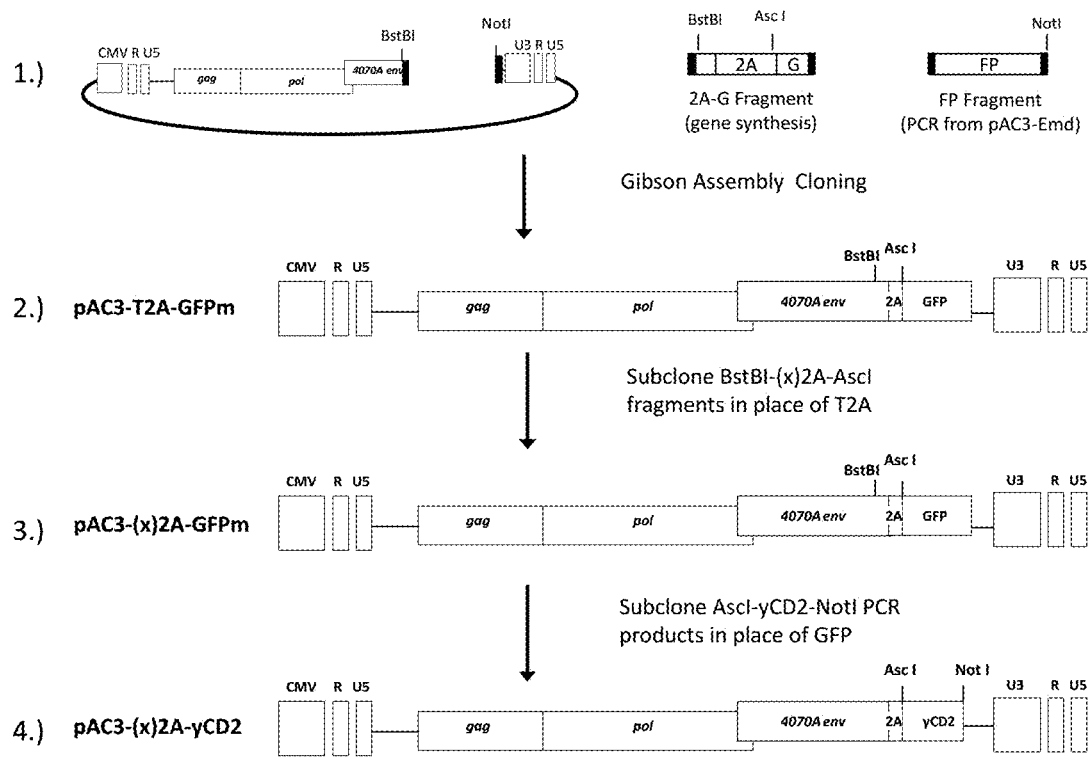
FIG. 3 shows cloning schemes of pAC3-(x)2A-GFPm and pAC3-(x)2A-yCD2 vector sets. Black box represents overlapping sequences utilized in Gibbson Assembly Cloning; (x) represents 2A peptide from Equine rhinitis A (E), Foot-and-mouth disease virus (F), Porcine teschovirus-1 (P) or *Thosea asigna* virus (T).

As used herein and in the appended claims, the singular forms "a," "and," and "the" include plural referents unless the context clearly dictates otherwise. Thus, for example, reference to "a cell" includes a plurality of such cells and reference to "the vector" includes reference to one or more vectors, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

General texts which describe molecular biological techniques useful herein, including the use of vectors, promoters and many other relevant topics, include: Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook"); Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"); and S. Carson, H. B. Miller & D. S. Witherow and Molecular Biology Techniques: A Classroom Laboratory Manual, Third Edition, Elsevier, San Diego (2012). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The publications discussed throughout the text are provided solely for their disclosure prior to the filing date of the present application. Nothing herein is to be construed as an admission that the inventors are not entitled to antedate such disclosure by virtue of prior disclosure.

The disclosure provides methods and compositions useful for gene or protein delivery to a cell or subject. Such methods and compositions can be used to treat various diseases and disorders in a subject including cancer and other cell proliferative diseases and disorders. The disclosure provides replication competent retroviral vectors for gene delivery to a cell.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise DNA or RNA, into which foreign DNA encoding a protein is inserted by restriction enzyme technology. A common type of vector is a "plasmid", which generally is a self-contained molecule of double-stranded DNA that can readily accept additional (foreign) DNA and which can be readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

A recombinant replication competent retroviral vector or retroviral replicating vector (RRV) refers to a vector based on a member of the retroviridae family of viruses. The structures of retroviruses are well characterized as described more fully below. Such vectors can be engineered using recombinant genetic techniques to modify the parent virus to be a non-naturally occurring RRV by inserting heterologous genes or sequences. Such modification can provide attributes to the vectors that allow them to deliver genes to be express to a host cell in vitro or in vivo.

Retroviruses have been classified in various ways but the nomenclature has been standardized in the last decade (see ICTVdB—The Universal Virus Database, v 4 on the World Wide Web (www) at ncbi.nlm.nih.gov/ICTVdb/ICTVdB/ and the text book "Retroviruses" Eds Coffin, Hughs and Varmus, Cold Spring Harbor Press 1997; the disclosures of which are incorporated herein by reference). In one embodiment, the replication competent retroviral vector can comprise an Orthoretrovirus or more typically a gamma retrovirus vector.

Retroviruses are defined by the way in which they replicate their genetic material. During replication the RNA is converted into DNA. Following infection of the cell a double-stranded molecule of DNA is generated from the two molecules of RNA which are carried in the viral particle by the molecular process known as reverse transcription. The DNA form becomes covalently integrated in the host cell genome as a provirus, from which viral RNAs are expressed with the aid of cellular and/or viral factors. The expressed viral RNAs are packaged into particles and released as infectious virion.

The retrovirus particle is composed of two identical RNA molecules. Each wild-type genome has a positive sense, single-stranded RNA molecule, which is capped at the 5' end and polyadenylated at the 3' tail. The diploid virus particle contains the two RNA strands complexed with gag proteins, viral enzymes (pol gene products) and host tRNA molecules within a 'core' structure of gag proteins. Surrounding and protecting this capsid is a lipid bilayer, derived from host cell membranes and containing viral envelope (env) proteins. The env proteins bind to a cellular receptor for the virus and the particle typically enters the host cell via receptor-mediated endocytosis and/or membrane fusion.

After release of the viral particle into a targeted cell, the outer envelope is shed, the viral RNA is copied into DNA by reverse transcription. This is catalyzed by the reverse transcriptase enzyme encoded by the pol region and uses the host cell tRNA packaged into the virion as a primer for DNA synthesis. In this way the RNA genome is converted into the more complex DNA genome.

The double-stranded linear DNA produced by reverse transcription may, or may not, have to be circularized in the nucleus. The provirus now has two identical repeats at either end, known as the long terminal repeats (LTR). The termini of the two LTR sequences produces the site recognized by a pol product—the integrase protein—which catalyzes integration, such that the provirus is always joined to host DNA two base pairs (bp) from the ends of the LTRs. A duplication of cellular sequences is seen at the ends of both LTRs, reminiscent of the integration pattern of transposable genetic elements. Retroviruses can integrate their DNAs at many sites in host DNA, but different retroviruses have different integration site preferences. HIV-1 and simian immunodeficiency virus DNAs preferentially integrate into expressed genes, murine leukemia virus (MLV) DNA preferentially integrates near transcriptional start sites (TSSs), and avian sarcoma leukosis virus (ASLV) and human T cell leukemia virus (HTLV) DNAs integrate nearly randomly, showing a slight preference for genes (Derse D, et al. (2007), J Virol 81:6731-6741; Lewinski M K, et al. (2006), PLoS Pathog 2:e601).

Transcription, RNA splicing and translation of the integrated viral DNA is mediated by host cell proteins. Variously spliced transcripts are generated. In the case of the human retroviruses HIV-1/2 and HTLV-I/II viral proteins are also used to regulate gene expression. The interplay between cellular and viral factors is a factor in the control of virus latency and the temporal sequence in which viral genes are expressed.

Retroviruses can be transmitted horizontally and vertically. Efficient infectious transmission of retroviruses requires the expression on the target cell of receptors which specifically recognize the viral envelope proteins, although viruses may use receptor-independent, nonspecific routes of entry at low efficiency. Normally a viral infection leads to a single or few copies of viral genome per cell because of receptor masking or down-regulation that in turn leads to resistance to superinfection (Ch3 p104 in "Retroviruses", J M Coffin, S H Hughes, & H E Varmus 1997 Cold Spring Harbor Laboratory Press, Cold Spring Harbor N.Y.; Fan et al. J. Virol 28:802, 1978). By manipulating the situation in tissue culture it is possible to get some level of multiple infection but this is typically less than 5 copies/diploid genome. In addition, the target cell type must be able to support all stages of the replication cycle after virus has bound and penetrated. Vertical transmission occurs when the viral genome becomes integrated in the germ line of the host. The provirus will then be passed from generation to generation as though it were a cellular gene. Hence endogenous proviruses become established which frequently lie latent, but which can become activated when the host is exposed to appropriate agents.

The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2) and simian immunodeficiency virus (SIV).

The oncoviruses have historically been further subdivided into groups A, B, C and D on the basis of particle morphology, as seen under the electron microscope during viral maturation. A-type particles represent the immature particles of the B- and D-type viruses seen in the cytoplasm of infected cells. These particles are no-infectious. B-type particles bud as mature virion from the plasma membrane by the enveloping of intracytoplasmic A-type particles. At the membrane they possess a toroidal core of 75 nm, from which long glycoprotein spikes project. After budding, B-type particles contain an eccentrically located, electron-dense core. The prototype B-type virus is mouse mammary tumor virus (MMTV). No intracytoplasmic particles can be observed in cells infected by C-type viruses. Instead, mature particles bud directly from the cell surface via a crescent 'C'-shaped condensation which then closes on itself and is enclosed by the plasma membrane. Envelope glycoprotein spikes may be visible, along with a uniformly electron-dense core. Budding may occur from the surface plasma membrane or directly into intracellular vacuoles. The C-type viruses are the most commonly studied and include many of the avian and murine leukemia viruses (MLV). Bovine leukemia virus (BLV), and the human T-cell leukemia viruses types I and II (HTLV-I/II) are similarly classified as C-type particles because of the morphology of their budding from the cell surface. However, they also have a regular hexagonal morphology and more complex genome structures than the prototypic C-type viruses such as the murine leukemia viruses (MLV). D-type particles resemble B-type particles in that they show as ring-like structures in the infected cell cytoplasm, which bud from the cell surface, but the virion incorporate short surface glycoprotein spikes. The electron-dense cores are also eccentrically located within the particles. Mason Pfizer monkey virus (MPMV) is the prototype D-type virus.

In many situations for using a recombinant replication competent retrovirus therapeutically, it is advantageous to have high levels of expression of the transgene that is encoded by the recombinant replication competent retrovirus. For example, with a prodrug activating gene such as the cytosine deaminase gene it is advantageous to have higher levels of expression of the CD protein in a cell so that the conversion of the prodrug 5-FC to 5-FU is more efficient. Similarly high levels of expression of siRNA or shRNA lead to more efficient suppression of target gene expression. Also for cytokines or single chain antibodies (scAbs) it is usually advantageous to express high levels of the cytokine or scAb. In addition, in the case that there are mutations in some copies of the vector that inactivate or impair the activity of the vector or transgene, it is advantageous to have multiple copies of the vector in the target cell as this provides a high probability of efficient expression of the intact transgene.

As mentioned above, the integrated DNA intermediate is referred to as a provirus. Prior gene therapy or gene delivery systems use methods and retroviruses that require transcription of the provirus and assembly into infectious virus while in the presence of an appropriate helper virus or in a cell line containing appropriate sequences enabling encapsidation without coincident production of a contaminating helper virus. As described below, a helper virus is not required for the production of the recombinant retrovirus of the disclosure, since the sequences for encapsidation are provided in the genome thus providing a replication competent retroviral vector for gene delivery or therapy.

The retroviral genome and the proviral DNA of the disclosure have at least three genes: the gag, the pol, and the env, these genes may be flanked by one or two long terminal (LTR) repeat, or in the provirus are flanked by two long terminal repeat (LTR) and sequences containing cis-acting sequences such as psi. The gag gene encodes the internal structural (matrix, capsid, and nucleocapsid) proteins; the pol gene encodes the RNA-directed DNA polymerase (reverse transcriptase), protease and integrase; and the env gene encodes viral envelope glycoproteins. The 5' and/or 3' LTRs serve to promote transcription and polyadenylation of the virion RNAs. The LTR contains all other cis-acting sequences necessary for viral replication. Lentiviruses have additional genes including vif, vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virion) are missing from the viral genome, the result is a cis defect which prevents encapsidation of genomic viral RNA. This type of modified vector is what has typically been used in prior gene delivery systems (i.e., systems lacking elements which are required for encapsidation of the virion) as 'helper' elements providing viral proteins in trans that package a non-replicating, but packageable, RNA genome.

The terms "express" and "expression" mean allowing or causing the information in a gene or DNA sequence to become manifest, for example producing a protein by activating the cellular functions involved in transcription and translation of a corresponding gene or DNA sequence or in the case of inhibitor RNA (RNAi) transcribing the RNAi molecule such that is processed and capable of inhibiting expression of a target gene.

A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

As mentioned above, in some instances the term "express" includes the production of inhibitory RNA molecules (RNAi). The expression of such molecules do not involve the translation machinery of the cell but rather utilize machinery in a cell to modify a host cell's gene expression. In some embodiments, a recombinant viral vector of the disclosure can be modified to express a coding sequence (e.g., a protein), express an RNAi molecule, or express both a coding sequence (e.g., express a protein) and express and RNAi molecule.

Typically a recombinant replication viral vector is modified to include a "cassette", which typically contain a heterologous gene or sequence to be expressed operably linked to elements that allow effective expression (e.g., a promoter, IRES or a read-through element that allows transcription and translation of the heterologous sequence).

Transgenes (e.g., the heterologous sequence to be expressed) can be inserted into a retroviral genome in number of locations including into the long-terminal repeats (LTR's), insertion downstream of the envelope and after splice acceptors, fusion with viral gag or pol proteins, internal IRES sequences or small internal promoters downstream of the envelope coding sequence. Insertion of transgenes into LTR's and introduction of extra splice acceptors have led to rapid destabilization of the vector genome, while the IRES and other methods have shown more promise. Expression and the constitution of the transgene can be affected, at least in part, by judicious changes in key sequences such as elimination of cryptic splice acceptors and humanization of transgene sequences (see, e.g., U.S. Pat. No. 8,722,867, the disclosure of which is incorporated herein by reference). The size of a transgene can also have an effect on vector statiblity. For example, in certain vectors as the size of the transgene increases the virus becomes unstable, and rapidly deletes at least part of the heterologous gene or sequence. This limitation is aggravated by the need to include expression enabling sequences such as the IRES (normally about 600 bp, see, e.g., U.S. Pat. No. 8,722,867) or small promoter (normally about 250-300 bp, see, e.g., International Application Publ. No. WO 2014/066700, which is incorporated herein by reference), potentially leaving only 900 to 1200 bp insert of heterologous gene or sequence in, e.g., MLV. Thus, it would be very useful to be able to maximize the available transgene size to include more choice of transgene or multiple transgenes.

Some examples of retroviruses that replicate efficiently in human cells include, amphotropic, polytropic, xenotropic and 10A1 strains of murine leukemia virus (MLV) as well as gibbon ape leukemia virus (GALV), Baboon endogenous virus and the feline virus RD114. Likewise, ecotropic strains of MLV that have been modified to contain a non-ecotropic envelope gene such as amphotropic-pseudotyped RRV can also efficiently replicate in a variety of species and cell types to be treated. However, the retroviral envelope can also be substituted by non-retroviral envelopes such as rhabdovirus, alphavirus, measles or influenza virus envelopes.

Several viruses including picornaviruses and encephalomyocarditis virus encode 2A or 2A-like peptides in their genomes in order to mediate multiple protein expression from a single ORF. 2A peptides are typically about 16-18 amino acid in sequence and share the consensus motif (D[V/I]EXNPGP (SEQ ID NO:1), wherein X is any amino acid). When the 2A peptide is encoded between ORFs in an artificial multicistronic mRNA, it causes the ribosome to halt at the C-terminus of 2A peptide in the translating polypeptide, thus resulting in separation of polypeptides derived from each ORF (Doronina et al., 2008). The separation point is at the C-terminus of 2A, with the first amino acid of the downstream ORF being proline (see, e.g., FIG. 1). The unique features of 2A peptide have led to its utilization as a molecular tool for multiple-protein expression from a single multicistronic mRNA configuration.

2A peptides are present in the viral genome of picornaviridae virus family, such as foot-and-mouth disease virus and equine rhinitis A virus, and other viruses such as the porcine teschovirus-1 and the insect virus *Thosea asigna* virus (FIG. 1). 2A peptides have near 100% "separation" efficiency in their native contexts, and often have lower "separation" efficiencies when they are introduced into non-native sequences. Other 2A-like sequences found in different classes of virus have also been shown to achieve ~85% "separation" efficiency in non-native sequences (Donnelly et al., 1997). There is a large number of 2A-like sequences (FIG. 2) that can be used in the methods and composition of this disclosure for expressing transgenes.

Although 2A sequences have been known to exist for about 20 years, their ability to function in non-native settings has been questioned. In particular the 2A sequences leaves approximately 17-22 extra amino acids on the C terminus of the preceding translated protein and adds a proline onto the N-terminus of the downstream protein, thus, possibly affecting the ability of the preceding protein to function. If the protein requires post-translation modifications in the endoplasmic and Golgi apparatus and/or during the maturation of the virions, as in the case for many viral enveloped proteins (T. Murakami, Mol Biol Int. 2012), there is further risk for functional incompetence for the preceding protein.

Figure 19:
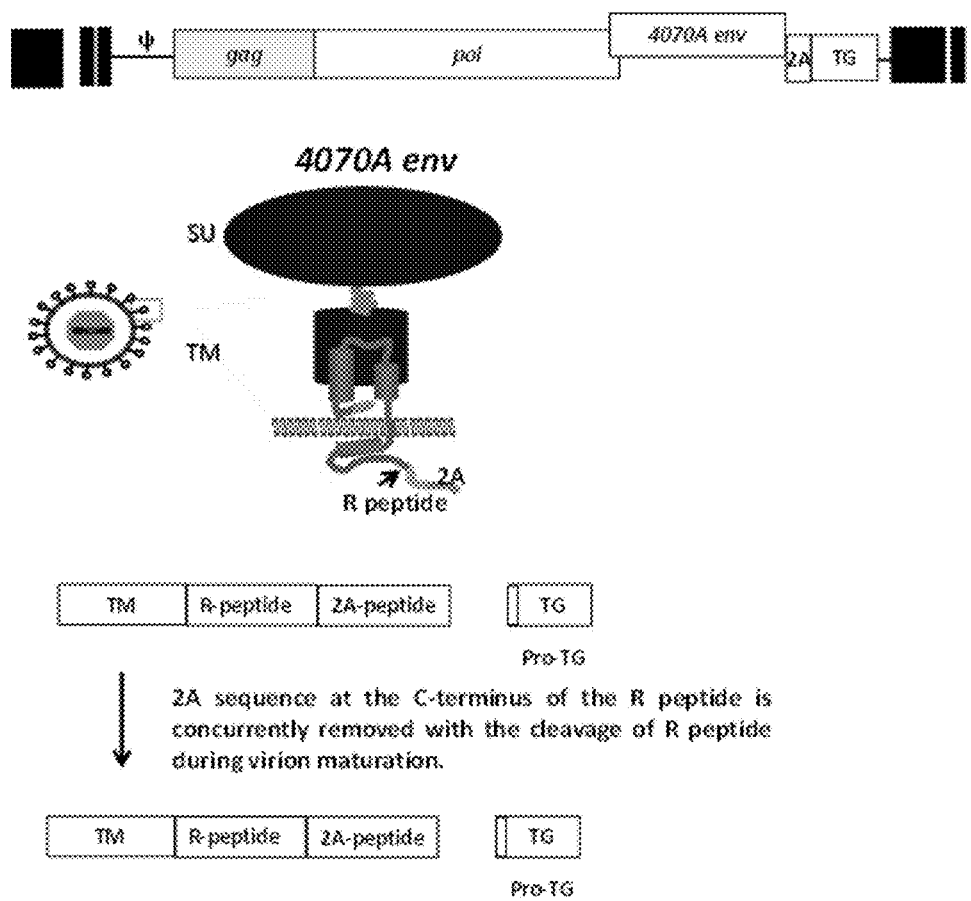
FIG. 19 shows MLV viral envelop protein processing during virion assembly and maturation. Normally, processing of a native MLV envelope protein involves cleavage of the precursor protein Pr85 to gp70 (SU) and p15E (TM) subunit which occurs in infected host cell. Cleavage of Pr85 is required for efficient incorporation of viral envelope protein into the viron during budding from the host cell. As the virion buds off from the host cell membrane, the virion undergoes a maturation processes in order to become infectious. One of the processes in MLV virion maturation involves the removal of the R-peptide located in the C-terminus of the TM subunit of the envelop protein by viral protease. The 2A peptide is expressed in-frame to the C-terminus of the R-peptide, making the length of R peptide increase from 16 amino acids to at least 32 amino acids, depending on the sequence of the 2A peptide. Although the length of the R-peptide is increased by addition of the 2A peptide sequence, the 2A peptide will be concurrently removed with the cleavage of R peptide, resulting a functional envelop protein.

FIG. 19 depicts processing of MLV envelope protein bearing a 2A peptide at the C-terminus of the envelope protein. Normally, processing of a native MLV envelope protein involves cleavage of the precursor protein Pr85 to gp70 (SU) and p15E (TM) subunit which occurs in infected host cell. Cleavage of Pr85 is required for efficient incorporation of viral envelope protein into the virion during budding from the host cell. As virion buds off from the host cell membrane, the virion undergoes a maturation processes in order to become infectious. One of the processes in MLV virion maturation involves the removal of R-peptide located in the C-terminus of the TM subunit of the envelop protein by viral protease. In the scenario depicted in FIG. 19, the 2A peptide except for the last amino acid residue proline (Pro) is expressed downstream of the R-peptide, making the length of R peptide from 16 amino acids to at least 32 amino acids, depending on the sequence of the 2A peptide. Although the length of the R-peptide is lengthened by addition of 2A peptide sequence, theoretically, the 2A peptide will be concurrently removed with the cleavage of R peptide, resulting in a functional envelop protein.

Thus, if the envelope sequence is non-functional or attenuated, the viral vector is likely not to be useful. There have been attempts to use a particular 2A sequence (from porcine teschovirus-1, "P2A") in a retroviral construct with a particular envelope (ecotropic) that infects only mice (S. Stavrou et al., PLoS Pathog 10(5):e1004145, 2014; and E. P. Browne, J. Virol. 89:155-64, 2015). However, these viruses do not infect human cells and there is no expectation that the general protein processing problem has been solved. Moreover, the viruses so constructed were designed to express genes that facilitates viral replication in vivo, rather than achieves a therapeutic effect.

The disclosure provides replication competent viral vectors the contain a heterologous polynucleotide encoding, for example, a cytosine deaminase or mutant thereof, an miRNA or siRNA, a cytokine, an antigen binding domain, or combinations of coding sequences etc., that can be delivered to a cell or subject. The viral vector can be an adenoviral vector, a measles vector, a herpes vector, a retroviral vector (including a lentiviral vector), a rhabdoviral vector such as a Vesicular Stomatitis viral vector, a reovirus vector, a Seneca Valley Virus vector, a poxvirus vector (including animal pox or vaccinia derived vectors), a parvovirus vector (including an AAV vector), an alphavirus vector or other viral vector known to one skilled in the art (see also, e.g., *Concepts in Genetic Medicine*, ed. Boro Dropulic and Barrie Carter, Wiley, 2008, Hoboken, N.J.; *The Development of Human Gene Therapy*, ed. Theodore Friedmann, Cold Springs Harbor Laboratory Press, Cold springs Harbor, New York, 1999; *Gene and Cell Therapy*, ed. Nancy Smyth Templeton, Marcel Dekker Inc., New York, N.Y., 2000 and *Gene & Cell Therapy: Therapeutic Mechanism and Strategies*, $3^{rd}$. ed., ed. Nancy Smyth Templetone, CRC Press, Boca Raton, Fla., 2008; the disclosures of which are incorporated herein by reference).

As described below, the RRV's of the disclosure can be derived from (i.e., the parental nucleotide sequence is obtained from) MLV, MoMLV, GALV, FELV and the like and are engineered to contain a 2A peptide or 2A likepeptide linked to a heterologous nucleotide sequence (sometimes referred to herein as a "2A-peptide cassette").

The RRVs of the disclosure can be engineered to modify their stability and/or expression. For example, changes in expression can occur due to the frequency with which inactivating or attenuating mutations accumulate in the replicating retroviral vector as it progressively replicates in tumor tissue. Investigation shows that one of the most frequent events is G to A mutations (corresponds to the C to T characteristic ApoBec mediated mutations in the negative strand single stranded DNA from the first replicative step in the reverse transcription step). This can cause changes in amino acid composition of the RRV proteins and a devastating change from TGG (Tryptophan) to stop codons (TAG or TGA). In one embodiment this inactivating change is avoided by substitution codons, without this possibility, of other amino acids with similar chemical or structural properties such as phenylalanine or tyrosine.

Thus, in addition to the 2A-peptide cassette the RRV can include a plurality of additional mutations that improve expression and/or stability of the construct in a host cell. Such mutations can include modifications of one or more codons in the GAG, POL and/or ENV coding sequences that change a tryptophan codon to a permissible codon that maintains the biological activity of the GAG, POL and/or ENV domains. It is known in the art that the codon for tryptophan is UGG (TGG in DNA). Moreover, it is known in the art that the "stop codon" is UAA, UAG or UGA (TAA, TAG or TGA in DNA). A single point mutation in the tryptophan codon and cause an unnatural stop codon (e.g., UGG→UAG or UGG→UGA). It is also known that human APOBEC3GF (hA3G/F) inhibits retroviral replication through G→A hypermutations (Neogi et al., J. Int. AIDS Soc., 16(1):18472, Feb. 25, 2013). Moreover, as described below long term expression and viral stability can be improved by avoiding use of tryptophan codons in coding sequence, thereby avoiding the incorporation of unnatural stop codons due to hypermutation cause by hA3G/F. For example, in one embodiment, an MLV derived nucleic acid sequence comprises GAG, POL and ENV coding domains (e.g., the gag nucleic acid domain comprises a sequence from about nucleotide number 1203 to about nucleotide 2819 of SEQ ID NO: 2, the pol domain comprises a sequence from about nucleotide number 2820 to about nucleotide 6358 of SEQ ID NO:2 and the env domain comprises a sequence from about nucleotide number 6359 to about nucleotide 8323 of SEQ ID NO:2). By modifying codons containing the nucleotides identified in Table 1 (nucleotide number referenced to SEQ ID NO:2), which are in tryptophan codons, one can provide hA3G/F resistant RRVs.

TABLE 1

Summary of recurrent G to A mutations that lead to tryptophan to stop codon changes. Nucleotide is the position in SEQ ID NO: 2 RRV genome, "gene" is the gene the nucleotide is located in and AA is the amino acid position in the polypeptide.

| nucleotide | gene | AA |
|---|---|---|
| 1306 | GAG | 35 |
| 5299 | POL | 718 |
| 5557 | POL | 804 |
| 5806 | POL | 887 |
| 6193 | POL | 1016 |
| 6232 | POL | 1029 |
| 6298 | POL | 1051 |
| 6801 | ENV | 148 |
| 6978 | ENV | 207 |
| 7578 | ENV | 407 |

Thus, in one embodiment of the disclosure, a recombinant replication competent retrovirus is provided that comprises one or more mutations in codons for tryptophan, wherein the mutation changes the codon to a codon for an amino acid other than tryptophan and that provide codons that are biocompatible (i.e., codons that do not disrupt the function of the vector). This vector is "ApoBec inactivation resistant". The recombinant ApoBec inactivation resistant vector can comprise an IRES cassette, promoter cassette and/or 2A peptide cassette. As used herein an IRES cassette comprises an internal ribosome entry site operably linked to a heterologous polynucleotide encoding a desired biological active molecule (see, e.g., U.S. Pat. No. 8,829,173, incorporated herein by reference). As used herein a promoter cassette comprises a regulatory domain that initiates transcription of a downstream heterologous polynucleotide encoding a desired biological active molecule (see, e.g., U.S. Pat. No. 8,829,173 and U.S. Pat. Publ. No. 2015/0273029A1, which are incorporated herein). The promoter can be a tissue specific promoter, a polIII promoter or a mini-promoter. A 2A peptide cassette is described elsewhere herein.

In one embodiment, the viral vector can be a replication competent retroviral vector capable of infecting only dividing mammalian cells. In one embodiment, a replication competent retroviral vector comprises a 2A peptide or 2A peptide-like sequence just downstream and operably linked to the retroviral envelope and just upstream of a heterologous nucleic acid sequence to be expressed. In certain embodiments, the vector can additional include an IRES cassette or a polIII (or minipromoter) cassette. The heterologous polynucleotide can encode, e.g., a cytosine deaminase, a thymidine kinase, cytokine, receptor, antibody or the like. Where a polIII promoter or minipromoter is included the vector can further express miRNA, siRNA, or other RNAi sequence.

In another embodiment, the disclosure provides an ENV-2A-heterologous gene cassette. The cassette can comprise an envelope chosen from one of amphotropic, polytropic, xenotropic, 10A1, GALV, Baboon endogenous virus, RD114, rhabdovirus, alphavirus, measles and influenza virus envelopes. The 2A peptide or 2A peptide-like coding sequence can be any of the sequences set forth in FIG. 1 or 2 operably linked to the C-terminus of the envelope coding sequence. In another embodiment, the 2A peptide or 2A peptide-like coding sequence is linked through a GSG linker sequence (e.g., ggaagcgga (SEQ ID NO:3)). The heterologous gene is operably linked to the C-terminus of the 2A peptide or 2A peptide-like sequence. The heterologous gene can be any desired gene to be delivered and expressed in a target cell. In one embodiment, the heterologous gene comprises 500-1500 bp in length or any numerical value therebetween (e.g., 1000 bp, 1100 bp, 1200 bp, 1300 bp, 1400 bp etc.). In another embodiment the heterologous gene comprises >1500 bp in length. In another embodiment, the cassette comprises two heterologous genes separated by a 2A peptide or 2A peptide-like sequence. In yet another embodiment, the cassette can comprise a 2A peptide or 2A peptide-like sequence operably linked between the C-terminus of the env and N-terminus of a heterologous gene, wherein the heterologous gene is followed by a second cassette comprising an IRES or promoter linked to a second heterologous sequence.

The disclosure provides modified retroviral vectors. The modified retroviral vectors can be derived from members of the retroviridae family and be engineered to contain an ENV-2A-transgene cassette. As mentioned above, the Retroviridae family consists of three groups: the spumaviruses-(or foamy viruses) such as the human foamy virus (HFV); the lentiviruses, as well as visna virus of sheep; and the oncoviruses (although not all viruses within this group are oncogenic).

In one embodiment, the disclosure provides a recombinant retrovirus capable of infecting a non-dividing cell, a dividing cell, or a cell having a cell proliferative disorder. The recombinant replication competent retrovirus of the disclosure comprises a polynucleotide sequence encoding a viral GAG, a viral POL, a viral ENV, a heterologous polynucleotide preceded by a 2A peptide or 2A peptide-like coding sequence immediately downstream (e.g., between 1 and 50 nucleotides (1-10, 10-15, 15-20, 20-25, 25-30, 30-35, 35-40, 40-45, 45-50 or any integer therebetween) of the viral ENV sequence and encapsulated within a virion.

The phrase "non-dividing" cell refers to a cell that does not go through mitosis. Non-dividing cells may be blocked at any point in the cell cycle, (e.g., $G_0/G_1$, $G_{1/S}$, $G_{2/M}$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). For example, a recombinant lentivirus vector is capable of infecting non-dividing cells. Examples of pre-existing non-dividing cells in the body include neuronal, muscle, liver, skin, heart, lung, and bone marrow cells, and their derivatives. For dividing cells oncoretroviral vectors can be used.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells. The term "cell proliferative disorder" refers to a condition characterized by an abnormal number of cell divisions. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous cell cancer, malignant melanoma, sinonasal undifferentiated carcinoma (SNUC), brain (including glioblastomas such as glioblastoma multiforme) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp 1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer, skin cancer and ovarian cancer. The cell proliferative disease also includes rheumatoid arthritis (O'Dell NEJM 350:2591 2004) and other auto-immune disorders (Mackay et al NEJM 345:340 2001) that are often characterized by inappropriate proliferation of cells of the immune system.

The heterologous nucleic acid sequence is operably linked to a sequence encoding a 2A peptide or 2A peptide-like sequence. As used herein, the term "heterologous" nucleic acid sequence or transgene refers to (i) a sequence that does not normally exist in a wild-type retrovirus, (ii) a sequence that originates from a foreign species, or (iii) if from the same species, it may be substantially modified from its original form. Alternatively, an unchanged nucleic acid sequence that is not normally expressed in a cell is a heterologous nucleic acid sequence.

Depending upon the intended use of the retroviral vector of the disclosure any number of heterologous polynucleotide or nucleic acid sequences may be inserted into the retroviral vector. For example, for in vitro studies commonly used marker genes or reporter genes may be used, including, antibiotic resistance and fluorescent molecules (e.g., GFP) or luminescent molecules. Additional polynucleotide sequences encoding any desired polypeptide sequence may also be inserted into the vector of the disclosure.

Where in vivo delivery of a heterologous nucleic acid sequence is sought both therapeutic and non-therapeutic sequences may be used. For example, in some embodiments an ENV-2A-transgene cassette can be followed by a polIII-RNAi cassette or an IRES-cassette. For example, where a minipromoter or polIII cassette is used, the cassette can comprise a heterologous sequence including miRNA, siRNA and the like directed to a particular gene associated with a cell proliferative disorder or other gene-associated disease or disorder. In other embodiments the heterologous gene downstream of the 2A peptide or 2A peptide-like sequence or IRES can be a suicide gene (e.g., HSV-tk or PNP or polypeptide having cytosine deaminase activity; either modified or unmodified), a growth factor or a therapeutic protein (e.g., Factor IX, IL2, and the like). Other therapeutic proteins applicable to the disclosure are easily identified in the art.

In one embodiment, the heterologous polynucleotide within the vector comprises a cytosine deaminase or thymidine kinase that has been optimized for expression in a human cell. In a further embodiment, the cytosine deaminase comprises a sequence that has been human codon optimized and comprises mutations that increase the cytosine deaminase's stability (e.g., reduced degradation or increased thermo-stability) and/or includes mutations that change a tryptophan codon to a non-tryptophan encoding codon compared to a wild-type cytosine deaminase. In yet another embodiment, the heterologous polynucleotide encodes a fusion construct comprising a polypeptide having cytosine deaminase activity (either human codon optimized or non-optimized, either mutated or non-mutated) operably linked to a polynucleotide encoding a polypeptide having UPRT or OPRT activity.

As mentioned above, human APOBEC3g causes hypermutations in viral vector sequences converting G→A. Accordingly, tryptophan codons in heterologous polynucleotides contained in the 2A peptide cassette are susceptible to being converted by hAPOBEC3 to stop codons. To avoid such mutations, tryptophan codons can be replaced with biologically permissible codons for other amino acids. For example, in one embodiment, a 2A-cassette of the disclosure can comprise a polynucleotide encoding a polypeptide having cytosine deaminase activity, wherein the polynucleotide comprises the sequence:

(SEQ ID NO: 28)

```
atg gtg acc ggc ggc atg gcc tcc aag tgg gat
caa aag ggc atg gat atc gct tac gag gag gcc
ctg ctg ggc tac aag gag ggc ggc gtg cct atc
ggc ggc tgt ctg atc aac aac aag gac ggc agt
gtg ctg ggc agg ggc cac aac atg agg ttc cag
aag ggc tcc gcc acc ctg cac ggc gag atc tcc
acc ctg gag aac tgt ggc agg ctg gag ggc aag
gtg tac aag gac acc acc ctg tac acc acc ctg
tcc cct tgt gac atg tgt acc ggc gct atc atc
atg tac ggc atc cct agg tgt gtg atc ggc gag
aac gtg aac ttc aag tcc aag ggc gag aag tac
```

```
ctg caa acc agg ggc cac gag gtg gtg gtt gtt gac gat gag agg tgt aag aag ctg atg aag cag ttc atc gac gag agg cct cag gac tgg ttc gag gat atc ggc gag taa
```

This sequence comprises two tryptophan codons (bold/underlined). In one embodiment of the disclosure these codons are independently changed to a codon providing an amino acid selected from the group consisting of D, M, T, E, S, Q, N, F, Y, A, K, H, P, R, V, L, G, I and C. The resulting polypeptide comprises a sequence:

(SEQ ID NO: 29)
M V T G G M A S K X D Q K G M D I A Y E E A L L G

Y K E G G V P I G G C L I N N K D G S V L G R G H

N M R F Q K G S A T L H G E I S T L E N C G R L E

G K V Y K D T T L Y T T L S P C D M C T G A I I M

Y G I P R C V I G E N V N F K S K G E K Y L Q T R

G H E V V V V D D E R C K K L M K Q F I D E R P Q

D X F E D I G E, wherein the polypeptide comprises cytosine deaminase activity, wherein X is any amino acid except tryptophan. In one embodiment, X in SEQ ID NO:29 are each independently selected from the group consisting of F, D, M, L, S or R.

In another embodiment, a replication competent retroviral vector can comprise a heterologous polynucleotide encoding a polypeptide comprising a cytosine deaminase (as described herein) and may further comprise a polynucleotide comprising a miRNA or siRNA molecule either as part of the primary transcript from the viral promoter or linked to a promoter, which can be cell-type or tissue specific. In yet a further embodiment, the miRNA or siRNA may be preceded by a pol III promoter.

MicroRNAs (miRNA) are small, non-coding RNAs. They are located within introns of coding or non-coding genes, exons of non-coding genes or in inter-genic regions. miRNA coding sequences are transcribed by RNA polymerase II that generate precursor polynucleotides called primary precursor miRNA (pri-miRNA). The pri-miRNA in the nucleus is processed by the ribonuclease Drosha to produce the miRNA precursor (pre-miRNA) that forms a short hairpin structure. Subsequently, pre-miRNA is transported to the cytoplasm via Exportin 5 and further processed by another ribonuclease called Dicer to generate an active, mature miRNA.

A mature miRNA is approximately 21 nucleotides in length. It exerts in function by binding to the 3' untranslated region of mRNA of targeted genes and suppressing protein expression either by repression of protein translation or degradation of mRNA. miRNA are involved in biological processes including development, cell proliferation, differentiation and cancer progression. Studies of miRNA profiling indicate that some miRNA expressions are tissue specific or enriched in certain tissues. For example, miR-142-3p, miR-181 and miR-223 expressions have demonstrated to be enriched in hematopoietic tissues in human and mouse (Baskerville et al., 2005 *RNA* 11, 241-247; Chen et al., 2004 *Science* 303, 83-86).

Some riRNAs have been observed to be up-regulated (oncogenic miRNA) or down-regulated (repressor) in several tumors (Spizzo et al., 2009 *Cell* 137, 586e1). For example, miR-21 is overexpressed in glioblastoma, breast, lung, prostate, colon, stomach, esophageal, and cervical cancer, uterine leiomyosarcoma, DLBCL, head and neck cancer. In contrast, members of let-7 have reported to be down-regulated in glioblastoma, lung, breast, gastric, ovary, prostate and colon cancers. Re-establishment of homeostasis of miRNA expression in cancer is an imperative mechanism to inhibit or reverse cancer progression.

miRNAs that are down-regulated in cancers could be useful as anticancer agents. Examples include mir-128-1, let-7, miR-26, miR-124, and miR-137 (Esquela-Kerscher et al., 2008 *Cell Cycle* 7, 759-764; Kumar et al., 2008 *Proc Natl Acad Sci USA* 105, 3903-3908; Kota et al., 2009 Cell 137, 1005-1017; Silber et al., 2008 BMC Medicine 6:14 1-17). miR-128 expression has reported to be enriched in the central nervous system and has been observed to be down-regulated in glioblastomas (Sempere et al., 2004 *Genome Biology* 5:R13.5-11; Godlewski et al., 2008 *Cancer Res* 68: (22) 9125-9130). miR-128 is encoded by two distinct genes, miR-128-1 and miR-128-2. Both are processed into identical mature sequence. Bmi-1 and E2F3a have been reported to be the direct targets of miR-128 (Godlewski et al., 2008 *Cancer Res* 68: (22) 9125-9130; Zhang et al., 2009 *J. Mol Med* 87:43-51). In addition, Bmi-1 expression has been observed to be up-regulated in a variety of human cancers, including gliomas, mantle cell lymphomas, non-small cell lung cancer B-cell non-Hodgkin's lymphoma, breast, colorectal and prostate cancer. Furthermore, Bmi-1 has been demonstrated to be required for the self-renewal of stem cells from diverse tissues, including neuronal stem cells as well as "stem-like" cell population in gliomas.

As used herein, the term "RNA interference" (RNAi) refers to the process of sequence-specific post-transcriptional gene silencing mediated by short interfering nucleic acids (siRNAs or microRNAs (miRNA)). The term "agent capable of mediating RNA interference" refers to siRNAs as well as DNA and RNA vectors that encode siRNAs when transcribed within a cell. The term siRNA or miRNA is meant to encompass any nucleic acid molecule that is capable of mediating sequence specific RNA interference, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others.

Suitable range for designing stem lengths of a hairpin duplex, includes stem lengths of 20-30 nucleotides, 30-50 nucleotides, 50-100 nucleotides, 100-150 nucleotides, 150-200 nucleotides, 200-300 nucleotides, 300-400 nucleotides, 400-500 nucleotides, 500-600 nucleotides, and 600-700 nucleotides. Suitable range for designing loop lengths of a hairpin duplex, includes loop lengths of 4-25 nucleotides, 25-50 nucleotides, or longer if the stem length of the hair duplex is substantial. In certain context, hairpin structures with duplexed regions that are longer than 21 nucleotides may promote effective siRNA-directed silencing, regardless of the loop sequence and length.

In yet another or further embodiment, the heterologous polynucleotide can comprise a cytokine such as an interleukin, interferon gamma or the like. Cytokines that may expressed from a retroviral vector of the disclosure include, but are not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, anti-CD40, CD40L, IFN-gamma and TNF-alpha, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TRANK, TR9 (International Publication No. WO 98/56892), TR10 (International Publication No. WO 98/54202), 312C2 (International Publication No. WO 98/06842), and TR12, and soluble forms CD154, CD70, and CD153. Angiogenic proteins may be useful in some embodiments, particularly for protein production from cell lines. Such angiogenic factors include, but are not limited to, Glioma Derived Growth Factor (GDGF), Platelet Derived Growth Factor-A (PDGF-A), Platelet Derived Growth Factor-B (PDGF-B), Placental Growth Factor (PIGF), Placental Growth Factor-2 (PIGF-2), Vascular Endothelial Growth Factor (VEGF), Vascular Endothelial Growth Factor-A (VEGF-A), Vascular Endothelial Growth Factor-2 (VEGF-2), Vascular Endothelial Growth Factor B (VEGF-3), Vascular Endothelial Growth Factor B-1 86 (VEGF-B186), Vascular Endothelial Growth Factor-D (VEGF-D), Vascular Endothelial Growth Factor-D (VEGF-D), and Vascular Endothelial Growth Factor-E (VEGF-E). Fibroblast Growth Factors may be delivered by a vector of the disclosure and include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15. Hematopoietic growth factors may be delivered using vectors of the disclosure, such growth factors include, but are not limited to, granulocyte macrophage colony stimulating factor (GM-CSF) (sargramostim), granulocyte colony stimulating factor (G-CSF) (filgrastim), macrophage colony stimulating factor (M-CSF, CSF-1) erythropoietin (epoetin alfa), stem cell factor (SCF, c-kit ligand, steel factor), megakaryocyte colony stimulating factor, PIXY321 (a GMCSF/IL-3) fusion protein and the like.

The term "regulatory nucleic acid sequence" refers collectively to promoter sequences/regions, polyadenylation signals, transcription termination sequences, upstream regulatory domains, origins of replication, enhancers and the like, which collectively provide for the replication, transcription and translation of a coding sequence in a recipient cell. Not all of these control sequences need always be present so long as the selected coding sequence is capable of being replicated, transcribed and translated in an appropriate host cell. One skilled in the art can readily identify regulatory nucleic acid sequence from public databases and materials. Furthermore, one skilled in the art can identify a regulatory sequence that is applicable for the intended use, for example, in vivo, ex vivo, or in vitro.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter.

A "2A peptide or 2A peptide-like sequence" refers to a peptide having the consensus sequence of SEQ ID NO:1, a sequence that is 97% identical to any of the sequences in FIGS. 1 and 2 and which contains the consensus sequence of SEQ ID NO:1. A sequence that "encodes" a 2A peptide or 2A peptide-like sequence is a polynucleotide sequence that encodes a 2A peptide or peptide-like sequence having, e.g., the consensus sequence of SEQ ID NO:1. The coding sequence is operably linked to and placed, in one embodiment, between an ENV and heterologous sequence, such that once the sequence is transcribed it is transcribed as a single transcript (e.g., polymRNA) and when the transcript is translated that two polypeptide are produced (e.g., the ENV and the heterologous polypeptide).

An internal ribosome entry sites ("IRES") refers to a segment of nucleic acid that promotes the entry or retention of a ribosome during translation of a coding sequence usually 3' to the IRES. In some embodiments the IRES may comprise a splice acceptor/donor site, however, preferred IRESs lack a splice acceptor/donor site. Normally, the entry of ribosomes into messenger RNA takes place via the cap located at the 5' end of all eukaryotic mRNAs. However, there are exceptions to this universal rule. The absence of a cap in some viral mRNAs suggests the existence of alternative structures permitting the entry of ribosomes at an internal site of these RNAs. To date, a number of these structures, designated IRES on account of their function, have been identified in the 5' noncoding region of uncapped viral mRNAs, such as that of picornaviruses, in particular the poliomyelitis virus (Pelletier et al., 1988, Mol. Cell. Biol., 8, 1103-1112) and the EMCV virus (encephalo-myocarditis virus (Jang et al., J. Virol., 62, 2636-2643 1988; B. T. Baranick et al., Proc Natl Acad Sci USA. 105:4733-8, 2008). The disclosure provides the use of an IRES in the context of a replication-competent retroviral vector.

The heterologous nucleic acid sequence is typically under control of either the viral LTR promoter-enhancer elements or an internal promoter, and retained elements within the retroviral LTR can still bring about efficient integration of the vector into the host cell genome. Accordingly, the recombinant retroviral vectors of the disclosure, the desired sequences, genes and/or gene fragments can be inserted at several sites and under different regulatory sequences. For example, a site for insertion can be the viral enhancer/promoter proximal site (i.e., 5' LTR-driven gene locus).

In one embodiment, the retroviral genome of the disclosure contains a 2A peptide or 2A peptide-like coding sequence comprising a cloning site downstream of the 2A peptide or 2A peptide-like coding sequence for insertion of a desired/heterologous polynucleotide. In one embodiment, the 2A peptide or 2A peptide-like coding sequence is located 3' to the env gene in the retroviral vector, but 5' to the desired heterologous polynucleotide. Accordingly, a heterologous polynucleotide encoding a desired polypeptide is operably linked to the 2A peptide or 2A peptide-like coding sequence.

In another embodiment, a targeting polynucleotide sequence is included as part of the recombinant retroviral vector of the disclosure. The targeting polynucleotide sequence is a targeting ligand (e.g., peptide hormones such as heregulin, a single-chain antibodies, a receptor or a ligand for a receptor), a tissue-specific or cell-type specific regulatory element (e.g., a tissue-specific or cell-type specific promoter or enhancer), or a combination of a targeting ligand and a tissue-specific/cell-type specific regulatory element. Preferably, the targeting ligand is operably linked to the env protein of the retrovirus, creating a chimeric retroviral env protein. The viral GAG, viral POL and viral ENV proteins can be derived from any suitable retrovirus (e.g., MLV or lentivirus-derived). In another embodiment, the viral ENV protein is non-retrovirus-derived (e.g., CMV or VSV).

In one embodiment, the recombinant retrovirus of the disclosure is genetically modified in such a way that the virus is targeted to a particular cell type (e.g., smooth muscle cells, hepatic cells, renal cells, fibroblasts, keratinocytes, mesenchymal stem cells, bone marrow cells, chondrocyte, epithelial cells, intestinal cells, mammary cells, neoplastic cells, glioma cells, neuronal cells and others known in the art) such that the recombinant genome of the retroviral vector is delivered to a target non-dividing, a target dividing cell, or a target cell having a cell proliferative disorder.

In one embodiment, the retroviral vector is targeted to the cell by binding to cells having a molecule on the external surface of the cell. This method of targeting the retrovirus utilizes expression of a targeting ligand on the coat of the retrovirus to assist in targeting the virus to cells or tissues that have a receptor or binding molecule which interacts with the targeting ligand on the surface of the retrovirus. After infection of a cell by the virus, the virus injects its nucleic acid into the cell and the retrovirus genetic material can integrate into the host cell genome.

By inserting a heterologous polynucleotide of interest into the viral vector of the disclosure, along with another gene which encodes, for example, the ligand for a receptor on a specific target cell, the vector is now target specific. Viral vectors can be made target specific by attaching, for example, a sugar, a glycolipid, or a protein. Targeting can be accomplished by using an antibody to target the viral vector. Those of skill in the art will know of, or can readily ascertain, specific polynucleotide sequences which can be inserted into the viral genome or proteins which can be attached to a viral envelope to allow target specific delivery of the viral vector containing the nucleic acid sequence of interest.

Thus, the disclosure includes in one embodiment, a chimeric env protein comprising a retroviral ENV protein operably linked to a targeting polypeptide. The targeting polypeptide can be a cell specific receptor molecule, a ligand for a cell specific receptor, an antibody or antibody fragment to a cell specific antigenic epitope or any other ligand easily identified in the art which is capable of binding or interacting with a target cell. Examples of targeting polypeptides or molecules include bivalent antibodies using biotin-streptavidin as linkers (Etienne-Julan et al., J. Of General Virol., 73, 3251-3255 (1992); Roux et al., Proc. Natl. Acad. Sci USA 86, 9079-9083 (1989)), recombinant virus containing in its envelope a sequence encoding a single-chain antibody variable region against a hapten (Russell et al., Nucleic Acids Research, 21, 1081-1085 (1993)), cloning of peptide hormone ligands into the retrovirus envelope (Kasahara et al., Science, 266, 1373-1376 (1994)), chimeric EPO/env constructs (Kasahara et al., 1994), single-chain antibody against the low density lipoprotein (LDL) receptor in the ecotropic MLV envelope, resulting in specific infection of HeLa cells expressing LDL receptor (Somia et al., Proc. Natl. Acad. Sci USA, 92, 7570-7574 (1995)), similarly the host range of ALV can be altered by incorporation of an integrin ligand, enabling the virus to now cross species to specifically infect rat glioblastoma cells (Valsesia-Wittmann et al., J. Virol. 68, 4609-4619 (1994)), and Dornberg and co-workers (Chu and Dornburg, J. Virol 69, 2659-2663 (1995); M. Engelstadter et al. Gene Therapy 8, 1202-1206 (2001)) have reported tissue-specific targeting of spleen necrosis virus (SNV), an avian retrovirus, using envelopes containing single-chain antibodies directed against tumor markers.

The disclosure provides a method of producing a recombinant retrovirus capable of infecting a target cell comprising transfecting a suitable host cell with the following: a vector comprising a polynucleotide sequence encoding a viral gag, a viral pol and a viral env, a 2A peptide or 2A peptide-like coding sequence operably linked and between the env and a heterologous polynucleotide, and recovering the recombinant virus.

The retrovirus and methods of the disclosure provide a replication competent retrovirus that does not require helper virus or additional nucleic acid sequence or proteins in order to propagate and produce virion. For example, the nucleic acid sequences of the retrovirus of the disclosure encode a group specific antigen and reverse transcriptase, (and integrase and protease-enzymes necessary for maturation and reverse transcription), respectively, as discussed above. The viral gag and pol can be derived from a lentivirus, such as HIV or an oncovirus or gammaretrovirus such as MoMLV. In addition, the nucleic acid genome of the retrovirus of the disclosure includes a sequence encoding a viral envelope (ENV) protein. The env gene can be derived from any retroviruses. The env may be an amphotropic envelope protein which allows transduction of cells of human and other species, or may be an ecotropic envelope protein, which is able to transduce only mouse and rat cells. Further, it may be desirable to target the recombinant virus by linkage of the envelope protein with an antibody or a particular ligand for targeting to a receptor of a particular cell-type. As mentioned above, retroviral vectors can be made target specific by inserting, for example, a glycolipid, or a protein. Targeting is often accomplished by using an antibody to target the retroviral vector to an antigen on a particular cell-type (e.g., a cell type found in a certain tissue, or a cancer cell type). Those of skill in the art will know of, or can readily ascertain without undue experimentation, specific methods to achieve delivery of a retroviral vector to a specific target. In one embodiment, the env gene is derived from a non-retrovirus (e.g., CMV or VSV). Examples of retroviral-derived env genes include, but are not limited to: Moloney murine leukemia virus (MoMuLV), Harvey murine sarcoma virus (HaMuSV), murine mammary tumor virus (MuMTV), gibbon ape leukemia virus (GaLV), human immunodeficiency virus (HIV) and Rous Sarcoma Virus (RSV). Other env genes such as Vesicular stomatitis virus (VSV) (Protein G), cytomegalovirus envelope (CMV), or influenza virus hemagglutinin (HA) can also be used.

In one embodiment, the retroviral genome is derived from an onco-retrovirus, and more particularly a mammalian oncoretrovirus. In a further embodiment, the retroviral genome is derived from a gamma retrovirus, and more particularly a mammalian gamma retrovirus. By "derived" is meant that the parent polynucleotide sequence is a wild-type oncovirus which has been modified by insertion or removal of naturally occurring sequences (e.g., insertion of 2A peptide or 2A peptide like coding sequence and a heterologous polynucleotide encoding a polypeptide and optionally one or more of an IRES, or polIII promoter linked to another heterologous polynucleotide or an inhibitory nucleic acid of interest, respectively).

In another embodiment, the disclosure provides retroviral vectors that are targeted using regulatory sequences. Cell- or tissue-specific regulatory sequences (e.g., promoters) can be utilized to target expression of gene sequences in specific cell populations. Suitable mammalian and viral promoters for the disclosure are described elsewhere herein. Accordingly, in one embodiment, the disclosure provides a retrovirus having tissue-specific promoter elements at the 5' end of the retroviral genome. Typically, the tissue-specific regulatory elements/sequences are in the U3 region of the LTR of the retroviral genome, including for example cell- or tissue-specific promoters and enhancers to neoplastic cells (e.g., tumor cell-specific enhancers and promoters), and inducible promoters (e.g., tetracycline).

Transcription control sequences of the disclosure can also include naturally occurring transcription control sequences naturally associated with a gene encoding a superantigen, a cytokine or a chemokine.

In some circumstances, it may be desirable to regulate expression. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV can be used. Other viral promoters that can be used include SV4C, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific or selective promoters may be used to effect transcription in specific tissues or cells so as to reduce potential toxicity or undesirable effects to non-targeted tissues. For example, promoters such as the PSA, probasin, prostatic acid phospharase or prostate-specific glandular kallikrein (hK2) may be used to target gene expression in the prostate. The Whey accessory protein (WAP) may be used for breast tissue expression (Andres et al., PNAS 84:1299-1303, 1987). Other promoters/regulatory domains that can be used are set forth below.

"Tissue-specific regulatory elements" are regulatory elements (e.g., promoters) that are capable of driving transcription of a gene in one tissue while remaining largely "silent" in other tissue types. It will be understood, however, that tissue-specific promoters may have a detectable amount of "background" or "base" activity in those tissues where they are expected to be silent. The degree to which a promoter is selectively activated in a target tissue can be expressed as a selectivity ratio (activity in a target tissue/activity in a control tissue). In this regard, a tissue specific promoter useful in the practice of the disclosure typically has a selectivity ratio of greater than about 5. Preferably, the selectivity ratio is greater than about 15.

In certain indications, it may be desirable to activate transcription at specific times after administration of the recombinant replication competent retrovirus of the disclosure (RRV). This may be done with promoters that are hormone or cytokine regulatable. For example, in therapeutic applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones may be used. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1990), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin. Tumor specific promoters such as osteocalcin, hypoxia-responsive element (HRE), MAGE-4, CEA, alpha-fetoprotein, GRP78/BiP and tyrosinase may also be used to regulate gene expression in tumor cells.

In addition, this list of promoters should not be construed to be exhaustive or limiting, those of skill in the art will know of other promoters that may be used in conjunction with the promoters and methods disclosed herein.

TABLE 2

TISSUE SPECIFIC PROMOTERS

| Tissue | Promoter |
| --- | --- |
| Pancreas | Insulin Elastin Amylase pdr-1 pdx-1 glucokinase |
| Liver | Albumin PEPCK HBV enhancer α fetoprotein apolipoprotein C α-1 antitrypsin vitellogenin, NF-AB Transthyretin |
| Skeletal muscle | Myosin H chain Muscle creatine kinase Dystrophin Calpain p94 Skeletal alpha-actin fast troponin 1 |
| Skin | Keratin K6 Keratin K1 |
| Lung | CFTR Human cytokeratin 18 (K18) Pulmonary surfactant proteins A, B and C CC-10 P1 |
| Smooth muscle | sm22 α SM-alpha-actin |
| Endothelium | Endothelin-1 E-selectin von Willebrand factor TIE (Korhonen et al., 1995) KDR/flk-1 Melanocytes Tyrosinase |
| Adipose tissue | Lipoprotein lipase (Zechner et al., 1988) Adipsin (Spiegelman et al., 1989) acetyl-CoA carboxylase (Pape and Kim, 1989) glycerophosphate dehydrogenase (Dani et al., 1989) adipocyte P2 (Hunt et al., 1986) |
| Breast | Whey Acidic Protien (WAP) (Andres et al. PNAS 84: 1299-1303 1987 |
| Blood | β-globin |

It will be further understood that certain promoters, while not restricted in activity to a single tissue type, may nevertheless show selectivity in that they may be active in one group of tissues, and less active or silent in another group. Such promoters are also termed "tissue-specific," and are contemplated for use with the disclosure. For example, promoters that are active in a variety of central nervous system (CNS) neurons may be therapeutically useful in protecting against damage due to stroke, which may affect any of a number of different regions of the brain. Accordingly, the tissue-specific regulatory elements used in the disclosure, have applicability to regulation of the heterologous proteins as well as an applicability as a targeting polynucleotide sequence in the present retroviral vectors.

In yet another embodiment, the disclosure provides plasmids comprising a recombinant retroviral derived construct. The plasmid can be directly introduced into a target cell or a cell culture such as ET1080, NIH 3T3 or other tissue culture cells. The resulting cells release the retroviral vector into the culture medium.

The disclosure provides a polynucleotide construct comprising from 5' to 3': a promoter or regulatory region useful for initiating transcription; a psi packaging signal; a gag encoding nucleic acid sequence, a pol encoding nucleic acid sequence; an env encoding nucleic acid sequence; a 2A peptide or 2A peptide-like coding sequence; a heterologous polynucleotide encoding a marker, therapeutic or diagnostic polypeptide; an optional IRES or polIII cassette; and a LTR nucleic acid sequence. As mentioned above, the gag, pol and env nucleic acid domains can be modified to remove tryptophan codons that are converted by ApoBec3 to stop codons. In certain other embodiments, the vector may further comprise a polIII cassette or IRES cassette downstream of the heterologous polynucleotide and upstream of the 3' LTR. As described elsewhere herein and as follows the various segment of the polynucleotide construct of the disclosure (e.g., a recombinant replication competent retroviral polynucleotide) are engineered depending in part upon the desired host cell, expression timing or amount, and the heterologous polynucleotide. A replication competent retroviral construct of the disclosure can be divided up into a number of domains that may be individually modified by those of skill in the art.

For example, the promoter can comprise a CMV promoter having a sequence as set forth in SEQ ID NO:2 from nucleotide 1 to about nucleotide 582 and may include modification to one or more (e.g., 2-5, 5-10, 10-20, 20-30, 30-50, 50-100 or more nucleic acid bases) so long as the modified promoter is capable of directing and initiating transcription. In one embodiment, the promoter or regulatory region comprises a CMV-R-U5 domain polynucleotide. The CMV-R-U5 domain comprises the immediately early promoter from human cytomegalovirus linked to the MLV R-U5 region. In one embodiment, the CMV-R-U5 domain polynucleotide comprises a sequence as set forth in SEQ ID NO:2 from about nucleotide 1 to about nucleotide 1202 or sequences that are at least 95% identical to a sequence as set forth in SEQ ID NO:2 wherein the polynucleotide promotes transcription of a nucleic acid molecule operably linked thereto. The gag domain of the polynucleotide may be derived from any number of retroviruses, but will typically be derived from an oncoretrovirus and more particularly from a mammalian oncoretrovirus such as MLV. In one embodiment, the gag domain comprises a sequence of SEQ ID NO:2 from about nucleotide number 1203 to about nucleotide 2819 or a sequence having at least 95%, 98%, 99% or 99.8% (rounded to the nearest $10^{th}$) identity thereto. The pol domain of the polynucleotide may be derived from any number of retroviruses, but will typically be derived from an oncoretrovirus and more particularly from a mammalian oncoretrovirus such as MLV. In one embodiment the pol domain comprises a sequence of SEQ ID NO:2 from about nucleotide number 2820 to about nucleotide 6358 or a sequence having at least 95%, 98%, 99% or 99.9% (roundest to the nearest $10^{th}$) identity thereto. The env domain of the polynucleotide may be derived from any number of retroviruses, but will typically be derived from an oncoretrovirus or gamma-retrovirus and more particularly from a mammalian oncoretrovirus or gamma-retrovirus such as MLV. In some embodiments the env coding domain comprises an amphotropic env domain. In one embodiment the env domain comprises a sequence of SEQ ID NO:2 from about nucleotide number 6359 to about nucleotide 8323 or a sequence having at least 95%, 98%, 99% or 99.8% (roundest to the nearest $10^{th}$) identity thereto. The 2A peptide or 2A peptide-like cassette is inserted after the env domain (e.g., at about nucleotide 8324) and continues to the end of a heterologous polynucleotide linked to the C-terminus of the 2A or 2A like-peptide. The heterologous domain may be followed by a polypurine rich domain or may be followed by a IRES cassette or polIII cassette. The 3' LTR can be derived from any number of retroviruses, typically an oncoretrovirus and preferably a mammalian oncoretrovirus such as MLV. In one embodiment, the 3' LTR comprises a U3-R-U5 domain. In yet another embodiment the LTR comprises a sequence as set forth in SEQ ID NO:2 from about nucleotide 9111 to about 11654 or a sequence that is at least 95%, 98% or 99.5% (rounded to the nearest $10^{th}$) identical thereto.

The disclosure also provides a recombinant retroviral vector comprising from 5' to 3' a CMV-R-U5, fusion of the immediate early promoter from human cytomegalovirus to the MLV R-U5 region; a PBS, primer binding site for reverse transcriptase; a 5' splice site; a t packaging signal; a gag, ORF for MLV group specific antigen; a pol, ORF for MLV polymerase polyprotein; a 3' splice site; a 4070A env, ORF for envelope protein of MLV strain 4070A; a 2A peptide or 2A peptide-like sequence; a modified cytosine deaminase (thermostabilized and codon optimized) with or without modifications to tryptophan codons (as described above); a PPT, polypurine tract; and a U3-R-U5, MLV long terminal repeat.

The disclosure also provides a retroviral vector comprising a sequence as set forth below.

The retroviral vectors can be used to treat a wide range of disease and disorders including a number of cell proliferative diseases and disorders (see, e.g., U.S. Pat. Nos. 4,405,712 and 4,650,764; Friedmann, 1989, Science, 244:1275-1281; Mulligan, 1993, Science, 260:926-932, R. Crystal, 1995, Science 270:404-410, each of which are incorporated herein by reference in their entirety, see also: The Development of Human Gene Therapy, Theodore Friedmann, Ed., Cold Spring Harbor Laboratory Press, Cold Spring Harbor, N.Y., 1999. ISBN 0-87969-528-5; Concepts in Genetic Medicine, ed. Boro Dropulic and Barrie Carter, Wiley, 2008, Hoboken, N.J.; Gene & Cell Therapy—Therapeutic Mechanism and Strategies, 3rd edition ed. Nancy Smyth Templeton, CRC Press, Boca Raton Fla. 2008 each of which is incorporated herein by reference in its entirety).

The disclosure also provides gene therapy for the treatment of cell proliferative disorders. Such therapy would achieve its therapeutic effect by introduction of an appropriate therapeutic polynucleotide (e.g., antisense, ribozymes, suicide genes, siRNA), into cells of subject having the proliferative disorder. Delivery of polynucleotide constructs can be achieved using the recombinant retroviral vector of the disclosure, particularly if it is based on MLV, which is capable of infecting dividing cells.

In addition, the therapeutic methods (e.g., the gene therapy or gene delivery methods) as described herein can be performed in vivo or ex vivo. It may be preferable to remove the majority of a tumor prior to gene therapy, for example surgically or by radiation. In some aspects, the retroviral therapy may be preceded or followed by surgery, chemotherapy or radiation therapy.

Thus, the disclosure provides a recombinant retrovirus capable of infecting a non-dividing cell, a dividing cell or a neoplastic cell, therein the recombinant retrovirus comprises a viral GAG; a viral POL; a viral ENV; a heterologous nucleic acid operably linked to a 2A peptide or peptide-like coding sequence; and cis-acting nucleic acid sequences necessary for packaging, reverse transcription and integration. The recombinant retrovirus can be a lentivirus, such as HIV, or can be an oncovirus. As described above for the method of producing a recombinant retrovirus, the recombinant retrovirus of the disclosure may further include at least one of VPR, VIF, NEF, VPX, TAT, REV, and VPU protein. While not wanting to be bound by a particular theory, it is believed that one or more of these genes/protein products are important for increasing the viral titer of the recombinant retrovirus produced (e.g., NEF) or may be necessary for infection and packaging of virion.

The disclosure also provides a method of nucleic acid transfer to a target cell to provide expression of a particular nucleic acid (e.g., a heterologous sequence). Therefore, in another embodiment, the disclosure provides a method for introduction and expression of a heterologous nucleic acid in a target cell comprising infecting the target cell with the recombinant virus of the disclosure and expressing the heterologous nucleic acid in the target cell, wherein the heterologous nucleic acid is engineered into the recombination viral vector downstream of the env domain and operably linked to a 2A or 2A like-peptide. As mentioned above, the target cell can be any cell type including dividing, non-dividing, neoplastic, immortalized, modified and other cell types recognized by those of skill in the art, so long as they are capable of infection by a retrovirus.

It may be desirable to transfer a nucleic acid encoding a biological response modifier (e.g., a cytokine) into a cell or subject. Included in this category are immunopotentiating agents including nucleic acids encoding a number of the cytokines classified as "interleukins". These include, for example, interleukins 1 through 38, as well as other response modifiers and factors described elsewhere herein. Also included in this category, although not necessarily working according to the same mechanisms, are interferons, and in particular gamma interferon, tumor necrosis factor (TNF) and granulocyte-macrophage-colony stimulating factor (GM-CSF). Other polypeptides include, for example, angiogenic factors and anti-angiogenic factors. It may be desirable to deliver such nucleic acids to bone marrow cells or macrophages to treat enzymatic deficiencies or immune defects. Nucleic acids encoding growth factors, toxic peptides, ligands, receptors, or other physiologically important proteins can also be introduced into specific target cells. Any of the foregoing biological response modifiers are engineered into the RRV of the disclosure downstream and operably liked to the 2A or 2A like-peptide.

The disclosure can be used for delivery of heterologous polynucleotides that promotes drug specific targeting and effects. For example, HER2, a member of the EGF receptor family, is the target for binding of the drug trastuzumab (Herceptin™, Genentech). Trastuzumab is a mediator of antibody-dependent cellular cytotoxicity (ADCC). Activity is preferentially targeted to HER2-expressing cells with 2+ and 3+ levels of overexpression by immunohistochemistry rather than 1+ and non-expressing cells (Herceptin prescribing information, Crommelin 2002). Enhancement of expression of HER2 by introduction of vector expressing HER2 or truncated HER2 (expressing only the extracellular and transmembrane domains) in HER2 low tumors may facilitate optimal triggering of ADCC and overcome the rapidly developing resistance to Herceptin that is observed in clinical use. In these instances the heterologous gene would encode HER2.

In another example, CD20 is the target for binding of the drug rituximab (Rituxan™, Genentech). Rituximab is a mediator of complement-dependent cytotoxicity (CDC) and ADCC. Cells with higher mean fluorescence intensity by flow cytometry show enhanced sensitivity to rituximab (van Meerten et al., Clin Cancer Res 2006; 12(13):4C21-4035, 2006). Enhancement of expression of CD20 by introduction of vector expressing CD20 in CD20 low B cells may facilitate optimal triggering of ADCC. In this instance the heterologous gene encodes CD20.

The disclosure provides methods for treating cell proliferative disorders such as cancer and neoplasms comprising administering an RRV vector of the disclosure followed by treatment with a chemotherapeutic agent or anti-cancer agent. In one aspect, the RRV vector is administered to a subject for a period of time prior to administration of the chemotherapeutic or anti-cancer agent that allows the RRV to infect and replicate. The subject is then treated with a chemotherapeutic agent or anti-cancer agent for a period of time and dosage to reduce proliferation or kill the cancer cells. In one aspect, if the treatment with the chemotherapeutic or anti-cancer agent reduces, but does not kill the cancer/tumor (e.g., partial remission or temporary remission), the subject may then be treated with a non-toxic therapeutic agent (e.g., 5-FC) that is converted to a toxic therapeutic agent in cells expression a cytotoxic gene (e.g., cytosine deaminase) from the RRV.

Using such methods the RRV vectors of the disclosure are spread during a replication process of the tumor cells, such cells can then be killed by treatment with an anti-cancer or chemotherapeutic agent and further killing can occur using the RRV treatment process described herein.

In yet another embodiment of the disclosure, the heterologous gene can comprise a coding sequence for a target antigen (e.g., a cancer antigen). In this embodiment, cells comprising a cell proliferative disorder are infected with an RRV comprising a heterologous polynucleotide encoding the target antigen to provide expression of the target antigen (e.g., overexpression of a cancer antigen). An anticancer agent comprising a targeting cognate moiety that specifically interacts with the target antigen is then administered to the subject. The targeting cognate moiety can be operably linked to a cytotoxic agent or can itself be an anticancer agent. Thus, a cancer cell infected by the RRV comprising the targeting antigen coding sequences increases the expression of target on the cancer cell resulting in increased efficiency/ efficacy of cytotoxic targeting.

In yet another embodiment, an RRV of the disclosure can comprise a coding sequence comprising a binding domain (e.g., an antibody, antibody fragment, antibody domain or receptor ligand) that specifically interacts with a cognate antigen or ligand. The RRV comprising the coding sequence for the binding domain can then be used to infect cells in a subject comprising a cell proliferative disorder such as a cancer cell or neoplastic cell. The infected cell will then express the binding domain or antibody. An antigen or cognate operably linked to a cytotoxic agent or which is cytotoxic itself can then be administered to a subject. The cytotoxic cognate will then selectively kill infected cells expressing the binding domain. Alternatively the binding domain itself can be an anti-cancer agent.

The disclosure provides a method of treating a subject having a cell proliferative disorder. The subject can be any mammal, and is preferably a human. The subject is contacted with a recombinant replication competent retroviral vector of the disclosure. The contacting can be in vivo or ex vivo. Methods of administering the retroviral vector of the disclosure are known in the art and include, for example, systemic administration, topical administration, intraperitoneal administration, intra-muscular administration, intracranial, cerebrospinal, as well as administration directly at the site of a tumor or cell-proliferative disorder. Other routes of administration known in the art.

Thus, the disclosure includes various pharmaceutical compositions useful for treating a cell proliferative disorder. The pharmaceutical compositions according to the disclosure are prepared by bringing a retroviral vector containing a heterologous polynucleotide sequence useful in treating or modulating a cell proliferative disorder according to the disclosure into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

In other embodiments, host cells transfected with a replication competent retroviral vector of the disclosure are provided. Host cells include eukaryotic cells such as yeast cells, insect cells, or animal cells. Host cells also include prokaryotic cells such as bacterial cells.

Also provided are engineered host cells that are transduced (transformed or transfected) with a vector provided herein (e.g., a replication competent retroviral vector). The engineered host cells can be cultured in conventional nutrient media modified as appropriate for activating promoters, selecting transformants, or amplifying a coding polynucleotide. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; or plant cells or explants, etc. Typically human cells or cell lines will be used; however, it may be desirable to clone vectors and polynucleotides of the disclosure into non-human host cells for purposes of sequencing, amplification and cloning.

The following Examples are intended to illustrate, but not to limit the disclosure. While such Examples are typical of those that might be used, other procedures known to those skilled in the art may alternatively be utilized.

EXAMPLES

Example 1: Design of RRV-2A-GFPm, RRV-GSG-2A, RRV-2A-yCD2 and RRV-GSG-2A-yCD2

RRV-yCD2 and RRV-GFP are Moloney MLV-based RRVs with an amphotropic envelope gene and an encephalomyocarditis virus internal ribosome entry site (IRES)—transgene cassette downstream of the env gene (Perez et al, 2012). RRV-2A-GFP (aka pAC3-2A-GFP) and RRV-2A-yCD2 (pAC3-2A-yCD2) vectors are based on RRV-GFP and RRV-yCD2 but the IRES region has been replaced with a variety of different 2A peptides in-frame with the amphotropic envelope protein and the transgene (GFP or yCD2). The overview of the cloning scheme for RRV-2A-GFP and RRV-yCD2 vectors is depicted in FIG. 3. The pAC3-T2A-GFP construct was first generated using Gibson Assembly Cloning Kit (NEB) containing 2 DNA fragments and pAC3-emd backbone digested with BstB I and Not I site. First, a pair of sense and antisense oligonucleotides containing sequence of the 3' end of the amphotropic env, 2A peptide from *Thosea asigna* virus (T2A), and 5' of GFP in 5'-to-3' order was synthesized (IDT) and hybridized to generate DNA fragment 2A-G. The second DNA fragment in the Gibson Assembly is the FP fragment (FIG. 3). FP fragment was generated by PCR using the following primers: GFP-F-Gib (5'-GAAGTTCG AGGGCGACAC-3') and GFP-R-Gib (5'-TAAAATCTTTTATTTTATCTGCGGCCGCAC-3').

In the 2A-G fragment, the 5' contains sequence that overlaps with the BstBI site in the amphotropic env of the pAC3 backbone; the 3' contains sequence that overlaps with the 5' of the FP DNA fragment. In addition, AscI restriction enzyme site was placed at the 3'-end of T2A, immediately upstream of the start codon for the second transgene, GFP. The inclusion of AscI site is for subsequent replacement of the T2A peptide with other 2A peptides. The inclusion of AscI restriction site with an additional nucleotide T followed by the AscI site resulted in an additional 3 amino acids (glycine-alanine-proline) C-terminus to the last proline residue in the T2A peptide. During the co-translation process, the separation of the GFP protein from envelope protein mediated by the T2A peptide resulted in an additional 4 amino acids P, G, A, and P at the N-terminus of the GFP. In the FP fragment, the 5'-end of the FP fragment contains sequence which overlaps to the 3'-end of the 2A-G fragment by 24 nucleotides and the 3'-end of the FP fragment overlaps the 5'-end of the pAC3-GFP backbone spanning the Not I site by 26 nucleotides. The resulting plasmid DNA from Gibson Assembly Cloning was designated pAC3-T2A-GFP (FIG. 3).

Additional RRV-2A-GFP vectors harboring three other commonly used 2A peptides derived from Porcine teschovirus-1 (P2A), Foot-and-mouth disease virus (F2A), and Equine rhinitis A virus (E2A), in two different configurations, were subsequently synthesized (IDT). Each DNA fragment contains sequence of 3' of amphotropic env gene and the designated 2A peptide in place of the T2A of the pAC3-T2A-GFP backbone at the BstBI and AscI site (FIG. 3). The resulting plasmid DNA are designated pAC3-P2A-GFP, pAC3-F2A-GFP, pAC3-E2A-GFP, pAC3-GSG-T2A-GFP, pAC3-GSG-P2A-GFP, pAC3-GSG-F2A-GFP, and pAC3-GSG-E2A-GFP.

It was later determined that RRV-2A-GFP plasmid DNAs described (pAC3-E2A-GFP, pAC3-F2A-GFP, pAC3-P2A-GFP, pAC3-T2A-GFP, pAC3-GSG-E2A-GFP, pAC3-GSG- F2A-GFP, pAC3-GSG-P2A-GFP, and pAC3-GSG-T2A-GFP) all contained a stop codon mutation at the 3'-end of GFP. The mutation was introduced in the GFP-R-Gib primer (5'-TAAAATCTTTTATTTTATCTGCGGCCGCAC-3' (SEQ ID NO:4)) when generating the FP PCR fragment. The stop codon mutation in the GFP derived from PCR resulted in read through of the GFP ORF for additional 11 amino acids (C-A-A-A-D-K-I-K-D-F-I (SEQ ID NO:5)) before reaching to a stop codon. The plasmids DNA were re-designated as pAC3-E2A-GFPm, pAC3-F2A-GFPm, pAC3-P2A-GFPm, pAC3-T2A-GFPm, pAC3-GSG-E2A-GFPm, pAC3-GSG-F2A-GFPm, pAC3-GSG-P2A-GFPm, and pAC3-GSG-T2A-GFPm. Hereafter, the two nomenclatures pAC3-E2A-GFP/pAC3-E2A-GFPm, pAC3-F2A-GFP/pAC3-F2A-GFPm, pAC3-P2A-GFP/pAC3-P2A-GFPm, pAC3-T2A-GFP/pAC3-T2A-GFPm, pAC3-GSG-E2A-GFP/pAC3-GSG-E2A-GFPm, pAC3-GSG-F2A-GFP/pAC3-GSG-F2A-GFPm, pAC3-GSG-P2A-GFP/pAC3-GSG-P2A-GFPm, and pAC3-GSG-T2A-GFP/pAC3-GSG-T2A-GFPm are used interchangeably.

An equivalent set of 4 RRV-2A-yCD2 vectors were generated by replacing the GFPm open reading frame with yCD2 ORF in the respective 2A peptide version of pAC3-P2A-GFPm, pAC3-GSG-P2A-GFPm, pAC3-T2A-GFPm and pAC3-GSG-T2A-GFPm plasmid DNA (FIG. 3). The AscI-yCD2-NotI PCR fragment was generated from the pAC3-yCD2 plasmid DNA using the primers: AscI-yCD2-F (5'-GATCGGCGCGCCTATGGTGACCGGCGGCATGGC-3' (SEQ ID NO:6) and 3-37 (5'-CCCCTTTTTCTGGA-GACTAAATAA-3' (SEQ ID NO:7). The PCR product and each of the four pAC3-2A-GFPm plasmid DNAs were restriction enzyme digested with AscI and NotI, and the AscI-yCD2-NotI digested PCR product was subcloned in place of GFPm to generate pAC3-P2A-yCD2, pAC3-GSG-P2A-yCD2, pAC3-T2A-yCD2, and pAC3-GSG-T2A-yCD2 (Table 3).

TABLE 3

Sequence, source of the 2A peptide, and RRV plasmid-2A peptide-transgene name.

| Nucleotide sequence (GSG-linker sequence underlined) | Source of 2A (infected species) | RRV-2A-GFP plasmid |
|---|---|---|
| GAGGGCAGAGGAAGTCTTCTAACATGCGGTGACGTGGAGGAGAATCCCGGCCCT (SEQ ID NO: 8) | Thosea asigna virus (insects) | pAC3-T2A-GFP |
| <u>GGAAGCGGA</u>GAGGGCAGAGGAAGTCTTCTAACATGCGGTGACGTGGAGGAGAATCCCGGCCCT (SEQ ID NO: 9) | Thosea asigna virus (insects) | pAC3-GSG-T2A-GFP |
| GCTACTAACTTCAGCCTGCTGAAGCAGGCTGGAGACGTGGAGGAGAACCCTGGACCT (SEQ ID NO: 10) | Porcine teschovirus-1 (mammals) | pAC3-P2A-GFP |
| <u>GGAAGCGGA</u>GCTACTAACTTCAGCCTGCTGAAGCAGGCTGGAGACGTGGAGGAGAACCCTGGACCT (SEQ ID NO: 11) | Porcine teschovirus-1 (mammals) | pAC3-GSG-P2A-GFP |
| GTGAAACAGACTTTGAATTTTGACCTTCTCAAGTTGGCGGGAGACGTGGAGTCCAACCCTGGACCT (SEQ ID NO: 12) | Foot-and-mouth disease virus (mammals) | pAC3-F2A-GFP |
| <u>GGAAGCGGA</u>GTGAAACAGACTTTGAATTTTGACCTTCTCAAGTTGGCGGGAGACGTGGAGTCCAACCCTGGACCT (SEQ ID NO: 13) | Foot-and-mouth disease virus (mammals) | pAC3-GSG-F2A-GFP |
| CAGTGTACTAATTATGCTCTCTTGAAATTGGCTGGAGATGTTGAGAGCAACCCTGGACCT (SEQ ID NO: 14) | Equine rhinitis A virus (mammals) | pAC3-E2A-GFP |
| <u>GGAAGCGGA</u>CAGTGTACTAATTATGCTCTCTTGAAATTGGCTGGAGATGTTGAGAGCAACCCTGGACCT (SEQ ID NO: 15) | Equine rhinitis A virus (mammals) | pAC3-GSG-E2A-GFP |

| Nucleotide sequence (GSG-linker sequence underlined) | Source of 2A (infected species) | RRV-2A-yCD2 plasmid |
|---|---|---|
| GAGGGCAGAGGAAGTCTTCTAACATGCGGTGACGTGGAGGAGAATCCCGGCCCT (SEQ ID NO: 16) | Thosea asigna virus (insects) | pAC3-T2A-yCD2 |
| <u>GGAAGCGGA</u>GAGGGCAGAGGAAGTCTTCTAACATGCGGTGACGTGGAGGAGAATCCCGGCCCT (SEQ ID NO: 17) | Thosea asigna virus (insects) | pAC3-GSG-T2A-yCD2 |
| GCTACTAACTTCAGCCTGCTGAAGCAGGCTGGAGACGTGGAGGAGAACCCTGGACCT (SEQ ID NO: 18) | Porcine teschovirus-1 (mammals) | pAC3-P2A-yCD2 |
| <u>GGAAGCGGA</u>GCTACTAACTTCAGCCTGCTGAAGCAGGCTGGAGACGTGGAGGAGAACCCTGGACCT (SEQ ID NO: 19) | Porcine teschovirus-1 (mammals) | pAC3-GSG-P2A-yCD2 |

Example 2: RRV-2A-GFPm and RRV-GSG-2A-GFPm Vectors Produced from 293T Cells are Infectious and Express GFP Protein HEK293T cells were seeded at 2e6 cells per 10 cm plates, 18 to 20 hours pre transfection. The next day, pAC3-2A-GFPm and pAC3-GSG-2A-GFPm plasmids were used for transient transfection of 20 μg of plasmid DNA at 20 h post-cell seeding using the calcium phosphate method. Eighteen hours post transfection, cells were washed with DMEM complete medium three times and incubated with fresh complete culture medium. Viral supernatant was collected approximately 42 h post-transfection and filtered through a 0.45 μm syringe filter. The viral titers of RRV-2A-GFPm, RRV-GSG-2A-GFPm and RRV-IRES-GFP from transient transfection of HEK293T cells were determined as described previously (Perez et al., 2012). Briefly, vector preparations titers were determined on PC3 cells by single-cycle infection of the vector. The single-cycle infection was guaranteed by azidothymidine treatment 24 h post-infection, followed by quantitative PCR (qPCR) of target cell genomic DNA specific for viral vector DNA (MLV LTR primer set; 5-MLV-U3-R (5'-AGCCCACAACCCCTCACTC-3' (SEQ ID NO:20)), 3-MLV-Psi (5'-TCTCCCGATCCCGGACGA-3' (SEQ ID NO:21)), and probe (5'-FAM-CCCCAAAT-GAAAGACCCCCGCTGACG-BHQ1-3' (SEQ ID NO:22)) 48 h post-infection, to quantify the number of viral DNA copies per cell genome. Viral titers, reported in transduction units (TU) per milliliter (TU/mL), were determined by calculation of threshold cycle (CT) values derived from a standard curve ranging from $2\times10^7$ copies to $2=10^1$ copies of plasmid DNA and from a known amount of genomic DNA input, the number of cells, and a dilution of the viral stock per reaction mixture. Table 4 shows that titers of RRV-2A-GFPm and RRV-GSG-2A-GFPm produced from HEK293T cells were comparable to that of RRV-IRES-GFP.

TABLE 4

Titers of RRV-2A-GFPm and RRV-GSG-2A-GFPm vectors produced from 293T cells

|  | TU/mL | Stdv |
| --- | --- | --- |
| pAC3-E2A-GFP | 1.15E+06 | 2.55E+05 |
| pAC3-F2A-GFP | 1.63E+06 | 2.58E+05 |
| pAC3-P2A-GFP | 1.81E+06 | 3.11E+05 |
| pAC3-T2A-GFP | 3.31E+06 | 1.32E+05 |
| pAC3-GSG-E2A-GFP | 1.65E+06 | 2.76E+05 |
| pAC3-GSG-F2A-GFP | 1.32E+06 | 7.57E+04 |
| pAC3-GSG-P2A-GFP | 1.31E+06 | 1.22E+05 |
| pAC3-GSG-T2A-GFP | 2.66E+06 | 2.14E+05 |
| pAC3emd | 1.65E+06 | 2.12E+05 |

Figure 4:
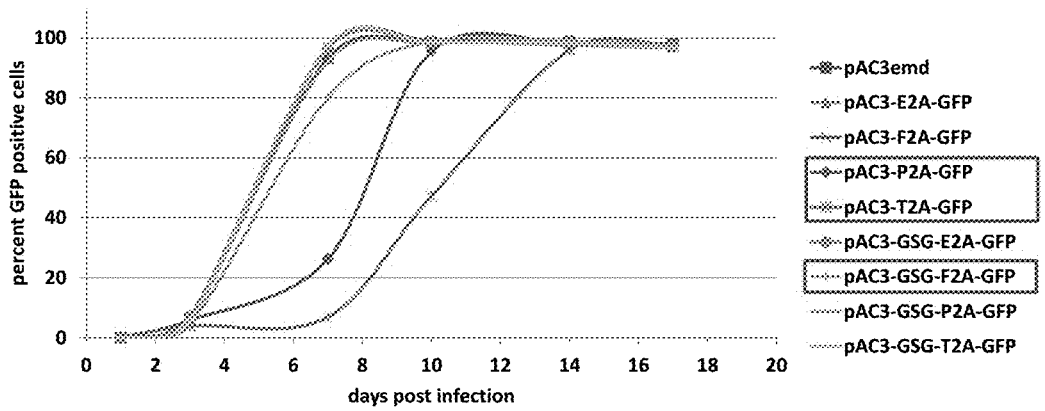
FIG. 4 shows replication kinetics of RRV-2A-GFPm and RRV-GSG-2A-GFPm vectors produced from transiently transfected HEK293T cells in U87-MG cells.
Figure 5:
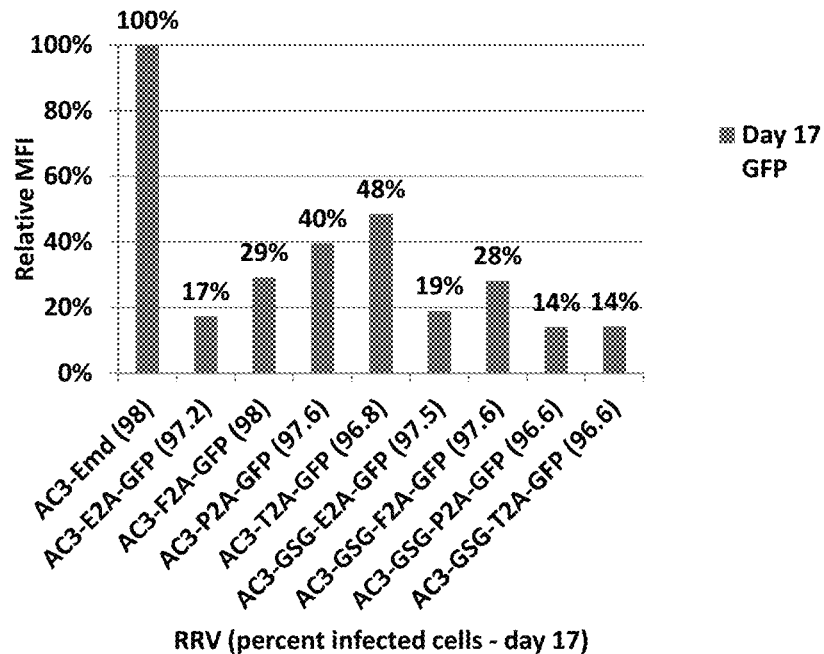
FIG. 5 shows GFP expression levels, indicated as mean fluorescent intensity (MFI), of RRV-2A-GFPm and RRV-GSG-2A-GFPm vectors in U87-MG cells. Percentage indicated is relative to MFI of RRV-IRES-GFP.

The RRV-2A-GFPm viruses produced from HEK293T cells were then used to infect U87-MG at a multiplicity of infection (MOI) of 0.01. U87-MG cells were seeded at $1\times10^5$ cells in 6-well plates for initial infection. The cells were passaged to a new well of a 6-well plate at a dilution of 1 to 4 at each passage and the remainder of the cells from each sample was harvested to assess viral spread by measuring percent of GFPm expressing cells and GFPm mean fluorescent intensity using BD FACS Canto II (BD Biosciences). The percentages of GFP-positive cells at each passage were plotted. The length of the assay was carried out until all RRV-2A-GFP viruses reached to maximum infectivity (~95% or greater GFP-positive cells). FIG. 4 shows that the RRV-2A-GFPm and RRV-GSG-2A-GFPm produced from HEK293T cells are infectious. The rate of viral spread among RRV-2A-GFPm and RRV-GSG-2A-GFPm were similar to RRV-IRES-GFP in infected U87-MG cells, with the exception of RRV-P2A-GFPm, RRV-T2A-GFPm and RRV-GSG-F2A-GFPm exhibiting a lag. Nevertheless, they reached maximally infectivity within 18 days. The GFPm expression levels also varied among RRV-2A-GFPm and RRV-GSG-2A-GFPm vectors but were all at approximately 20 to 50% of that expressed from RRV-IRES-GFP infected U87-MG cells (FIG. 5).

Figure 6:
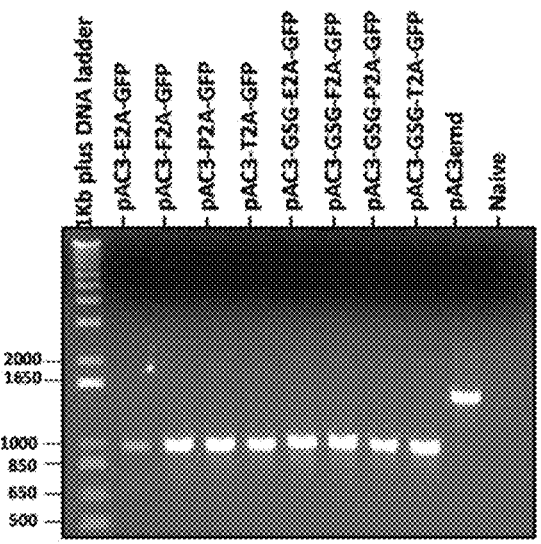
FIG. 6 shows vector stability of RRV-2A-GFPm and RRV-GSG-2A-GFPm vectors in U87-MG cells.

Example 3: RRV-2A-GFPm and RRV-GSG-2A-GFPm Vectors are Stable in U87-MG Cells To ensure that the reduced GFP expression in RRV-2A-GFPm and RRV-GSG-2A-GFPm infected U87-MG cells is not due to deletion of GFP gene in viral genome, the integrity of 2A-GFPm region was assessed by end-point PCR using primer set which span the 3'env and 3'UTR region of proviral DNA. At maximal infectivity of the U87-MG cells, cells were subsequently cultured to reach confluency in a T75 flask, at which time the media was replaced with fresh media, followed by the collection of virus containing supernatant and 0.45 μM filtration at 18-24 h post media change. The collected cell supernatant was aliquoted and stored at −80° C. until being used for immunoblotting and re-infection experiments. At the same time, the cells were split into two fractions; $\frac{1}{10}^{th}$ for isolation of genomic DNA and $\frac{9}{10}^{th}$ for isolation of total cell lysates. The genomic DNA was extracted from the cell pellet by resuspending in 400 μL 1×PBS and isolated using the Promega Maxwell 16 Cell DNA Purification Kit (Promega). One-hundred nanogram of genomic DNA was then use as the template for PCR with a primer set: IRES-F (5'-CTGATCT-TACTCTTTGGACCTTG-3' (SEQ ID NO:23)) and IRES-R (5'-CCCCTTTTTCTGGAGACTAAATAA-3' (SEQ ID NO:24)). The resultant PCR products were analyzed on 1% agarose gel. The data show that the 2A-GFPm and GSG-2A-GFPm region in proviral DNA of RRV-2A-GFPm and RRV-GSG-2A-GFPm vectors are stable in U87-MG cells during the time course of viral replication (FIG. 6).

Figure 7:
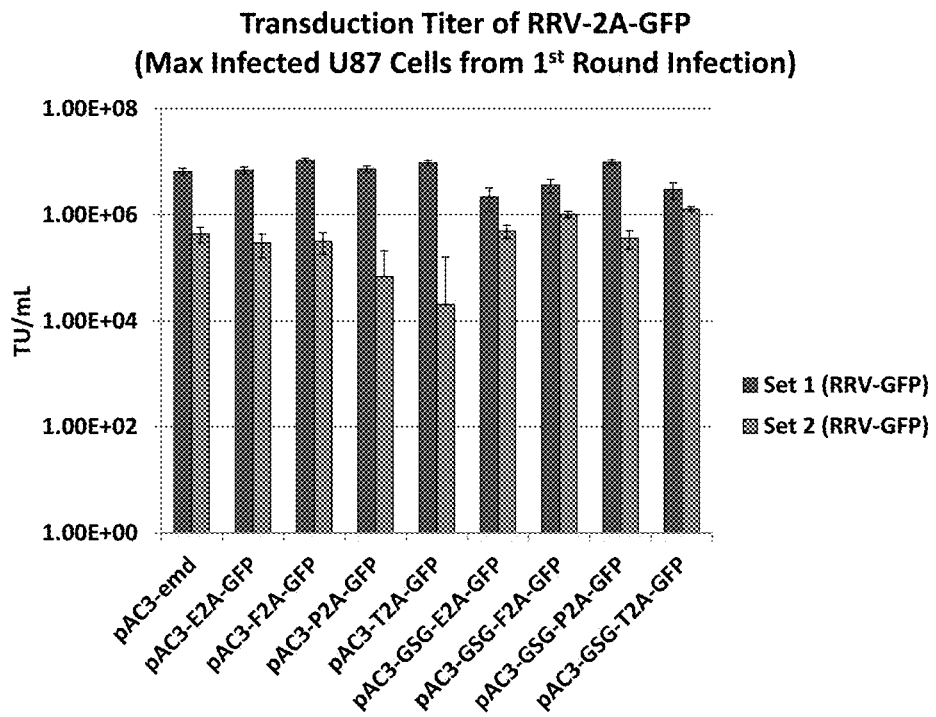
FIG. 7 shows titers of RRV-2A-GFPm and RRV-GSG-2A-GFPm vectors produced from maximally infected U87-MG cells. Titers values presented are from 2 independent experiments.

Example 4: RRV-2A-GFPm and RRV-GSG-2A-GFPm Produced from Maximally Infected U87-MG Cells Remain Infectious in the Subsequently Infection Cycle As long-term infectivity is one of the many important criteria to sustain therapeutic effect delivered by RRV, infectivity of RRV-2A-GFPm and RRV-GSG-2A-GFPm produced from maximally infected U87-MG cells was evaluated by performing an additional cycle of infection in naïve U87-MG cells. Viral supernatants collected from maximally infected U87-MG cells were first titered as described then re-infected back onto naïve U87-MG cells at an MOI of 0.01. FIG. 7 shows that titers produced from maximally infected U87-MG cells were similar to those obtained from transiently transfected HEK293T cells are comparable among RRV-2A-GFPm, RRV-GSG-2A-GFPm vectors as well as RRV-IRES-GFP vector.

Figure 8:
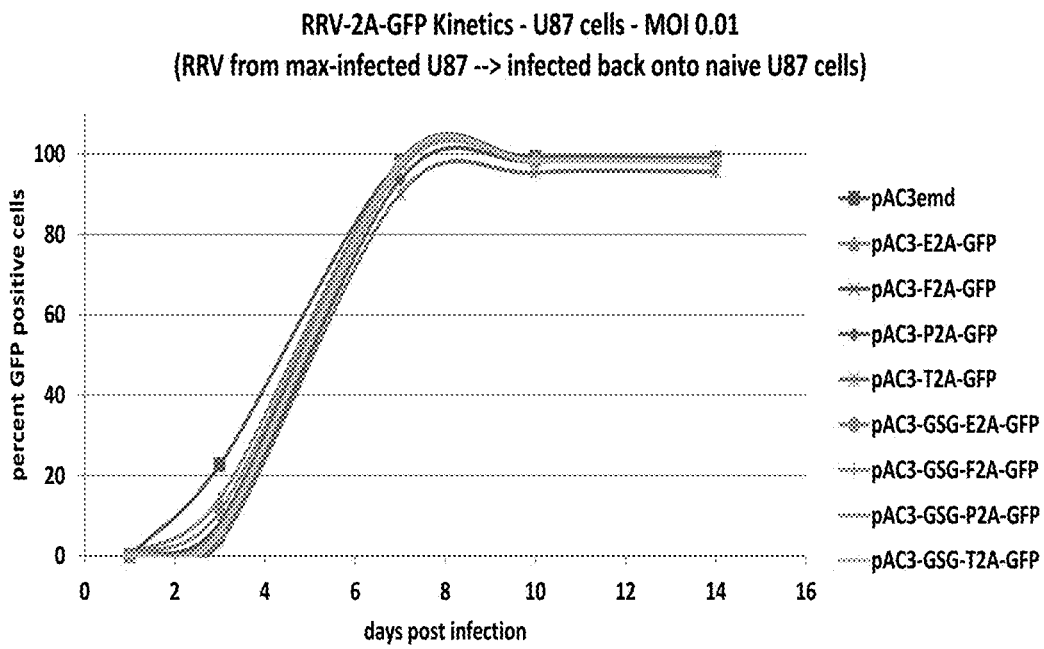
FIG. 8 shows replication kinetics of RRV-2A-GFPm and RRV-GSG-2A-GFPm vectors produced in maximally infected U87-MG cells followed by subsequent infection cycle in naïve U87-MG cells.
Figure 9:
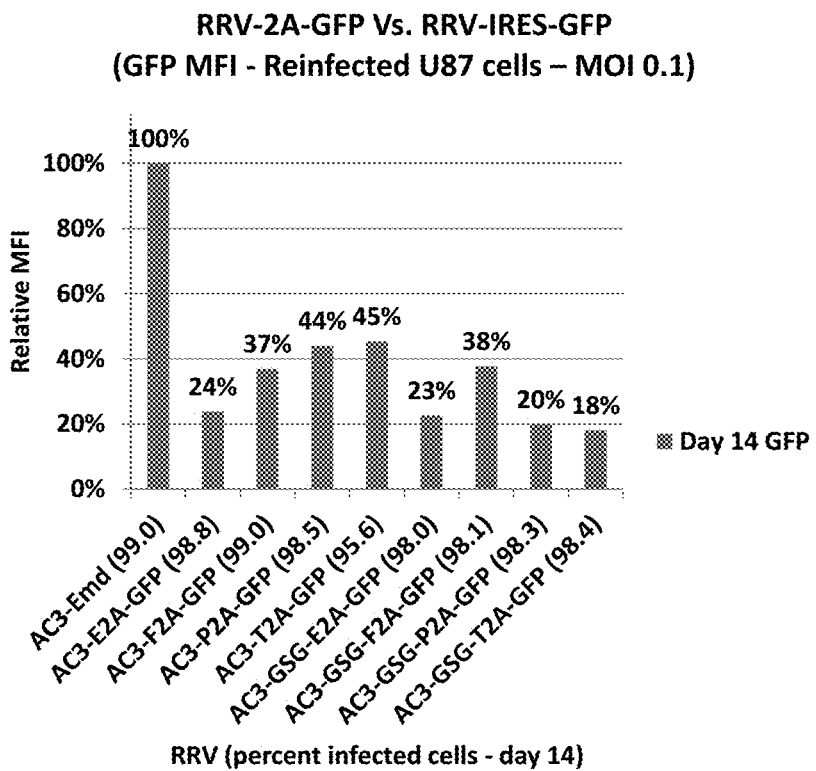
FIG. 9 shows MFI of GFPm expression in RRV-2A-GFPm and RRV-GSG-2A-GFPm vectors in maximally infected U87-MG cells from the second infection cycle. Percentage indicated is relative to MFI of RRV-IRES-GFP.

The viral spread of RRV-2A-GFPm and RRV-GSG-2A-GFPm was monitored at each cell passage as described. In contrast to the viral spread rate observed in the first infection cycle using the viral supernatant produced from transiently transfected HEK293T cells, FIG. 8 shows that all vectors spread at the rate comparable to RRV-IRES-GFP. However, the GFP expression levels from RRV-2A-GFPm and RRV- GSG-2A-GFPm infected U87-MG cells in this infection cycle remained at 20 to 50% of that expressed by RRV-IRES-GFP cells, as previously observed (FIG. 9).

Figure 10:
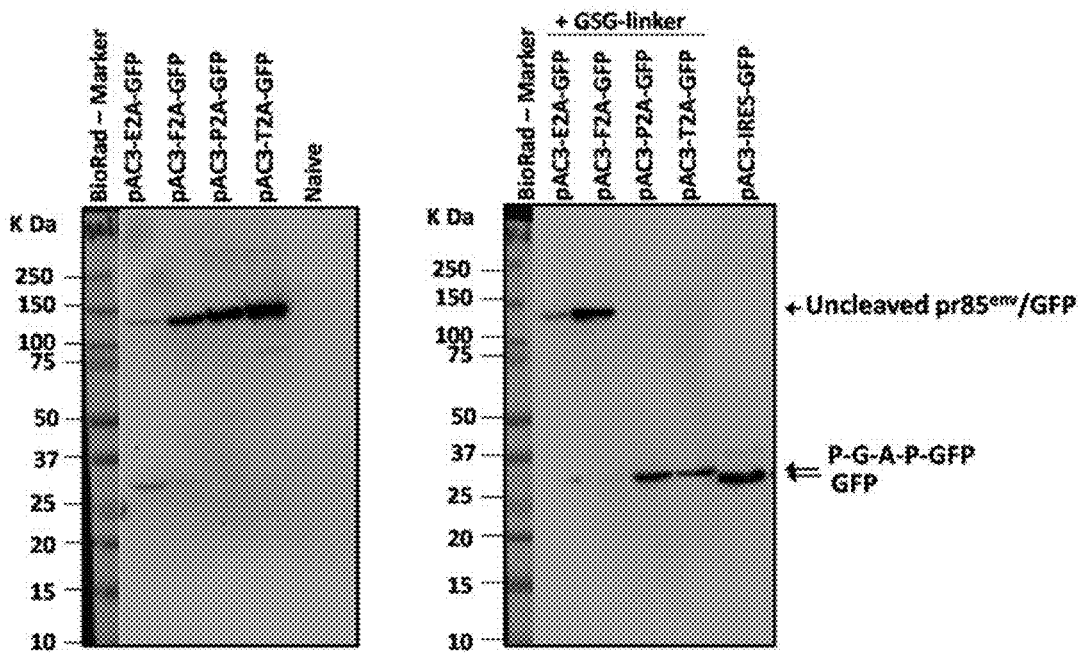
FIG. 10 shows anti-GFP immunoblot of cell lysates from RRV-2A-GFPm and RRV-GSG-2A-GFPm infected U87-MG cells. Protein band detected at ~120 KDa represents the viral envelope-GFPm fusion polyprotein. Protein band detected at ~27 KDa represents the native GFP or 2A-GFPm protein separated from the Env-GFPm fusion polyprotein.
Figure 11:
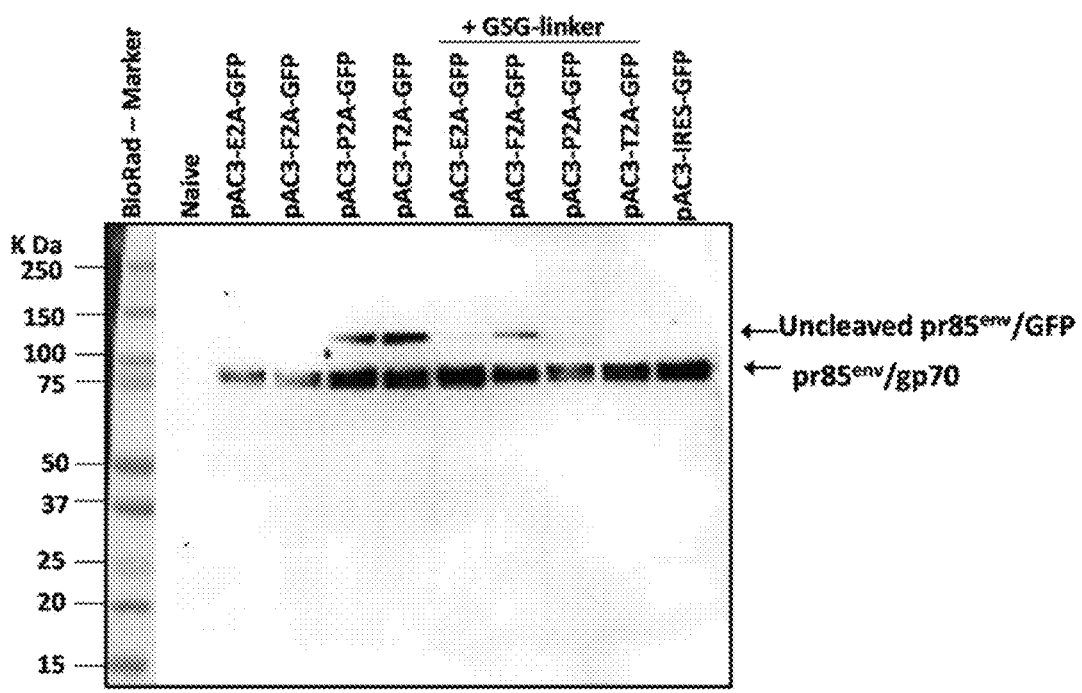
FIG. 11 shows anti-gp70 immunoblot of cell lysates from RRV-2A-GFPm and RRV-GSG-2A-GFPm infected U87-MG cells. Protein band detected at ~120 KDa represents the viral envelope-GFPm fusion polyprotein. Protein band detected at ~75 KDa represents the Pr85/gp70 viral envelope protein separated from the fusion polyprotein.

Example 5: The Viral Envelope and GFPm Proteins of RRV-2A-GFPm and RRV-GSG-2A-GFPm Vectors are Processed at Different Efficiency in Infected U87-MG Cells To assess the GFPm expression, the separation efficiency of GFPm from the viral envelope protein, and the proper processing of the viral envelope protein, cell lysates were generated from infected U87-MG cells. U87-MG cells at maximal infectivity, confluent cell monolayer was washed once in 1×PBS, disassociated by TrpZean (Sigma), resuspended in complete DMEM, washed again in 1×PBS, followed by cell lysis in 200 µL of RIPA lysis buffer (Thermo Scientific) on ice for 30 minutes. The lysates were clarified of cellular debris by centrifugation at 14,000 rpm for 15 m at 4° C. and the supernatants collected and transferred to a new tube. The cell lysates were then assayed for their protein concentration using BCA precipitation assay (Thermo Scientific) and 20 µg protein was subjected to SDS-PAGE. The proteins were resolved on 4-12% XT-Tris SDS-PAGE gels (BioRad) for 45 minutes at 200 volts. Subsequently the proteins were transferred onto PVDF membranes (Life Technologies) using an iBlot dry blotting system at 20 volts for 7 minutes. The membranes were assayed for the expression of the gp70 subunit of the envelope protein and the GFPm, using anti-gp70 (rat anti-gp70, clone 83A25; 1:500 dilution) and anti-GFP (rabbit anti-GFP; 1:1000 dilution). Protein expression was detected using the corresponding secondary antibody conjugated to horseradish peroxidase. The result show that GFPm protein from RRV-F2A-GFPm, RRV-P2A-GFPm, and RRV-T2A-GFPm, RRV-GSG-F2A-GFPm and RRV-GSG-F2A-GFPm were separated inefficiently from the viral envelope protein, as indicated by the high molecular weight of the env-2A-GFPm fusion protein at ~120 KDa, using the anti-GFP antibody (FIG. 10). In contrast, the separation of GFPm from the viral envelope protein was relative efficient for RRV-E2A-GFPm, RRV-GSG-P2A-GFPm and RRV-GSG-T2A-GFPm vectors compared to that from RRV-IRES-GFP (FIG. 10). In parallel, the processing of the viral envelope protein in infected U87-MG was examined using the anti-gp70 antibody. The result show the viral enveloped in either precursor (Pr85) or processed form (gp70) were detected in all RRV-2A-GFPm and RRV-GSG-2A-GFPm vectors (FIG. 11), suggesting separation of the viral envelope protein from the GFPm as seen in the anti-GFP immunoblot. In addition, the efficiency of separation observed in the anti-gp70 blot is somewhat consistent with that observed in the anti-GFP immunoblot. Although the protein expression of the fusion polyprotein, Env-GFPm, varied among the RRV-2A-GFPm and RRV-GSG-2A-GFPm vectors, RRV-GSG-P2A-GFPm and RRV-T2A-GFPm appear to have most efficient separation as indicated by the lack of detection of the viral envelope-GFPm fusion polyprotein in both anti-GFP and anti-gp70 immunoblots.

Figure 12:
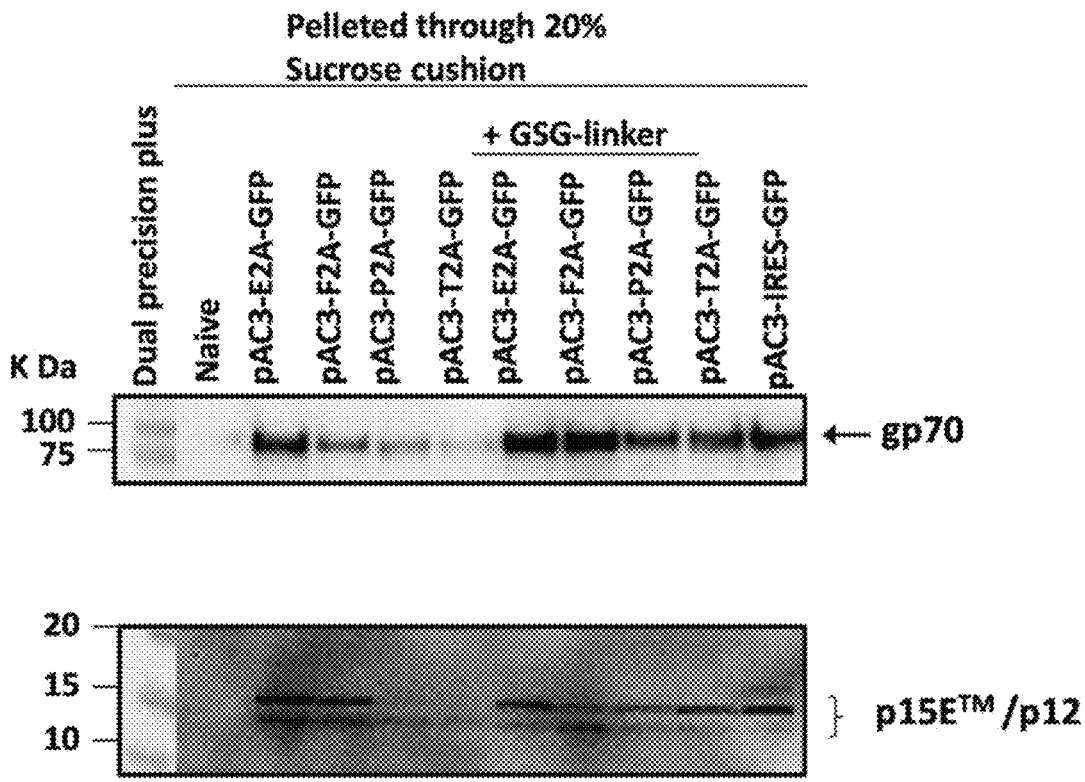
FIG. 12 shows immunoblot of viron-associated, properly processed viral envelope protein containing the gp70 and p15E subunit detected by anti-gp70 and anti-TM antibody, respectively. The anti-p15E antibody detects both the precursor TM subunit p15E and R-peptide cleaved TM subunit p12E.

Example 6: The Level of Incorporation of Properly Processed Viral Envelope Protein Correlates with the Efficiency of Separation Between the Viral Envelope and GFPm Proteins Viral supernatants from RRV-2A-GFPm and RRV-GSG-2A-GFPm maximally infected U87-MG cells were pelleted through a 20% sucrose gradient at 14000 rpm for 30 m at 4° C., and subsequently resuspended in 20 µL of 1× Laemmli Buffer containing 5% 2-mercaptoethanol and subjected to SDS PAGE on 4-20% Tris Glycine gels (BioRad). The electrophoresis and protein transfer were performed as described. Properly processed viron-associated viral envelope protein expression was examined using anti-gp70 (rat raised anti-gp70, clone 83A25; 1:500 dilution) and the anti-p15E (mouse raised anti-TM, clone 372; 1:25C dilution). Protein expression was detected using the corresponding secondary antibody conjugated to horseradish peroxidase. The data indicate that properly processed envelope protein, gp70 and p12E/p15E of RRV-2A-GFPm and RRV-GSG-2A-GFPm, except RRV-P2A-GFPm and RRV-T2A-GFPm vectors, were detected at levels comparable to that of RRV-IRES-GFP in virions (FIG. 12). As expected, RRV-GSG-P2A-GFPm and RRV-T2A-GFPm which showed lowest level of virion-associated envelope protein expressed highest level of fusion polyprotein in cell lysates. Consistent with published data, the data support the notation that unprocessed envelope protein precursor protein Pr8b or in this case the viral envelope-GFPm fusion polyprotein does not get incorporated into virion. Furthermore, the cleavage of the R peptide bearing the 2A peptide leading to "fusogenic" p12E also appears to be sufficient during virion maturation to produce infectious viral particles as indicated by the titer produced from maximally infected U87-MG cells (FIG. 7). The nature of p15E/p12E ratio and its role in membrane fusion during infection is unclear. All together, the data suggest that the level of viral envelope protein incorporation does not correlate with titer values measured in target cells. The unexpected lack of difference in titer values among vectors, particularly the RRV-GSG-P2A-GFPm and RRV-T2A-GFPm vectors suggests that a range of envelope expression levels can be tolerated on the RRV particles without affecting titer on these cells.

Example 7: RRV-P2A-yCD2 and RRV-T2A-yCD2, RRV-GSG-P2A-yCD2 and RRV-GSG-T2A-yCD2 Vectors Produced from 293T Cells are Infectious and Express yCD2 Protein HEK293T cells were seeded at 2e6 cells per 10 cm plates, 18 to 20 hours pre transfection. The next day, pAC3-P2A-yCD2, pAC3-T2A-yCD2, pAC3-GSG-P2A-yCD2, and pAC3-GSG-T2A-yCD2 plasmids were used for transient transfection of 20 µg of plasmid DNA at 20 h post-cell seeding using the calcium phosphate method. Eighteen hours post transfection, cells were washed with DMEM complete medium three times and incubated with fresh complete culture medium. Viral supernatant was collected approximately 42 h post-transfection and filtered through a 0.45 µm syringe filter. The viral titers of RRV-P2A-yCD2, RRV-T2A-yCD2, RRV-GSG-P2A-yCD2, and RRV-GSG-T2A-yCD2 from transient transfection of HEK293T cells were determined as described previously (Perez et al., 2012). Briefly, vector preparations titers were determined on PC3 cells by single-cycle infection of the vector. The single-cycle infection was guaranteed by azidothymidine treatment 24 h post-infection, followed by quantitative PCR (qPCR) of target cell genomic DNA specific for viral vector DNA (MLV LTR primer set; 5-MLV-U3-R (5'-AGCC-CACAACCCCTCACTC-3' (SEQ ID NO:20)), 3-MLV-Psi (5'-TCTCCCGATCCCGGACGA-3' (SEQ ID NO:21)) and probe (5'-FAM-CCCCAAATGAAAGACCCCCGCTG-ACG-BHQ1-3' (SEQ ID NO:22)) 48 h post-infection, to quantify the number of viral DNA copies per cell genome. Viral titers, reported in transduction units (TU) per milliliter (TU/mL), were determined by calculation of threshold cycle (CT) values derived from a standard curve ranging from $2 \times 10^7$ copies to $2 \times 10^1$ copies of plasmid DNA and from a known amount of genomic DNA input, the number of cells, and a dilution of the viral stock per reaction mixture. Table 5 shows that titers of RRV-P2A-yCD2, RRV-T2A-yCD2, RRV-GSG-P2A-yCD2, and RRV-GSG-T2A-yCD2 produced from HEK293T cells were comparable to that of RRV-IRES-yCD2.

TABLE 5

Titers of RRV-P2A-yCD2, RRV-T2A-yCD2, RRV-GSG-P2A-yCD2 and RRV-GSG-T2A-yCD2 vectors produced from 293T cells

|  | TU/mL | Stdv |
| --- | --- | --- |
| pAC3P2AyCD2 | 3.06E+06 | 4.59E+05 |
| pAC3GSGP2AyCD2 | 1.15E+06 | 2.45E+05 |
| pAC3T2AyCD2 | 2.32E+06 | 3.78E+05 |
| pAC3GSGT2AyCD2 | 1.88E+06 | 4.64E+05 |
| pAC3-yCD2 | 1.76E+06 | 1.84E+05 |

Figure 13:
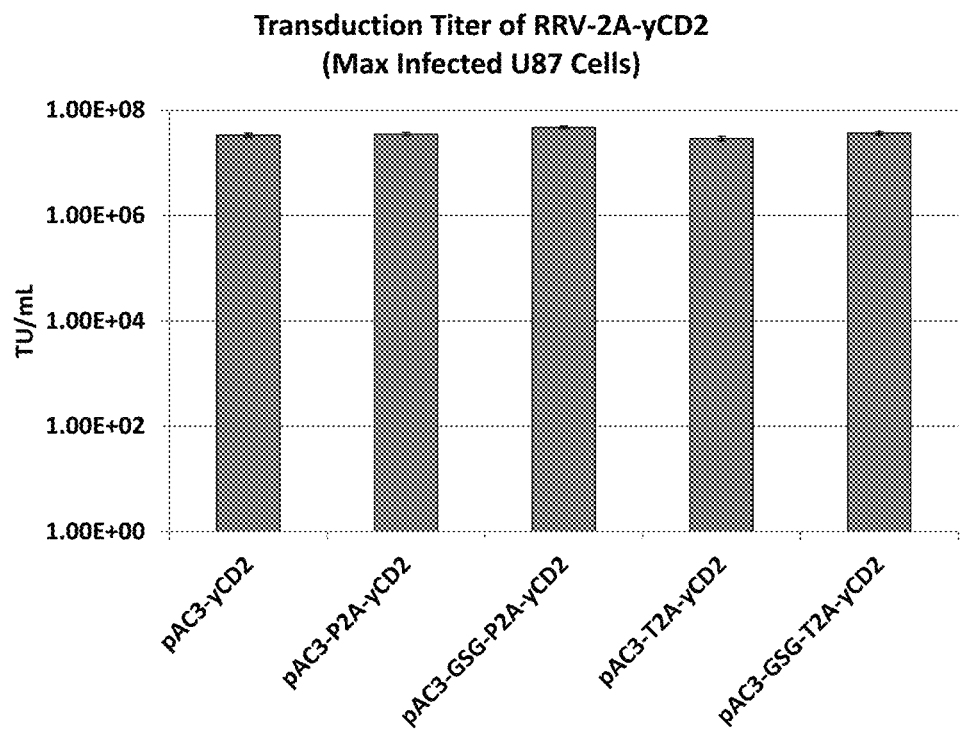
FIG. 13 shows titers of RRV-P2A-yCD2, RRV-T2A-yCD2, RRV-GSG-P2A-yCD2 and RRV-GSG-T2A-yCD2 vectors produced from maximally infected U87-MG cells.

In addition, viral supernatants collected from maximally infected U87-MG cells were titered as described to ensure they remain infectious. The primer set used for titer have similar priming efficiency as the primer set containing the, 5-MLV-U3-R, 3-MLV-Psi primers and probe. The primer set used for tittering the RRV-P2A-yCD2, RRV-T2A-yCD2, RRV-GSG-P2A-yCD2 and RRV-GSG-T2A-yCD2 vectors from infected U87-MG cells are: Env2 For: 5'-ACCCT-CAACCTCCCCTACAAGT-3' (SEQ ID NO:25), Env2 Rev: 5'-GTTAAGCGCCTGATAGGCTC-3' (SEQ ID NO:26) and probe 5'-FAM-CCCCAAATGAAAGACCCCCGCTG-ACG-BHQ1-3' (SEQ ID NO:27). FIG. 13 shows that titers produced from maximally infected U87-MG cells were similar to those obtained from transiently transfected HEK293T cells and comparable among RRV-IRES-yCD2 vector.

Figure 14:
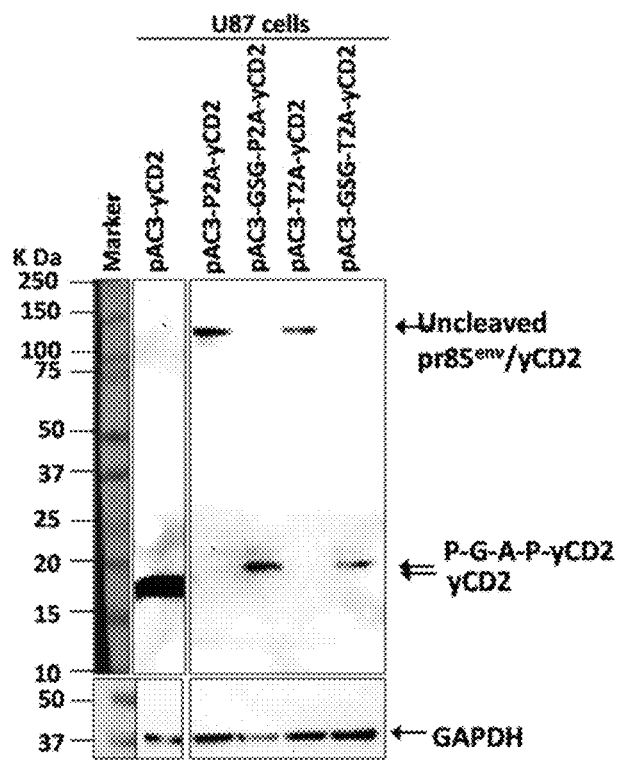
FIG. 14 shows anti-yCD2 immunoblot of cell lysates from RRV-P2A-yCD2, RRV-T2A-yCD2, RRV-GSG-P2A-yCD2 and RRV-GSG-T2A-yCD2 infected U87-MG cells. Protein band detected at ~110 KDa represents the viral envelope-GFPm fusion polyprotein. Protein band detected at ~15 KDa represents the yCD2 or 2A-yCD2 protein separated from the Env-yCD2 fusion polyprotein.
Figure 15:
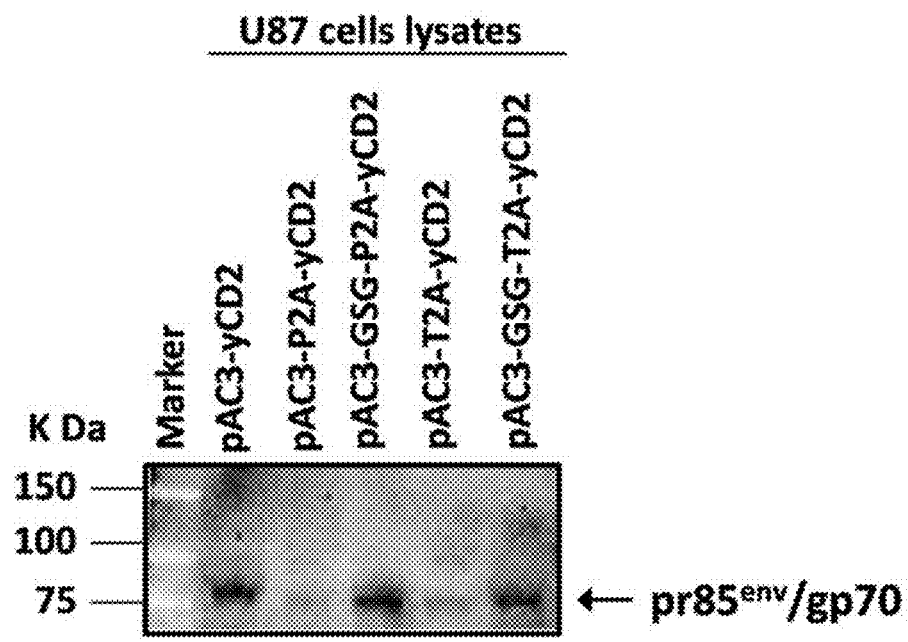
FIG. 15 shows anti-gp20 immunoblot of cell lysates from RRV-P2A-yCD2, RRV-T2A-yCD2, RRV-GSG-P2A-yCD2 and RRV-GSG-T2A-yCD2 infected U87-MG cells. Protein band detected at ~110 KDa represents the viral envelope-yCD2 fusion polyprotein. Protein band detected at ~75 KDa represents the Pr85/gp70 viral envelope protein separated from the fusion polyprotein.

Example 8: The Viral Envelope and yCD2 Proteins of RRV-P2A-yCD2 and RRV-T2A-yCD2, RRV-GSG-P2A-yCD2 and RRV-GSG-T2A-yCD2 Vectors in Infected U87-MG Cells are Processed at Different Efficiency To assess the yCD2 expression, the separation efficiency of yCD2 protein from the viral envelope protein, and the proper processing of the viral envelope protein, cell lysates were generated from infected U87-MG cells. U87-MG cells at maximal infectivity, confluent cell monolayer was washed once in 1×PBS, dissociated by TrpZean (Sigma), resuspended in complete DMEM, washed again in 1×PBS, followed by cell lysis in 200 µL of RIPA lysis buffer (Thermo Scientific) on ice for 30 minutes. The lysates were clarified of cellular debris by centrifugation at 14,000 rpm for 15 minutes at 4° C. and the supernatants collected and transferred to a new tube. The cell lysates were then assayed for their protein concentration using BCA precipitation assay (Thermo Scientific) and 20 µg protein was subjected to SDS-PAGE. The proteins were resolved on 4-12% XT-Tris SDS-PAGE gels (BioRad) for 45 minutes at 200 volts. Subsequently the proteins were transferred onto PVDF membranes (Life Technologies) using an iBlot dry blotting system at 20 volts for 7 minutes. The membranes were assayed for the expression of the gp70 subunit of the envelope protein and the yCD2, using anti-gp70 (rat anti-gp70, clone 83A25; 1:500 dilution) and anti-yCD2 (mouse anti-yCD2; 1:1000 dilution). Protein expression was detected using the corresponding secondary antibody conjugated to horseradish peroxidase. The result show that yCD2 protein from RRV-P2A-yCD2 and RRV-T2A-yCD2 were separated inefficiently from the viral envelope protein, as indicated by the high molecular weight of the env-2A-yCD2 fusion polyprotein at ~110 KDa, using the anti-yCD2 antibody (FIG. 14). In contrast, the separation of yCD2 protein from the viral envelope protein was relative efficient for RRV-GSG-P2A-yCD2 and RRV-GSG-T2A-yCD2 compared to that from RRV-IRES-yCD2 (FIG. 14). In parallel, the processing of the viral envelope protein in infected U87-MG was examined using the anti-gp70 antibody. The result showed the viral enveloped in either precursor (Pr85) or processed form (gp70) were readily detectable in RRV-GSG-P2A-yCD2, RRV-GSG-T2A-yCD2 vector, but at much lower level in RRV-P2A-yCD2 and RRV-T2A-yCD2 vectors (FIG. 15). In addition, the level of Pr85/gp70 viral envelope protein is somewhat consistent with that observed in the anti-yCD2 immunoblot. However, unlike RRV-2A-GFPm or RRV-GSG-2A-GFPm vectors, viral envelope-yCD2 fusion polyprotein could not be detected using the anti-gp70 antibody or anti-2A antibody (Cat #A3S31, EMD Millipore). Among the 4 vectors, RRV-GSG-P2A-yCD2 and RRV-GSG-T2A-yCD2 vectors showed most efficient separation of fusion polyprotein as indicated by the lack of detection of the viral envelope-yCD2 fusion polyprotein in the anti-yCD2 immunoblot. All together the data suggest that GSG-P2A and GSG-T2A configuration give rise to the most efficient polyprotein separation in the context of RRV envelope protein open reading frame.

Figure 16:
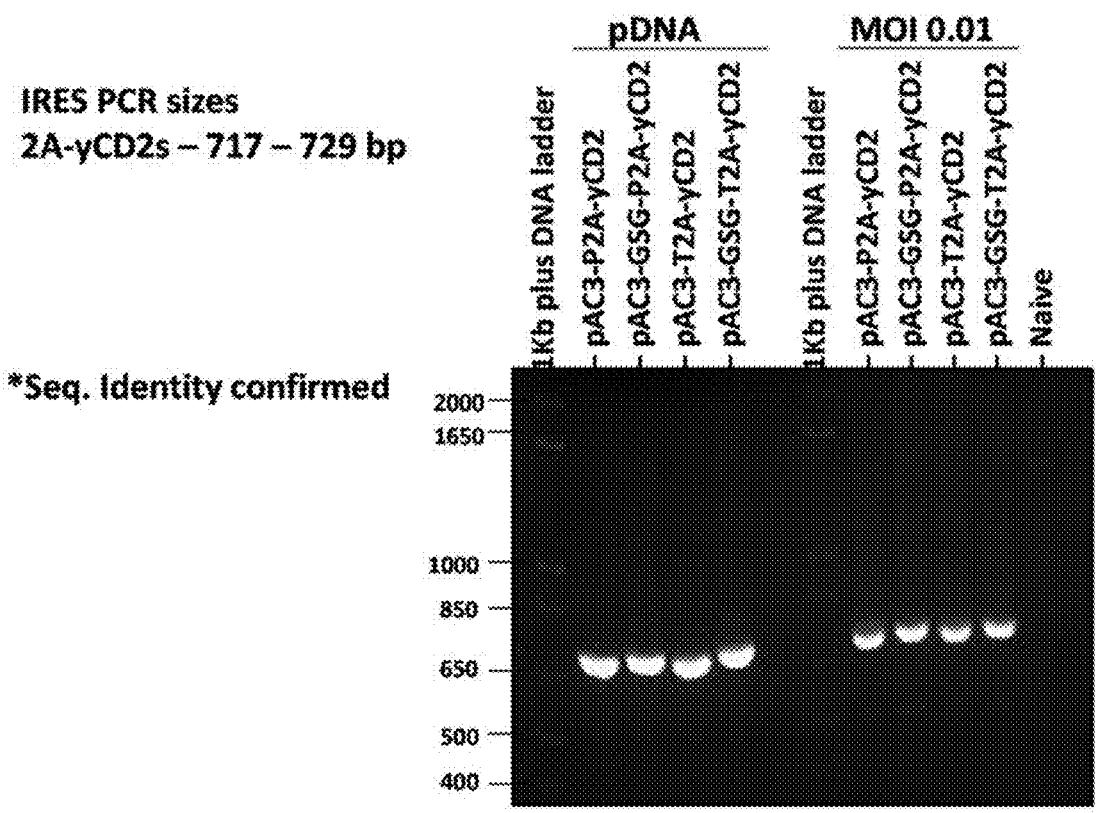
FIG. 16 shows long-term vector stability of RRV-P2A-yCD2 and RRV-T2A-yCD2, RRV-GSG-P2A-yCD2 and RRV-GSG-T2A-yCD2 vectors in U87-MG cells over 16 cycles of infection. pDNA are plasmid DNA of pAC3-P2A-yCD2 and pAC3-T2A-yCD2, pAC3-GSG-P2A-yCD2 and pAC3-GSG-T2A-yCD2 which were included as positive controls.

Example 9: RRV-G2G-P2A-YCD2 and RRV-GSG-T2A-yCD2 have Long-Term Stability in U87-MG Cells Serial infection was performed to evaluate long-term vector stability of RRV-GSG-P2A-yCD2 and RRV-GSG-T2A-yCD2 in U87-MG cells. Approximately $10^5$ naive U87-MG cells seeded in 6-well plates were initially infected with the viral vectors at a MOI of 0.1 and cultured for 1 week to complete a single cycle of infection. 100 µL of the 2 ml of viral supernatant from fully infected cells is used to infect $10^5$ naïve cells and repeated up to 16 cycles. The genomic DNA was extracted from the small pellet by resuspending in 400 µL 1×PBS and isolated using the Promega Maxwell 16 Cell DNA Purification Kit (Promega). One-hundred nanogram of genomic DNA was then use as the template for PCR with a primer pair that spans the transgene cassette; IRES-F (5'-CTGATCTTACTCTTTGGACCTTG-3' (SEQ ID NO:23)) and IRES-R (5'-CCCCTTTTTCTGGA-GACTAAATAA-3' (SEQ ID NO:24)). Vector stability of the 2A-yCD2 region is evaluated by PCR amplification of the integrated provirus from the infected cells. The expected PCR product size is approximately 0.73 kb. The appearance of any bands smaller than 0.73 kb indicates deletion in the 2A-yCD2 region. FIG. 16A shows that IRES-yCD2 (1.2 Kb) region in RRV-yCD2 is stable up to infection cycle 16 as previously reported (Perez et al., 2012). Similarly, 2A-yCD2 region in both RRV-GSG-P2A-yCD2 and RRV-GSG-T2A-yCD2 also remains stable up to infection cycle 16. However, 2A-yCD2 region in RRV-GSG-T2A-yCD2 is slightly less stable than RRV-GSG-P2A-yCD2 as deletion (0.4 kb) deletion emerged from infection cycle 13 but remains stable throughout cycle 16 (FIGS. 16B and 16C).

Figure 17:
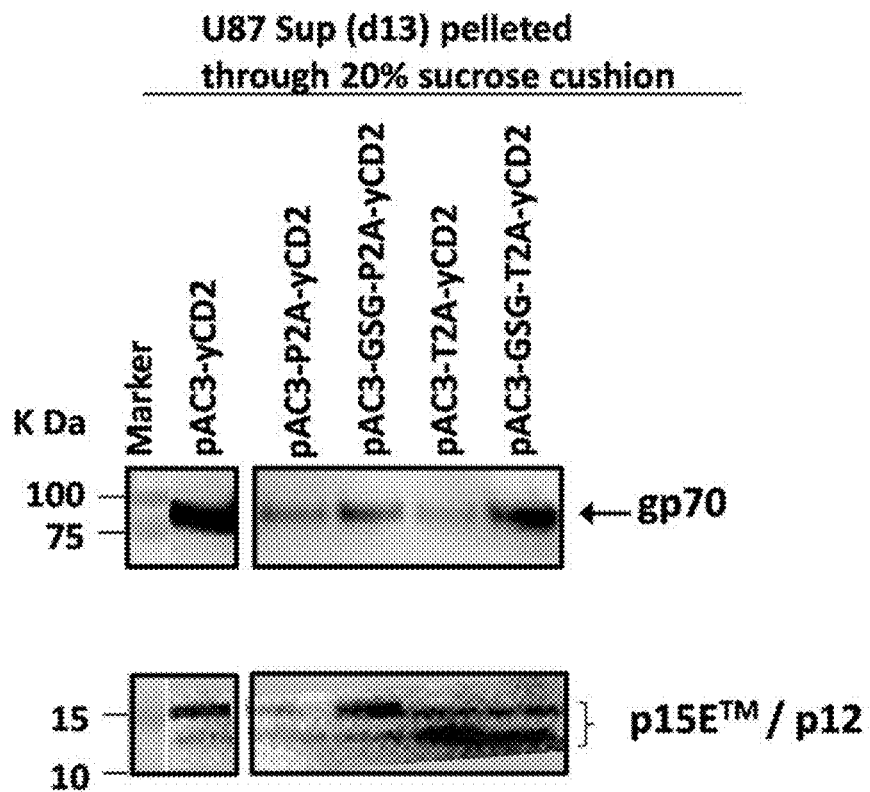
FIG. 17 shows an immunoblot of viron-associated, properly processed viral envelope protein containing the gp20 and p15E subunit detected by anti-gp70 and anti-TM antibody, respectively. The anti-p15E antibody detects both the precursor TM subunit p15E and R-peptide cleaved TM subunit p12E.

Example 10: Incorporation of Properly Processed Viral Envelope Protein Correlates with the Efficiency of Separation Between the Viral Envelope and yCD2 Proteins in U87-MG Cells Infected with RRV-P2A-yCD2 and RRV-T2A-yCD2, RRV-GSG-P2A-yCD2 and RRV-GSG-T2A-yCD2 Vectors Viral supernatants produced from RRV-2A-yCD2 and RRV-GSG-2A-yCD2 maximally infected U87-MG cells, were pelleted through a 20% sucrose gradient at 14,000 rpm for 30 minutes at 4° C., and subsequently resuspended in 20 uL of 1× Laemmli Buffer containing 5% 2-mercaptoethanol and subjected to SDS PAGE on 4-20% Tris Glycine gels (BioRad, Hercules Calif.). The electrophoresis and protein transfer were performed as described. Properly processed virion viral envelop protein expression and maturation was assayed for using anti-gp70 (rat raised anti-gp70, clone 83A25; 1:500 dilution) and anti-p15E (mouse raised anti-TM, clone 372; 1:250 dilution). Protein expression was detected using the corresponding secondary antibody conjugated to horseradish peroxidase. The data show that properly processed envelope protein, gp70 of RRV-GSG-P2A-yCD2 and RRV-GSG-T2A-yCD2, but not RRV-P2A-yCD2 and RRV-T2A-yCD2, were detected at levels comparable to that of RRV-IRES-yCD2 in virions (FIG. 17).

Importantly, the data suggest that the level of incorporation of properly processed viral envelope protein does not correlate with titer values.

Figure 18:
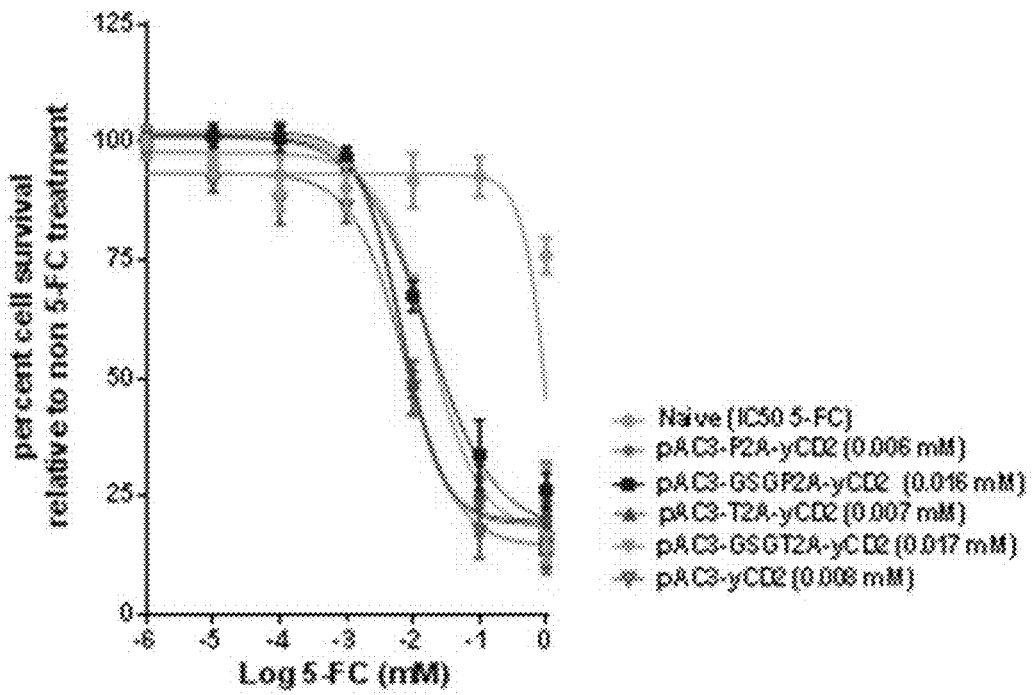
FIG. 18 shows the 5-FC-mediated killing of RRV-IRES-GFP, RRV-P2A-yCD2 and RRV-T2A-yCD2, RRV-GSG-P2A-yCD2 and RRV-GSG-T2A-yCD2 infected U87-MG cells at day 7 post 5-FC treatment. Percent of cell survival was calculated relative to non 5-FC treated but RRV-infected cells. Naïve U87-MG cells were included as a control to determine concentration of non-5-FU mediated cytotoxic effect of 5-FC.

Example 11: yCD2 Protein Expression Level Varied in RRV-P2A-yCD2 and RRV-T2A-yCD2, RRV-GSG-P2A-yCD2 and RRV-GSG-T2A-yCD2 Infected U87-MG Cells but Exhibited Comparable 5-FC Sensitivity to that of RRV-IRES-yCD2 Infected U87-MG Cells As the immunoblots of RRV-P2A-yCD2 and RRV-T2A-yCD2, RRV-GSG-P2A-yCD2 and RRV-GSG-T2A-yCD2 showed that the amount of yCD2 protein expressed either as separated protein from the viral envelope protein or as a fusion polyprotein varied in infected U87-MG cells, their 5-FC sensitivity was measured by performing a $LD_{50}$ experiment. Maximally infected U87-MG cells with RRV-P2A-yCD2 and RRV-T2A-yCD2, RRV-GSG-P2A-yCD2 and RRV-GSG-T2A-yCD2 vectors were used to determine their 5-FC $LD_{50}$ by MTS assay. For each infected or non-infected U87-MG cell line, 1×10³ cells/well/100 μL culture media were seeded in triplicate in 96-well plates. Cells were treatmented with 5-FC (cat #F7129, Sigma) in a series of 1:10 dilutions ranging from 0.00001 mM-1 mM. No 5-FC treatment was included as a control. 5-FC was added 1 day after plating and then replenished with complete medium plus 5-FC every 2 days. Naïve U87-MG cells were included as a control to determine non-5-FU mediated cytotoxic effect of 5-FC. The cells were monitored over a 7-day incubation time, and cell death was measured every 2 days by using the CellTiter 96 AQueous One Solution Cell Proliferation Assay System (Promega). Following the addition of the MTS, OD value at 490 nm were acquired using the Infinite M200 (Tecan) plate reader at 60-minute post MTS incubation. Averaged OD values from triplicates of each sample were converted to percentage of cell survival relative to untreated, but RRV-infected cells. Subsequently, the percentage values were plotted against 5-FC concentrations in log scale using GraphPad Prim to generate LD50 graphs. $LD_{50}$ values were calculated by the software using nonlinear four-parameter fit of the data points acquired. The data indicate that although the level of "separated" yCD2 protein were higher in RRV-GSG-P2A-yCD2 and RRV-GSG-T2A-yCD2 infected U87-MG cells than RRV-P2A-yCD2 and RRV-T2A-yCD2 infected U87-MG cells, the viral envelope-yCD2 fusion polyprotein observed in RRV-P2A-yCD2 and RRV-T2A-yCD2 infected U87-MG cells are enzymatically active in converting 5-FC to 5-FU to achieve cytotoxicitic effect at a $LC_{50}$ concentration similar to that of RRV-IRES-yCD2 (FIG. 18).

Example 12: RRV-GSG-P2A-yCD2 and RRV-GSG-T2A-yCD2 Infected Tu2449 Cells Exhibited Comparable 5-FC Sensitivity to that of RRV-IRES-yCD2

Figure 20A:
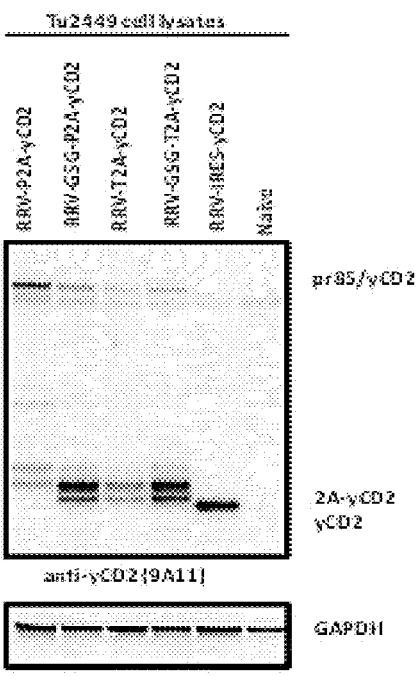
FIG. 20A-B shows (A) yCD2 protein expression of, and (B) 5-FC sensitivity of, RRV-P2A-yCD2, RRV-GSG-P2A-yCD2, RRV-T2A-yCD2 and RRV-GSG-T2A-yCD2 in maximally infected Tu-2449 cells.
Figure 20B:
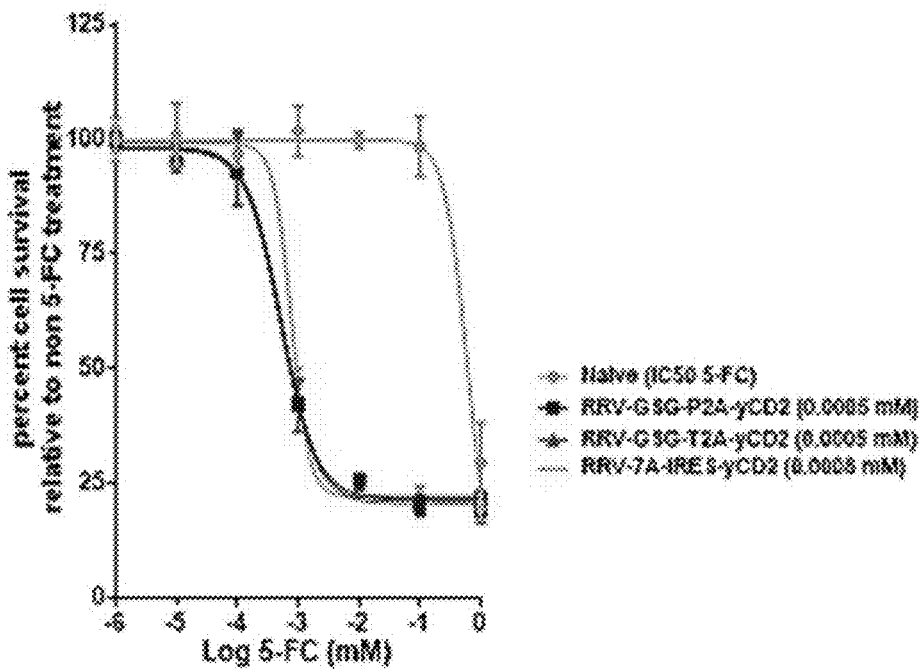

Maximally infected U87-MG cells with RRV-GSG-P2A-GMCSF-T2A-yCD2 was used to determine its 5-FC LD50 by MTS assay as described. RRV-IRES-yCD2 was included as a control. Treatment with 5-FC (cat #F7129, Sigma) in a series of 1:10 dilutions ranging from 0.00001 mM-1 mM was used. No 5-FC treatment was included as a control. 5-FC was added 1 day after plating and then replenished with complete medium plus 5-FC every 2 days. Naïve U87-MG cells were included as a control to determine non-5-FU mediated cytotoxic effect of 5-FC. The cells were monitored over a 7-day incubation time, and cell death was measured every 2 days by using the CellTiter 96 AQueous One Solution Cell Proliferation Assay System (Promega). Following the addition of the MTS, OD value at 490 nm were acquired using the Infinite M200 (Tecan) plate reader at 60-minute post MTS incubation. Averaged OD values from triplicates of each sample were converted to percentage of cell survival relative to untreated, but RRV-infected cells. The percentage values were plotted against 5-FC concentrations in log scale using GraphPad Prim to generate $LD_{50}$ graphs. $LD_{50}$ values were calculated by the software using nonlinear four-parameter fit of the data points acquired. The data indicate that yCD2 protein expressed by RRV-GSG-P2A-yCD2 and RRV-GSG-T2A-yCD2 infected Tu-2449 cells (FIG. 20A) are enzymatically active in converting 5-FC to 5-FU to achieve cytotoxicitic effect at a $LC_{50}$ concentration similar to that of RRV-IRES-yCD2 (FIG. 20B).

Example 13: Subcutaneous, Syngeneic Glioma Mice Treated RRV-GSG-T2A-yCD2 Showed Delayed Tumor Growth Comparable to that of RRV-IRES-yCD2

Figure 21:
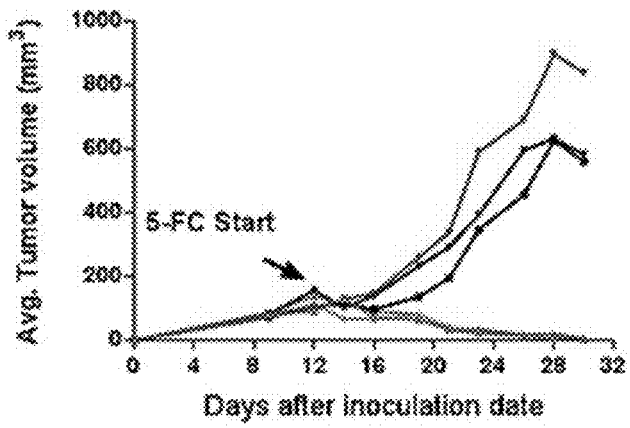
FIG. 21 shows tumor growth delay of tumor treated with RRV-GSG-T2A-yCD2+5-FC compare to that treated with RRV-IRES-yCD2+5-FC.

The syngeneic cell line Tu-2449 was used as an orthotopic brain tumour model in B6C3F1 mice (Ostertag et al., 2012). A subline of Tu-2449 cells (Tu-2449SQ) was established for subcutaneous tumor modeling. A mixture of 98, naïve Tu-2449 SQ cells and 2% RRV-GSG-2A-yCD2 infected Tu-2449SQ cells were prepared in vitrol and resuspended in phosphate-buffered saline (PBS; Hyclone) for subcutaneous tumor implantation. A mixture of 98% naïve Tu-2449SQ cells and 2%, RRV-IRES-yCD2 infected Tu-2449SQ cells was included as a positive control as well as a comparator. B6C3F1 mice in each group (n=10 per group) undergo subcutaneous implantation of 1×10⁶ tumor cells on day 0. On day 12 post tumor implant (at the time approximately >75% of tumors are infected with RRV), mice are administered with either PBS or 5-FC (500 mg per kg body weight per dose, i.p., b.i.d.) for 45 consecutive days, followed by 2 days without drug to allow vector spread from the remaining infected cells. Cycles of 5-day on, 2-day off drug treatment were repeated two additional times. The tumor volumetric measurement was taken daily. The results indicate that mice bearing tumor carrying RRV-IRES-yCD2 or REV-GSG-T2A without 5-FC treatment continue to grow. In contrast, mice bearing tumor carrying RRV-GSG-T2A followed by 5-FC treatment delayed tumor growth or pre-established tumor and is comparable to that treated with RRV-IRES-yCD2+5-FC (FIG. 21). The data suggest that in subcutaneous, syngeneic glioma mouse model, RRV-GSG-T2A-yCD2 have comparable therapeutic efficacy as RRV-IRES-yCD2.

Example 14: RRV-GSG-T2A-GMCSF-GSG-P2A-yCD2 and RRV-GSG-T2A-yCD2-GSG-PS2-GMCSF Vectors Produced from HEK293T Cells Express GMCSF and yCD2 Proteins and are Infectious pAC3-GSG-T2A-GMCSF-GSG-P2A-yCD2 and RRV-GSG-T2A-yCD2-GSG-P2A-GMCSF were generated by cloning of the human GMCSF-GSG-P2A-yCD2 and yCD2-GSG-P2A-GMCSF cassette chemically synthesized (Genewiz) with AscI and NotI restriction site present at the 5' and 3' end, respectively, into pAC3-GSG-T2A-yCD2 backbone digested with AscI and NotI restriction enzymes. The resultant GMCSF-GSG-P2A-yCD2 and yCD2-GSG-P2A-GMCSF cassette are in-frame with GSG-T2A at the N-terminus (5' upstream of the AscI restriction site) of the cassette.

HEK293T cells were seeded at 2e6 cells per 10-cm plates, 18 to 20 hours pre transfection. The next day, 20 µg of pAC3-GSG-T2A-GMCSF-GSG-P2A-yCD2 ro pAC3-GSG-T2A-yCD2-GSG-P2A-GMCSF plasmid was used for transient transfection at 20 hours post-cell seeding using the calcium phosphate method. Eighteen hours post-transfection, cells were washed with CMEM medium three times and incubated with fresh complete medium. Viral supernatant was collected approximately 42 hours post-transfection and filtered through a 0.45 µm syringe filter. The viral titers of RRV-GSG-T2A-GMCSF-GSG-P2A-yCD2 from transient transfection of HEK293T cells was determined as described. The data show that titers of RRV-GSG-T2A-GMCSF-GSG-P2A-yCD2 and pAC3-GSG-T2A-yCD2-GSG-P2A-GMCSF (~2E6 TU/mL) are comparable to that of RRV-IRES-yCD2.

Figure 22A:
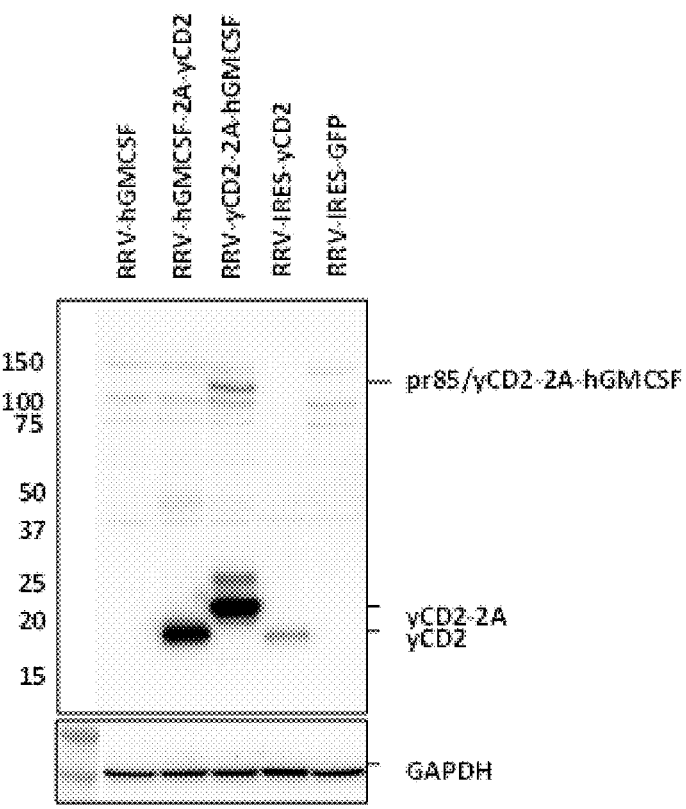
FIG. 22A-B shows (A) anti-yCD2 immunoblot of cell lysates from RRV-GSG-T2A-GMCSF-GSG-P2A-yCD2 and RRV-GSG-T2A-yCD2-GSG-P2A-GMCSF transiently transfected HEK293T cells. Protein band detected at ~110 KDa represents the viral envelope-GFPm fusion polyprotein. Protein band detected at ~15 KDa represents the yCD2 or 2A-yCD2 protein separated from the fusion polyprotein. (B) GMCSF secreted to the culture medium from RRV-GSG-T2A-GMCSF-GSG-P2A-yCD2 and RRV-GSG-T2A-yCD2-GSG-P2A-GMCSF transiently transfected HEK293T cells.

To assess the yCD2 protein expression, cell lysates were generated from pAC3-GSG-P2A-GMCSF-GSG-T2A-yCD2 or pAC3-GSG-T2A-yCD2-GSG-P2A-GMCSF transiently transfected 293T cells. In this experiment, pAC3-IRES-yCD2 and pAC3-IRES-GMCSF were also included as controls. For GMCSF expression, supernatants transiently transfected 293T cells were collected for measurement by ELISA (Cat #DGM00, R & D Systems). The whole cell lysates were assayed for yCD2 protein expression as described. The anti-yCD2 result shows that yCD2 protein from pAC3-GSG-P2A-GMCSF-GSG-T2A-yCD2 or pAC3-GSG-T2A-yCD2-GSG-P2A-GMCSF is separated efficiently from the GMCSF, as indicated by the ~15 KDa band (FIG. 22A). However, the separation of the yCD2 from GMCSF (pAC3-GSG-P2A-GMCSF-GSG-T2A-yCD2) or from viral envelope protein (pAC3-GSG-T2A-yCD2-GSG-P2A-GMCSF) mediated by the 2A peptide in both configurations are remarkably different, with proper separation of yCD2 protein from GMCSF as indicated by the size of yCD2 in comparison to yCD2 from RRV-IRES-yCD2 (FIG. 22A). In contrast, yCD2 protein separation from the viral env has slightly higher molecular weight (denoted as 2A-yCD2 in FIG. 22A) and is consistent with that of RRV-GSG-P2A-GFP, RRV-GSG-T2A-GFP, RRV-GSG-P2A-yCD2 and RRV-GSG-T2A-yCD2 constructs shown in FIG. 10 and FIG. 14. The data suggest that the yCD2 separation from the Env may not occur precisely at the theoretically expected amino acid sequence. But when yCD2 is placed downstream of another secreted protein (i.e. GMCSF), proper separation of yCD2 protein is observed. However, it is important to note that the enzymatic activity of 2A-yCD2 protein expressed from RRV-GSG-P2A-yCD2 and RRV-GSG-T2A-yCD2 appear not to affect the 5-FC sensitivity and cytotoxic effect both in vitro and in vivo (FIG. 20).

Figure 22B:
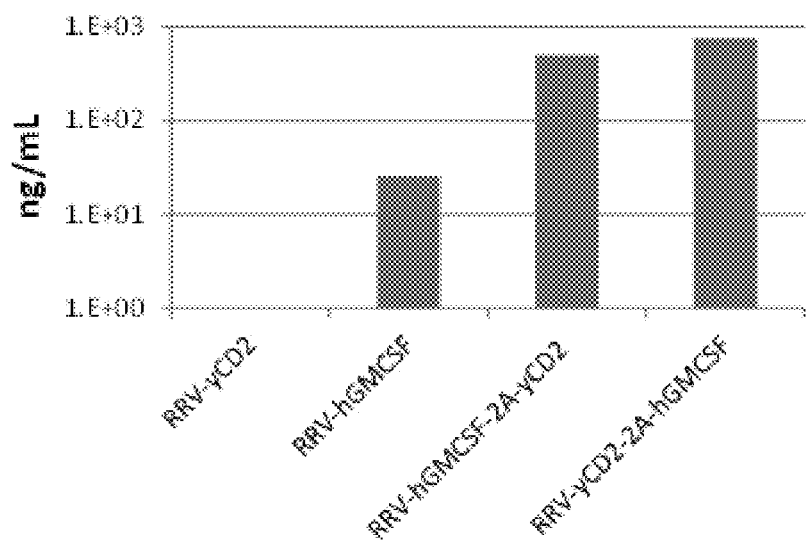

Although the separation efficiency of GMCSF protein from the viral envelope protein in pAC3-GSG-P2A-GMCSF-GSG-T2A-yCD2 construct or from yCD2 in pAC3-GSG-T2A-yCD2-GSG-P2A-GMCSF construct is undetermined, GMCSF ELISA results indicate that the amount of secreted GMCSF is ~500 ng/mL for RRV-GSG-P2A-GMCSF-GSG-T2A-yCD2 and ~760 ng/mL for RRV-GSG-T2A-yCD2-GSG-P2A-GMCSF (FIG. 22B). In both cases, the amount of GMCSF expressed is about 20- to 30-fold more than that of RRV-IRES-GMCSF (25 ng/mL). In parallel, the processing of the viral envelope protein in infected U87-MG is examined using the anti-gp70 antibody. The result shows that the viral envelope protein in either the precursor (Pr85) or processed form (gp70) is readily detectable. Together the data suggest that both Env-GSG-T2A-GMCSF-GSG-P2A-yCD2 and Env-GSG-T2A-yCD2-GSG-P2A-GMCSF polyprotein configurations can express GMCSF and yCD2 proteins.

In addition, viral supernatants collected from maximally infected U87-MG cells are titered as described to ensure the virus remain infectious. The data show that titers (~3E6 TU/mL) produced from maximally infected U87-MG cells are similar to those obtained from transiently transfected HEK293T cells and are comparable to RRV-IRES-yCD2.

Example 15: RRV-GSG-T2A-GMCSF-P2A-yCD2 and RRV-GSG-T2A-yCD2-P2A-GMCSF Vectors Exhibit Comparable 5-FC Sensitivity to that of RRV-IRES-yCD2 Infected U87-MG Cells Maximally infected U87-MG cells with RRV-GSG-T2A-GMCSF-GSG-P2A-yCD2 or RRV-GSG-T2A-yCD2-GSG-P2A-GMCSF are used to determine its 5-FC $LD_{50}$ by MTS assay as described. RRV-IRES-yCD2 is included as a control. The data indicate that the amount of "separated" yCD2 protein detected in infected U87-MG cells is able to achieve cytotoxic effect at a $LD_{50}$ concentration of 0.008 mM, which is similar to that of RRV-IRES-yCD2.

Example 16: RRV-GSG-T2A-GMCSF-RSV-yCD2 and Vector Produced from HEK293T Cells and Maximally Infected U87-MG Cells is Infectious and Express GMCSF and yCD2 Proteins pAC3-GSG-T2A-GMCSF-RSV-yCD2 is generated by cloning of the human GMCSF-RSV-yCD2 cassette chemically synthesized (Genewiz) with AscI and NotI restriction site present at the 5' and 3' end, respectively, into pAC3-GSG-T2A-yCD2 backbone digested AscI and NotI restriction enzymes. The chemically synthesized GMCSF-RSV-yCD2 cassette contains a stop codon at the 3' end of GMCSF ORF.

HEK293T cells are seeded at 2e6 cells per 10-cm plates, 18 to 20 hours pre transfection. The next day, 20 µg of pAC3-GSG-T2A-GMCSF-RSV-yCD2 plasmid is used for transient transfection at 20 h post-cell seeding using the calcium phosphate method. Eighteen hours post transfection, cells were washed with DMEM medium three times and incubated with fresh complete culture medium. Viral supernatant was collected approximately 42 h post-transfection and filtered through a 0.45 µm syringe filter. The viral titers of RRV-GSG-T2A-GMCSF-RSV-yCD2 from transient transfection of HEK293T cells is determined as described. The data show that titer of RRV-GSG-T2A-GMCSF-RSV-yCD2 (~2E6 TU/mL) is comparable to that of RRV-IRES-yCD2.

In addition, viral supernatants collected from maximally infected U87-MG cells is titered to ensure the virus remains infectious. The data show that titer (~2E6 TU/mL) produced from maximally infected U87-MG cells is similar to those obtained from transiently transfected HEK293T cells and is comparable to RRV-IRES-yCD2.

To assess the GMCSF and yCD2 protein expression, cell lysates are generated from RRV-GSG-T2A-GMCSF-RSV-yCD2 infected U87-MG cells. In this experiment, RRV-IRES-yCD2 and RRV-IRES-GMCSF are included as controls. Supernatant from maximally infected U87-MG cells is collected for measuring the protein expression level of GMCSF by ELISA (R & D Systems). The whole cell lysates are assayed for yCD2 protein expression as described. The anti-yCD2 immunoblot result shows that yCD2 protein from RRV-GSG-T2A-GMCSF-RSV-yCD2 infected U87-MG cells is expressed at the level ~2-3 times less than that of RRV-IRES-yCD2. In parallel, the processing of the viral envelope protein in infected U87-MG is examined using the anti-gp70 antibody. The result shows that the viral envelope protein in either precursor (Pr85) or processed form (gp70) is readily detectable. As expected, viral envelope-GMCSF fusion polyprotein is also detected in cell lysates using the anti-gp70 antibody. Although the separation of GMCSF protein from the viral envelope protein is undetermined, GMCSF ELISA result indicates that the amount of secreted GMCSF is ~300 ng/mL and is about 10-fold more than that of RRV-IRES-GMCSF (30 ng/mL). Together the data suggest that viral envelop protein-GSG-T2A-GMCSF-RSV-yCD2 polyprotein configuration can produce infectious virus as well GMCSF and yCD2 protein in the context of RRV.

Example 17: RRV-GSG-T2A-GMCSF-RSV-yCD2 Vector Exhibits Comparable 5-FC Sensitivity to that of RRV-IRES-yCD2 Infected U87-MG Cells Maximally infected U87-MG cells with RRV-GSG-T2A-GMCSF-RSV-yCD2 vector is used to determine its 5-FC LD50 by MTS assay as described. In this experiment, RRV-IRES-yCD2 is included as a control. The data indicate that the amount of yCD2 protein expressed in infected U87-MG cells is able to achieve cytotoxicitic effect at a $LD_{50}$ concentration of 0.010 mM and is comparable to that of RRV-IRES-yCD2.

Example 18: RRV-GSG-P2A-yCD2-RSV-PDL1miR30shRNA Vector Produced from 293T Cells and Infected U87-MG Cells is Infectious and Express yCD2 Protein pAC3-GSG-T2A-yCD2-RSV-miRPDL1 is generated by cloning of the human yCD2-RSV-miRPDL1 cassette chemically synthesized (Genewiz) with AscI and NotI restriction site present at the 5' and 3' end, respectively, into pAC3-GSG-T2A-yCD2 backbone digested AscI and NotI restriction enzymes. The chemically synthesized yCD2-RSV-miRPDL1 cassette contains a stop codon at the end of yCD2 ORF.

HEK293T cells are seeded at 2e6 cells per 10-cm plates, 18 to 20 hours pre transfection. The next day, 20 µg of pAC3-GSG-T2A-yCD2-RSV-miRPDL1 plasmid is used for transient transfection at 20 h post-cell seeding using the calcium phosphate method. Eighteen hours post transfection, cells were washed with DMEM medium three times and incubated with fresh complete culture medium. Viral supernatant was collected approximately 42 h post-transfection and filtered through a 0.45 µm syringe filter. The viral titers of RRV-GSG-T2A-yCD2-RSV-mrRPDL1 from transient transfection of HEK293T cells is determined as described. The data show that titer of RRV-GSG-T2A-yCD2-RSV-miRPDL1 (~2E6 TU/mL) is comparable to that of RRV-IRES-yCD2.

In addition, viral supernatants collected from maximally infected U87-MG cells is titered to ensure the virus remains infectious. The data show that titer (~2E6 TU/mL) produced from maximally infected U87-MG cells is similar to those obtained from transiently transfected HEK293T cells and is comparable to RRV-IRES-yCD2.

To measure the expression of yCD2 protein and PDL1 cell surface expression, maximally infected U87-MG cells are harvested and the whole cell lysates are assayed for yCD2 protein expression as described. The anti-yCD2 immunoblot result shows that yCD2 protein from RRV-GSG-T2A-yCD2-RSV-miRPDL1 infected U87-MG cells is separated efficiently from the viral envelope protein, as indicated by the ~15 KDa band using the anti-yCD2 antibody. As expected, viral envelope-yCD2 fusion polyprotein is also detected in the cell lysates using both anti-yCD2 and anti-gp70 antibodies. In parallel, the processing of the viral envelope protein in infected U87-MG is examined using the anti-gp70 antibody. The result shows that the viral envelope protein in either precursor (Pr85) or processed form (gp70) is readily detectable. In addition, fusion polyproteins are detected as seen in the anti-yCD2 immunoblot.

Example 19: RRV-GSG-T2A-yCD2-RSV-miRPDL1 Infected U87-MG Cells Exhibits Comparable 5-FC Sensitivity to that of RRV-IRES-yCD2 Infected U87-MG Cells Maximally infected U87-MG cells with RRV-GSG-T2A-yCD2-RSV-miRPDL1 vector is used to determine its 5-EC $LD_{50}$ by MTS assay as described. In this experiment RRV-IRES-yCD2 is included as a control. The data indicate that the amount of "separated" yCD2 protein detected in infected U87-MG cells is able to achieve cytotoxicitic effect at a $LD_{50}$ concentration (0.008 mM) comparable to that of RRV-IRES-yCD2.

Example 20: RRV-GSG-P2A-yCD2-RSV-miRPDL1 Infected MDA-MB231 Cells Exhibits Potent PD-L1 Knockdown on the Cell Surface To assess PDL1 knockdown activity of RRV-GSG-T2A-yCD2-RSV-miRPDL1, a MOI of 0.1 is used to infect MDA-MB231 cells which have been shown to express marked level of PDL1. In this experiment, RRV-RSV-miRPDL1 is included as a positive control for assessing PDL1 knockdown activity. Approximately at day 14 post infection, cells are harvested and cell surface staining is performed to measure the level of PDL1 protein by FACS.

The data shows that the cell surface expression of PDL1 in MDA-MB231 cells infected with RRV-GSG-T2A-yCD2-RSV-miRPDL1 is decreased by approximately 75% and is comparable to that of RRV-RSV-miRPDL1. Together the data suggest that viral envelope protein-GSG-T2A-yCD2-RSV-miRPDL1 configuration can produce infectious virus, yCD2 protein and miRPDL1 in the context of RRV.

Example 21: RRV-P2A-TKO RRV-GSG-P2A-TKO, RRV-T2A-TKO and RRV-GSG-T2A-TKO Vectors Produced from HEK293T Cells and Maximally Infected U87-MG Cells are Infectious and Express TKO Protein pAC3-P2A-TKO, pAC3-GSG-P2A-TKO, pAC3-T2A-TKO and pAC3-GSG-T2A-TKO were generated by cloning of a Sr39-tk (Black et al., Cancer Res., 61:3022-3026, 2001; Kokoris et al., *Protein Science* 11:2267-2272, 2002) with human codon optimization (TKO), (see, International Application Publ. No. WO2014/066700, incorporated herein by reference) cassette into pAC3-2A backbone. Sequence of TKO was chemically synthesized (Genewiz) with AscI and NotI restriction site present at the 5' and 3' end, respectively, into pAC3-GSG-P2A-yCD2 or pAC3-GSG-T2A-yCD2 backbone digested with AscI and NotI restriction enzymes.

HEK293T cells were seeded at 2e6 cells per 10-cm plates, 18 to 20 hours pre transfection. The next day, 20 μg of pAC3-GSG-P2A-TKO or pAC3-GSG-T2A-TKO plasmid was used for transient transfection at 20 h post-cell seeding using the calcium phosphate method. Eighteen hours post transfection, cells were washed with DMEM medium three times and incubated with fresh complete medium. Viral supernatant was collected approximately 42 h post-transfection and filtered through a 0.45 μm syringe filter. The viral titers of RRV-P2A-TKO, RRV-GSG-P2A-TKO, RRV-T2A-TKO and RRV-GSG-T2A-TKO from transient transfection of HEK293T cells was determined as described. The data show that titers are comparable to that of RRV-IRES-yCD2 (Table 6).

Figure 23:
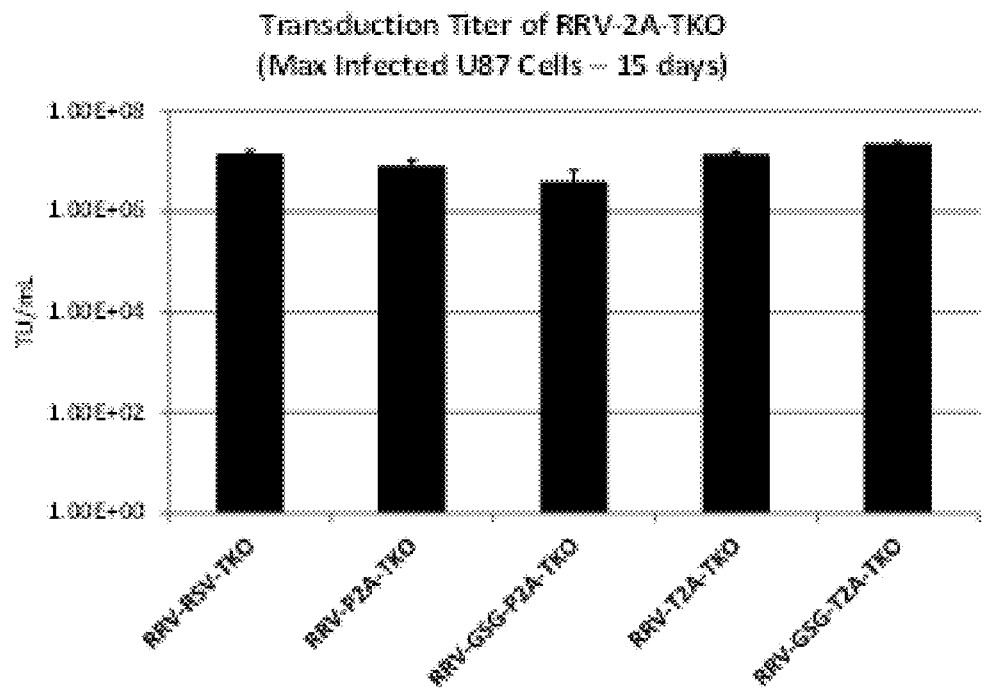
FIG. 23 shows titers of RRV-P2A-TKO, RRV-T2A-TKO, RRV-GSG-P2A-TKO and RRV-GSG-T2A-TKO vectors produced from maximally infected U87-MG cells.

In addition, viral supernatants collected from maximally infected U87-MG cells is titered as described to ensure the virus remain infectious. The data show that titers produced from maximally infected U87-MG cells are comparable to those obtained from transiently transfected HEK293T cells (FIG. 23).

Figure 24:
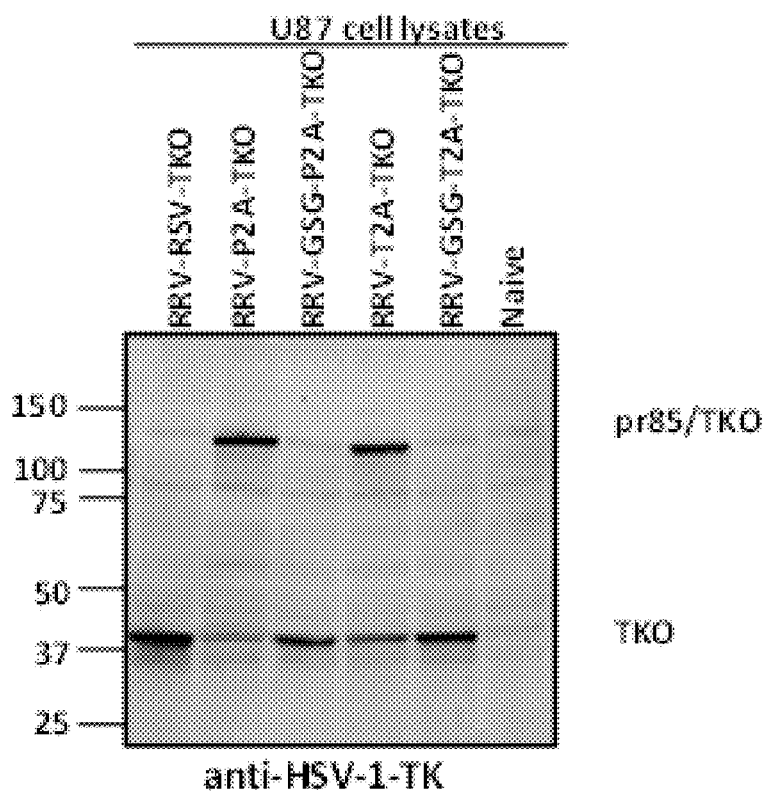
FIG. 24 shows an anti-HSV-tk immunoblot of cell lysates from RRV-P2A-TKO, RRV-T2A-TKO, RRV-GSG-P2A-TKO and RRV-GSG-T2A-TKO infected U87-MG cells.

To assess the TKO protein expression, cell lysates were generated from RRV-P2A-TKO RRV-GSG-P2A-TKO, RRV-T2A-TKO and RRV-GSG-T2A-TKO infected U87-MG cells. The whole cell lysates were assayed for TKO protein expression using anti-HSV-tk antibody (Cat #sc28037, Santa Cruz Biotech Inc) at 1:200. The result shows that TKO protein from RRV-P2A-TKO and RRV-T2A-TKO infected U87-MG cells is separated less efficiently than RRV-GSG-P2A-TKO and RRV-GSG-T2A-TKO (FIG. 24) as seen previously with GFP and yCD2 transgenes.

Figure 25:
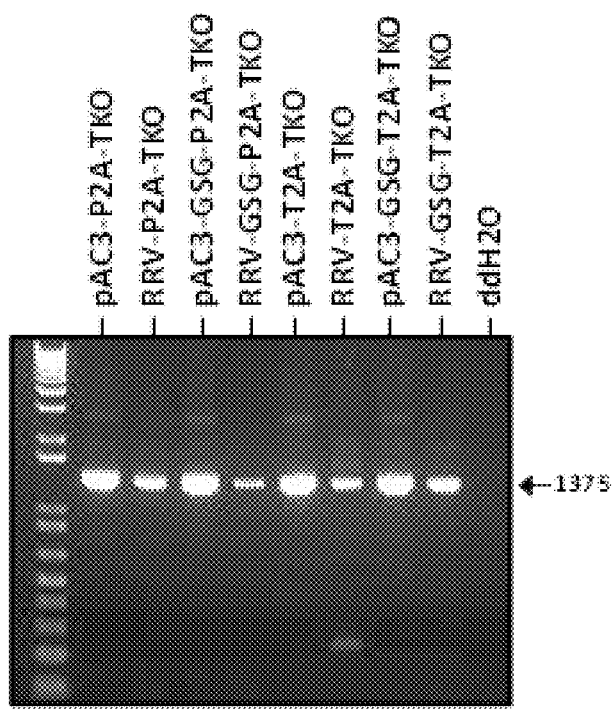
FIG. 25 shows vector stability of RRV-P2A-TKO, RRV-T2A-TKO, RRV-GSG-P2A-TKO and RRV-GSG-T2A-TKO vectors in U87-MG cells over 16 cycles of infection. pAC3-P2A-TKO plasmid DNA is used as a positive control.

Example 22: RRV-P2A-TKO RRV-GSG-P2A-TKO, RRV-T2A-TKO and RRV-GSG-T2A-TKO Vectors are Stable in U87-MG Cells To evaluate the vector stability in maximally infected U87-MG cells, genomic DNA was extracted from cells using the Promega Maxwell 16 Cell DNA Purification Kit (Promega). One-hundred nanogram of genomic DNA was then use as the template for PCR with a primer pair that spans the transgene cassette; IRES-F (5'-CTGATCT-TACTCTTTGGACCTTG-3' (SEQ ID NO:23)) and IRES-R (5'-CCCCTTTTTCTGGAGACTAAATAA-3' (SEQ ID NO:24)) as previously described. The expected PCR product for all RRV-2A-TKO constructs is 1.4 kb. The data show that the 2A-TKO and GSG-2A-TKO region in proviral DNA RRV-P2A-TKO RRV-GSG-P2A-TKO, RRV-T2A-TKO and RRV-GSG-T2A-TKO vectors are stable in U87-MG cells during the time course of viral replication (FIG. 25).

TABLE 6

Titer of RRV-P2A-TKO RRV-GSG-P2A-TKO, RRV-T2A-TKO and RRV-GSG-T2A-TKO vectors produced from HER293T cells

| | | Titer of qPCR replicates (TU/mL) | | | Mean of dilution reps | | |
|---|---|---|---|---|---|---|---|
| Sample Titered | dilution | Well 1 | Well 2 | Well 3 | Trans rep | Std Dev | CV (%) |
| 5 RRV-RSV-GFP | 1 | 7.90E+05 | 6.97E+05 | 8.71E+05 | 8.05E+05 | 1.03E+05 | 12.80% |
| 6 RRV-RSV-GFP | 1 | 8.42E+05 | 6.81E+05 | 9.47E+05 | | | |
| 7 RRV-RSV-TKO | 1 | 4.85E+05 | 5.63E+05 | 4.91E+05 | 4.97E+05 | 4.29E+04 | 8.63% |
| 8 RRV-RSV-TKO | 1 | 5.13E+05 | 4.31E+05 | 4.99E+05 | | | |
| 9 RRV-P2A-TKO | 1 | 1.14E+06 | 1.26E+06 | 1.28E+06 | 1.12E+06 | 1.59E+05 | 14.21% |
| 10 RRV-P2A-TKO | 1 | 1.16E+06 | 8.69E+05 | 1.00E+06 | | | |
| 11 RRV-GSG-P2A-TKO | 1 | 1.03E+06 | 9.75E+05 | 9.84E+05 | 1.07E+06 | 8.04E+04 | 7.85% |
| 12 RRV-GSG-P2A-TKO | 1 | 1.18E+06 | 1.14E+06 | 1.12E+06 | | | |
| 13 RRV-12A-TKO | 1 | 9.51E+05 | 1.09E+06 | 1.07E+06 | 1.15E+06 | 1.34E+05 | 11.66% |
| 14 RRV-T2A-TKO | 1 | 1.28E+06 | 1.21E+06 | 1.29E+06 | | | |
| 15 RRV-GSG-T2A-TKO | 1 | 1.17E+06 | 1.55E+06 | 1.36E+06 | 1.53E+06 | 2.42E+05 | 15.78% |
| 16 RRV-GSG-T2A-TKO | 1 | 1.62E+06 | 1.88E+06 | 1.60E+06 | | | |
| 17 RRV-GSG-T2A-GFP | 1 | 2.16E+06 | 1.80E+06 | 1.42E+06 | 1.65E+06 | 3.09E+05 | 18.70% |
| 18 RRV-GSG-T2A-GFP | 1 | 1.73E+06 | 1.38E+06 | 1.41E+06 | | | |
| 19 RRV-IRES-GFP | 1 | 8.12E+05 | 9.68E+05 | 7.31E+05 | 7.73E+05 | 1.18E+05 | 15.25% |
| 20 RRV-IRES-GFP | 1 | 7.73E+05 | 7.45E+05 | 6.07E+05 | | | |
| 21 Mock 293T Sup | 1 | #VALUE! | #VALUE! | #VALUE! | #VALUE! | #VALUE! | #VALUE! |
| 22 Mock 293T Sup | 1 | 5.17E+06 | #VALUE! | #VALUE! | | | |
| 23 NBTGOT033pg01-R00137 (Exp273) | 200 | 2.38E+08 | 1.66E+08 | 1.64E+08 | 1.93E+08 | 4.11E+07 | 21.32% |
| 24 NRTC-GOT033pg01-R00137 (Exo273) | 200 | 2.53E+08 | 1.70E+08 | 1.66E+08 | | | |

Figure 26A:
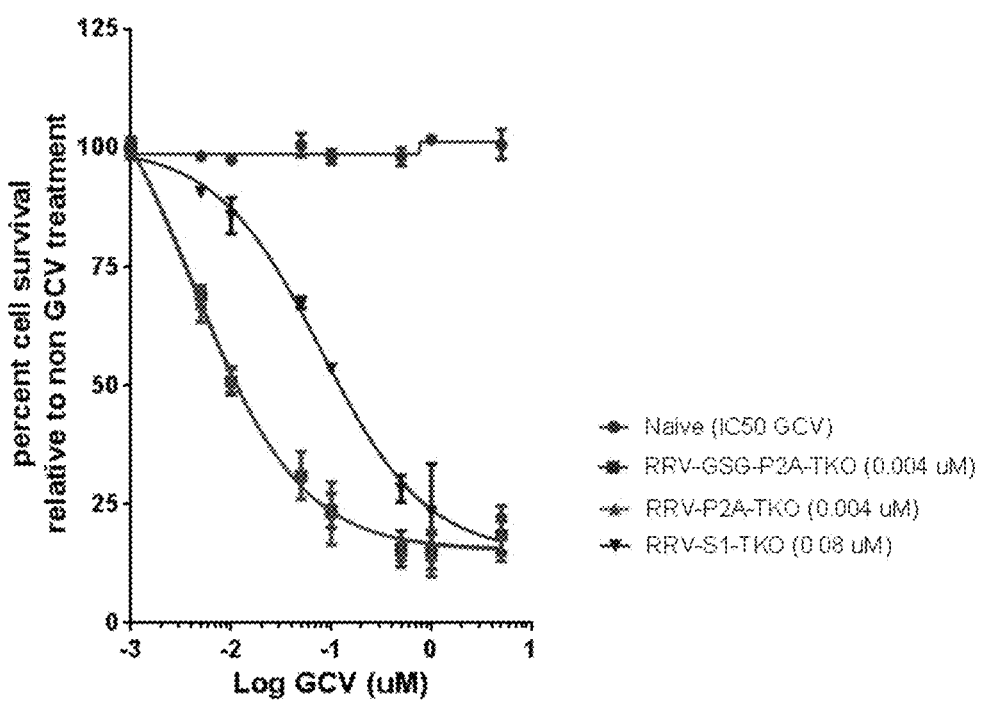
FIG. 26A-B shows the GCV sensitivity of RRV-P2A-TKO, RRV-T2A-TKO, RRV-GSG-P2A-TKO and RRV-GSG-T2A-TKO infected U87-MG cells at different doses.
Figure 26B:
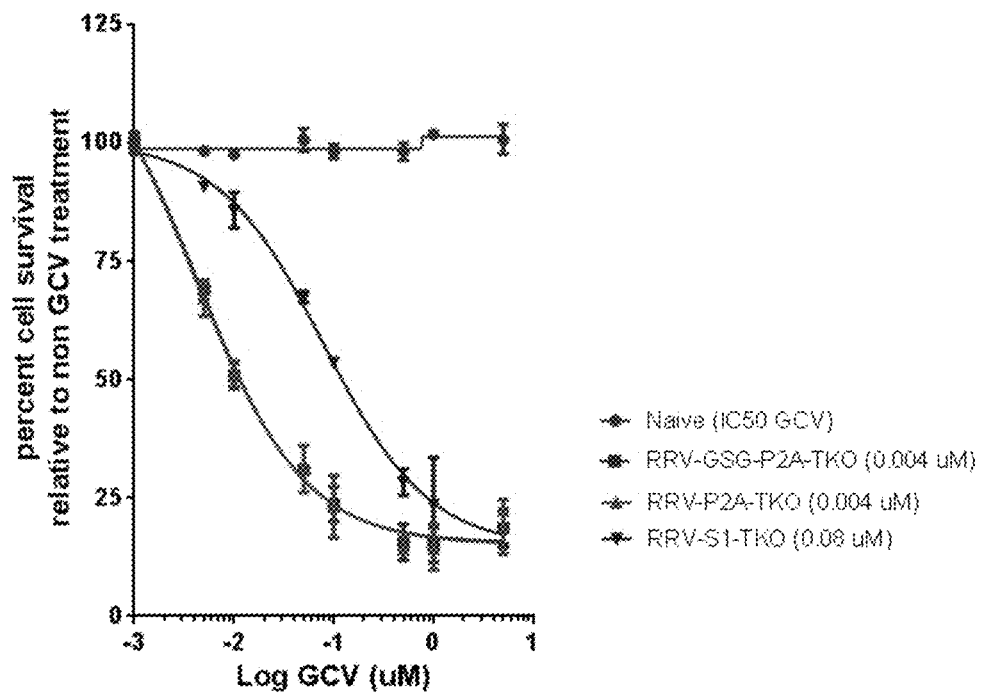

Example 23: RRV-P2A-TKO, RRV-GSG-P2A-TKO, RRV-T2A-TKO and RRV-GSG-T2A-TKO Infected U87-MG Cells Exhibited Superior GCV Sensitivity to that of RRV-S1-TKO Maximally infected U87-MG cells with RRV-P2A-TKO, RRV-GSG-P2A-TKO, RRV-T2A-TKO and RRV-GSG-T2A-TKO were used to determine its GCV $LD_{50}$ by MTS assay. RRV-S1-TKO of which the TKO expression driven by a synthetic minimal promoter (see, International Pat. Publ. No. WO2014/066700, incorporated herein by reference) was included as a control. Treatment with GCV (cat #345700-50MG, EMD Millipore) was performed in a series of 1:2 dilutions ranging from 0.0001 µM-0.5 µM. No GCV treatment was included as a control. GCV was added 1 day after plating and then replenished with complete medium plus GCV every 2 days. Naïve U87-MG cells were included as a control to determine cytotoxic effect of GCV. The cells were monitored over a 7-day incubation time, and cell death was measured every 2 days by using the CellTiter 96 AQueous One Solution Cell Proliferation Assay System (Promega). Following the addition of the MTS, OD value at 490 nm were acquired using the Infinite M200 (Tecan) plate reader at 60-minute post MTS incubation. Averaged OD values from triplicates of each sample were converted to percentage of cell survival relative to untreated, but RRV-infected cells. The percentage values were plotted against GCV concentrations in log scale using GraphPad Prim to generate $LD_{50}$ graphs. $LD_{50}$ values were calculated by the software using nonlinear four-parameter fit of the data points acquired. The data indicate that the TKO protein expressed by RRV-P2A-TKO, RRV-GSG-P2A-TKO, RRV-T2A-TKO and RRV-GSG-T2A-TKO is enzymatically active in converting GCV to cytotoxic GCV at tenth of millimolar range to achieve cytotoxicitic effect (FIG. 26). In comparison to RRV-S1-TKO, RRV-P2A-TKO, RRV-GSG-P2A-TKO, RRV-T2A-TKO and RRV-GSG-T2A-TKO show 12.5-20-fold higher GCV sensitivity. In addition, there was no significant difference in GCV LD50 between RRV-P2A-TKO vs RRV-GSG-P2A-TKO or RRV-T2A-TKO vs RRV-GSG-T2A-TKO despite the difference in TKO separation from the Env-TKO fusion polyprotein. Similar to 2A-yCD2, the data suggest that the amount of TKO protein expressed in the cells is sufficient to convert GCV to cytotoxic GCV.

Example 24: Subcutaneous, Syngeneic Glioma Mice Treated RRV-GSG-P2A-TKO and RRV-GSG-T2A-TKO Show Delayed Tumor Growth Comparable to that of RRV-IRES-yCD2

The syngeneic cell line Tu-2449 was used as an orthotopic brain tumor model in B6C3F1 mice (Ostertag et al., 2012). A subline of Tu-2449 cells (Tu-2449SQ) was established at Tocagen for subcutaneous tumor model. A mixture of 98% naïve Tu-2449SQ cells and 2% RRV-GSG-P2A-TKO, RRV-GSG-T2A-TKO or RRV-S1-TKO infected Tu-2449SQ cells were prepared in vitro and resuspended in phosphate-buffered saline (PBS; Hyclone) for subcutaneous tumor implantation. A mixture of 98% naïve Tu-2449SQ cells and 2% RRV-IRES-yCD2 infected Tu-2449SQ cells was included as a positive control as well as a comparator. B6C3F1 mice in each group (n=10 per group) undergo subcutaneous implantation of $1 \times 10^6$ tumor cells on day 0. On day 12 post rumor implant (at the time approximately >75% of tumors are infected with RRV), mice are administered with either PBS, 5-FC (500 mg per kg body weight per dose, i.p., b.i.d.) or GCV (50 mg per kg body weight per dose, i.p., b.i.d.) for 5 consecutive days, followed by 2 days without drug to allow vector spread from the remaining 10 infected cells. Cycles of 5-day on, 2-day off drug treatment were repeated two additional times. The tumor volumetric measurement was taken daily. The results indicate that mice bearing tumor carrying RRV-GSG-P2A-TKO, RRV-GSG-T2A-TKO or RRV-S1-TKO without GCV or RRV-IRES-yCD2 without 5-FC treatment continue to grow. In contrast, mice bearing tumor treated RRV-GSG-P2A-TKO, RRV-GSG-T2A-TKO+GCV delay tumor growth of pre-established tumor. Furthermore, mice breaking tumor treated with RRV-S1-TKO+GCV also shows delay in tumor growth although at lesser extent and longer time than tumor treated RRV-GSG-P2A-TKO, RRV-GSG-T2A-TKO+GCV, possibly due reduced TKO expression. Together, the data indicate that the delay in tumor growth of RRV-GSG-P2A-TKO+GCV and RRV-GSG-T2A-TKO+GCV is comparable to that treated with RRV-IRES-yCD2+5-FC. The data suggest that in subcutaneous syngeneic glioma mouse model, RRV-GSG-P2A-TKO and RRV-GSG-T2A-TKO have comparable therapeutic efficacy as RRV-IRES-yCD2.

Example 25: RRV-GSG-T2A-PDL1scFv and RRV-GSG-T2A-PDL1scFvFc Vectors Produced from HEK293T Cells and Maximally Infected U87-MG Cells are Infectious and Express scFv and scFvFc Protein pAC3-T2A-PDL1scFv, pAC3-T2A-PDL1scFv-Tag, pAC3-T2A-PDL1scFvFc and pAC3-T2A-PDL1scFvFc-Tag were generated to function as a blocking single chain variable fragment (scFv) against human and mouse PDL1. The PDL1scFv cassettes are designed with or without the fragment crystallizable (Fc) region of human $IgG_1$. In addition, the matching cassettes with HA and Flag epitope tags incorporated at the C-terminus of the scFv or ScFvFc were also generated for detection of scFv or scFvFc protein expression. Sequence of each cassettes (PDL1scFv, PDL1scFv-Tag, PDL1scFvFc and PDL1scFvFC-Tag) was chemically synthesized (Genewiz) with AscI and NotI restriction site present at the 5' and 3' end, respectively, and cloned into pAC3-GSG-T2A-yCD2 backbone digested with AscI and NotI restriction enzymes.

HEK293T cells were seeded at 2e6 cells per 10-cm plates, 18 to 20 hours pre transfection. The next day, 20 µg of pAC3-T2A-PDL1scFv, pAC3-T2A-PDL1scFv-Tag, pAC3-T2A-PDL1scFvFc and pAC3-T2A-PDL1scFvFc-Tag plasmid was used for transient transfection at 20 h post-cell seeding using the calcium phosphate method. Eighteen hours post transfection, cells were washed with DMEM medium three times and incubated with fresh complete medium. Viral supernatant was collected approximately 42 h post-transfection and filtered through a 0.45 µm syringe filter. The viral titers of RRV-GSG-T2A-GMCSF-GSG-P2A-yCD2 from transient transfection of HEK293T cells was determined as described. The data show that titer values of RRV-GSG-T2A-PDL1scFv, RRV-GSG-T2A-PDL1scFvFc, RRV-GSG-T2A-PDL1scFv-Tag, RRV-GSG-T2A-PDL1scFvFc-Tag are comparable to that of RRV-IRES-yCD2 (Table 7).

TABLE 7

Titer values of RRV-GSG-T2A-PDL1scFv, RRV-GSG-T2A-PDL1scFvFc, RRV-GSG-T2A-PDL1scFv-Tag, RRV-GSG-T2A-PDL1scFvFc-Tag from transiently transfected HEK293T cells

|  | TU/mL | Std Dev |
| --- | --- | --- |
| RRV-PDL 1scFv | 2.09E+06 | 4.80E+05 |
| RRV-PDL 1scFv Fc | 1.98E+06 | 4.38E+05 |
| RRV-PDL 1scFv-Tag | 2.08E+06 | 6.73E+05 |
| RRV-PDL 1scFv Fc-Tag | 1.29E+06 | 1.87E+05 |

Figure 27A:
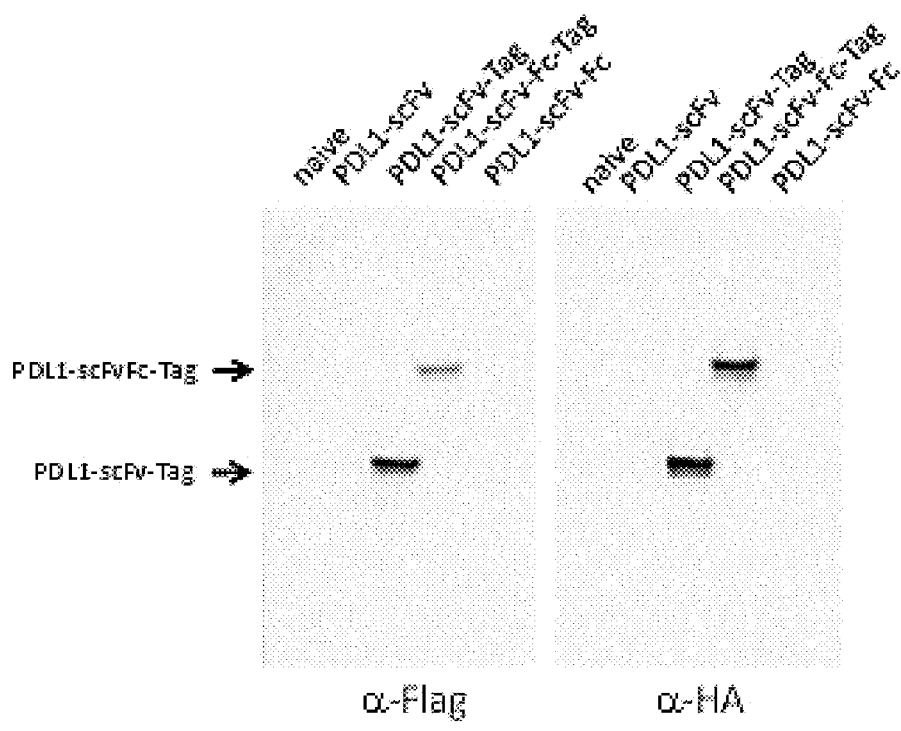
FIG. 27A-B shows PDL1scFv and PDL1scFvFc protein expression and the separation efficiency of Env-scFv and Env-ScFvFc polyproteins in transiently transfected 293T cells. (A) scFv-Tag (~30 KDa) and scFvFc-Tag (~55 Kd) protein expression from HEK293T cells transiently transfected with of pAC3-GSG-T2A-PDL1scFv, pAC3-GSG-T2A-PDL1scFvFc, pAC3-GSG-T2A-PDL1scFv-Tag, pAC3-GSG-T2A-PDL1scFvFc-Tag. (B) Anti-2A immunoblot of cell lysates from transiently transfected 293T cells. The protein band detected above ~110 KDa represents the Env-scFv and Env-ScFvFc fusion polyproteins. The protein band detected at ~85 KDa represents the Pr85 viral envelope protein separated from the fusion polyprotein, and protein band detected at ~15 KDa represents the p15E-2A protein processed from the Pr85 viral envelope protein.

To evaluate the scFv protein expression, cell lysates were generated from RRV-GSG-T2A-PDL1scFv and RRV-GSG-T2A-PDL1scFvFc transfected HEK293T cells. The whole cell lysates were assayed for scFv protein expression using anti-Flag and anti-HA antibody (Cat #1804 and Cat #H3663, Sigma Aldrich) at 1:1,000. The result shows that PDL1scFv-Tag and PDL1scFvFc-Tag protein expression from RRV-GSG-T2A-PDL1scFv-Tag, RRV-GSG-T2A-PDL1scFvFc-Tag transiently transfected HEK293T cells are separated from the Env-scFv polyprotein (FIG. 27A) as seen previously with GFP and yCD2 and TKO transgenes.

Figure 27B:
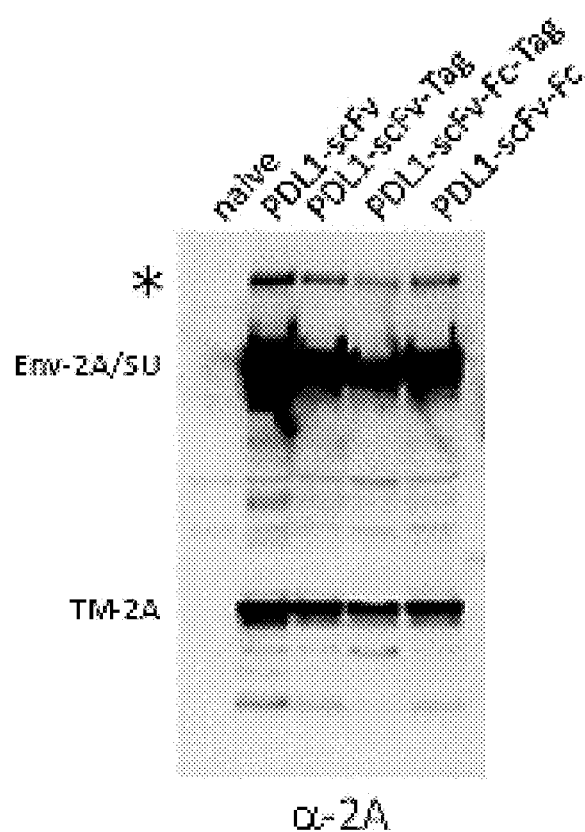

In parallel, the processing of the viral envelope protein in HEK293T cells was examined using the anti-2A antibody. The result show the viral enveloped in either precursor (Pr85) or processed form (p15E) containing the 2A peptide sequence were detected in all 4 vectors (FIG. 27B), suggesting separation of the viral envelope protein from the scFv and scFvFc protein as seen in the anti-Flag and anti-HA immunoblots. Although fusion polyprotein, Env-scFv or Env-scFvFc, expression are detected in the cell lysates, significant amount of PDL1scFv and PDL1scFvFc protein are separated from the fusion polyprotein as indicated by immunoblots from cell lysates and supernatant.

Similarly, abundant scFv-Tag and scFvFc-Tag protein expression are also detected in supernatant from transiently transfected HEK293T cells by immunoprecipitation with anti-Flag antibody followed by detection with anti-HA and vice versa. Furthermore, scFv-Tag and scFvFc-Tag protein expression cell lysates as well as supernatant are also detected from maxilly infected MDA-MB231 (human breast cancer cell line) and CT-26 (murine colorectal cancer cell line) cells at the levels approximately 2-3 times less than that from transiently transfected HEK293T cells.

Example 26: RRV-GSG-T2A-PDL1scFv and RRV-GSG-T2A-PDL1scFvFc Restore PRA-Stimulated T-Cell Activation and Shows Equivalence of PDL1 Blocking Antibody In Vitro To determine if PDL1 blocking on tumor cells by RRV-GSG-T2A-PDL1scFv or RRV-GSG-T2A-PDL1scFvFc could alleviate PDL1-mediated T-cell suppression, we perform a PDL1-mediated trans-suppression co-culture experiment. Here, we evaluate if modulation of PDL1 expression on various tumor cell lines could alter PHA-stimulated activation of healthy donor PBMC as measured by intracellular expression of IFNγ or release of IFNγ into the supernatant. To eliminate the potential pleiotropic effects of IFNγ pre-treatment in the trans-suppression co-culture assay, we set up a co-culture system using the human breast cancer cell line MDA-MB-231, which has a high PDL1 basal cell surface expression level. To confirm the necessity of PDL1 engagement in this assay, anti-PDL1 blocking antibody is also included. PDL1$^+$ tumor cells MDA-MB-231 cells in the presence of anti-PDL1 blocking antibody is unable to suppress CD8+ T-cell activation as indicated by the increased frequency of IFNγ+/CD8+ T cells. Similarly, MDA-MB-231 cells infected with RRV-GSG-T2A-scFv or RRV-GSG-T2A-scFvFc equally restored CD8$^+$ T-cell activation. The data indicate that disruption of the PDL1:PD1 axis on tumor cells and lymphocytes by PDL1 blocking scFv show comparable activity as anti-PDL1 blocking antibody and provides evidence for a substantial immunological benefit from RRV-GSG-T2A-PDL1scFv and RRV-GSG-T2A-PDL1scFvFc.

Example 27: RRV, TOCA-511, Mutation Profiling

Various tumor types are variably able to support rapid RRV replication, and this variability can alter the susceptibility of different tumors to RRV based therapeutic treatment such as for the RRV Toca 511 (aka T5.0002) and prodrug Toca FC treatment for high grade glioma (T. F. Cloughsey et al., Sci Transl Med., 8(341):341ra75, Jun. 1, 2016, doi: 10.1126/scitranslmed.aad9784.) This variability is attributable to various factors but one that appears relevant, from our sequencing data of RRV encoding a modified yeast cytosine deaminase that have been recovered from patients' blood or tumor, is modification by the APOBEC function, particularly APOBEC3B and APOBEC3B (B. P. Doehle et al., J. Virol. 79: 8201-8207, 2005). Modification of expression is deduced from the frequency with which inactivating or attenuating mutations accumulate in the replicating retroviral vector as it progressively replicates in tumor tissue. Investigation shows that one of the most frequent events is G to A mutations, which corresponds to the C to T transition characteristic of APOBEC mediated mutations on the negative strand single stranded DNA from the first replicative step in the reverse transcription step. These mutations can cause changes in amino acid composition of the RRV proteins, for instance a devastating change from TGG (Tryptophan) to stop codons (TAG, TGA or TAA). It has been shown that some tumors (in particular bladder, cervix, lung (adenocarcinoma and squamous cell carcinoma), head and neck, and breast cancers, APOBEC3B activity is upregulated, and this upregulation correlates with increased mutational load with changes that are consistent with APOBEC3B activity (M B. Burns et al., Nature Genetics 45: 977-83, 2013; doi: 10.1038/ng.2701). The driver behind this upregulation is proposed to be that the higher mutational rate favors tumor evolution and selection for a tumor advantageous genotype and phenotype. In one embodiment, the inactivating change in the virus is avoided by substitution of codons for other amino acids with similar chemical or structural properties such as phenylalanine or tyrosine that will not be converted by APOBEC. Toca 511 is an MLV derived RRV that encodes a thermostable codon optimized yeast cytosine deaminase linked to an IRES, which catalyzes conversion of prodrug 5-FC to cytotoxic 5-FU. In the course of Toca 511 treatment, Toca 511 is susceptible to mutations, due to errors in reverse transcription and cellular anti-viral defense mechanisms such as APOBEC-mediated cytidine deaminase. APOBEC proteins target single stranded DNA, primarily during reverse transcription of Toca 511 RNA genome, manifesting as G to A point.

Figure 28:
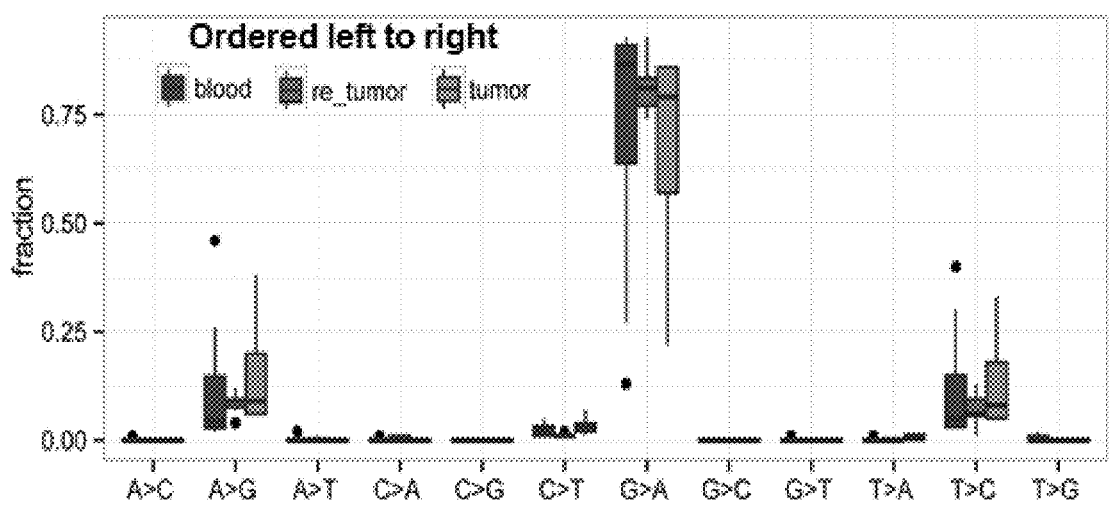
FIG. 28 shows meta-analysis of RRV (Toca 511, Tocagen Inc.) point mutations from 20 patient samples taken from blood and tumor. All point mutations passing quality filters with a frequency of detection of at least 1% were compiled for each sample and the total of each of the possible pairwise point mutations were calculated and transformed into relative frequency. This plot shows relative frequency of the different point mutations, grouped according to sample type: blood=blood sample from patient, tumor resected tumor following IV administration of Toca 511, re_tumor=re-resected tumor from patient treated with Toca 511 at time of initial resection.

Toca 511 sequence mutation spectrum were profiled by high throughput sequencing of Toca 511 from clinical samples isolated from tumor and blood. G to A point mutation is the most common mutation type in Toca 511, consistent with APOBEC activity (FIG. 28). This is the first characterization of gamma-retroviral gene therapy mutation spectrum from human samples via high throughput sequencing. An analysis of the G to A mutations shows that these usually lead to nonsynonymous changes in coding sequences. Within the gene encoding the cytosine deaminase polypeptide there were two positions with recurrent G to A mutations in samples from multiple patients (Table 8). These mutations convert codon TGG encoding tryptophan to TGA, TAG or TAA stop codons and thus terminate CD translation after only nine amino acids. These results highlight that tryptophan codons are a potential source of inactivation of retroviral gene therapies.

TABLE 8

Summary of point mutations in recombinant cytosine deaminase (SEQ ID NO:28-29) of Toca 511. Position is the amino acid position within the CD protein. Samples indicated the number of clinical samples from blood or tumor that showed mutation. Codon and change show the original codon sequence and the subsequent change. AA is the original amino acid encoded by the original codon and change shows what the amino acid is changed to after the codon mutation.

| nucleotide | position | samples | codon | change | AA | change |
|---|---|---|---|---|---|---|
| 29 | 10 | 17 | TGG | TAG | W | STOP |
| 30 | 10 | 5 | TGG | TGA | W | STOP |
| 31 | 11 | 1 | GAT | AAT | D | N |
| 40 | 14 | 1 | GGC | AGC | G | S |
| 45 | 15 | 1 | ATG | ATA | M | I |
| 105 | 35 | 2 | GGC | GAC | G | D |
| 144 | 48 | 1 | AGG | AAG | R | K |
| 159 | 53 | 1 | AGG | AAG | R | K |
| 168 | 56 | 6 | AAG | AAA | R | K |
| 216 | 72 | 1 | GGC | GAC | G | S |
| 357 | 119 | 1 | GAG | AAG | E | K |
| 456 | 152 | 4 | TGG | TAG | Q | STOP |

Accordingly, changing tryptophan codons to alternative codons that encode amino acids compatible with protein function can mitigate APOBEC mediated inactivation of retroviral gene therapies.

To test the effects of mutations on stability, Toca 511 genome sequence (see, e.g., U.S. Pat. No. 8,722,867, SEQ ID Nos: 19, 20 and 22 of the '867 patent, which are incorporated herein by reference) is engineered to change the codons that that show ApoBec hypermutation to codons that encode an alternative amino acid that preserves stability and function (e.g., changing codons for tryptophan to some other permissible amino acid). The Toca 511 polypeptide having cytosine deaminase activity (see, SEQ ID NO:29) is closely related to naturally occurring fungal cytosine deaminase proteins and high resolution structures of such cytosine deaminases are available. Thus it is possible to utilize the combination of structural and multiple sequence alignments from phylogenetically diverse fungal CD proteins to identify potential amino acid substitutions that will not have adverse effects on biological function, for instance using ROSETTA, Provean, PSIpred or similar programs. A set of putative amino acid substitutions are then tested, by altering Toca 511 genome and measuring enzyme and biological activity, solubility, thermostability in solution as well as the ability to function in cell culture assays and mouse tumors models such as conversion of 5-FC to 5-FU, initiate cell death, and activate the immune response against tumors to achieve durable responses. A similar analysis can be used for GAG, POL and ENV sequence to modify such sequences to remove codon susceptible to ApoBec hypermutations.

Example 28: APOBEC-Resistant yCD Viral Vectors are Therapeutic in an Intracranial Human Xenograft (T98G) in Nude Mice An intracranial xenograft model using the T98G human glioma cell line that highly expresses APOBEC is established to test RRV vector spread and biodistribution as well as therapeutic efficacy of APOBEC-resistant RCR-vector mediated cytosine deaminase suicide gene therapy in a nude mouse host under high APOBEC activity conditions.

Following acclimation, mice are randomly assigned to one of 9 Treatment groups (see group description below). Eight groups undergo intracranial administration into the right striatum of $1\times10^5$ T98G cells administered/mouse on Day 0. Group 9 mice are not implanted with tumor. At Day 5, mice are injected with Formulation Buffer only, T5.0002 (APOBEC-sensitive RRV expressing yCD; group 3) at $9\times10^5$ TU/5 µl or an APOBEC-resistant RCR vector (T5.002A) at $9\times10^5$ TU/5 µl, $9\times10^4$ TU/5 µl, or $9\times10^3$ TU/5 µl. Randomized 5-FC dosing is performed at 500 mg/kg/day, administered as a single IP injection, beginning on Day 19, or some group are given no 5-FC (Groups, 1, 4, 8). Mice receiving vector at mid-dose all receive 5-F (i.e., No separate control group for this dose). 5-FC administration continues daily for 7 consecutive days followed by 15 days of no treatment. Cycles of drug plus rest are repeated up to 4 cycles. 10 mice from each group except group 8 are randomly assigned to the survival analysis category. The remaining mice are sacrificed according to a predetermined schedule.

| | | | | | N per Analysis Category | |
|---|---|---|---|---|---|---|
| Group | Test article | Volume | Drug TX | N | (A) Survival analysis | (B) Scheduled Sacrifice |
| 1 | Form buffer | 5 µl | none | 4 | | 4 before first drug cycle |
| 2 | Form buffer | 5 µl | 5-FC | 10 | 10 | |
| 3 | T5.0002 | 9e5/5 µl | 5FC | 25 | 10 | 3 before start of each cycle, 15 total |
| 4 | T5.0002A | 9e5/5 µl | PBS | 10 | 10 | |
| 5 | T5.0002A | 9e5/5 µl | 5FC | 25 | 10 | 3 before start of each cycle, 15 total |
| 6 | T5.0002A | 9e4/5 µl | 5FC | 10 | 10 | |
| 7 | T5.0002A | 9e3/5 µl | 5FC | 25 | 10 | 3 before start of each cycle, 15 total |
| 8 | T5.0002A | 9e3/5 µl | PBS | 10 | 10 | |
| 9 NO TUMOR | none | | 5FC | 15 | | 3 before start of each cycle, 15 total |
| Total Number of Animals | | | | 134 | 70 | 64 |

Intravenous dosing is performed via injection into the tail vein. Intraperitoneal dosing is performed via injection into the abdomen with care taken to avoid the bladder. For intracranial injection mice are anesthetized with isoflurane and positioned in a stereotaxic device with blunt ear bars. The skin is shaved and betadine is used to treat the scalp to prepare the surgical site. The animal is placed on a heating pad and a scalpel is used under sterile conditions to make a midline incision through the skin. Retraction of the skin and reflection of the fascia at the incision site will allow for visualization of the skull. A guide cannula with a 3 mm projection, fitted with a cap with a 3.5 mm projection, is inserted through a small burr hole in the skull and attached with dental cement and three small screws to the skull. After hardening of the cement, the skin is closed with sutures. The projected stereotaxic coordinates are AP=0.5-1.0 mm, ML=1.8-2.0 mm, DV=3.0 mm. Exact stereotaxic coordinates for the cohort of animals is determined in a pilot experiment (2-3 animals) by injecting dye and determining its location. The animals are monitored during anesthesia recovery. Analgesics, buprenorphine, is administered subcutaneously (SC) before the end of the procedure then buprenorphine is administered approximately every 12 hrs for up to 3 days. Animals are monitored on a daily basis. Cells or vector are intracranially infused through an injection cannula with a 3.5 mm projection inserted through the guide cannula. The rate is controlled with a syringe pump fitted with a Hamilton syringe and flexible tubing. For cell injection, 1 microliter of cells is delivered at a flow rate of 0.2 microliters per minute (5 minutes total). For vector injection, 5 microliters of vector is delivered at a flow rate of 0.33 microliters per minute (15 minutes total).

APOBEC-resistant Vector is delivered and calculated as transforming units (TU) per gram of brain weight to the mice. Using such calculation the translation of dose can be calculated for other mammals including humans. APOBEC-resistant Vector shows an effective dose-response while vectors sensitive to APOBEC activity show a diminished effective response. The same experiment is conducted in U87 cell lines transfected with an expression vector for human APOBEC3G or APOBEC3B that express these proteins at least 3 fold above the U87 natural levels that are implanted in a xenograft model. These experiments show that the modified codon virus designed to be APOBEC-resistant has a replication and/or therapeutic response advantage in the U87 lines with increased APOBEC levels over the original RRV that is without codon modification for APOBEC resistance.

Example 29: APOBEC-Resistant yCD Viral Vector is Therapeutic in a Syngeneic Mouse Model of Brain Cancer Additional experiments to demonstrate the methods and compositions of the disclosure in a syngeneic animal model are performed.

An intracranial implant model using the CT26 colorectal cancer cell line stably transfected to produce murine APOBEC3 in syngeneic BALB/c mice is established to test APOBEC-resistant RRV vector spread and biodistribution as well as therapeutic efficacy of RRV-vector mediated cytosine deaminase suicide gene therapy and its immunological impact.

This study includes 129 animals, 0 Male, 119 Female and 10 contingency animals (10 Female). Following acclimation, mice are randomly assigned to one of 9 Treatment groups (see group description below). Eight groups undergo intracranial administration into the right striatum of $1\times10^4$ APOBEC-expressing CT26 cells administered/mouse on Day 0. Group 9 mice are not implanted with tumor. At Day 4, mice are injected with Formulation Buffer only, control vector that is still sensitive to APOBEC (T5.0002) at $9\times10^5$ TU/5 µl, or APOBEC-resistant vector (T5.0002A) at $9\times10^5$ TU/5 µl, $9\times10^4$ TU/5 µl, or $9\times10^3$ TU/5 µl. Mice receiving no vector, or vector at $9\times10^5$ TU/5 µl or $9\times10^3$ TU/5 µl are randomized to receive 5-FC (500 mg/kg/BID), administered by IP injection, beginning on Day 13, or no 5-FC as indicated (PBS). Mice receiving vector at mid dose receive 5-FC (i.e., No separate control group for this dose). 5-FC administration continues daily for 7 consecutive days followed by 10 days of no treatment. Cycles of drug plus rest are repeated up to 4 cycles. 10 mice from each group except group 9 are randomly assigned to the survival analysis category. The remaining mice are sacrificed according to a predetermined schedule.

Naïve sentinel mice are co-housed with the scheduled sacrifice animals and taken down at the same time points to assess vector transmittal through shedding.

| | | | | N per Analysis Category | | |
|---|---|---|---|---|---|---|
| Group | Test article | Volume | Drug TX | N | (A) Survival analysis | (B) Scheduled Sacrifice | (C) Sentinels |
| 1 | Form buffer | 5 µl | PBS | 4 | | 4 before first drug cycle | |
| 2 | Form buffer | 5 µl | 5FC | 10 | 10 | | |
| 3 | T5.0002A | 9E5/5 µl | PBS | 10 | 10 | | |
| 4 | T5.0002 | 9E5/5 µl | 5FC | 10 | 10 | 3 before start of each cycle, 15 total | 1 before start of each cycle, 5 total |
| 5 | T5.0002A | 9E5/5 µl | 5FC | 25 | 10 | 3 before start of each cycle, 15 total | 1 before start of each cycle, 5 total |
| 6 | T5.0002A | 9E4/5 µl | 5FC | 10 | 10 | | |
| 7 | T5.0002A | 9E3/5 µl | 5FC | 25 | 10 | 3 before start of each cycle, 15 total | 1 before start of each cycle, 5 total |
| 8 | T5.0002A | 9E3/5 µl | PBS | 10 | 10 | | |
| 9 NO TUMOR | none | | 5FC | 15 | | 3 before start of each cycle, 15 total | |
| Total Number of Animals | | | | 119 | 70 | 64 | 15 |

Group Assignments and Dose Levels

Intravenous dosing is performed via injection into the tail vein. Intraperitoneal dosing is performed via injection into the abdomen with care taken to avoid the bladder. For intracranial administration, mice with a guide cannula with a 3.2 mm projection implanted into the right striatum, and fitted with a cap with a 3.7 mm projection are used. The projected stereotaxic coordinates are AP=0.5-1.0 mm, ML=1.8-2.0 mm, DV=3.2 mm (from bregma). Cells or vector are intracranially infused through an injection cannula with a 3.7 mm projection inserted through the guide cannula. The rate is controlled with a syringe pump fitted with a Hamilton syringe and flexible tubing.

For cell injection, 1 microliter of cells is delivered at a flow rate of 0.2 microliter per minute (5 minutes total). For vector injection, 5 microliter of vector is delivered at a flow rate of 0.33 microliter per minute (15 minutes total).

Vector is delivered and calculated as transforming units (TU) per gram of brain weight to the mice. Using such calculation the translation of dose can be calculated for other mammals including humans. Results from this study will show that APOBEC-resistant virus spreads throughout tumor, maintains yCD integrity and is more effective at treating the tumor in combination with 5FC when compared to APOBEC-sensitive RRV. APOBEC-resistant RRV also does not horizontally spread to naïve cage mates.

As described above, an RRV contains a "2A cassette". For example, SEQ ID NO:AA provides a general construct containing a 2A cassette. The cassette can be replaced with a number of different cassettes. For example, the following cassettes can be prepare and cloned into the SEQ ID NO:AA vector backbone replacing the cassette in SEQ ID NO:AA.

Using the methods and sequences provided herein a number of vectors were designed as follows:

pAC3-T2A-GFPm (SEQ ID NO: 43)

pAC3-GSG-T2A-GFPm (SEQ ID NO: 44)

pAC3-P2A-GFPm (SEQ ID NO: 45)

pAC3-GSG-P2A-GFPm (SEQ ID NO: 46)

pAC3-E2A-GFP (SEQ ID NO: 47)

pAC3-GSG-E2A-GFPm (SEQ ID NO: 48)

pAC3-F2A-GFPm (SEQ ID NO: 49)

pAC3-GSG-F2A-GFPm (SEQ ID NO: 50)

pAC3-T2A-yCD2 (SEQ ID NO: 51)

pAC3-GSG-T2A-yCD2 (SEQ ID NO: 52)

pAC3-P2A-yCD2 (SEQ ID NO: 53)

pAC3-GSG-P2A-yCD2 (SEQ ID NO: 54)

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A recombinant replication competent retrovirus comprising:
   a retroviral GAG protein;
   a retroviral POL protein;
   a retroviral envelope;
   a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain;
   a cassette comprising a 2A peptide or 2A peptide-like coding sequence that encodes the peptide of any one of SEQ ID Nos: 55-58 and is operably linked to a heterologous polynucleotide encoding a polypeptide having cytosine deaminase activity comprising the amino acid sequence as set forth in SEQ ID NO: 29, wherein the amino acid residue at position 10 and 152 of SEQ ID NO: 29 is F, D, M, L, or R, and wherein the cassette is positioned 5' to the 3' LTR and 3' to the env nucleic acid domain encoding the retroviral envelope; and
   cis-acting sequences necessary for reverse transcription, packaging and integration in a target cell.

2. The recombinant replication competent retrovirus of claim 1, wherein the envelope is chosen from one of amphotropic, polytropic, xenotropic, 10A1, GALV, Baboon endogenous virus, RD114, rhabdovirus, alphavirus, measles or influenza virus envelopes.

3. The retrovirus of claim 1, wherein the retroviral polynucleotide sequence is engineered from a virus selected from the group consisting of murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD 114, squirrel monkey retrovirus, Xenotropic murine leukemia virus-related virus (XMRV), avian reticuloendotheliosis virus (REV), and Gibbon ape leukemia virus (GALV) to contain the cassette.

4. The retrovirus of claim 1, wherein the retrovirus is a gammaretrovirus.

5. The retrovirus of claim 1, wherein the 2A peptide or 2A peptide like coding sequence encodes the peptide sequence as set forth in SEQ ID NO: 55.

6. The retrovirus of claim 1, wherein the 2A peptide or 2A peptide-like coding sequence encodes the peptide sequence as set forth in SEQ ID NO: 56.

7. The retrovirus of claim 1, wherein the 2A peptide or 2A peptide-like coding sequence encodes the peptide sequence as set forth in SEQ ID NO: 57.

8. The retrovirus of claim 1, further comprising a second cassette downstream of the cassette, wherein the second cassette comprises an internal ribosome entry site (IRES) or a minipromoter or a polIII promoter or a second 2A peptide or 2A peptide-like coding sequence operably linked to a second heterologous polynucleotide.

9. A recombinant replication competent retrovirus comprising:
   a retroviral GAG protein;
   a retroviral POL protein;
   a retroviral envelope;
   a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain;
   a cassette comprising regulatory domain operably linked to a first heterologous polynucleotide encoding a polypeptide having cytosine deaminase activity comprising the amino acid sequence as set forth in SEQ ID NO: 29, wherein the amino acid residue at position 10 and 152 of SEQ ID NO: 29 is F, D, M, L, or R, and operably linked to at least one 2A cassette comprising a GSG linker coding sequence and a 2A peptide or 2A peptide-like coding sequence that encodes a peptide of any one of SEQ ID Nos: 55-58 and is operably linked to a second heterologous polynucleotide, wherein the cassette is positioned 5' to the 3' LTR and 3' to the env nucleic acid domain encoding the retroviral envelope and wherein the 2A cassette is downstream of the first heterologous polynucleotide; and
   cis-acting sequences necessary for reverse transcription, packaging and integration in a target cell.

10. The retrovirus of claim 9, wherein the envelope is chosen from one of amphotropic, polytropic, xenotropic, 10A1, GALV, Baboon endogenous virus, RD 114, rhabdovirus, alphavirus, measles or influenza virus envelopes.

11. The retrovirus of claim 9, wherein the retrovirus is a gammaretrovirus.

12. The retrovirus of claim 9, wherein the 2A peptide or 2A peptide-like coding sequence encodes the peptide sequence as set forth in SEQ ID NO: 55.

13. The retrovirus of claim 9, wherein the 2A peptide or 2A peptide-like coding sequence encodes the peptide sequence as set forth in SEQ ID NO: 56.

14. The retrovirus of claim 9, wherein the second heterologous nucleic acid sequence encodes an immunopotentiating cytokine.

15. The retrovirus according to claim 9, wherein the second heterologous nucleic acid sequence encodes a receptor domain, an antigen binding domain, an antibody, or antibody fragment.

16. The retrovirus according to claim 8, wherein the second cassette comprises an inhibitory polynucleotide.

17. The retrovirus according to claim 16, wherein the inhibitory polynucleotide comprises an miRNA, RNAi or siRNA sequence.

18. A recombinant polynucleotide comprising a cassette comprising a 2A peptide or 2A peptide-like coding sequence that encodes the peptide of any one of SEQ ID Nos: 55-58 and is operably linked to a heterologous polynucleotide encoding a polypeptide having cytosine deaminase activity comprising the amino acid sequence as set forth in SEQ ID NO: 29, wherein the amino acid residue at position 10 and 152 of SEQ ID NO: 29 is F, D, M, L, or R, for producing the retrovirus of claim 1.

19. The recombinant replication competent retrovirus of claim 1, wherein the retroviral polynucleotide or the heterologous polynucleotide has been engineered to remove tryptophan codons susceptible to human APOBEC hypermutations.

20. The recombinant replication competent retrovirus of claim 9, wherein the retroviral polynucleotide or the first or the second heterologous polynucleotide has been engineered to remove tryptophan codons susceptible to human APOBEC hypermutation.

21. The recombinant replication competent retrovirus of claim 1, wherein the recombinant replication competent retrovirus is resistant to inactivation by human APOBEC by engineering codons in a retroviral polynucleotide susceptible to APOBEC hypermutation to a non-susceptible codon.

22. The recombinant replication competent retrovirus of claim 21, wherein the retrovirus comprises an IRES cassette, promoter cassette and/or 2A peptide cassette downstream of the env gene.

\* \* \* \* \*

SEQUENCE LISTING

```
<160> NUMBER OF SEQ ID NOS: 125

<210> SEQ ID NO 1
<211> LENGTH: 8
<212> TYPE: PRT
<213> ORGANISM: Artificial Sequence
<220> FEATURE:
<223> OTHER INFORMATION: 2A peptide consensus sequence
<220> FEATURE:
<221> NAME/KEY: MISC_FEATURE
<222> LOCATION: (2)..(2)
<223> OTHER INFORMATION: Xaa is V or I
<220> FEATURE:
<221> NAME/KEY: MISC_FEATURE
<222> LOCATION: (4)..(4)
<223> OTHER INFORMATION: Xaa is any amino acid

<400> SEQUENCE: 1

Asp Xaa Glu Xaa Asn Pro Gly Pro
1               5

<210> SEQ ID NO 2
<211> LENGTH: 11654
<212> TYPE: DNA
<213> ORGANISM: Artificial Sequence
<220> FEATURE:
<223> OTHER INFORMATION: RRV vector containing 2A-cassette

<400> SEQUENCE: 2
tagttattaa tagtaatcaa ttacggggtc attagttcat agcccatata tggagttccg     60
```

-continued

```
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgcc ccattgacg  caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcggggggtc    720 tttcatttgg gggctcgtcc gggatcggga gaccccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960 cggggggccgt ttttgtggcc cgacctgagt ccaaaaatcc cgatcgtttt ggactctttg    1020 gtgcacccccc cttagaggag ggatatgtgg ttctggtagg agacgagaac ctaaaacagt    1080
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaga    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaaccttt aacgtcggat ggccgcgaga cggcaccttt aaccgagacc    1380
tcatcaccca ggttaagatc aaggtctttt cacctggccc gcatggacac ccagaccagg    1440 tccccctacat cgtgacctgg gaagccttgg cttttgaccc ccctccctgg gtcaagccct    1500
ttgtacaccc taagcctccg cctcctcttc tccatccgc  cccgtctctc cccttgaac     1560 ctcctcgttc gaccccgcct cgatcctccc tttatccagc cctcactcct tctctaggcg    1620
ccaaacctaa acctcaagtt cttttctgaca gtggggggcc gctcatcgac ctacttacag    1680
aagacccccc gccttatagg gacccaagac cacccccttc cgacagggac ggaaatggtg    1740
gagaagcgac ccctgcggga gaggcaccgg acccctcccc aatggcatct cgcctacgtg    1800
ggagacggga gcccctgtg  gccgactcca ctacctcgca ggcattcccc ctccgcgcag    1860
gaggaaacgg acagcttcaa tactggccgt tctcctcttc tgacctttac aactggaaaa    1920
ataataaccc ttcttttttct gaagatccag gtaaactgac agctctgatc gagtctgttc    1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
```

-continued

```
ttggagattt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc gggggcaac     2880 ccgtcacctt cctggtagat actggggccc aacactccgt gctgacccaa atcctggac     2940 ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagcccac atacagagac     3420 tgttggacca gggaatactg gtaccctgcc agtccccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttctgc ctgagactcc      3660 accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg ggtatcgggc ctcggccaag aaagcccaaa    3960
tttgccagaa acaggtcaag tatctgggt atcttctaaa agagggtcag agatggctga     4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gcccttgaa ctctttgtcg acgagaagca gggctacgcc aaaggtgtcc      4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc ccgaccgct ggctttccaa cgcccggatg actcactatc      4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
```

```
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca gcggcccga aaggcagcca    5160 tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagttttttat agataccttt tctggctgga    5640
tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc tactaccaagaa caactggacc gaccggtgg acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt agacggcatc gcagcttgga    6300
tacacgccgc ccacgtgaag gctgccgacc ccggggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttg acttttacgt gtgccctggg cataccgtaa agtcggggtg    6720
tgggggacca ggagagggct actgtggtaa atgggggtgt gaaaccaccg acaggcttta    6780
ctggaagccc acatcatcgt gggacctaat ctcccttaag cgcggtaaca cccccctggga    6840 cacgggatgc tctaaagttg cctgtggccc ctgctacgac ctctccaaag tatccaattc    6900
cttccaaggg gctactcgag ggggcagatg caaccctcta gtcctagaat tcactgatgc    6960 aggaaaaag gctaactggg acgggcccaa atcgtgggga ctgagactgt accggacagg    7020
aacagatcct attaccatgt tctccctgac ccggcaggtc cttaatgtgg gaccccgagt    7080
ccccataggg cccaacccag tattacccga ccaaagactc ccttcctcac caatagagat    7140
tgtaccggct ccacagccac ctagccccct caataccagt taccccccctt ccactaccag    7200
```

```
tacaccctca acctccccta caagtccaag tgtcccacag ccaccccag gaactggaga      7260
tagactacta gctctagtca aaggagccta tcaggcgctt aacctcacca atcccgacaa      7320
gacccaagaa tgttggctgt gcttagtgtc gggacctcct tattacgaag gagtagcggt      7380
cgtgggcact tataccaatc attccaccgc tccggccaac tgtacggcca cttcccaaca      7440
taagcttacc ctatctgaag tgacaggaca gggcctatgc atgggggcag tacctaaaac      7500
tcaccaggcc ttatgtaaca ccacccaaag cgccggctca ggatcctact accttgcagc      7560
acccgccgga acaatgtggg cttgcagcac tggattgact ccctgcttgt ccaccacggt      7620
gctcaatcta accacagatt attgtgtatt agttgaactc tggcccagag taatttacca      7680
ctcccccgat tatatgtatg gtcagcttga acagcgtacc aaatataaaa gagagccagt      7740
atcattgacc ctggcccttc tactaggagg attaaccatg ggagggattg cagctggaat      7800
agggacgggg accactgcct taattaaaac ccagcagttt gagcagcttc atgccgctat      7860
ccagacagac ctcaacgaag tcgaaaagtc aattaccaac ctagaaaagt cactgacctc      7920
gttgtctgaa gtagtcctac agaaccgcag aggcctagat ttgctattcc taaaggaggg      7980
aggtctctgc gcagccctaa aagaagaatg ttgtttttat gcagaccaca cggggctagt      8040
gagagacagc atggccaaat taagagaaag gcttaatcag agacaaaaac tatttgagac      8100
aggccaagga tggttcgaag ggctgtttaa tagatccccc tggttaccca ccttaatctc      8160
caccatcatg ggacctctaa tagtactctt actgatctta ctctttggac cttgcattct      8220
caatcgattg gtccaatttg ttaaagacag gatctcagtg gtccaggctc tggttttgac      8280
tcagcaatat caccagctaa aacccataga gtacgagcca gtgaaacaga ctttgaattt      8340
tgaccttctc aagttggcgg gagacgtgga gtccaacccct ggacctggcg cgcctatggc      8400
cagcaagggc gaggagctgt tcaccggggt ggtgcccatc ctggtcgagc tggacggcga      8460
cgtaaacggc cacaagttca gcgtgtccgg cgaaggagag ggcgatgcca cctacggcaa      8520
gctgaccctg aagttcatct gcaccaccgg caagctgccc gtgccctggc ccaccctcgt      8580
gaccaccttg acctacggcg tgcagtgctt cgcccgctac cccgaccaca tgaagcagca      8640
cgacttcttc aagtccgcca tgcccgaagg ctacgtccag gagcgcacca tcttcttcaa      8700
ggacgacggc aactacaaga cccgcgccga ggtgaagttc gagggcgaca ccctggtgaa      8760
ccgcatcgag ctgaagggca tcgacttcaa ggaggacggc aacatcctgg ggcacaagct      8820
ggagtacaac tacaacagcc acaaggtcta tatcaccgcc gacaagcaga agaacggcat      8880
caaggtgaac ttcaagaccc gccacaacat cgaggacggc agcgtgcagc tcgccgacca      8940
ctaccagcag aacaccccca tcggcgacgg ccccgtgctg ctgcccgaca accactacct      9000
gagcacccag tccgccctga gcaaagaccc caacgagaag cgcgatcaca tggtcctgct      9060
ggagttcgtg accgccgccg ggatcactct cggcatggac gagctgtaca agtgtgcggc      9120
cgcagataaa ataaaagatt ttatttagtc tccagaaaaa gggggaatg aaagacccca      9180
cctgtaggtt tggcaagcta gcttaagtaa cgccattttg caaggcatgg aaaaatacat      9240
aactgagaat agagaagttc agatcaaggt caggaacaga tggaacagct gaatatgggc      9300
caaacaggat atctgtggta agcagttcct gccccggctc agggccaaga acagatggaa      9360
cagctgaata tgggccaaac aggatatctg tggtaagcag ttcctgcccc ggctcagggc      9420
caagaacaga tggtccccag atgcggtcca gccctcagca gtttctagag aaccatcaga      9480
tgtttccagg gtgccccaag gacctgaaat gaccctgtgc cttatttgaa ctaaccaatc      9540
```

```
agttcgcttc tcgcttctgt tcgcgcgctt ctgctcccog agctcaataa aagagcccac    9600
aaccectcac tcggggcgcc agtcctccga ttgactgagt cgcccgggta cccgtgtatc    9660
caataaaccc tcttgcagtt gcatccgact tgtggtctcg ctgttccttg ggagggtctc    9720
ctctgagtga ttgactaccc gtcagcgggg gtctttcatt acatgtgagc aaaaggccag    9780
caaaaggcca ggaaccgtaa aaggccgcg ttgctggcgt ttttccatag gctccgcccc    9840
cctgacgagc atcacaaaaa tcgacgctca agtcagaggt ggcgaaaccc gacaggacta    9900
taaagatacc aggcgtttcc ccctggaagc tccctcgtgc gctctcctgt tccgaccctg    9960
ccgcttaccg gatacctgtc cgcctttctc ccttcgggaa gcgtggcgct ttctcaatgc   10020
tcacgctgta ggtatctcag ttcggtgtag gtcgttcgct ccaagctggg ctgtgtgcac   10080
gaaccccccg ttcagcccga ccgctgcgcc ttatccggta actatcgtct tgagtccaac   10140
ccggtaagac acgacttatc gccactggca gcagccactg gtaacaggat tagcagagcg   10200
aggtatgtag gcggtgctac agagttcttg aagtggtggc ctaactacgg ctacactaga   10260
aggacagtat ttggtatctg cgctctgctg aagccagtta ccttcggaaa aagagttggt   10320
agctcttgat ccggcaaaca aaccaccgct ggtagcggtg gtttttttgt ttgcaagcag   10380
cagattacgc gcagaaaaaa aggatctcaa gaagatcctt tgatctttc tacgggtct   10440
gacgctcagt ggaacgaaaa ctcacgttaa gggattttgg tcatgagatt atcaaaaagg   10500
atcttcacct agatcctttt aaattaaaaa tgaagtttta aatcaatcta agtatatat    10560
gagtaaactt ggtctgacag ttaccaatgc ttaatcagtg aggcacctat ctcagcgatc   10620
tgtctatttc gttcatccat agttgcctga ctccccgtcg tgtagataac tacgatacgg   10680
gagggcttac catctggccc cagtgctgca atgataccgc gagacccacg ctcaccggct   10740
ccagatttat cagcaataaa ccagccagcc ggaagggccg agcgcagaag tggtcctgca   10800
actttatccg cctccatcca gtctattaat tgttgccggg aagctagagt aagtagttcg   10860
ccagttaata gtttgcgcaa cgttgttgcc attgctgcag gcatcgtggt gtcacgctcg   10920
tcgtttggta tggcttcatt cagctccggt tcccaacgat caaggcgagt tacatgatcc   10980
cccatgttgt gcaaaaaagc ggttagctcc ttcggtcctc cgatcgttgt cagaagtaag   11040
ttggccgcag tgttatcact catggttatg gcagcactgc ataattctct tactgtcatg   11100
ccatccgtaa gatgctttc tgtgactggt gagtactcaa ccaagtcatt ctgagaatag   11160
tgtatgcggc gaccgagttg ctcttgcccg gcgtcaacac gggataatac cgcgccacat   11220
agcagaactt aaaagtgct catcattgga aaacgttctt cggggcgaaa actctcaagg   11280
atcttaccgc tgttgagatc cagttcgatg taacccactc gtgcacccaa ctgatcttca   11340
gcatctttta ctttcaccag cgtttctggg tgagcaaaaa caggaaggca aaatgccgca   11400
aaaaagggaa taagggcgac acggaaatgt tgaatactca tactcttcct ttttcaatat   11460
tattgaagca tttatcaggg ttattgtctc atgagcggat acatatttga atgtatttag   11520
aaaaataaac aaatagggt tccgcgcaca tttccccgaa aagtgccacc tgacgtctaa   11580
gaaaccatta ttatcatgac attaacctat aaaaataggc gtatcacgag gcccctttcgt   11640
cttcaagaat tcat                                                     11654

<210> SEQ ID NO 3
<211> LENGTH: 9
<212> TYPE: DNA
<213> ORGANISM: Artificial Sequence
<220> FEATURE:
<223> OTHER INFORMATION: GSG linker sequence
```

```
<400> SEQUENCE: 3 ggaagcgga                                                                9

<210> SEQ ID NO 4
<211> LENGTH: 30
<212> TYPE: DNA
<213> ORGANISM: Artificial Sequence
<220> FEATURE:
<223> OTHER INFORMATION: GFP-R-Gib primer

<400> SEQUENCE: 4 taaaatctt tattttatct gcggccgcac                                         30

<210> SEQ ID NO 5
<211> LENGTH: 11
<212> TYPE: PRT
<213> ORGANISM: Artificial Sequence
<220> FEATURE:
<223> OTHER INFORMATION: Peptide readthrough sequence

<400> SEQUENCE: 5

Cys Ala Ala Ala Asp Lys Ile Lys Asp Phe Ile
1               5                   10

<210> SEQ ID NO 6
<211> LENGTH: 33
<212> TYPE: DNA
<213> ORGANISM: Artificial Sequence
<220> FEATURE:
<223> OTHER INFORMATION: Ascl-yCD2 formard primer

<400> SEQUENCE: 6
gatcggcgcg cctatggtga ccggcggcat ggc                                    33

<210> SEQ ID NO 7
<211> LENGTH: 24
<212> TYPE: DNA
<213> ORGANISM: Artificial Sequence
<220> FEATURE:
<223> OTHER INFORMATION: 3-37 primer

<400> SEQUENCE: 7
cccctttttc tggagactaa ataa                                              24

<210> SEQ ID NO 8
<211> LENGTH: 54
<212> TYPE: DNA
<213> ORGANISM: Artificial Sequence
<220> FEATURE:
<223> OTHER INFORMATION: 2A peptide sequence

<400> SEQUENCE: 8
gagggcagag gaagtcttct aacatgcggt gacgtggagg agaatcccgg ccct             54

<210> SEQ ID NO 9
<211> LENGTH: 63
<212> TYPE: DNA
<213> ORGANISM: Artificial Sequence
<220> FEATURE:
<223> OTHER INFORMATION: 2A peptide sequence

<400> SEQUENCE: 9
ggaagcggag agggcagagg aagtcttcta acatgcggtg acgtggagga gaatcccggc       60
cct                                                                     63
```

<210> SEQ ID NO 10
<211> LENGTH: 57
<212> TYPE: DNA
<213> ORGANISM: Artificial Sequence
<220> FEATURE:
<223> OTHER INFORMATION: 2A peptide sequence

<400> SEQUENCE: 10
gctactaact tcagcctgct gaagcaggct ggagacgtgg aggagaaccc tggacct      57

<210> SEQ ID NO 11
<211> LENGTH: 66
<212> TYPE: DNA
<213> ORGANISM: Artificial Sequence
<220> FEATURE:
<223> OTHER INFORMATION: 2A peptide sequence

<400> SEQUENCE: 11
ggaagcggag ctactaactt cagcctgctg aagcaggctg agacgtgga ggagaaccct    60 ggacct                                                               66

<210> SEQ ID NO 12
<211> LENGTH: 66
<212> TYPE: DNA
<213> ORGANISM: Artificial Sequence
<220> FEATURE:
<223> OTHER INFORMATION: 2A peptide sequence

<400> SEQUENCE: 12
gtgaaacaga ctttgaattt tgaccttctc aagttggcgg gagacgtgga gtccaaccct    60
ggacct                                                               66

<210> SEQ ID NO 13
<211> LENGTH: 75
<212> TYPE: DNA
<213> ORGANISM: Artificial Sequence
<220> FEATURE:
<223> OTHER INFORMATION: 2A peptide sequence

<400> SEQUENCE: 13
ggaagcggag tgaaacagac tttgattttt gaccttctca gttggcggg agacgtggag     60 tccaaccctg gacct                                                     75

<210> SEQ ID NO 14
<211> LENGTH: 60
<212> TYPE: DNA
<213> ORGANISM: Artificial Sequence
<220> FEATURE:
<223> OTHER INFORMATION: 2A peptide sequence

<400> SEQUENCE: 14
cagtgtacta attatgctct cttgaaattg gctggagatg ttgagagcaa ccctggacct    60

<210> SEQ ID NO 15
<211> LENGTH: 69
<212> TYPE: DNA
<213> ORGANISM: Artificial Sequence
<220> FEATURE:
<223> OTHER INFORMATION: 2A peptide sequence

<400> SEQUENCE: 15
ggaagcggac agtgtactaa ttatgctctc ttgaaattgg ctggagatgt tgagagcaac    60
cctggacct                                                           69

<210> SEQ ID NO 16
<211> LENGTH: 54
<212> TYPE: DNA
<213> ORGANISM: Artificial Sequence
<220> FEATURE:
<223> OTHER INFORMATION: 2A peptide sequence

<400> SEQUENCE: 16
gagggcagag gaagtcttct aacatgcggt gacgtggagg agaatcccgg ccct         54

<210> SEQ ID NO 17
<211> LENGTH: 63
<212> TYPE: DNA
<213> ORGANISM: Artificial Sequence
<220> FEATURE:
<223> OTHER INFORMATION: 2A peptide sequence

<400> SEQUENCE: 17
ggaagcggag agggcagagg aagtcttcta acatgcggtg acgtggagga gaatcccggc   60
cct                                                                 63

<210> SEQ ID NO 18
<211> LENGTH: 57
<212> TYPE: DNA
<213> ORGANISM: Artificial Sequence
<220> FEATURE:
<223> OTHER INFORMATION: 2A peptide sequence

<400> SEQUENCE: 18
gctactaact tcagcctgct gaagcaggct ggagacgtgg aggagaaccc tggacct      57

<210> SEQ ID NO 19
<211> LENGTH: 66
<212> TYPE: DNA
<213> ORGANISM: Artificial Sequence
<220> FEATURE:
<223> OTHER INFORMATION: 2A peptide sequence

<400> SEQUENCE: 19
ggaagcggag ctactaactt cagcctgctg aagcaggctg agacgtgga ggagaaccct    60 ggacct                                                              66

<210> SEQ ID NO 20
<211> LENGTH: 19
<212> TYPE: DNA
<213> ORGANISM: Artificial Sequence
<220> FEATURE:
<223> OTHER INFORMATION: 5-MLV-U3-R primer

<400> SEQUENCE: 20
agcccacaac ccctcactc                                                19

<210> SEQ ID NO 21
<211> LENGTH: 18
<212> TYPE: DNA
<213> ORGANISM: Artificial Sequence
<220> FEATURE:
<223> OTHER INFORMATION: 3-MLV-Psi primer sequence

<400> SEQUENCE: 21
tctcccgatc ccggacga                                                 18

```
<210> SEQ ID NO 22
<211> LENGTH: 26
<212> TYPE: DNA
<213> ORGANISM: Artificial Sequence
<220> FEATURE:
<223> OTHER INFORMATION: Probe sequence

<400> SEQUENCE: 22
ccccaaatga aagaccoccg ctgacg                                           26

<210> SEQ ID NO 23
<211> LENGTH: 23
<212> TYPE: DNA
<213> ORGANISM: Artificial Sequence
<220> FEATURE:
<223> OTHER INFORMATION: IRES forward primer

<400> SEQUENCE: 23
ctgatcttac tctttggacc ttg                                              23

<210> SEQ ID NO 24
<211> LENGTH: 24
<212> TYPE: DNA
<213> ORGANISM: Artificial Sequence
<220> FEATURE:
<223> OTHER INFORMATION: IRES reverse primer

<400> SEQUENCE: 24 ccccttttc tggagactaa ataa                                              24

<210> SEQ ID NO 25
<211> LENGTH: 22
<212> TYPE: DNA
<213> ORGANISM: Artificial Sequence
<220> FEATURE:
<223> OTHER INFORMATION: ENV forward primer

<400> SEQUENCE: 25
accctcaacc tcccctacaa gt                                               22

<210> SEQ ID NO 26
<211> LENGTH: 20
<212> TYPE: DNA
<213> ORGANISM: Artificial Sequence
<220> FEATURE:
<223> OTHER INFORMATION: ENV reverse primer

<400> SEQUENCE: 26
gttaagcgcc tgataggctc                                                  20

<210> SEQ ID NO 27
<211> LENGTH: 26
<212> TYPE: DNA
<213> ORGANISM: Artificial Sequence
<220> FEATURE:
<223> OTHER INFORMATION: Env probe sequence

<400> SEQUENCE: 27
ccccaaatga aagaccoccg ctgacg                                           26

<210> SEQ ID NO 28
<211> LENGTH: 477
<212> TYPE: DNA
<213> ORGANISM: Artificial Sequence
<220> FEATURE:
<223> OTHER INFORMATION: Human codon optimized heat stabilized CD coding
      sequence
```

<400> SEQUENCE: 28

```
atggtgaccg gcggcatggc ctccaagtgg gatcaaaagg gcatggatat cgcttacgag      60
gaggccctgc tgggctacaa ggagggcggc gtgcctatcg gcggctgtct gatcaacaac     120
aaggacggca gtgtgctggg cagggccac aacatgaggt tccagaaggg ctccgccacc      180
ctgcacggcg agatctccac cctggagaac tgtggcaggc tggagggcaa ggtgtacaag     240
gacaccaccc tgtacaccac cctgtcccct tgtgacatgt gtaccggcgc tatcatcatg     300
tacggcatcc ctaggtgtgt gatcggcgag aacgtgaact tcaagtccaa gggcgagaag     360
tacctgcaaa ccaggggcca cgaggtggtg gttgttgacg atgagaggtg taagaagctg     420
atgaagcagt tcatcgacga gaggcctcag gactggttcg aggatatcgg cgagtaa       477
```

<210> SEQ ID NO 29
<211> LENGTH: 158
<212> TYPE: PRT
<213> ORGANISM: Artificial Sequence
<220> FEATURE:
<223> OTHER INFORMATION: Heat stabilized APOBEC modified CD polypeptide
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (152)..(152)
<223> OTHER INFORMATION: Xaa is any amino acid

<400> SEQUENCE: 29

```
Met Val Thr Gly Gly Met Ala Ser Lys Xaa Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Asp Asp Glu Arg Cys Lys Lys Leu Met Lys Gln Phe
    130                 135                 140

Ile Asp Glu Arg Pro Gln Asp Xaa Phe Glu Asp Ile Gly Glu
145                 150                 155
```

<210> SEQ ID NO 30
<211> LENGTH: 54
<212> TYPE: DNA
<213> ORGANISM: Artificial Sequence
<220> FEATURE:
<223> OTHER INFORMATION: 2A peptide coding sequence

<400> SEQUENCE: 30

```
gagggcagag gaagtcttct aacatgcggt gacgtggagg agaatcccgg ccct           54
```

<210> SEQ ID NO 31
<211> LENGTH: 1062
<212> TYPE: DNA
<213> ORGANISM: Artificial Sequence
<220> FEATURE:
<223> OTHER INFORMATION: BstBI-env-T2A-GFPm of pAC3-T2A-GFPm

<400> SEQUENCE: 31

| | | | | | |
|---|---|---|---|---|---|
| ttcgaagggc | tgtttaatag | atcccctgg | tttaccacct | taatctccac | catcatggga | 60 |
| cctctaatag | tactcttact | gatcttactc | tttggacctt | gcattctcaa | tcgattggtc | 120 |
| caatttgtta | aagacaggat | ctcagtggtc | caggctctgg | ttttgactca | gcaatatcac | 180 |
| cagctaaaac | ccatagagta | cgagccagag | ggcagaggaa | gtcttctaac | atgcggtgac | 240 |
| gtggaggaga | atcccggccc | tggcgcgcct | atggccagca | agggcgagga | gctgttcacc | 300 |
| ggggtggtgc | ccatcctggt | cgagctggac | ggcgacgtaa | acggccacaa | gttcagcgtg | 360 |
| tccggcgaag | gagagggcga | tgccacctac | ggcaagctga | ccctgaagtt | catctgcacc | 420 |
| accggcaagc | tgcccgtgcc | ctggcccacc | ctcgtgacca | ccttgaccta | cggcgtgcag | 480 |
| tgcttcgccc | gctaccccga | ccacatgaag | cagcacgact | tcttcaagtc | cgccatgccc | 540 |
| gaaggctacg | tccaggagcg | caccatcttc | ttcaaggacg | acggcaacta | caagacccgc | 600 |
| gccgaggtga | agttcgaggg | cgacaccctg | gtgaaccgca | tcgagctgaa | gggcatcgac | 660 |
| ttcaaggagg | acggcaacat | cctggggcac | aagctggagt | acaactacaa | cagccacaag | 720 |
| gtctatatca | ccgccgacaa | gcagaagaac | ggcatcaagg | tgaacttcaa | gacccgccac | 780 |
| aacatcgagg | acggcagcgt | gcagctcgcc | gaccactacc | agcagaacac | ccccatcggc | 840 |
| gacggccccg | tgctgctgcc | cgacaaccac | tacctgagca | cccagtccgc | cctgagcaaa | 900 |
| gaccccaacg | agaagcgcga | tcacatggtc | ctgctggagt | tcgtgaccgc | cgccgggatc | 960 |
| actctcggca | tggacgagct | gtacaagtgt | gcggccgcag | ataaaataaa | agatttatt | 1020 |
| tagtctccag | aaaaagggg | gaatgaaaga | ccccacctgt | ag | | 1062 |

<210> SEQ ID NO 32
<211> LENGTH: 1026
<212> TYPE: DNA
<213> ORGANISM: Artificial Sequence
<220> FEATURE:
<223> OTHER INFORMATION: BstBI-env-P2A-GFPm of pAC3-P2A-GFPm

<400> SEQUENCE: 32

| | | | | | |
|---|---|---|---|---|---|
| ttcgaagggc | tgtttaatag | atcccctgg | tttaccacct | taatctccac | catcatggga | 60 |
| cctctaatag | tactcttact | gatcttactc | tttggacctt | gcattctcaa | tcgattggtc | 120 |
| caatttgtta | aagacaggat | ctcagtggtc | caggctctgg | ttttgactca | gcaatatcac | 180 |
| cagctaaaac | ccatagagta | cgagccagct | actaacttca | gcctgctgaa | gcaggctgga | 240 |
| gacgtggagg | agaaccctgg | acctggcgcg | cctatggcca | gcaagggcga | ggagctgttc | 300 |
| accggggtgg | tgcccatcct | ggtcgagctg | gacggcgacg | taaacggcca | caagttcagc | 360 |
| gtgtccggcg | aaggagaggg | cgatgccacc | tacggcaagc | tgaccctgaa | gttcatctgc | 420 |
| accaccggca | agctgcccgt | gccctggccc | accctcgtga | ccaccttgac | ctacggcgtg | 480 |
| cagtgcttcg | cccgctaccc | cgaccacatg | aagcagcacg | acttcttcaa | gtccgccatg | 540 |
| cccgaaggct | acgtccagga | gcgcaccatc | ttcttcaagg | acgacggcaa | ctacaagacc | 600 |
| cgcgccgagg | tgaagttcga | gggcgacacc | ctggtgaacc | gcatcgagct | gaagggcatc | 660 |
| gacttcaagg | aggacggcaa | catcctgggg | cacaagctgg | agtacaacta | caacagccac | 720 |

```
aaggtctata tcaccgccga caagcagaag aacggcatca aggtgaactt caagacccgc    780
cacaacatcg aggacggcag cgtgcagctc gccgaccact accagcagaa cacccccatc    840
ggcgacggcc ccgtgctgct gcccgacaac cactacctga gcacccagtc cgccctgagc    900
aaagacccca acgagaagcg cgatcacatg gtcctgctgg agttcgtgac cgccgccggg    960
atcactctcg gcatggacga gctgtacaag tgtgcggccg cagataaaat aaaagatttt   1020
atttag                                                              1026
```

<210> SEQ ID NO 33
<211> LENGTH: 1029
<212> TYPE: DNA
<213> ORGANISM: Artificial Sequence
<220> FEATURE:
<223> OTHER INFORMATION: BstBI-env-E2A-GFPm of pAC3-E2A-GFPm

<400> SEQUENCE: 33

```
ttcgaagggc tgtttaatag atccccctgg tttaccacct taatctccac catcatggga     60
cctctaatag tactcttact gatcttactc tttggacctt gcattctcaa tcgattggtc    120
caatttgtta aagacaggat ctcagtggtc caggctctgg ttttgactca gcaatatcac    180
cagctaaaac ccatagagta cgagccacag tgtactaatt atgctctctt gaaattggct    240
ggagatgttg agagcaaccc tggacctggc gcgccatggg ccagcaaggg cgaggagctg    300
ttcaccgggg tggtgcccat cctggtcgag ctggacggcg acgtaaacgg ccacaagttc    360
agcgtgtccg gcgaaggaga gggcgatgcc acctacggca agctgaccct gaagttcatc    420
tgcaccaccg gcaagctgcc cgtgccctgg cccaccctcg tgaccacctt gacctacggc    480
gtgcagtgct tcgcccgcta ccccgaccac atgaagcagc acgacttctt caagtccgcc    540
atgcccgaag gctacgtcca ggagcgcacc atcttcttca aggacgacgg caactacaag    600
acccgcgccg aggtgaagtt cgagggcgac accctggtga accgcatcga gctgaagggc    660
atcgacttca aggaggacgg caacatcctg ggcacaagc tggagtacaa ctacaacagc    720
cacaaggtct atatcaccgc cgacaagcag aagaacggca tcaaggtgaa cttcaagacc    780
cgccacaaca tcgaggacgg cagcgtgcag ctcgccgacc actaccagca gaacaccccc    840
atcggcgacg gccccgtgct gctgcccgac aaccactacc tgagcaccca gtccgccctg    900
agcaaagacc ccaacgagaa gcgcgatcac atggtcctgc tggagttcgt gaccgccgcc    960
gggatcactc tcggcatgga cgagctgtac aagtgtgcgg ccgcagataa aataaaagat   1020
tttatttag                                                           1029
```

<210> SEQ ID NO 34
<211> LENGTH: 1035
<212> TYPE: DNA
<213> ORGANISM: Artificial Sequence
<220> FEATURE:
<223> OTHER INFORMATION: BstBI-env-F2A-GFPm of pAC3-F2A-GFPm

<400> SEQUENCE: 34

```
ttcgaagggc tgtttaatag atccccctgg tttaccacct taatctccac catcatggga     60
cctctaatag tactcttact gatcttactc tttggacctt gcattctcaa tcgattggtc    120
caatttgtta aagacaggat ctcagtggtc caggctctgg ttttgactca gcaatatcac    180
cagctaaaac ccatagagta cgagccagtg aaacagactt tgaattttga ccttctcaag    240
ttggcgggag acgtggagtc caaccctgga cctggcgcgc ctatggccag caagggcgag    300
```

```
gagctgttca ccggggtggt gcccatcctg gtcgagctgg acggcgacgt aaacggccac    360
aagttcagcg tgtccggcga aggagagggc gatgccacct acggcaagct gaccctgaag    420
ttcatctgca ccaccggcaa gctgcccgtg ccctggccca ccctcgtgac caccttgacc    480
tacggcgtgc agtgcttcgc ccgctacccc gaccacatga gcagcacga cttcttcaag     540 tccgccatgc ccgaaggcta cgtccaggag cgcaccatct tcttcaagga cgacggcaac    600
tacaagaccc gcgccgaggt gaagttcgag ggcgacaccc tggtgaaccg catcgagctg    660
aagggcatcg acttcaagga ggacggcaac atcctggggc acaagctgga gtacaactac    720
aacagccaca aggtctatat caccgccgac aagcagaaga cggcatcaa ggtgaacttc      780 aagacccgcc acaacatcga ggacggcagc gtgcagctcg ccgaccacta ccagcagaac    840
acccccatcg cgacggcccc cgtgctgctg cccgacaacc actacctgag cacccagtcc    900
gccctgagca agacccccaa cgagaagcgc gatcacatgg tcctgctgga gttcgtgacc    960
gccgccggga tcactctcgg catggacgag ctgtacaagt gtgcggccgc agataaaata   1020
aaagatttta tttag                                                    1035

<210> SEQ ID NO 35
<211> LENGTH: 1032
<212> TYPE: DNA
<213> ORGANISM: Artificial Sequence
<220> FEATURE:
<223> OTHER INFORMATION: BstBI-env-GSG-T2A-GFPm of pAC3-GSG-T2A-GFPm

<400> SEQUENCE: 35
ttcgaagggc tgtttaatag atcccctgg tttaccacct taatctccac catcatggga      60
cctctaatag tactcttact gatcttactc tttggacctt gcattctcaa tcgattggtc    120
caatttgtta aagacaggat ctcagtggtc caggctctgg ttttgactca gcaatatcac    180
cagctaaaac ccatagagta cgagccagga agcggagagg cagaggaag tcttctaaca     240 tgcggtgacg tggaggagaa tcccggccct ggcgcgccta tggccagcaa gggcgaggag    300
ctgttcaccg gggtggtgcc catcctggtc gagctggacg gcgacgtaaa cggccacaag    360
ttcagcgtgt ccggcgaagg agagggcgat gccacctacg gcaagctgac cctgaagttc    420
atctgcacca ccggcaagct gcccgtgccc tggccacccc tcgtgaccac cttgacctac    480
ggcgtgcagt gcttcgcccg ctaccccgac cacatgaagc agcacgactt cttcaagtcc    540
gccatgcccg aaggctacgt ccaggagcgc accatcttct tcaaggacga cggcaactac    600
aagacccgcg ccgaggtgaa gttcgagggc gacaccctgg tgaaccgcat cgagctgaag    660
ggcatcgact tcaaggagga cggcaacatc ctggggcaca gctggagta caactacaac     720 agccacaagg tctatatcac cgccgacaag cagaagaacg gcatcaaggt gaacttcaag    780
acccgccaca catcgagga cggcagcgtg cagctcgccg accactacca gcagaacacc     840
cccatcggcg acggccccgt gctgctgccc gacaaccact acctgagcac ccagtccgcc    900
ctgagcaaag accccaacga gaagcgcgat cacatggtcc tgctggagtt cgtgaccgcc    960
gccgggatca ctctcggcat ggacgagctg tacaagtgtg cggccgcaga taaataaaa   1020 gattttattt ag                                                       1032

<210> SEQ ID NO 36
<211> LENGTH: 1035
<212> TYPE: DNA
<213> ORGANISM: Artificial Sequence
<220> FEATURE:
<223> OTHER INFORMATION: BstBI-env-GSG-P2A-GFPm of pAC3-GSG-P2A-GFPm
```

<400> SEQUENCE: 36

```
ttcgaagggc tgtttaatag atcccctgg tttaccacct taatctccac catcatggga      60
cctctaatag tactcttact gatcttactc tttggacctt gcattctcaa tcgattggtc    120
caatttgtta aagacaggat ctcagtggtc caggctctgg ttttgactca gcaatatcac    180
cagctaaaac ccatagagta cgagccagga agcggagcta ctaacttcag cctgctgaag    240
caggctggag acgtggagga gaaccctgga cctggcgcgc tatggccag caagggcgag    300
gagctgttca ccggggtggt gcccatcctg gtcgagctgg acggcgacgt aaacggccac    360
aagttcagcg tgtccggcga aggagagggc gatgccacct acggcaagct gaccctgaag    420
ttcatctgca ccaccggcaa gctgcccgtg cctggcccca cctcgtgac caccttgacc    480
tacggcgtgc agtgcttcgc ccgctaccc gaccacatga gcagcacga cttcttcaag    540
tccgccatgc cgaaggcta cgtccaggag cgcaccatct tcttcaagga cgacggcaac    600
tacaagaccc gcgccgaggt gaagttcgag ggcgacaccc tggtgaaccg catcgagctg    660
aagggcatcg acttcaagga ggacggcaac atcctggggc acaagctgga gtacaactac    720
aacagccaca aggtctatat caccgccgac aagcagaaga cggcatcaa ggtgaacttc    780
aagacccgcc acaacatcga ggacggcagc gtgcagctcg ccgaccacta ccagcagaac    840
accccccatcg cgacggccc cgtgctgctg cccgacaacc actacctgag cacccagtcc    900
gccctgagca agacccca cgagaagcgc gatcacatgg tcctgctgga gttcgtgacc    960
gccgccggga tcactctcgg catggacgag ctgtacaagt gtgcggccgc agataaaata   1020
aaagatttta tttag                                                     1035
```

<210> SEQ ID NO 37
<211> LENGTH: 1044
<212> TYPE: DNA
<213> ORGANISM: Artificial Sequence
<220> FEATURE:
<223> OTHER INFORMATION: BstBI-env-GSG-F2A-GFPm of pAC3-GSG-F2A-GFPm

<400> SEQUENCE: 37

```
ttcgaagggc tgtttaatag atcccctgg tttaccacct taatctccac catcatggga      60
cctctaatag tactcttact gatcttactc tttggacctt gcattctcaa tcgattggtc    120
caatttgtta aagacaggat ctcagtggtc caggctctgg ttttgactca gcaatatcac    180
cagctaaaac ccatagagta cgagccagga agcggagtga acagactttt gaattttgac    240
cttctcaagt tggcgggaga cgtggagtcc aaccctggac ctggcgcgcc tatggccagc    300
aagggcgagg agctgttcac cggggtggtg cccatcctgg tcgagctgga cggcgacgta    360
aacggccaca agttcagcgt gtccggcgaa ggagagggcg atgccaccta cggcaagctg    420
accctgaagt tcatctgcac caccggcaag ctgcccgtgc ctggcccac cctcgtgacc    480
accttgacct acggcgtgca gtgcttcgcc cgctacccg accacatgaa gcagcacgac    540
ttcttcaagt ccgccatgcc cgaaggctac gtccaggagc gcaccatctt cttcaaggac    600
gacggcaact acaagacccg cgccgaggtg aagttcgagg gcgacaccct ggtgaaccgc    660
atcgagctga agggcatcga cttcaaggag gacggcaaca tcctgggca agctggag    720
tacaactaca acagccacaa ggtctatatc accgccgaca agcagaagaa cggcatcaag    780
gtgaacttca gacccgcca acatcgag acggcagcg tgcagctcgc cgaccactac    840
cagcagaaca ccccatcgg cgacggcccc gtgctgctgc ccgacaacca ctacctgagc    900
```

| | | |
|---|---|---|
| acccagtccg ccctgagcaa agaccccaac gagaagcgcg atcacatggt cctgctggag | 960 | |
| ttcgtgaccg ccgccgggat cactctcggc atggacgagc tgtacaagtg tgcggccgca | 1020 | |
| gataaaataa aagattttat ttag | 1044 | |

<210> SEQ ID NO 38
<211> LENGTH: 1038
<212> TYPE: DNA
<213> ORGANISM: Artificial Sequence
<220> FEATURE:
<223> OTHER INFORMATION: BstBI-env-GSG-E2A-GFPm of pAC3-GSG-E2A-GFPm

<400> SEQUENCE: 38

| | | |
|---|---|---|
| ttcgaagggc tgtttaatag atcccctgg tttaccacct taatctccac catcatggga | 60 | |
| cctctaatag tactcttact gatcttactc tttggacctt gcattctcaa tcgattggtc | 120 | |
| caatttgtta aagacaggat ctcagtggtc caggctctgg ttttgactca gcaatatcac | 180 | |
| cagctaaaac ccatagagta cgagccagga agcggacagt gtactaatta tgctctcttg | 240 | |
| aaattggctg agatgttga gagcaaccct ggacctggcg cgcctatggc cagcaagggc | 300 | |
| gaggagctgt tcaccggggt ggtgcccatc ctggtcgagc tggacggcga cgtaaacggc | 360 | |
| cacaagttca gcgtgtccgg cgaaggagag ggcgatgcca cctacggcaa gctgaccctg | 420 | |
| aagttcatct gcaccaccgg caagctgccc gtgccctggc ccaccctcgt gaccaccttg | 480 | |
| acctacggcg tgcagtgctt cgcccgctac cccgaccaca tgaagcagca cgacttcttc | 540 | |
| aagtccgcca tgcccgaagg ctacgtccag gagcgcacca tcttcttcaa ggacgacggc | 600 | |
| aactacaaga cccgcgccga ggtgaagttc gagggcgaca ccctggtgaa ccgcatcgag | 660 | |
| ctgaagggca tcgacttcaa ggaggacggc aacatcctgg gcacaagct ggagtacaac | 720 | |
| tacaacagcc acaaggtcta tatcaccgcc gacaagcaga gaacggcat caaggtgaac | 780 | |
| ttcaagaccc gccacaacat cgaggacggc agcgtgcagc tcgccgacca ctaccagcag | 840 | |
| aacaccccca tcggcgacgg ccccgtgctg ctgcccgaca accactacct gagcacccag | 900 | |
| tccgccctga gcaaagaccc caacgagaag cgcgatcaca tggtcctgct ggagttcgtg | 960 | |
| accgccgccg ggatcactct cggcatggac gagctgtaca agtgtgcggc cgcagataaa | 1020 | |
| ataaaagatt ttatttag | 1038 | |

<210> SEQ ID NO 39
<211> LENGTH: 548
<212> TYPE: DNA
<213> ORGANISM: Artificial Sequence
<220> FEATURE:
<223> OTHER INFORMATION: T2A-AscI-yCD2 of pAC3-T2A-yCD2

<400> SEQUENCE: 39

| | | |
|---|---|---|
| gagggcagag gaagtcttct aacatgcggt gacgtggagg agaatcccgg ccctggcgcg | 60 | |
| cctatggtga ccggcggcat ggcctccaag tgggatcaaa agggcatgga tatcgcttac | 120 | |
| gaggaggccc tgctgggcta caaggagggc ggcgtgccta tcggcggctg tctgatcaac | 180 | |
| aacaaggacg gcagtgtgct gggcaggggc cacaacatga ggttccagaa gggctccgcc | 240 | |
| accctgcacg gcgagatctc caccctggag aactgtggca ggctggaggg caaggtgtac | 300 | |
| aaggacacca cccctgtaca caccctgtcc ccttgtgaca tgtgtaccgg cgctatcatc | 360 | |
| atgtacggca tccctaggtg tgtgatcggc gagaacgtga acttcaagtc caagggcgag | 420 | |
| aagtacctgc aaaccagggg ccacgaggtg gtggttgttg acgatgagag gtgtaagaag | 480 | |
| ctgatgaagc agttcatcga cgagaggcct caggactggt tcgaggatat cggcgagtaa | 540 | |

<210> SEQ ID NO 40
<211> LENGTH: 551
<212> TYPE: DNA
<213> ORGANISM: Artificial Sequence
<220> FEATURE:
<223> OTHER INFORMATION: P2A-AscI-yCD2 of pAC3-P2A-yCD2

<400> SEQUENCE: 40

```
gctactaact tcagcctgct gaagcaggct ggagacgtgg aggagaaccc tggacctggc      60
gcgcctatgg tgaccggcgg catggcctcc aagtgggatc aaaagggcat ggatatcgct     120
tacgaggagg ccctgctggg ctacaaggag ggcggcgtgc ctatcggcgg ctgtctgatc     180
aacaacaagg acggcagtgt gctgggcagg ggccacaaca tgaggttcca gaagggctcc     240
gccaccctgc acggcgagat ctccaccctg agaactgtg  gcaggctgga gggcaaggtg     300
tacaaggaca ccaccctgta caccaccctg tccccttgtg acatgtgtac cggcgctatc     360
atcatgtacg gcatccctag tgtgtgatc  ggcgagaacg tgaacttcaa gtccaagggc     420
gagaagtacc tgcaaaccag gggccacgag gtggtggttg ttgacgatga gaggtgtaag     480
aagctgatga agcagttcat cgacgagagg cctcaggact ggttcgagga tatcggcgag     540
taagcggccg c                                                          551
```

<210> SEQ ID NO 41
<211> LENGTH: 557
<212> TYPE: DNA
<213> ORGANISM: Artificial Sequence
<220> FEATURE:
<223> OTHER INFORMATION: GSG-T2A-AscI-yCD2 of pAC3-GSG-T2A-yCD2

<400> SEQUENCE: 41

```
ggaagcggag agggcagagg aagtcttcta acatgcggtg acgtggagga gaatcccggc      60
cctggcgcgc ctatggtgac cggcggcatg gcctccaagt gggatcaaaa gggcatggat     120
atcgcttacg aggaggccct gctgggctac aaggagggcg gcgtgcctat cggcggctgt     180
ctgatcaaca acaaggacgg cagtgtgctg gcaggggcc  acaacatgag gttccagaag     240
ggctccgcca ccctgcacgg cgagatctcc accctggaga actgtggcag gctggagggc     300
aaggtgtaca aggacaccac cctgtacacc accctgtccc cttgtgacat gtgtaccggc     360
gctatcatca tgtacggcat ccctaggtgt gtgatcggcg agaacgtgaa cttcaagtcc     420
aagggcgaga agtacctgca aaccaggggc cacgaggtgg tggttgttga cgatgagagg     480
tgtaagaagc tgatgaagca gttcatcgac gagaggcctc aggactggtt cgaggatatc     540
ggcgagtaag cggccgc                                                    557
```

<210> SEQ ID NO 42
<211> LENGTH: 560
<212> TYPE: DNA
<213> ORGANISM: Artificial Sequence
<220> FEATURE:
<223> OTHER INFORMATION: GSG-P2A-AscI-yCD2 of pAC3-GSG-P2A-yCD2

<400> SEQUENCE: 42

```
ggaagcggag ctactaactt cagcctgctg aagcaggctg agacgtgga  ggagaaccct      60
ggacctggcg cgcctatggt gaccggcggc atggcctcca gtgggatca  aaagggcatg     120
gatatcgctt acgaggaggc cctgctgggc tacaaggagg gcggcgtgcc tatcggcggc     180
```

| | |
|---|---|
| tgtctgatca acaacaagga cggcagtgtg ctgggcaggg gccacaacat gaggttccag | 240 |
| aagggctccg ccaccctgca cggcgagatc tccaccctgg agaactgtgg caggctggag | 300 |
| ggcaaggtgt acaaggacac caccctgtac accaccctgt ccccttgtga catgtgtacc | 360 |
| ggcgctatca tcatgtacgg catccctagg tgtgtgatcg gcgagaacgt gaacttcaag | 420 |
| tccaagggcg agaagtacct gcaaaccagg ggccacgagg tggtggttgt tgacgatgag | 480 |
| aggtgtaaga agctgatgaa gcagttcatc gacgagaggc ctcaggactg gttcgaggat | 540 |
| atcggcgagt aagcggccgc | 560 |

<210> SEQ ID NO 43
<211> LENGTH: 11642
<212> TYPE: DNA
<213> ORGANISM: Artificial Sequence
<220> FEATURE:
<223> OTHER INFORMATION: pAC3-T2A-GFPm

<400> SEQUENCE: 43

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta acaactccgc cccattgacg caaatgggcg gtaggcgtgt | 540 |
| acggtgggag gtctatataa gcagagctgg tttagtgaac cggcgccagt cctccgattg | 600 |
| actgagtcgc ccgggtaccc gtgtatccaa taaaccctct tgcagttgca tccgacttgt | 660 |
| ggtctcgctg ttccttggga gggtctcctc tgagtgattg actaccgtc agcggggtc | 720 |
| tttcatttgg ggctcgtcc gggatcggga accctgcc cagggaccac cgacccacca | 780 |
| ccgggaggta agctggccag caacttatct gtgtctgtcc gattgtctag tgtctatgac | 840 |
| tgattttatg cgcctgcgtc ggtactagtt agctaactag ctctgtatct ggcggacccg | 900 |
| tggtggaact gacgagttcg gaacacccgg ccgcaaccct gggagacgtc cagggactt | 960 |
| cggggggccgt ttttgtggcc cgacctgagt ccaaaaatcc cgatcgtttt ggactctttg | 1020 |
| gtgcaccccc cttagaggag ggatatgtgg ttctggtagg agacgagaac ctaaaacagt | 1080 |
| tcccgcctcc gtctgaattt ttgctttcgg tttgggaccg aagccgcgcc gcgcgtcttg | 1140 |
| tctgctgcag catcgttctg tgttgtctct gtctgactgt gtttctgtat ttgtctgaga | 1200 |
| atatgggcca gactgttacc actcccttaa gtttgacctt aggtcactgg aaagatgtcg | 1260 |
| agcggatcgc tcacaaccag tcggtagatg tcaagaagag acgttgggtt accttctgct | 1320 |
| ctgcagaatg gccaaccttt aacgtcggat ggccgcgaga cggcaccttt aaccgagacc | 1380 |
| tcatcaccca ggttaagatc aaggtctttt cacctggccc gcatggacac ccagaccagg | 1440 |
| tccccctacat cgtgacctgg gaagccttgg cttttgaccc cctccctggg tcaagccct | 1500 |
| ttgtacaccc taagcctccg cctcctcttc ctccatccgc cccgtctctc cccttgaac | 1560 |
| ctcctcgttc gaccccgcct cgatcctccc tttatccagc cctcactcct tctctaggcg | 1620 |
| ccaaacctaa acctcaagtt ctttctgaca gtggggggcc gctcatcgac ctacttacag | 1680 |

```
aagaccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttcttttct gaagatccag gtaaactgac agctctgatc gagtctgttc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa atcctggac   2940 ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagccctg caagtgttga   3180 ccctaaatat agaagatgag catcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagcccac atacagagac   3420 tgttggacca gggaatactg gtaccctgcc agtcccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc cttttttctgc ctgagactcc   3660 accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaaccta gggaacctcg ggtatcgggc ctcggccaag aaagcccaaa   3960
tttgccagaa acaggtcaag tatctggggt atcttctaaa agagggtcag agatggctga   4020
```

```
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gcccttt gaa ctctttgtcg acgagaagca gggctacgcc aaaggtgtcc    4320
taacgcaaaa actgggacct tggcgtcggc cggtggccta cctgtccaaa agctagacc     4380 cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca gcggcccga aaggcagcca    5160 tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagttttat agataccttt tctggctgga    5640
tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atgcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccaccg ccctcaaagt agacggcatc gcagcttgga    6300
tacacgccgc ccacgtgaag gctgccgacc ccggggtgg accatcctct agactgacat    6360
ggcgcgttca acgctctcaa aaccccctca agataagatt aacccgtgga agcccttaat    6420
```

```
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcaggag    6660 acagcggacc cggacttttg acttttacgt gtgccctggg cataccgtaa agtcggggtg    6720
tgggggacca ggagagggct actgtggtaa atggggggtgt gaaaccaccg gacaggctta    6780
ctggaagccc acatcatcgt gggacctaat ctcccttaag cgcggtaaca ccccctggga    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accgacagg    7020 aacagatcct attaccatgt tctccctgac ccggcaggtc cttaatgtgg gaccccgagt    7080
ccccataggg cccaacccag tattacccga ccaaagactc ccttcctcac caatagagat    7140
tgtaccggct ccacagccac ctagcccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatatataaaa gagagccagt    7740 atcattgacc ctgcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagatg ttgtttttat gcagaccaca cggggctagt    8040
gagagacagc atggccaaat taagagaaag gcttaatcag agacaaaaaac tatttgagac    8100 aggccaagga tggttcgaag ggctgtttaa tagatccccc tggttttacca ccttaatctc    8160 caccatcatg ggacctctaa tagtactctt actgatctta ctctttggac cttgcattct    8220
caatcgattg gtccaatttg ttaaagacag atctcagtg gtccaggctc tggttttgac    8280
tcagcaatat caccagctaa aacccataga gtacgagcca gagggcagag aagtcttct    8340 aacatgcggt gacgtggagg agaatccggg ccctggggcg cctatggcca gcaagggcga    8400
ggagctgttc accggggtgg tgcccatcct ggtcgagctg gacggcgacg taaacggcca    8460
caagttcagc gtgtccggcg aaggagaggg cgatgccacc tacggcaagc tgaccctgaa    8520
gttcatctgc accaccggca agctgcccgt gccctggccc acccctgtga ccaccttgac    8580
ctacggcgtg cagtgcttcg cccgctaccc cgaccacatg aagcagcacg acttcttcaa    8640
gtccgccatg cccgaaggct acgtccagga gcgcaccatc ttcttcaagg acgacggcaa    8700
ctacaagacc cgcgccgagg tgaagttcga gggcgacacc ctggtgaacc gcatcgagct    8760
```

-continued

```
gaagggcatc gacttcaagg aggacggcaa catcctgggg cacaagctgg agtacaacta    8820
caacagccac aaggtctata tcaccgccga caagcagaag aacggcatca aggtgaactt    8880
caagacccgc cacaacatcg aggacggcag cgtgcagctc gccgaccact accagcagaa    8940
cacccccatc ggcgacggcc ccgtgctgct gcccgacaac cactacctga gcacccagtc    9000
cgccctgagc aaagacccca acgagaagcg cgatcacatg gtcctgctgg agttcgtgac    9060
cgccgccggg atcactctcg gcatggacga gctgtacaag tgtgcggccg cagataaaat    9120
aaaagatttt atttagtctc cagaaaaagg ggggaatgaa agacccacc tgtaggtttg    9180 gcaagctagc ttaagtaacg ccattttgca aggcatggaa aatacataa ctgagaatag    9240 agaagttcag atcaaggtca ggaacagatg gaacagctga atatgggcca aacaggatat    9300
ctgtggtaag cagttcctgc cccggctcag ggccaagaac agatggaaca gctgaatatg    9360
ggccaaacag gatatctgtg gtaagcagtt cctgccccgg ctcagggcca agaacagatg    9420
gtccccagat gcggtccagc cctcagcagt ttctagagaa ccatcagatg tttccagggt    9480
gccccaagga cctgaaatga ccctgtgcct tatttgaact aaccaatcag ttcgcttctc    9540
gcttctgttc gcgcgcttct gctccccgag ctcaataaaa gagcccacaa cccctcactc    9600
ggggcgccag tcctccgatt gactgagtcg cccgggtacc cgtgtatcca ataaaccctc    9660
ttgcagttgc atccgacttg tggtctcgct gttccttggg agggtctcct ctgagtgatt    9720 gactaccgt cagcggggt cttcattac atgtgagcaa aaggccagca aaggccagg    9780 aaccgtaaaa aggccgcgtt gctggcgttt ttccataggc tccgccccc tgacgagcat    9840 cacaaaaatc gacgctcaag tcagaggtgg cgaaaccga caggactata agataccag    9900 gcgtttcccc ctggaagctc cctcgtgcgc tctcctgttc cgaccctgcc gcttaccgga    9960
tacctgtccg cctttctccc ttcgggaagc gtggcgcttt ctcaatgctc acgctgtagg   10020
tatctcagtt cggtgtaggt cgttcgctcc aagctgggct gtgtgcacga accccccgtt   10080
cagcccgacc gctgcgcctt atccggtaac tatcgtcttg agtccaaccc ggtaagacac   10140
gacttatcgc cactggcagc agccactggt aacaggatta gcagagcgag gtatgtaggc   10200
ggtgctacag agttcttgaa gtggtggcct aactacggct acactagaag gacagtattt   10260
ggtatctgcg ctctgctgaa gccagttacc ttcggaaaaa gagttggtag ctcttgatcc   10320
ggcaaacaaa ccaccgctgg tagcggtggt ttttttgttt gcaagcagca gattacgcgc   10380
agaaaaaaag gatctcaaga agatcctttg atcttttcta cggggtctga cgctcagtgg   10440
aacgaaaact cacgttaagg gattttggtc atgagattat caaaaaggat cttcacctag   10500
atccttttaa attaaaaatg aagttttaaa tcaatctaaa gtatatatga gtaaacttgg   10560
tctgacagtt accaatgctt aatcagtgag gcacctatct cagcgatctg tctatttcgt   10620
tcatccatag ttgcctgact ccccgtcgtg tagataacta cgatacggga gggcttacca   10680
tctggcccca gtgctgcaat gataccgcga gacccacgct caccggctcc agatttatca   10740
gcaataaacc agccagccgg aagggccgag cgcagaagtg gtcctgcaac tttatccgcc   10800
tccatccagt ctattaattg ttgccgggaa gctagagtaa gtagttcgcc agttaatagt   10860
ttgcgcaacg ttgttgccat tgctgcaggc atcgtggtgt cacgctcgtc gtttggtatg   10920
gcttcattca gctccggttc ccaacgatca aggcgagtta catgatcccc catgttgtgc   10980
aaaaaagcgg ttagctcctt cggtcctccg atcgttgtca gaagtaagtt ggccgcagtg   11040
ttatcactca tggttatggc agcactgcat aattctctta ctgtcatgcc atccgtaaga   11100
tgcttttctg tgactggtga gtactcaacc aagtcattct gagaatagtg tatgcggcga   11160
```

```
ccgagttgct cttgcccggc gtcaacacgg gataataccg cgccacatag cagaacttta    11220
aaagtgctca tcattggaaa acgttcttcg gggcgaaaac tctcaaggat cttaccgctg    11280
ttgagatcca gttcgatgta acccactcgt gcacccaact gatcttcagc atcttttact    11340
ttcaccagcg tttctgggtg agcaaaaaca ggaaggcaaa atgccgcaaa aaagggaata    11400
agggcgacac ggaaatgttg aatactcata ctcttccttt ttcaatatta ttgaagcatt    11460
tatcagggtt attgtctcat gagcggatac atatttgaat gtatttagaa aaataaacaa    11520
ataggggttc cgcgcacatt tccccgaaaa gtgccacctg acgtctaaga aaccattatt    11580
atcatgacat taacctataa aaataggcgt atcacgaggc cctttcgtct tcaagaattc    11640
at                                                                  11642
```

<210> SEQ ID NO 44
<211> LENGTH: 11651
<212> TYPE: DNA
<213> ORGANISM: Artificial Sequence
<220> FEATURE:
<223> OTHER INFORMATION: pAC3-GSG-T2A-GFPm

<400> SEQUENCE: 44

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actacccgtc agcggggtc      720 tttcatttgg gggctcgtcc gggatcggga gaccctgcc cagggaccac cgacccacca      780
ccgggaggta agctggccag caacttatct gtgtctgtcc gattgtctag tgtctatgac     840
tgattttatg cgcctgcgtc ggtactagtt agctaactag ctctgtatct ggcggacccg     900
tggtggaact gacgagttcg gaacacccgg ccgcaaccct gggagacgtc cagggactt      960 cgggggccgt ttttgtggcc cgacctgagt ccaaaaatcc cgatcgtttt ggactctttg    1020
gtgcaccccc cttagaggag ggatatgtgg ttctggtagg agacgagaac ctaaaacagt    1080
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaga    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaaccttt aacgtcggat ggccgcgaga cggcaccttt aaccgagacc    1380
tcatcaccca ggttaagatc aaggtctttt cacctggccc gcatggacac ccagaccagg    1440
tcccctacat cgtgacctgg gaagccttgg cttttgaccc cctccctgg gtcaagccct    1500
```

-continued

```
ttgtacaccc taagcctccg cctcctcttc ctccatccgc cccgtctctc cccttgaac     1560 ctcctcgttc gacccccgcct cgatcctccc tttatccagc cctcactcct tctctaggcg    1620
ccaaacctaa acctcaagtt cttttctgaca gtggggggcc gctcatcgac ctacttacag    1680 aagaccccc gccttatagg gacccaagac cacccccttc cgacagggac ggaaatggtg     1740
gagaagcgac ccctgcggga gaggcaccgg accctcccc aatggcatct cgcctacgtg     1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttcttttct gaagatccag gtaaactgac agctctgatc gagtctgttc    1980
tcatcaccca tcagcccacc tgggacgact gtcagcagct gttggggact ctgctgaccg    2040
gagaagaaaa acaacgggtg ctcttagagg ctagaaaggc ggtgcgggc gatgatgggc     2100 gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc gggggcaac    2880 ccgtcacctt cctggtagat actggggccc aacactccgt gctgacccaa aatcctggac    2940
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gatttttcctc aggcctgggc ggaaaccggg ggcatgggac    3300
tggcagttcg ccaagctcct ctgatcatac ctctgaaagc aacctctacc cccgtgtcca    3360
taaaacaata cccccatgtca caagaagcca gactgggat caagccccac atacagagac    3420
tgttggacca gggaatactg gtaccctgcc agtcccctg gaacacgccc ctgctacccg     3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttttctgc ctgagactcc    3660 accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
```

```
gggccctgtt acaaaccctca gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg ggttgccag     4260 atttgactaa gcccctttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040 taaaagcccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatgctat aaatatcttc tagtttttat agatacctt tctggctgga    5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttgggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcacccct taccgagtcg    6180 gcgacacagt gtgggtccgc cgacaccaga ctaagaacct agaacctcgc tggaaaggac    6240
```

```
cttacacagt cctgctgacc acccccaccg ccctcaaagt agacggcatc gcagcttgga    6300
tacacgccgc ccacgtgaag gctgccgacc ccggggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggacttttg acttttacgt gtgccctggg cataccgtaa agtcggggtg    6720
tgggggacca ggagagggct actgtggtaa atgggggtgt gaaaccaccg gacaggctta    6780
ctggaagccc acatcatcgt gggacctaat ctcccttaag cgcggtaaca cccccctggga    6840 cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680 ctccccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat tgctattcc taaaggaggg    7980 aggtctctgc gcagccctaa agaagaatg ttgtttttat gcagaccaca cggggctagt    8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca ggaagcggag agggcagagg    8340
aagtcttcta acatgcggtg acgtggagga gaatcccggc cctggcgcgc ctatggccag    8400
caagggcgag gagctgttca ccggggtggt gcccatcctg gtcgagctgg acggcgacgt    8460
aaacggccac aagttcagcg tgtccggcga aggagagggc gatgccacct acggcaagct    8520
gaccctgaag ttcatctgca ccaccggcaa gctgcccgtg ccctggccca ccctcgtgac    8580
caccttgacc tacggcgtgc agtgcttcgc ccgctacccc gaccacatga agcagcacga    8640
```

```
cttcttcaag tccgccatgc ccgaaggcta cgtccaggag cgcaccatct tcttcaagga   8700
cgacggcaac tacaagaccc gcgccgaggt gaagttcgag ggcgacaccc tggtgaaccg   8760
catcgagctg aagggcatcg acttcaagga ggacggcaac atcctggggc acaagctgga   8820
gtacaactac aacagccaca aggtctatat caccgccgac aagcagaaga acggcatcaa   8880
ggtgaacttc aagacccgcc acaacatcga ggacggcagc gtgcagctcg ccgaccacta   8940
ccagcagaac ccccatcg cgacggccc cgtgctgctg cccgacaacc actacctgag   9000
cacccagtcc gccctgagca agacccccaa cgagaagcgc gatcacatgg tcctgctgga   9060
gttcgtgacc gccgccggga tcactctcgg catggacgag ctgtacaagt gtgcggccgc   9120
agataaaata aaagatttta tttagtctcc agaaaaaggg gggaatgaaa gacccccacct  9180
gtaggtttgg caagctagct taagtaacgc cattttgcaa ggcatggaaa atacataac   9240
tgagaataga aagttcaga tcaaggtcag gaacagatgg aacagctgaa tatgggccaa   9300
acaggatatc tgtggtaagc agttcctgcc ccggctcagg gccaagaaca gatggaacag   9360
ctgaatatgg gccaaacagg atatctgtgg taagcagttc ctgccccggc tcagggccaa   9420
gaacagatgt ccccagatg cggtccagcc ctcagcagtt tctagagaac catcagatgt   9480
ttccagggtg ccccaaggac ctgaaatgac cctgtgcctt atttgaacta accaatcagt   9540
tcgcttctcg cttctgttcg cgcgcttctg ctccccgagc tcaataaaag agcccacaac   9600
ccctcactcg gggcgccagt cctccgattg actgagtcgc ccgggtaccc gtgtatccaa   9660
taaaccctct tgcagttgca tccgacttgt ggtctcgctg ttccttggga gggtctcctc   9720
tgagtgattg actacccgtc agcgggggtc tttcattaca tgtgagcaaa aggccagcaa   9780
aaggccagga accgtaaaaa ggccgcgttg ctggcgtttt tccataggct ccgcccccct   9840
gacgagcatc acaaaaatcg acgctcaagt cagaggtggc gaaacccgac aggactataa   9900
agataccagg cgtttccccc tggaagctcc ctcgtgcgct ctcctgttcc gaccctgccg   9960
cttaccggat acctgtccgc ctttctccct tcgggaagcg tggcgctttc tcaatgctca  10020
cgctgtaggt atctcagttc ggtgtaggtc gttcgctcca agctgggctg tgtgcacgaa  10080
cccccgttc agcccgaccg ctgcgcctta tccggtaact atcgtcttga gtccaacccg  10140
gtaagacacg acttatcgcc actggcagca gccactggta acaggattag cagagcgagg  10200
tatgtaggcg gtgctacaga gttcttgaag tggtggccta actacggcta cactagaagg  10260
acagtatttg gtatctgcgc tctgctgaag ccagttacct tcggaaaaag agttggtagc  10320
tcttgatccg gcaaacaaac caccgctggt agcggtggtt tttttgtttg caagcagcag  10380
attacgcgca gaaaaaaagg atctcaagaa gatcctttga tcttttctac ggggtctgac  10440
gctcagtgga acgaaaactc acgttaaggg attttggtca tgagattatc aaaaaggatc  10500
ttcacctaga tccttttaaa ttaaaaatga agttttaaat caatctaaag tatatatgag  10560
taaacttggt ctgacagtta ccaatgctta atcagtgagg cacctatctc agcgatctgt  10620
ctatttcgtt catccatagt tgcctgactc cccgtcgtgt agataactac gatacgggag  10680
ggcttaccat ctggccccag tgctgcaatg ataccgcgag acccacgctc accggctcca  10740
gatttatcag caataaacca gccagccgga agggccgagc gcagaagtgg tcctgcaact  10800
ttatccgcct ccatccagtc tattaattgt tgccgggaag ctagagtaag tagttcgcca  10860
gttaatagtt tgcgcaacgt tgttgccatt gctgcaggca tcgtggtgtc acgctcgtcg  10920
tttggtatgg cttcattcag ctccggttcc caacgatcaa ggcgagttac atgatccccc  10980
```

```
atgttgtgca aaaaagcggt tagctccttc ggtcctccga tcgttgtcag aagtaagttg    11040
gccgcagtgt tatcactcat ggttatggca gcactgcata attctcttac tgtcatgcca    11100
tccgtaagat gcttttctgt gactggtgag tactcaacca agtcattctg agaatagtgt    11160
atgcggcgac cgagttgctc ttgcccggcg tcaacacggg ataataccgc gccacatagc    11220
agaactttaa aagtgctcat cattggaaaa cgttcttcgg ggcgaaaact ctcaaggatc    11280
ttaccgctgt tgagatccag ttcgatgtaa cccactcgtg cacccaactg atcttcagca    11340
tcttttactt tcaccagcgt ttctgggtga gcaaaaacag gaaggcaaaa tgccgcaaaa    11400
aagggaataa gggcgacacg gaaatgttga atactcatac tcttcctttt tcaatattat    11460
tgaagcattt atcagggtta ttgtctcatg agcggataca tatttgaatg tatttagaaa    11520
aataaacaaa taggggttcc gcgcacattt ccccgaaaag tgccacctga cgtctaagaa    11580
accattatta tcatgacatt aacctataaa aataggcgta tcacgaggcc ctttcgtctt    11640
caagaattca t                                                        11651

<210> SEQ ID NO 45
<211> LENGTH: 11645
<212> TYPE: DNA
<213> ORGANISM: Artificial Sequence
<220> FEATURE:
<223> OTHER INFORMATION: pAC3-P2A-GFPm

<400> SEQUENCE: 45
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta caactccgcc ccattgacg caaatgggcg gtaggcgtgt     540
acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actacccgtc agcgggggtc     720
tttcatttgg gggctcgtcc gggatcggga ccccctgcc cagggaccac cgacccacca     780 ccggaggta agctggccag caacttatct gtgtctgtcc gattgtctag tgtctatgac     840 tgatttatg cgcctgcgtc ggtactagtt agctaactag ctctgtatct ggcggacccg     900
tggtggaact gacgagttcg gaacacccgg ccgcaaccct gggagacgtc cagggactt     960 cgggggccgt ttttgtggcc cgacctgagt ccaaaaatcc cgatcgtttt ggactctttg    1020
gtgcaccccc cttagaggag ggatatgtgg ttctggtagg agacgagaac ctaaaacagt    1080
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaga    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaaccttt aacgtcggat ggccgcgaga cggcaccttt aaccgagacc    1380
```

```
tcatcaccca ggttaagatc aaggtctttt cacctggccc gcatggacac ccagaccagg    1440 tccccctacat cgtgacctgg gaagccttgg cttttgaccc ccctccctgg gtcaagccct    1500
ttgtacaccc taagcctccg cctcctcttc ctccatccgc ccgtctctc ccccttgaac     1560 ctcctcgttc gaccccgcct cgatcctccc tttatccagc cctcactcct tctctaggcg    1620
ccaaacctaa acctcaagtt cttttctgaca gtgggggcc gctcatcgac ctacttacag    1680 aagaccccc gccttatagg gacccaagac cacccccttc cgacagggac ggaaatggtg     1740
gagaagcgac ccctgcggga gaggcaccgg acccctcccc aatggcatct cgcctacgtg    1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttcttttttct gaagatccag gtaaactgac agctctgatc gagtctgttc    1980
tcatcaccca tcagcccacc tgggacgact gtcagcagct gttggggact ctgctgaccg    2040
gagaagaaaa acaacggtg ctcttagagg ctagaaaggc ggtgcggggc gatgatgggc     2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc cccctgaac ccaggataac cctcaaagtc ggggggcaac     2880
ccgtcacctt cctggtagat actggggccc aacactccgt gctgacccaa aatcctggac    2940
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagccccac atacagagac    3420
tgttggacca gggaatactg gtaccctgcc agtcccctg gaacacgccc ctgctacccg     3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgctttgatt taaaggatgc cttttttctgc ctgagactcc    3660 accccaccag tcagcctctc ttcgcctttg agtggagaga tccagagatg ggaatctcag    3720
```

```
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaaccta gggaacctcg ggtatcgggc ctcggccaag aaagcccaaa     3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gcccttttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cggacatcc gctcagcggg     4860 ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580 agccccggatt gtatggctat aaatatcttc tagtttttat agatacctt tctggctgga   5640 tagaagccct cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
```

```
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt agacggcatc gcagcttgga    6300
tacacgccgc ccacgtgaag gctgccgacc ccggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttg acttttacgt gtgccctggg cataccgtaa agtcggggtg    6720
tgggggacca ggagagggct actgtggtaa atggggtgt gaaaccaccg gacaggctta    6780
ctggaagccc acatcatcgt gggacctaat ctcccttaag cgcggtaaca cccctgggga    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg gaccccgagt    7080
ccccataggg cccaacccag tattacccga ccaaagactc ccttcctcac caatagagat    7140
tgtaccggct ccacagccac ctagcccect caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgaccte    7920 gttgtctgaa gtagtcctac agaaccgcag aggcctagat tgctattcc taaggagggg    7980 aggtctctgc gcagccctaa agaagaatg ttgtttttat gcagaccaca cggggctagt    8040
gagagacagc atggccaaat taagagaaag gcttaatcag agacaaaaac tatttgagac    8100
aggccaagga tggttcgaag gctgttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca gctactaact tcagcctgct    8340
gaagcaggct ggagacgtgg aggagaaccc tggacctggc gcgccatgg ccagcaaggg    8400 cgaggagctg ttcaccgggg tggtgcccat cctggtcgag ctggacggcg acgtaaacgg    8460
```

```
ccacaagttc agcgtgtccg gcgaaggaga gggcgatgcc acctacggca agctgaccct   8520
gaagttcatc tgcaccaccg gcaagctgcc cgtgccctgg cccaccctcg tgaccacctt   8580
gacctacggc gtgcagtgct tcgcccgcta ccccgaccac atgaagcagc acgacttctt   8640
caagtccgcc atgcccgaag gctacgtcca ggagcgcacc atcttcttca aggacgacgg   8700
caactacaag acccgcgccg aggtgaagtt cgagggcgac accctggtga accgcatcga   8760
gctgaagggc atcgacttca aggaggacgg caacatcctg gggcacaagc tggagtacaa   8820
ctacaacagc cacaaggtct atatcaccgc cgacaagcag aagaacggca tcaaggtgaa   8880
cttcaagacc cgccacaaca tcgaggacgg cagcgtgcag ctcgccgacc actaccagca   8940
gaacaccccc atcggcgacg gccccgtgct gctgcccgac aaccactacc tgagcaccca   9000
gtccgccctg agcaaagacc ccaacgagaa gcgcgatcac atggtcctgc tggagttcgt   9060
gaccgccgcc gggatcactc tcggcatgga cgagctgtac aagtgtgcgg ccgcagataa   9120
aataaaagat tttatttagt ctccagaaaa aggggggaat gaaagacccc acctgtaggt   9180
ttggcaagct agcttaagta acgccatttt gcaaggcatg gaaaaataca taactgagaa   9240
tagagaagtt cagatcaagg tcaggaacag atggaacagc tgaatatggg ccaaacagga   9300
tatctgtggt aagcagttcc tgccccggct cagggccaag aacagatgga cagctgaat   9360
atgggccaaa caggatatct gtggtaagca gttcctgccc cggctcaggg ccaagaacag   9420
atggtcccca gatgcggtcc agccctcagc agtttctaga accatcag atgtttccag    9480
ggtgccccaa ggacctgaaa tgaccctgtg ccttatttga actaaccaat cagttcgctt   9540
ctcgcttctg ttcgcgcgct tctgctcccc gagctcaata aaagagccca aacccctca   9600
ctcggggcgc cagtcctccg attgactgag tcgcccgggt accgtgtat ccaataaacc    9660
ctcttgcagt tgcatccgac ttgtggtctc gctgttcctt ggagggtct cctctgagtg    9720
attgactacc cgtcagcggg ggtctttcat tacatgtgag caaaaggcca gcaaaaggcc   9780
aggaaccgta aaaaggccgc gttgctggcg ttttttccata ggctccgccc cctgacgag   9840
catcacaaaa atcgacgctc aagtcagagg tggcgaaacc cgacaggact ataaagatac   9900
caggcgtttc cccctggaag ctccctcgtg cgctctcctg ttccgaccct gccgcttacc   9960
ggatacctgt ccgcctttct cccttcggga agcgtggcgc tttctcaatg ctcacgctgt  10020
aggtatctca gttcggtgta ggtcgttcgc tccaagctgg gctgtgtgca cgaaccccc   10080
gttcagcccg accgctgcgc cttatccggt aactatcgtc ttgagtccaa cccggtaaga  10140
cacgacttat cgccactggc agcagccact ggtaacagga ttagcagagc gaggtatgta  10200
ggcggtgcta cagagttctt gaagtggtgg cctaactacg gctacactag aaggacagta  10260
tttggtatct gcgctctgct gaagccagtt accttcggaa aaagagttgg tagctcttga  10320
tccggcaaac aaaccaccgc tggtagcggt ggtttttttg tttgcaagca gcagattacg  10380
cgcagaaaaa aaggatctca agaagatcct ttgatctttt ctacgggggtc tgacgctcag  10440
tggaacgaaa actcacgtta agggattttg gtcatgagat tatcaaaaag gatcttcacc  10500
tagatccttt taaattaaaa atgaagtttt aaatcaatct aaagtatata tgagtaaact  10560
tggtctgaca gttaccaatg cttaatcagt gaggcaccta tctcagcgat ctgtctattt  10620
cgttcatcca tagttgcctg actccccgtc gtgtagataa ctacgatacg ggagggctta  10680
ccatctggcc ccagtgctgc aatgatacccg cgagacccac gctcaccggc tccagattta  10740
tcagcaataa accagccagc cggaagggcc gagcgcagaa gtggtcctgc aactttatcc  10800
gcctccatcc agtctattaa ttgttgccgg gaagctagag taagtagttc gccagttaat  10860
```

```
agtttgcgca acgttgttgc cattgctgca ggcatcgtgg tgtcacgctc gtcgtttggt     10920
atggcttcat tcagctccgg ttcccaacga tcaaggcgag ttacatgatc ccccatgttt     10980
tgcaaaaaag cggttagctc cttcggtcct ccgatcgttg tcagaagtaa gttggccgca     11040
gtgttatcac tcatggttat ggcagcactg cataattctc ttactgtcat gccatccgta     11100
agatgctttt ctgtgactgg tgagtactca accaagtcat tctgagaata gtgtatgcgg     11160
cgaccgagtt gctcttgccc ggcgtcaaca cgggataata ccgcgccaca tagcagaact     11220
ttaaaagtgc tcatcattgg aaaacgttct cggggcgaaa actctcaag gatcttaccg      11280 ctgttgagat ccagttcgat gtaacccact cgtgcaccca actgatcttc agcatctttt     11340
actttcacca gcgtttctgg gtgagcaaaa acaggaaggc aaaatgccgc aaaaaaggga     11400
ataagggcga cacggaaatg ttgaatactc atactcttcc ttttcaata ttattgaagc      11460 atttatcagg gttattgtct catgagcgga tacatatttg aatgtattta gaaaaataaa     11520 caaataggg ttccgcgcac atttccccga aaagtgccac ctgacgtcta agaaaccatt      11580
attatcatga cattaaccta taaaaatagg cgtatcacga ggccctttcg tcttcaagaa     11640
ttcat                                                                 11645

<210> SEQ ID NO 46
<211> LENGTH: 11654
<212> TYPE: DNA
<213> ORGANISM: Artificial Sequence
<220> FEATURE:
<223> OTHER INFORMATION: pAC3-GSG-P2A-GFPm

<400> SEQUENCE: 46
tagttattaa tagtaatcaa ttacggggtc attagttcat agcccatata tggagttccg       60
cgttacataa cttacggtaa atggcccgcc tggctgaccg cccaacgacc cccgcccatt      120
gacgtcaata atgacgtatg ttcccatagt aacgccaata gggactttcc attgacgtca      180
atgggtggag tatttacggt aaactgccca cttggcagta catcaagtgt atcatatgcc      240
aagtacgccc cctattgacg tcaatgacgg taaatggccc gcctggcatt atgcccagta      300
catgacctta tgggactttc ctacttggca gtacatctac gtattagtca tcgctattac      360
catggtgatg cggttttggc agtacatcaa tgggcgtgga tagcggtttg actcacgggg      420
atttccaagt ctccacccca ttgacgtcaa tgggagtttg ttttggcacc aaaatcaacg      480
ggactttcca aaatgtcgta acaactccgc cccattgacg caaatgggcg gtaggcgtgt      540
acggtgggag gtctatataa gcagagctgg tttagtgaac cggcgccagt cctccgattg      600
actgagtcgc ccgggtaccc gtgtatccaa taaaccctct tgcagttgca tccgacttgt      660
ggtctcgctg ttccttggga gggtctcctc tgagtgattg actacccgtc agcgggggtc      720
tttcatttgg ggctcgtcc gggatcggga ccccctgcc cagggaccac cgacccacca       780 ccggaggta agctggccag caacttatct gtgtctgtcc gattgtctag tgtctatgac      840
tgattttatg cgcctgcgtc ggtactagtt agctaactag ctctgtatct ggcggacccg      900
tggtggaact gacgagttcg gaacacccgg ccgcaaccct gggagacgtc cagggactt      960 cgggggccgt ttttgtggcc cgacctgagt ccaaaaatcc cgatcgtttt ggactctttg     1020
gtgcaccccc cttagaggag ggatatgtgg ttctggtagg agacgagaac ctaaaacagt     1080
tcccgcctcc gtctgaattt ttgctttcgg tttgggaccg aagccgcgcc gcgcgtcttg     1140
tctgctgcag catcgttctg tgttgtctct gtctgactgt gtttctgtat ttgtctgaga     1200
```

```
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaacctttt aacgtcggat ggccgcgaga cggcacctttt aaccgagacc    1380 tcatcaccca ggttaagatc aaggtctttt cacctggccc gcatggacac ccagaccagg    1440 tccctacat cgtgacctgg gaagccttgg cttttgaccc cctccctgg gtcaagccct    1500 ttgtacaccc taagcctccg cctcctcttc tccatccgc cccgtctctc cccttgaac    1560 ctcctcgttc gaccccgcct cgatcctccc tttatccagc cctcactcct tctctaggcg    1620
ccaaacctaa acctcaagtt ctttctgaca gtgggggggcc gctcatcgac ctacttacag    1680 aagaccccccc gccttatagg gacccaagac caccccctttc cgacagggac ggaaatggtg    1740
gagaagcgac ccctgcggga gaggcaccgg acccctcccc aatggcatct cgcctacgtg    1800
ggagacggga gcccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttcttttttct gaagatccag gtaaactgac agctctgatc gagtctgttc    1980
tcatcaccca tcagcccacc tgggacgact gtcagcagct gttggggact ctgctgaccg    2040
gagaagaaaa acaacggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta cgccagttg ctcctagcgg    2220 gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460 ttggagatt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc gggggggcaac    2880 ccgtcacctt cctggtagat actggggccc aacactccgt gctgacccaa atcctggac    2940 ccctaagtga taagtctgcc tgggtccaag ggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagccccac atacagagac    3420
tgttggacca gggaatactg gtaccctgcc agtcccctg gaacacgccc tgctacccg    3480 ttaagaaacc agggactaat gattataggc ctgtccagga tctgagagaa gtcaacaagc    3540
gggtggaaga catccacccc accgtgccca accttacaa cctcttgagc gggctcccac    3600
```

```
cgtcccacca gtggtacact gtgcttgatt taaaggatgc cttttctgc ctgagactcc      3660 acccccaccag tcagcctctc ttcgcctttg agtggagaga tccagagatg ggaatctcag    3720
gacaattgac ctggaccaga ctcccacagg gtttcaaaaa cagtcccacc ctgtttgatg     3780
aggcactgca cagagaccta gcagacttcc ggatccagca cccagacttg atcctgctac     3840
agtacgtgga tgacttactg ctggccgcca cttctgagct agactgccaa caaggtactc     3900
gggccctgtt acaaaccta gggaacctcg ggtatcgggc ctcggccaag aaagcccaaa      3960
tttgccagaa acaggtcaag tatctggggt atcttctaaa agagggtcag agatggctga     4020
ctgaggccag aaaagagact gtgatggggc agcctactcc gaagacccct cgacaactaa     4080
gggagttcct agggacggca ggcttctgtc gcctctggat ccctgggttt gcagaaatgg     4140
cagccccctt gtaccctctc accaaaacgg ggactctgtt taattggggc ccagaccaac     4200
aaaaggccta tcaagaaatc aagcaagctc ttctaactgc cccagccctg gggttgccag     4260
atttgactaa gcccttttgaa ctctttgtcg acgagaagca gggctacgcc aaaggtgtcc    4320
taacgcaaaa actgggacct tggcgtcggc cggtggccta cctgtccaaa aagctagacc     4380
cagtagcagc tgggtggccc ccttgcctac ggatggtagc agccattgcc gtactgacaa     4440
aggatgcagg caagctaacc atgggacagc cactagtcat tctggccccc catgcagtag     4500
aggcactagt caaacaaccc cccgaccgct ggctttccaa cgcccggatg actcactatc     4560
aggccttgct tttggacacg gaccgggtcc agttcggacc ggtggtagcc ctgaacccgg     4620
ctacgctgct cccactgcct gaggaagggc tgcaacacaa ctgccttgat atcctggccg     4680
aagcccacgg aacccgaccc gacctaacgg accagccgct cccagacgcc gaccacacct     4740
ggtacacgga tggaagcagt ctcttacaag agggacagcg taaggcggga gctgcggtga     4800
ccaccgagac cgaggtaatc tgggctaaag ccctgccagc cgggacatcc gctcagcggg     4860
ctgaactgat agcactcacc caggcccctaa agatggcaga aggtaagaag ctaaatgttt     4920
atactgatag ccgttatgct tttgctactg cccatatcca tggagaaata tacagaaggc     4980
gtgggttgct cacatcagaa ggcaaagaga tcaaaaataa agacgagatc ttggccctac     5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttttactt  5340 ttgaattatt agactttctt catcagctga ctcacctcag cttctcaaaa atgaaggctc     5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacctttt tctggctgga    5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttgggat tgattggaaa ttacattgtg      5820
catacagacc ccaaagctca ggccaggtag aaagaatgaa tagaaccatc aaggagactt    5880
taactaaatt aacgcttgca actggctcta gagactgggt gctcctactc cccttagccc    5940
```

```
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccaccg ccctcaaagt agacggcatc gcagcttgga    6300
tacacgccgc ccacgtgaag gctgccgacc ccggggtgg accatcctct agactgacat    6360
ggcgcgttca acgctctcaa aaccccctca agataagatt aacccgtgga agcccttaat    6420
agtcatggga gtcctgttag gagtagggat ggcagagagc cccatcagg tctttaatgt     6480 aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttg actttacgt gtgccctggg cataccgtaa agtcggggtg      6720
tgggggacca ggagagggct actgtggtaa atggggggtgt gaaaccaccg gacaggctta   6780
ctggaagccc acatcatcgt gggacctaat ctcccttaag cgcggtaaca cccctgggaa    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg gacccccgagt   7080 ccccataggg cccaacccag tattacccga ccaaagactc ccttcctcac caatagagat    7140
tgtaccggct ccacagccac ctagccccct caataccagt taccccccctt ccactaccag   7200 tacaccctca acctcccta caagtccaag tgtcccacag ccaccccag gaactggaga     7260 tagactacta gctctagtca aaggagccta tcaggcgctt aacctcacca atcccgacaa    7320
gacccaagaa tgttggctgt gcttagtgtc gggaccctcct tattacgaag gagtagcggt   7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggccccttc tactaggagg attaaccatg ggagggattg cagctggaat   7800
agggacgggg accactgcct taattaaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa agaagaatg ttgtttttat gcagaccaca cggggctagt     8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca ggaagcggag ctactaactt    8340
```

```
cagcctgctg aagcaggctg gagacgtgga ggagaaccct ggacctggcg cgcctatggc    8400
cagcaagggc gaggagctgt tcaccggggt ggtgcccatc ctggtcgagc tggacggcga    8460
cgtaaacggc cacaagttca gcgtgtccgg cgaaggagag ggcgatgcca cctacggcaa    8520
gctgaccctg aagttcatct gcaccaccgg caagctgccc gtgccctggc ccaccctcgt    8580
gaccaccttg acctacggcg tgcagtgctt cgcccgctac cccgaccaca tgaagcagca    8640
cgacttcttc aagtccgcca tgcccgaagg ctacgtccag gagcgcacca tcttcttcaa    8700
ggacgacggc aactacaaga cccgcgccga ggtgaagttc gagggcgaca ccctggtgaa    8760
ccgcatcgag ctgaagggca tcgacttcaa ggaggacggc aacatcctgg ggcacaagct    8820
ggagtacaac tacaacagcc acaaggtcta tatcaccgcc gacaagcaga agaacggcat    8880
caaggtgaac ttcaagaccc gccacaacat cgaggacggc agcgtgcagc tcgccgacca    8940
ctaccagcag aacacccca tcggcgacgg ccccgtgctg ctgcccgaca ccactacct    9000
gagcacccag tccgccctga gcaaagaccc aacgagaag cgcgatcaca tggtcctgct    9060
ggagttcgtg accgccgccg ggatcactct cggcatggac gagctgtaca agtgtgcggc    9120
cgcagataaa ataaaagatt ttatttagtc tccagaaaaa gggggaatg aaagacccca    9180
cctgtaggtt tggcaagcta gcttaagtaa cgccattttg caaggcatgg aaaaatacat    9240
aactgagaat agagaagttc agatcaaggt caggaacaga tggaacagct gaatatgggc    9300
caaacaggat atctgtggta agcagttcct gccccggctc agggccaaga acagatggaa    9360
cagctgaata tgggccaaac aggatatctg tggtaagcag ttcctgcccc ggctcagggc    9420
caagaacaga tggtccccag atgcggtcca gccctcagca gtttctagag aaccatcaga    9480
tgtttccagg gtgccccaag gacctgaaat gaccctgtgc cttatttgaa ctaaccaatc    9540
agttcgcttc tcgcttctgt tcgcgcgctt ctgctcccg agctcaataa aagagcccac    9600
aaccctcac tcggggcgcc agtcctccga ttgactgagt cgcccgggta cccgtgtatc    9660
caataaaccc tcttgcagtt gcatccgact tgtggtctcg ctgttccttg ggagggtctc    9720
ctctgagtga ttgactaccc gtcagcgggg gtctttcatt acatgtgagc aaaaggccag    9780
caaaaggcca ggaaccgtaa aaaggccgcg ttgctggcgt ttttccatag gctccgcccc    9840
cctgacgagc atcacaaaaa tcgacgctca gtcagaggt ggcgaaaccc gacaggacta    9900
taaagatacc aggcgtttcc ccctggaagc tccctcgtgc gctctcctgt tccgaccctg    9960
ccgcttaccg gatacctgtc cgcctttctc ccttcgggaa gcgtggcgct ttctcaatgc   10020
tcacgctgta ggtatctcag ttcggtgtag tcgttcgct ccaagctggg ctgtgtgcac   10080
gaaccccccg ttcagcccga ccgctgcgcc ttatccggta actatcgtct tgagtccaac   10140
ccggtaagac acgacttatc gccactggca gcagccactg gtaacaggat tagcagagcg   10200
aggtatgtag gcggtgctac agagttcttg aagtggtggc ctaactacgg ctacactaga   10260
aggacagtat ttggtatctg cgctctgctg aagccagtta ccttcggaaa aagagttggt   10320
agctcttgat ccggcaaaca aaccaccgct ggtagcggtg gttttttgt ttgcaagcag   10380
cagattacgc gcagaaaaaa aggatctcaa gaagatcctt tgatctttc tacggggtct   10440
gacgctcagt ggaacgaaaa ctcacgttaa gggattttgg tcatgagatt atcaaaaagg   10500
atcttcacct agatcctttt aaattaaaaa tgaagtttta atcaatcta agtatatat   10560
gagtaaactt ggtctgacag ttaccaatgc ttaatcagtg aggcacctat ctcagcgatc   10620
tgtctatttc gttcatccat agttgcctga ctccccgtcg tgtagataac tacgatacgg   10680
```

```
gagggcttac catctggccc cagtgctgca atgataccgc gagacccacg ctcaccggct    10740
ccagatttat cagcaataaa ccagccagcc ggaagggccg agcgcagaag tggtcctgca    10800
actttatccg cctccatcca gtctattaat tgttgccggg aagctagagt aagtagttcg    10860
ccagttaata gtttgcgcaa cgttgttgcc attgctgcag gcatcgtggt gtcacgctcg    10920
tcgtttggta tggcttcatt cagctccggt tcccaacgat caaggcgagt tacatgatcc    10980
cccatgttgt gcaaaaaagc ggttagctcc ttcggtcctc cgatcgttgt cagaagtaag    11040
ttggccgcag tgttatcact catggttatg gcagcactgc ataattctct tactgtcatg    11100
ccatccgtaa gatgcttttc tgtgactggt gagtactcaa ccaagtcatt ctgagaatag    11160
tgtatgcggc gaccgagttg ctcttgcccg gcgtcaacac gggataatac cgcgccacat    11220
agcagaactt taaaagtgct catcattgga aaacgttctt cggggcgaaa actctcaagg    11280
atcttaccgc tgttgagatc cagttcgatg taacccactc gtgcacccaa ctgatcttca    11340
gcatctttta ctttcaccag cgtttctggg tgagcaaaaa caggaaggca aaatgccgca    11400
aaaaagggaa taagggcgac acggaaatgt tgaatactca tactcttcct ttttcaatat    11460
tattgaagca tttatcaggg ttattgtctc atgagcggat acatatttga atgtatttag    11520
aaaaataaac aaataggggt tccgcgcaca tttccccgaa aagtgccacc tgacgtctaa    11580
gaaaccatta ttatcatgac attaacctat aaaaataggc gtatcacgag gccctttcgt    11640
cttcaagaat tcat                                                     11654

<210> SEQ ID NO 47
<211> LENGTH: 11648
<212> TYPE: DNA
<213> ORGANISM: Artificial Sequence
<220> FEATURE:
<223> OTHER INFORMATION: pAC3-E2A-GFP

<400> SEQUENCE: 47
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta caactccgcc ccattgacg caaatgggcg gtaggcgtgt     540
acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actacccgtc agcgggggtc     720
tttcatttgg ggctcgtcc gggatcggga gaccctgcc cagggaccac cgacccacca     780 ccggaggta agctggccag caacttatct gtgtctgtcc gattgtctag tgtctatgac     840
tgattttatg cgcctgcgtc ggtactagtt agctaactag ctctgtatct ggcggacccg     900
tggtggaact gacgagttcg gaacacccgg ccgcaaccct gggagacgtc cagggactt     960 cgggggccgt ttttgtggcc cgacctgagt ccaaaaatcc cgatcgtttt ggactctttg    1020
gtgcaccccc cttagaggag ggatatgtgg ttctggtagg agacgagaac ctaaaacagt    1080
```

```
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaga    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaaccttt aacgtcggat ggccgcgaga cggcacctttt aaccgagacc    1380 tcatcaccca ggttaagatc aaggtctttt cacctggccc gcatggacac ccagaccagg    1440 tccctacat cgtgacctgg gaagccttgg cttttgaccc ccctccctgg gtcaagccct     1500
ttgtacaccc taagcctccg cctcctcttc tccatccgc cccgtctctc cccttgaac      1560 ctcctcgttc gaccccgcct cgatcctccc tttatccagc cctcactcct tctctaggcg    1620
ccaaacctaa acctcaagtt ctttctgaca gtggggggcc gctcatcgac ctacttacag    1680 aagaccccc gccttatagg acccaagac caccccttc cgacagggac ggaaatggtg       1740
gagaagcgac ccctgcggga gaggcaccgg acccctcccc aatggcatct cgcctacgtg    1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttcttttttct gaagatccag gtaaactgac agctctgatc gagtctgttc   1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc gggggcaac     2880 ccgtcaccttt cctggtagat actggggccc aacactccgt gctgacccaa atcctggac    2940 ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactgggat caagcccac atacagagac    3420
```

| | |
|---|---|
| tgttggacca gggaatactg gtaccctgcc agtcccctg gaacacgccc ctgctacccg | 3480 |
| ttaagaaacc agggactaat gattataggc ctgtccagga tctgagagaa gtcaacaagc | 3540 |
| gggtggaaga catccacccc accgtgccca acccttacaa cctcttgagc gggctcccac | 3600 |
| cgtcccacca gtggtacact gtgcttgatt taaaggatgc cttttttctgc ctgagactcc | 3660 |
| accccaccag tcagcctctc ttcgcctttg agtggagaga tccagagatg ggaatctcag | 3720 |
| gacaattgac ctggaccaga ctcccacagg gtttcaaaaa cagtcccacc ctgtttgatg | 3780 |
| aggcactgca cagagaccta gcagacttcc ggatccagca cccagacttg atcctgctac | 3840 |
| agtacgtgga tgacttactg ctggccgcca cttctgagct agactgccaa caaggtactc | 3900 |
| gggccctgtt acaaacccta gggaacctcg ggtatcgggc ctcggccaag aaagcccaaa | 3960 |
| tttgccagaa acaggtcaag tatctggggt atcttctaaa agagggtcag agatggctga | 4020 |
| ctgaggccag aaaagagact gtgatggggc agcctactcc gaagacccct cgacaactaa | 4080 |
| gggagttcct agggacggca ggcttctgtc gcctctggat ccctgggttt gcagaaatgg | 4140 |
| cagcccccct gtaccctctc accaaaacgg ggactctgtt taattggggc ccagaccaac | 4200 |
| aaaaggccta tcaagaaatc aagcaagctc ttctaactgc cccagccctg gggttgccag | 4260 |
| atttgactaa gcccttgtaa ctctttgtcg acgagaagcg gggctacgcc aaaggtgtcc | 4320 |
| taacgcaaaa actgggaacct tggcgtcggc cggtggccta cctgtccaaa aagctagacc | 4380 |
| cagtagcagc tgggtggccc ccttgcctac ggatggtagc agccattgcc gtactgacaa | 4440 |
| aggatgcagg caagctaacc atgggacagc cactagtcat tctggccccc catgcagtag | 4500 |
| aggcactagt caaacaaccc cccgaccgct ggctttccaa cgcccggatg actcactatc | 4560 |
| aggccttgct tttggacacg gaccgggtcc agttcggacc ggtggtagcc ctgaacccgg | 4620 |
| ctacgctgct cccactgcct gaggaagggc tgcaacacaa ctgccttgat atcctggccg | 4680 |
| aagcccacgg aacccgaccc gacctaacgg accagccgct cccagacgcc gaccacacct | 4740 |
| ggtacacgga tggaagcagt ctcttacaag agggacagcg taaggcggga gctgcggtga | 4800 |
| ccaccgagac cgaggtaatc tgggctaaag ccctgccagc cgggacatcc gctcagcggg | 4860 |
| ctgaactgat agcactcacc caggcccctaa agatggcaga aggtaagaag ctaaatgttt | 4920 |
| atactgatag ccgttatgct tttgctactg cccatatcca tggagaaata tacagaaggc | 4980 |
| gtgggttgct cacatcagaa ggcaaagaga tcaaaaataa agacgagatc ttggccctac | 5040 |
| taaaagccct ctttctgccc aaaagactta gcataatcca ttgtccagga catcaaaagg | 5100 |
| gacacagcgc cgaggctaga ggcaaccgga tggctgacca gcggcccga aaggcagcca | 5160 |
| tcacagagac tccagacacc tctaccctcc tcatagaaaa ttcatcaccc tacacctcag | 5220 |
| aacattttca ttacacagtg actgatataa aggacctaac caagttgggg gccatttatg | 5280 |
| ataaaacaaa gaagtattgg gtctaccaag gaaaacctgt gatgcctgac cagtttactt | 5340 |
| ttgaattatt agactttctt catcagctga ctcacctcag cttctcaaaa atgaaggctc | 5400 |
| tcctagagag aagccacagt ccctactaca tgctgaaccg ggatcgaaca ctcaaaaata | 5460 |
| tcactgagac ctgcaaagct tgtgcacaag tcaacgccag caagtctgcc gttaaacagg | 5520 |
| gaactagggt ccgcgggcat cggcccgca ctcattggga gatcgatttc accgagataa | 5580 |
| agcccggatt gtatggctat aaatatcttc tagttttat agatacctttt ctggctgga | 5640 |
| tagaagcctt cccaaccaag aaagaaaccg ccaaggtcgt aaccaagaag ctactagagg | 5700 |
| agatcttccc caggttcggc atgcctcagg tattgggaac tgacaatggg cctgccttcg | 5760 |
| tctccaaggt gagtcagaca gtggccgatc tgttggggat tgattggaaa ttacattgtg | 5820 |

```
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000 gggcacccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt gacggcatc gcagcttgga    6300 tacacgccgc ccacgtgaag gctgccgacc ccggggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggacttttg acttttacgt gtgccctggg cataccgtaa agtcggggtg    6720
tgggggacca ggagagggct actgtggtaa atgggggtgt gaaaccaccg gacaggctta    6780
ctggaagccc acatcatcgt gggacctaat ctcccttaag cgcggtaaca cccctgggta    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accgacagg    7020 aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaaa ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa agaagaatg ttgttttat gcagaccaca cggggctagt    8040
gagagacagc atgccaaaat taagagaag gcttaatcag agacaaaaac tatttgagac    8100
aggccaagga tggttcgaag ggctgtttaa tagatccccc tggtttacca ccttaatctc    8160
```

```
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca cagtgtacta attatgctct   8340
cttgaaattg gctggagatg ttgagagcaa ccctggacct ggcgcgccta tggccagcaa   8400
gggcgaggag ctgttcaccg gggtggtgcc catcctggtc gagctggacg gcgacgtaaa   8460
cggccacaag ttcagcgtgt ccggcgaagg agagggcgat gccacctacg gcaagctgac   8520
cctgaagttc atctgcacca ccggcaagct gcccgtgccc tggcccaccc tcgtgaccac   8580
cttgacctac ggcgtgcagt gcttcgcccg ctaccccgac cacatgaagc agcacgactt   8640
cttcaagtcc gccatgcccg aaggctacgt ccaggagcgc accatcttct tcaaggacga   8700
cggcaactac aagacccgcg ccgaggtgaa gttcgagggc gacaccctgg tgaaccgcat   8760
cgagctgaag ggcatcgact tcaaggagga cggcaacatc ctggggcaca agctggagta   8820
caactacaac agccacaagg tctatatcac cgccgacaag cagaagaacg gcatcaaggt   8880
gaacttcaag acccgccaca acatcgagga cggcagcgtg cagctcgccg accactacca   8940
gcagaacacc cccatcggcg acggccccgt gctgctgccc gacaaccact acctgagcac   9000
ccagtccgcc ctgagcaaag accccaacga gaagcgcgat cacatggtcc tgctggagtt   9060
cgtgaccgcc gccgggatca ctctcggcat ggacgagctg tacaagtgtg cggccgcaga   9120
taaaataaaa gattttattt agtctccaga aaaagggggg aatgaaagac cccacctgta   9180
ggtttggcaa gctagcttaa gtaacgccat tttgcaaggc atggaaaaat acataactga   9240
gaatagagaa gttcagatca aggtcaggaa cagatgaaac agctgaatat gggccaaaca   9300
ggatatctgt ggtaagcagt tcctgccccg gctcagggcc aagaacagat ggaacagctg   9360
aatatgggcc aaacaggata tctgtggtaa gcagttcctg ccccggctca gggccaagaa   9420
cagatggtcc ccagatgcgg tccagccctc agcagtttct agagaaccat cagatgtttc   9480
cagggtgccc caaggacctg aaatgaccct gtgccttatt tgaactaacc aatcagttcg   9540
cttctcgctt ctgttcgcgc gcttctgctc cccgagctca ataaaagagc ccacaacccc   9600
tcactcgggg cgccagtcct ccgattgact gagtcgcccg ggtacccgtg tatccaataa   9660
accctcttgc agttgcatcc gacttgtggt ctcgctgttc cttgggaggg tctcctctga   9720
gtgattgact acccgtcagc gggggtcttt cattacatgt gagcaaaagg ccagcaaaag   9780
gccaggaacc gtaaaaaggc cgcgttgctg gcgttttcc ataggctccg ccccctgac    9840 gagcatcaca aaaatcgacg ctcaagtcag aggtggcgaa acccgacagg actataaaga   9900
taccaggcgt ttccccctgg aagctccctc gtgcgctctc ctgttccgac cctgccgctt   9960
accggatacc tgtccgcctt tctcccttcg ggaagcgtgg cgctttctca atgctcacgc   10020
tgtaggtatc tcagttcggt gtaggtcgtt cgctccaagc tgggctgtgt gcacgaaccc   10080
cccgttcagc ccgaccgctg cgccttatcc ggtaactatc gtcttgagtc caacccggta   10140
agacacgact tatcgccact ggcagcagcc actggtaaca ggattagcag agcgaggtat   10200
gtaggcggtg ctacagagtt cttgaagtgg tggcctaact acggctacac tagaaggaca   10260
gtatttggta tctgcgctct gctgaagcca gttaccttcg gaaaaagagt tggtagctct   10320
tgatccggca aacaaaccac cgctggtagc ggtggttttt ttgtttgcaa gcagcagatt   10380
acgcgcagaa aaaaggatc tcaagaagat cctttgatct tttctacggg gtctgacgct   10440
cagtggaacg aaaactcacg ttaagggatt ttggtcatga gattatcaaa aaggatcttc   10500
acctagatcc ttttaaatta aaaatgaagt tttaaatcaa tctaaagtat atatgagtaa   10560
```

```
acttggtctg acagttacca atgcttaatc agtgaggcac ctatctcagc gatctgtcta    10620
tttcgttcat ccatagttgc ctgactcccc gtcgtgtaga taactacgat acgggagggc    10680
ttaccatctg gccccagtgc tgcaatgata ccgcgagacc cacgctcacc ggctccagat    10740
ttatcagcaa taaaccagcc agccggaagg gccgagcgca gaagtggtcc tgcaacttta    10800
tccgcctcca tccagtctat taattgttgc cgggaagcta gagtaagtag ttcgccagtt    10860
aatagtttgc gcaacgttgt tgccattgct gcaggcatcg tggtgtcacg ctcgtcgttt    10920
ggtatggctt cattcagctc cggttcccaa cgatcaaggc gagttacatg atcccccatg    10980
ttgtgcaaaa aagcggttag ctccttcggt cctccgatcg ttgtcagaag taagttggcc    11040
gcagtgttat cactcatggt tatggcagca ctgcataatt ctcttactgt catgccatcc    11100
gtaagatgct tttctgtgac tggtgagtac tcaaccaagt cattctgaga atagtgtatg    11160
cggcgaccga gttgctcttg cccggcgtca acacgggata ataccgcgcc acatagcaga    11220
actttaaaag tgctcatcat tggaaaacgt tcttcggggc gaaaactctc aaggatctta    11280
ccgctgttga gatccagttc gatgtaaccc actcgtgcac ccaactgatc ttcagcatct    11340
tttactttca ccagcgtttc tgggtgagca aaaacaggaa ggcaaaatgc cgcaaaaaag    11400
ggaataaggg cgacacggaa atgttgaata ctcatactct tcctttttca atattattga    11460
agcatttatc agggttattg tctcatgagc ggatacatat ttgaatgtat ttagaaaaat    11520
aaacaaatag gggttccgcg cacatttccc cgaaaagtgc cacctgacgt ctaagaaacc    11580
attattatca tgacattaac ctataaaaat aggcgtatca cgaggccctt tcgtcttcaa    11640
gaattcat                                                             11648
```

<210> SEQ ID NO 48
<211> LENGTH: 11657
<212> TYPE: DNA
<213> ORGANISM: Artificial Sequence
<220> FEATURE:
<223> OTHER INFORMATION: pAC3-GSG-E2A-GFPm

<400> SEQUENCE: 48

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg taggcgtgt     540
acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actacccgtc agcggggtc      720
tttcatttgg ggctcgtcc gggatcggga  gacccctgcc  cagggaccac cgacccacca    780
ccggaggta agctgccag caacttatct gtgtctgtcc gattgtctag tgtctatgac       840
tgattttatg cgcctgcgtc ggtactagtt agctaactag ctctgtatct ggcggacccg     900
```

```
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc cccttgaac    1560 ctcctcgttc gaccccgcct cgatcctccc tttatccagc cctcactcct tctctaggcg   1620
ccaaacctaa acctcaagtt cttctgaca gtgggggcc gctcatcgac ctacttacag     1680 aagaccccc gccttatagg gacccaagac caccccttc cgacagggac ggaaatggtg     1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttcttttttct gaagatccag gtaaactgac agctctgatc gagtctgttc   1980
tcatcaccca tcagcccacc tgggacgact gtcagcagct gttggggact ctgctgaccg   2040
gagaagaaaa acaacggtg ctcttagagg ctagaaaggc ggtgcggggc gatgatgggc    2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc cccctgaac ccaggataac cctcaaagtc ggggggcaac    2880
ccgtcacctt cctggtagat actggggccc aacactccgt gctgacccaa atcctggac    2940 ccctaagtga taagtctgcc tgggtccaag gggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag catcggctac atgagacctc aaaagagcca gatgtttctc   3240
tagggtccac atggctgtct gattttcctc aggcctgggc ggaaaccggg ggcatgggac   3300
```

| | |
|---|---|
| tggcagttcg ccaagctcct ctgatcatac ctctgaaagc aacctctacc cccgtgtcca | 3360 |
| taaaacaata ccccatgtca caagaagcca gactggggat caagccccac atacagagac | 3420 |
| tgttggacca gggaatactg gtaccctgcc agtcccctg gaacacgccc ctgctacccg | 3480 |
| ttaagaaacc agggactaat gattataggc ctgtccagga tctgagagaa gtcaacaagc | 3540 |
| gggtggaaga catccacccc accgtgccca acccttacaa cctcttgagc gggctcccac | 3600 |
| cgtcccacca gtggtacact gtgcttgatt taaaggatgc cttttctgc ctgagactcc | 3660 |
| accccaccag tcagcctctc ttcgcctttg agtggagaga tccagagatg gaatctcag | 3720 |
| gacaattgac ctggaccaga ctcccacagg gtttcaaaaa cagtcccacc ctgtttgatg | 3780 |
| aggcactgca cagagaccta gcagacttcc ggatccagca cccagacttg atcctgctac | 3840 |
| agtacgtgga tgacttactg ctggccgcca cttctgagct agactgccaa caaggtactc | 3900 |
| ggccctgtt acaaacccta gggaacctcg ggtatcgggc ctcggccaag aaagcccaaa | 3960 |
| tttgccagaa acaggtcaag tatctggggt atcttctaaa agagggtcag agatggctga | 4020 |
| ctgaggccag aaaagagact gtgatggggc agcctactcc gaagacccct cgacaactaa | 4080 |
| gggagttcct agggacggca ggcttctgtc gcctctggat ccctgggttt gcagaaatgg | 4140 |
| cagcccccctt gtaccctctc accaaaacgg ggactctgtt taattggggc ccagaccaac | 4200 |
| aaaaggccta tcaagaaatc aagcaagctc ttctaactgc cccagccctg gggttgccag | 4260 |
| atttgactaa gcccctttgaa ctctttgtcg acgagaagca gggctacgcc aaaggtgtcc | 4320 |
| taacgcaaaa actgggacct tggcgtcggc cggtggccta cctgtccaaa aagctagacc | 4380 |
| cagtagcagc tgggtggccc ccttgcctac ggatggtagc agccattgcc gtactgacaa | 4440 |
| aggatgcagg caagctaacc atgggacagc cactagtcat tctggcccc catgcagtag | 4500 |
| aggcactagt caaacaaccc cccgaccgct ggctttccaa cgcccggatg actcactatc | 4560 |
| aggccttgct tttggacacg gaccgggtcc agttcggacc ggtggtagcc ctgaacccgg | 4620 |
| ctacgctgct cccactgcct gaggaagggc tgcaacacaa ctgccttgat atcctggccg | 4680 |
| aagcccacgg aacccgaccc gacctaacgg accagccgct cccagacgcc gaccacacct | 4740 |
| ggtacacgga tggaagcagt ctcttacaag agggacagcg taaggcggga gctgcggtga | 4800 |
| ccaccgagac cgaggtaatc tgggctaaag ccctgccagc cgggacatcc gctcagcggg | 4860 |
| ctgaactgat agcactcacc caggcccctaa agatggcaga aggtaagaag ctaaatgttt | 4920 |
| atactgatag ccgttatgct tttgctactg cccatatcca tggagaaata tacagaaggc | 4980 |
| gtgggttgct cacatcagaa ggcaaagaga tcaaaaataa agacgagatc ttggccctac | 5040 |
| taaaagccct ctttctgccc aaaagactta gcataatcca ttgtccagga catcaaaagg | 5100 |
| gacacagcgc cgaggctaga ggcaaccgga tggctgacca gcggccccga aaggcagcca | 5160 |
| tcacagagac tccagacacc tctaccctcc tcatagaaaa ttcatcaccc tacacctcag | 5220 |
| aacatttttca ttacacagtg actgatataa aggacctaac caagtggggg gccattatg | 5280 |
| ataaaacaaa gaagtattgg gtctaccaag gaaaacctgt gatgcctgac cagtttactt | 5340 |
| ttgaattatt agactttctt catcagctga ctcacctcag cttctcaaaa atgaaggctc | 5400 |
| tcctagagag aagccacagt ccctactaca tgctgaaccg ggatcgaaca ctcaaaaata | 5460 |
| tcactgagac ctgcaaagct tgtgcacaag tcaacgccag caagtctgcc gttaaacagg | 5520 |
| gaactagggt ccgcgggcat cggccccgca ctcattggga gatcgatttc accgagataa | 5580 |
| agcccggatt gtatggctat aaatatcttc tagttttttat agataccttt tctggctgga | 5640 |

-continued

```
tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt gacggcatc gcagcttgga    6300 tacacgccgc ccacgtgaag gctgccgacc ccggggggtgg accatcctct agactgacat    6360
ggcgcgttca acgctctcaa aacccctca agataagatt aacccgtgga agcccttaat    6420
agtcatggga gtcctgttag gagtagggat ggcagagagc cccatcagg tctttaatgt    6480 aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcaggag    6660 acagcggacc cggactttg acttttacgt gtgccctggg cataccgtaa agtcggggtg    6720
tgggggacca ggagagggct actgtggtaa atggggtgt gaaaccaccg gacaggctta    6780
ctggaagccc acatcatcgt gggacctaat ctcccttaag cgcggtaaca ccccctggga    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagcccccct caataccagt taccccccctt ccactaccag    7200 tacaccctca acctcccctta caagtccaag tgtcccacag ccaccccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atggggcag tacctaaaac    7500 tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgtttttat gcagaccaca cggggctagt    8040
```

-continued

```
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca ggaagcggac agtgtactaa   8340
ttatgctctc ttgaaattgg ctggagatgt tgagagcaac cctggacctg gcgcgcctat   8400
ggccagcaag ggcgaggagc tgttcaccgg ggtggtgccc atcctggtcg agctggacgg   8460
cgacgtaaac ggccacaagt tcagcgtgtc cggcgaagga gagggcgatg ccacctacgg   8520
caagctgacc ctgaagttca tctgcaccac cggcaagctg cccgtgccct ggcccaccct   8580
cgtgaccacc ttgacctacg gcgtgcagtg cttcgcccgc tacccgacc acatgaagca   8640 gcacgacttc ttcaagtccg ccatgcccga aggctacgtc caggagcgca ccatcttctt   8700
caaggacgac ggcaactaca agacccgcgc cgaggtgaag ttcgagggcg acaccctggt   8760
gaaccgcatc gagctgaagg gcatcgactt caaggaggac ggcaacatcc tggggcacaa   8820
gctggagtac aactacaaca gccacaaggt ctatatcacc gccgacaagc agaagaacgg   8880
catcaaggtg aacttcaaga cccgccacaa catcgaggac ggcagcgtgc agctcgccga   8940
ccactaccag cagaacaccc ccatcggcga cggccccgtg ctgctgcccg acaaccacta   9000
cctgagcacc cagtccgccc tgagcaaaga ccccaacgag aagcgcgatc acatggtcct   9060
gctggagttc gtgaccgccg ccgggatcac tctcggcatg gacgagctgt acaagtgtgc   9120
ggccgcagat aaaataaaag attttattta gtctccagaa aagggggga atgaaagacc   9180 ccacctgtag gtttggcaag ctagcttaag taacgccatt ttgcaaggca tggaaaaata   9240
cataactgag aatagagaag ttcagatcaa ggtcaggaac agatggaaca gctgaatatg   9300
ggccaaacag gatatctgtg gtaagcagtt cctgccccgg ctcagggcca agaacagatg   9360
gaacagctga atatgggcca acaggatat ctgtggtaag cagttcctgc cccggctcag   9420
ggccaagaac agatggtccc cagatgcggt ccagccctca gcagtttcta gagaaccatc   9480
agatgtttcc agggtgcccc aaggacctga aatgaccctg tgccttattt gaactaacca   9540
atcagttcgc ttctcgcttc tgttcgcgcg cttctgctcc ccgagctcaa taaaagagcc   9600
cacaacccct cactcggggc gccagtcctc cgattgacta gtcgcccgg gtacccgtgt   9660 atccaataaa ccctcttgca gttgcatccg acttgtggtc tcgctgttcc ttgggagggt   9720
ctcctctgag tgattgacta cccgtcagcg ggggtctttc attacatgtg agcaaaaggc   9780
cagcaaaagg ccaggaaccg taaaaaggcc gcgttgctgg cgttttccca taggctccgc   9840
cccccctgac agcatcacaa aaatcgacgc tcaagtcaga ggtggcgaaa cccgacagga   9900
ctataaagat accaggcgtt tcccctggaa gctccctcg tgcgctctcc tgttccgacc   9960
ctgccgctta ccggatacct gtccgccttt ctcccttcgg gaagcgtggc gctttctcaa  10020
tgctcacgct gtaggtatct cagttcggtg taggtcgttc gctccaagct gggctgtgtg  10080
cacgaacccc ccgttcagcc cgaccgctgc gccttatccg gtaactatcg tcttgagtcc  10140
aacccggtaa gacacgactt atcgccactg gcagcagcca ctggtaacag gattagcaga  10200
gcgaggtatg taggcggtgc tacagagttc ttgaagtggt ggcctaacta cggctacact  10260
agaaggacag tatttggtat ctgcgctctg ctgaagccag ttaccttcgg aaaaagagtt  10320
ggtagctctt gatccggcaa acaaaccacc gctggtagcg gtggttttt tgtttgcaag  10380
```

| | |
|---|---|
| cagcagatta cgcgcagaaa aaaaggatct caagaagatc ctttgatctt ttctacgggg | 10440 |
| tctgacgctc agtggaacga aaactcacgt taagggattt tggtcatgag attatcaaaa | 10500 |
| aggatcttca cctagatcct tttaaattaa aaatgaagtt ttaaatcaat ctaaagtata | 10560 |
| tatgagtaaa cttggtctga cagttaccaa tgcttaatca gtgaggcacc tatctcagcg | 10620 |
| atctgtctat ttcgttcatc catagttgcc tgactcccccg tcgtgtagat aactacgata | 10680 |
| cgggagggct taccatctgg ccccagtgct gcaatgatac cgcgagaccc acgctcaccg | 10740 |
| gctccagatt tatcagcaat aaaccagcca gccggaaggg ccgagcgcag aagtggtcct | 10800 |
| gcaactttat ccgcctccat ccagtctatt aattgttgcc gggaagctag agtaagtagt | 10860 |
| tcgccagtta atagtttgcg caacgttgtt gccattgctg caggcatcgt ggtgtcacgc | 10920 |
| tcgtcgtttg gtatggcttc attcagctcc ggttcccaac gatcaaggcg agttacatga | 10980 |
| tcccccatgt tgtgcaaaaa agcggttagc tccttcggtc ctccgatcgt tgtcagaagt | 11040 |
| aagttggccg cagtgttatc actcatggtt atggcagcac tgcataattc tcttactgtc | 11100 |
| atgccatccg taagatgctt ttctgtgact ggtgagtact caaccaagtc attctgagaa | 11160 |
| tagtgtatgc ggcgaccgag ttgctcttgc ccggcgtcaa cacgggataa taccgcgcca | 11220 |
| catagcagaa ctttaaaagt gctcatcatt ggaaaacgtt cttcggggcg aaaactctca | 11280 |
| aggatcttac cgctgttgag atccagttcg atgtaaccca ctcgtgcacc caactgatct | 11340 |
| tcagcatctt ttactttcac cagcgtttct gggtgagcaa aaacaggaag gcaaaatgcc | 11400 |
| gcaaaaaagg gaataagggc gacacggaaa tgttgaatac tcatactctt ccttttcaa | 11460 |
| tattattgaa gcatttatca gggttattgt ctcatgagcg gatacatatt tgaatgtatt | 11520 |
| tagaaaaata aacaaatagg ggttccgcgc acatttcccc gaaaagtgcc acctgacgtc | 11580 |
| taagaaacca ttattatcat gacattaacc tataaaaata ggcgtatcac gaggcccttt | 11640 |
| cgtcttcaag aattcat | 11657 |

<210> SEQ ID NO 49
<211> LENGTH: 11654
<212> TYPE: DNA
<213> ORGANISM: Artificial Sequence
<220> FEATURE:
<223> OTHER INFORMATION: pAC3-F2A-GFPm

<400> SEQUENCE: 49

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta acaactccgc cccattgacg caaatgggcg gtaggcgtgt | 540 |
| acggtgggag gtctatataa gcagagctgg tttagtgaac cggcgccagt cctccgattg | 600 |
| actgagtcgc ccgggtaccc gtgtatccaa taaaccctct tgcagttgca tccgacttgt | 660 |
| ggtctcgctg ttccttggga gggtctcctc tgagtgattg actacccgtc agcgggggtc | 720 |
| tttcatttgg gggctcgtcc gggatcggga gacccctgcc cagggaccac cgacccacca | 780 |

-continued

| | | | |
|---|---|---|---|
| ccgggaggta agctggccag caacttatct gtgtctgtcc gattgtctag tgtctatgac | 840 |
| tgattttatg cgcctgcgtc ggtactagtt agctaactag ctctgtatct ggcggacccg | 900 |
| tggtggaact gacgagttcg gaacacccgg ccgcaaccct gggagacgtc ccagggactt | 960 |
| cggggggccgt ttttgtggcc cgacctgagt ccaaaaatcc cgatcgtttt ggactctttg | 1020 |
| gtgcaccccc cttagaggag ggatatgtgg ttctggtagg agacgagaac ctaaaacagt | 1080 |
| tcccgcctcc gtctgaattt ttgctttcgg tttgggaccg aagccgcgcc gcgcgtcttg | 1140 |
| tctgctgcag catcgttctg tgttgtctct gtctgactgt gtttctgtat ttgtctgaga | 1200 |
| atatgggcca gactgttacc actcccttaa gtttgacctt aggtcactgg aaagatgtcg | 1260 |
| agcggatcgc tcacaaccag tcggtagatg tcaagaagag cgttgggtt accttctgct | 1320 |
| ctgcagaatg ccaaccttt aacgtcggat ggccgcgaga cggcaccttt aaccgagacc | 1380 |
| tcatcaccca ggttaagatc aaggtctttt cacctggccc gcatggacac ccagaccagg | 1440 |
| tccctacat cgtgacctgg gaagccttgg cttttgaccc ccctccctgg gtcaagccct | 1500 |
| ttgtacaccc taagcctccg cctcctcttc ctccatccgc ccgtctctc ccccttgaac | 1560 |
| ctcctcgttc gacccgcct cgatcctccc tttatccagc cctcactcct tctctaggcg | 1620 |
| ccaaacctaa acctcaagtt cttttctgaca gtgggggcc gctcatcgac ctacttacag | 1680 |
| aagacccccc gccttatagg gacccaagac caccccttc cgacagggac ggaaatggtg | 1740 |
| gagaagcgac ccctgcggga gaggcaccgg acccctcccc aatggcatct cgcctacgtg | 1800 |
| ggagacggga gccccctgtg gccgactcca ctacctcgca ggcattcccc ctccgcgcag | 1860 |
| gaggaaacgg acagcttcaa tactggccgt tctcctcttc tgacctttac aactggaaaa | 1920 |
| ataataaccc ttcttttct gaagatccag gtaaactgac agctctgatc gagtctgttc | 1980 |
| tcatcaccca tcagcccacc tgggacgact gtcagcagct gttggggact ctgctgaccg | 2040 |
| gagaagaaaa acaacgggtg ctcttagagg ctagaaaggc ggtgcggggc gatgatgggc | 2100 |
| gccccactca actgcccaat gaagtcgatg ccgcttttcc cctcgagcgc ccagactggg | 2160 |
| attacaccac ccaggcaggt aggaaccacc tagtccacta tcgccagttg ctcctagcgg | 2220 |
| gtctccaaaa cgcgggcaga agccccacca atttggccaa ggtaaaagga ataacacaag | 2280 |
| ggcccaatga gtctccctcg gccttcctag agagacttaa ggaagcctat cgcaggtaca | 2340 |
| ctccttatga ccctgaggac ccagggcaag aaactaatgt gtctatgtct ttcatttggc | 2400 |
| agtctgcccc agacattggg agaaagttag agaggttaga agatttaaaa aacaagacgc | 2460 |
| ttggagattt ggttagagag gcagaaaaga tctttaataa cgagaaaccc ccggaagaaa | 2520 |
| gagaggaacg tatcaggaga gaaacagagg aaaagaaga cgccgtagg acagaggatg | 2580 |
| agcagaaaga gaaagaaga gatcgtagga gacatagaa gatgagcaag ctattggcca | 2640 |
| ctgtcgttag tggacagaaa caggatagac agggaggaga acgaaggagg tcccaactcg | 2700 |
| atcgcgacca gtgtgcctac tgcaaagaaa aggggcactg ggctaaagat tgtcccaaga | 2760 |
| aaccacgagg acctcgggga ccaagacccc agacctccct cctgacccta gatgactagg | 2820 |
| gaggtcaggg tcaggagccc ccccctgaac ccaggataac cctcaaagtc gggggggcaac | 2880 |
| ccgtcacctt cctggtagat actggggccc aacactccgt gctgacccaa atcctggac | 2940 |
| ccctaagtga taagtctgcc tgggtccaag gggctactgg aggaaagcgg tatcgctgga | 3000 |
| ccacggatcg caaagtacat ctagctaccg gtaaggtcac ccactctttc ctccatgtac | 3060 |
| cagactgtcc ctatcctctg ttaggaagag atttgctgac taaactaaaa gcccaaatcc | 3120 |

```
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactgggat caagcccac atacagagac     3420 tgttggacca gggaatactg gtaccctgcc agtcccctg gaacacgccc ctgctacccg     3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttctgc ctgagactcc     3660 accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gcccttttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040 taaaagcccct ctttctgccc aaaagactta gcataatcca ttgtccagga catcaaaagg    5100
gacacagcgc cgaggctaga ggcaaccgga tggctgacca gcggccgga aaggcagcca     5160 tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
```

```
gaactagggt ccgcgggcat cggcccggca ctcattggga gatcgatttc accgagataa    5580
agcccggatt gtatggctat aaatatcttc tagtttttat agatacctttt tctggctgga    5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt agacggcatc gcagcttgga    6300
tacacgccgc ccacgtgaag gctgccgacc ccggggggtgg accatcctct agactgacat    6360
ggcgcgttca acgctctcaa aaccccctca agataagatt aacccgtgga gcccttaat    6420 agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggacttttg acttttacgt gtgccctggg cataccgtaa agtcggggtg    6720
tgggggacca ggagagggct actgtggtaa atggggggtgt gaaaccaccg gacaggctta    6780
ctggaagccc acatcatcgt gggacctaat ctcccttaag cgcggtaaca cccccctggga    6840 cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctgccccttc tactaggagg attaaccatg ggagggattg cagctggaat    7800
agggacgggg accactgcct taattaaaac ccagcagttt gagcagcttc atgccgctat    7860
```

| | |
|---|---|
| ccagacagac ctcaacgaag tcgaaaagtc aattaccaac ctagaaaagt cactgacctc | 7920 |
| gttgtctgaa gtagtcctac agaaccgcag aggcctagat ttgctattcc taaaggaggg | 7980 |
| aggtctctgc gcagccctaa aagaagaatg ttgtttttat gcagaccaca cggggctagt | 8040 |
| gagagacagc atggccaaat taagagaaag gcttaatcag agacaaaaac tatttgagac | 8100 |
| aggccaagga tggttcgaag ggctgtttaa tagatccccc tggtttacca ccttaatctc | 8160 |
| caccatcatg ggacctctaa tagtactctt actgatctta ctctttggac cttgcattct | 8220 |
| caatcgattg gtccaatttg ttaaagacag gatctcagtg gtccaggctc tggttttgac | 8280 |
| tcagcaatat caccagctaa aacccataga gtacgagcca gtgaaacaga ctttgaattt | 8340 |
| tgaccttctc aagttggcgg gagacgtgga gtccaaccct ggacctggcg cgcctatggc | 8400 |
| cagcaagggc gaggagctgt tcaccggggt ggtgcccatc ctggtcgagc tggacggcga | 8460 |
| cgtaaacggc cacaagttca gcgtgtccgg cgaaggagag ggcgatgcca cctacggcaa | 8520 |
| gctgaccctg aagttcatct gcaccaccgg caagctgccc gtgccctggc ccaccctcgt | 8580 |
| gaccaccttg acctacggcg tgcagtgctt cgcccgctac cccgaccaca tgaagcagca | 8640 |
| cgacttcttc aagtccgcca tgcccgaagg ctacgtccag gagcgcacca tcttcttcaa | 8700 |
| ggacgacggc aactacaaga cccgcgccga ggtgaagttc gagggcgaca ccctggtgaa | 8760 |
| ccgcatcgag ctgaagggca tcgacttcaa ggaggacggc aacatcctgg ggcacaagct | 8820 |
| ggagtacaac tacaacagcc acaaggtcta tatcaccgcc gacaagcaga agaacggcat | 8880 |
| caaggtgaac ttcaagaccc gccacaacat cgaggacggc agcgtgcagc tcgccgacca | 8940 |
| ctaccagcag aacaccccca tcggcgacgg ccccgtgctg ctgcccgaca ccactacct | 9000 |
| gagcacccag tccgccctga gcaaagaccc caacgagaag cgcgatcaca tggtcctgct | 9060 |
| ggagttcgtg accgccgccg ggatcactct cggcatggac gagctgtaca gtgtgcggc | 9120 |
| cgcagataaa ataaaagatt ttatttagtc tccagaaaaa ggggggaatg aaagacccca | 9180 |
| cctgtaggtt tggcaagcta gcttaagtaa cgccattttg caaggcatgg aaaaatacat | 9240 |
| aactgagaat agagaagttc agatcaaggt caggaacaga tggaacagct gaatatgggc | 9300 |
| caaacaggat atctgtggta agcagttcct gccccggctc agggccaaga acagatggaa | 9360 |
| cagctgaata tgggccaaac aggatatctg tggtaagcag ttcctgcccc ggctcagggc | 9420 |
| caagaacaga tggtccccag atgcggtcca gccctcagca gtttctagag aaccatcaga | 9480 |
| tgtttccagg gtgccccaag gacctgaaat gaccctgtgc cttatttgaa ctaaccaatc | 9540 |
| agttcgcttc tcgcttctgt tcgcgcgctt ctgctcccg agctcaataa aagagcccac | 9600 |
| aaccccctcac tcggggcgcc agtcctccga ttgactgagt cgcccgggta cccgtgtatc | 9660 |
| caataaaccc tcttgcagtt gcatccgact tgtggtctcg ctgttccttg ggagggtctc | 9720 |
| ctctgagtga ttgactaccc gtcagcgggg gtctttcatt acatgtgagc aaaaggccag | 9780 |
| caaaaggcca ggaaccgtaa aaaggccgcg ttgctggcgt ttttccatag gctccgcccc | 9840 |
| cctgacgagc atcacaaaaa tcgacgctca agtcagaggt ggcgaaaccc gacaggacta | 9900 |
| taaagatacc aggcgtttcc ccctggaagc tccctcgtgc gctctcctgt tccgaccctg | 9960 |
| ccgcttaccg gatacctgtc cgcctttctc ccttcgggaa gcgtggcgct ttctcaatgc | 10020 |
| tcacgctgta ggtatctcag ttcggtgtag gtcgttcgct ccaagctggg ctgtgtgcac | 10080 |
| gaaccccccg ttcagcccga ccgctgcgcc ttatccggta actatcgtct tgagtccaac | 10140 |
| ccggtaagac acgacttatc gccactggca gcagccactg gtaacaggat tagcagagcg | 10200 |
| aggtatgtag gcggtgctac agagttcttg aagtggtggc ctaactacgg ctacactaga | 10260 |

```
aggacagtat ttggtatctg cgctctgctg aagccagtta ccttcggaaa aagagttggt    10320
agctcttgat ccggcaaaca aaccaccgct ggtagcggtg ttttttttgt ttgcaagcag    10380
cagattacgc gcagaaaaaa aggatctcaa gaagatcctt tgatcttttc tacggggtct    10440
gacgctcagt ggaacgaaaa ctcacgttaa gggattttgg tcatgagatt atcaaaaagg    10500
atcttcacct agatcctttt aaattaaaaa tgaagtttta atcaatcta aagtatatat     10560
gagtaaactt ggtctgacag ttaccaatgc ttaatcagtg aggcacctat ctcagcgatc    10620
tgtctatttc gttcatccat agttgcctga ctccccgtcg tgtagataac tacgatacgg    10680
gagggcttac catctggccc cagtgctgca atgataccgc gagacccacg ctcaccggct    10740
ccagatttat cagcaataaa ccagccagcc ggaagggccg agcgcagaag tggtcctgca    10800
actttatccg cctccatcca gtctattaat tgttgccggg aagctagagt aagtagttcg    10860
ccagttaata gtttgcgcaa cgttgttgcc attgctgcag gcatcgtggt gtcacgctcg    10920
tcgtttggta tggcttcatt cagctccggt tcccaacgat caaggcgagt tacatgatcc    10980
cccatgttgt gcaaaaaagc ggttagctcc ttcggtcctc cgatcgttgt cagaagtaag    11040
ttggccgcag tgttatcact catggttatg gcagcactgc ataattctct tactgtcatg    11100
ccatccgtaa gatgcttttc tgtgactggt gagtactcaa ccaagtcatt ctgagaatag    11160
tgtatgcggc gaccgagttg ctcttgcccg gcgtcaacac gggataatac cgcgccacat    11220
agcagaactt taaaagtgct catcattgga aaacgttctt cggggcgaaa actctcaagg    11280
atccttaccgc tgttgagatc cagttcgatg taacccactc gtgcacccaa ctgatcttca    11340
gcatctttta ctttcaccag cgtttctggg tgagcaaaaa caggaaggca aaatgccgca    11400
aaaaagggaa taagggcgac acggaaatgt tgaatactca tactcttcct ttttcaatat    11460
tattgaagca tttatcaggg ttattgtctc atgagcggat acatatttga atgtatttag    11520
aaaaataaac aaataggggt tccgcgcaca tttccccgaa aagtgccacc tgacgtctaa    11580
gaaaccatta ttatcatgac attaacctat aaaaataggc gtatcacgag gccctttcgt    11640
cttcaagaat tcat                                                      11654
```

<210> SEQ ID NO 50
<211> LENGTH: 11663
<212> TYPE: DNA
<213> ORGANISM: Artificial Sequence
<220> FEATURE:
<223> OTHER INFORMATION: pAC3-GSG-F2A-GFPm

<400> SEQUENCE: 50

```
tagttattaa tagtaatcaa ttacggggtc attagttcat agcccatata tggagttccg    60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgcc ccattgacg caaatgggcg gtaggcgtgt    540
acggtgggag gtctatataa gcagagctgg tttagtgaac cggcgccagt cctccgattg    600
```

```
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga daccccctgcc cagggaccac cgacccacca    780 ccggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacaccggg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcacccttt aaccgagacc   1380 tcatcccca ggttaagatc aaggtcttttt cacctggccc gcatggacac ccagaccagg   1440 tccccctacat cgtgacctgg gaagccttgg cttttgaccc ccctcccctgg gtcaagcccct   1500 ttgtacaccc taagcctccg cctcctcttc ctccatccgc ccgtctctc ccccttgaac   1560 ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680 aagaccccc gccttatagg gacccaagac caccccttc cgacagggac ggaaatggtg   1740
gagaagcgac ccctgcggga gaggcaccgg accccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttcttttttct gaagatccag gtaaactgac agctctgatc gagtctgttc   1980
tcatcaccca tcagcccacc tgggacgact gtcagcagct gttggggact ctgctgaccg   2040
gagaagaaaa acaacggtg ctcttagagg ctagaaaggc ggtgcgggc gatgatgggc   2100 gccccactca actgcccaat gaagtcgatg ccgcttttcc cctcgagcgc ccagactggg   2160
attacaccac ccaggcaggt aggaaccacc tagtccacta cgccagttg ctcctagcgg   2220 gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgaccctaa gatgactagg   2820 gaggtcaggg tcaggagccc cccctgaac ccaggataac cctcaaagtc gggggggcaac   2880 ccgtcacctt cctggtagat actggggccc aacactccgt gctgacccaa aatcctggac   2940
ccctaagtga taagtctgcc tgggtccaag ggctactgg aggaaagcgg tatcgctgga   3000
```

-continued

```
ccacggatcg caaagtacat ctagctaccg gtaaggtcac ccactctttc ctccatgtac      3060
cagactgtcc ctatcctctg ttaggaagag atttgctgac taaactaaaa gcccaaatcc      3120
actttgaggg atcaggagcc caggttatgg gaccaatggg gcagccctg caagtgttga       3180 ccctaaatat agaagatgag catcggctac atgagacctc aaaagagcca gatgtttctc      3240
tagggtccac atggctgtct gattttcctc aggcctgggc ggaaaccggg ggcatgggac     3300
tggcagttcg ccaagctcct ctgatcatac ctctgaaagc aacctctacc cccgtgtcca      3360
taaaacaata ccccatgtca caagaagcca gactggggat caagccccac atacagagac     3420
tgttggacca gggaatactg gtaccctgcc agtcccctg gaacacgccc ctgctacccg      3480
ttaagaaacc agggactaat gattataggc ctgtccagga tctgagagaa gtcaacaagc     3540
gggtggaaga catccacccc accgtgccca acccttacaa cctcttgagc gggctcccac    3600
cgtcccacca gtggtacact gtgcttgatt taaaggatgc ctttttctgc ctgagactcc     3660
accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc     3900
gggccctgtt acaaacccta gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg     4140
cagccccctt gtaccctctc accaaaacgg ggactctgtt taattgggc ccagaccaac    4200 aaaaggccta tcaagaaatc aagcaagctc ttctaactgc cccagccctg gggttgccag    4260
atttgactaa gccccttgaa ctctttgtcg acgagaagca gggctacgcc aaaggtgtcc     4320
taacgcaaaa actgggacct tggcgtcggc cggtggccta cctgtccaaa aagctagacc     4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg     4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga   4800
ccaccgagac cgaggtaatc tgggctaaag ccctgccagc cggacatccc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg     5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttcacacagtg actgatataa aggacctaac caagttgggg gccatttatg     5280
ataaaacaaa gaagtattgg gtctaccaag gaaaacctgt gatgcctgac cagtttactt     5340
```

```
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacccttt tctggctgga   5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccccaccg ccctcaaagt agacggcatc gcagcttgga   6300
tacacgccgc ccacgtgaag gctgccgacc ccggggtgg accatcctct agactgacat     6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttttg acttttacgt gtgccctggg cataccgtaa agtcggggtg    6720
tgggggacca ggagagggct actgtggtaa atgggggtgt gaaaccaccg gacaggctta    6780
ctggaagccc acatcatcgt gggacctaat ctcccttaag cgcggtaaca cccccctggga   6840 cacgggatgc tctaaagttg cctgtggccc ctgctacgac ctctccaaag tatccaattc    6900
cttccaaggg gctactcgag ggggcagatg caacccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg gaccccgagt    7080
ccccataggg cccaacccag tattacccga ccaaagactc ccttcctcac caatagagat    7140
tgtaccggct ccacagccac ctagcccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atccgacaa    7320 gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
```

```
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgtttttat gcagaccaca cggggctagt    8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca ggaagcggag tgaaacagac    8340
tttgaatttt gaccttctca agttggcggg agacgtggag tccaaccctg gacctggcgc    8400
gcctatggcc agcaagggcg aggagctgtt caccggggtg gtgcccatcc tggtcgagct    8460
ggacggcgac gtaaacggcc acaagttcag cgtgtccggc gaggagaggg gcgatgccac    8520
ctacggcaag ctgaccctga agttcatctg caccaccggc aagctgcccg tgccctggcc    8580
caccctcgtg accaccttga cctacggcgt gcagtgcttc gcccgctacc ccgaccacat    8640
gaagcagcac gacttcttca gtccgccat gcccgaaggc tacgtccagg agcgcaccat    8700
cttcttcaag gacgacggca actacaagac ccgcgccgag gtgaagttcg agggcgacac    8760
cctggtgaac cgcatcgagc tgaagggcat cgacttcaag gaggacggca acatcctggg    8820
gcacaagctg gagtacaact acaacagcca caaggtctat atcaccgccg acaagcagaa    8880
gaacggcatc aaggtgaact tcaagacccg ccacaacatc gaggacggca gcgtgcagct    8940
cgccgaccac taccagcaga acacccccat cggcgacggc cccgtgctgc tgcccgacaa    9000
ccactacctg agcacccagt ccgccctgag caaagacccc aacgagaagc gcgatcacat    9060
ggtcctgctg gagttcgtga ccgccgccgg gatcactctc ggcatggacg agctgtacaa    9120
gtgtgcggcc gcagataaaa taaaagattt tatttagtct ccagaaaaag ggggaatga    9180 aagacccccac ctgtaggttt ggcaagctag cttaagtaac gccattttgc aaggcatgga    9240
aaaatacata actgagaata gagaagttca gatcaaggtc aggaacagat ggaacagctg    9300
aatatgggcc aaacaggata tctgtggtaa gcagttcctg ccccggctca gggccaagaa    9360
cagatggaac agctgaatat gggccaaaca ggatatctgt ggtaagcagt tcctgccccg    9420 gctcagggc aagaacagat ggtccccaga tgcggtccag ccctcagcag tttctagaga    9480
accatcagat gtttccaggg tgccccaagg acctgaaatg accctgtgcc ttatttgaac    9540
taaccaatca gttcgcttct cgcttctgtt cgcgcgcttc tgctcccga gctcaataaa    9600 agagcccaca cccctcact cggggcgcca gtcctccgat tgactgagtc gcccgggtac    9660
ccgtgtatcc aataaaccct cttgcagttg catccgactt gtggtctcgc tgttccttgg    9720
gagggtctcc tctgagtgat tgactacccg tcagcggggg tctttcatta catgtgagca    9780
aaaggccagc aaaaggccag gaaccgtaaa aaggccgcgt tgctggcgtt tttccatagg    9840
ctccgccccc ctgacgagca tcacaaaaat cgacgctcaa gtcagaggtg gcgaaacccg    9900
acaggactat aaagatacca ggcgtttccc cctggaagct ccctcgtgcg ctctcctgtt    9960
ccgaccctgc cgcttaccgg atacctgtcc gcctttctcc cttcgggaag cgtggcgctt    10020
tctcaatgct cacgctgtag gtatctcagt tcggtgtagg tcgttcgctc caagctgggc    10080
```

| | |
|---|---|
| tgtgtgcacg aacccccgt tcagcccgac cgctgcgcct tatccggtaa ctatcgtctt | 10140 |
| gagtccaacc cggtaagaca cgacttatcg ccactggcag cagccactgg taacaggatt | 10200 |
| agcagagcga ggtatgtagg cggtgctaca gagttcttga agtggtggcc taactacggc | 10260 |
| tacactagaa ggacagtatt tggtatctgc gctctgctga agccagttac cttcggaaaa | 10320 |
| agagttggta gctcttgatc cggcaaacaa accaccgctg gtagcggtgg ttttttttgtt | 10380 |
| tgcaagcagc agattacgcg cagaaaaaaa ggatctcaag aagatccttt gatcttttct | 10440 |
| acggggtctg acgctcagtg aacgaaaac tcacgttaag ggattttggt catgagatta | 10500 |
| tcaaaaagga tcttcaccta gatccttta aattaaaaat gaagttttaa atcaatctaa | 10560 |
| agtatatatg agtaaacttg gtctgacagt taccaatgct taatcagtga ggcacctatc | 10620 |
| tcagcgatct gtctatttcg ttcatccata gttgcctgac tccccgtcgt gtagataact | 10680 |
| acgatacggg agggcttacc atctggcccc agtgctgcaa tgataccgcg agacccacgc | 10740 |
| tcaccggctc cagatttatc agcaataaac cagccagccg aagggccga gcgcagaagt | 10800 |
| ggtcctgcaa ctttatccgc ctccatccag tctattaatt gttgccggga agctagagta | 10860 |
| agtagttcgc cagttaatag tttgcgcaac gttgttgcca ttgctgcagg catcgtggtg | 10920 |
| tcacgctcgt cgtttggtat ggcttcattc agctccggtt cccaacgatc aaggcgagtt | 10980 |
| acatgatccc ccatgttgtg caaaaaagcg gttagctcct tcggtcctcc gatcgttgtc | 11040 |
| agaagtaagt tggccgcagt gttatcactc atggttatgg cagcactgca taattctctt | 11100 |
| actgtcatgc catccgtaag atgcttttct gtgactggtg agtactcaac caagtcattc | 11160 |
| tgagaatagt gtatgcggcg accgagttgc tcttgcccgg cgtcaacacg ggataatacc | 11220 |
| gcgccacata gcagaacttt aaaagtgctc atcattggaa aacgttcttc ggggcgaaaa | 11280 |
| ctctcaagga tcttaccgct gttgagatcc agttcgatgt aacccactcg tgcacccaac | 11340 |
| tgatcttcag catcttttac tttcaccagc gtttctgggt gagcaaaaac aggaaggcaa | 11400 |
| aatgccgcaa aaaagggaat aagggcgaca cggaaatgtt gaatactcat actcttcctt | 11460 |
| tttcaatatt attgaagcat ttatcagggt tattgtctca tgagcggata catatttgaa | 11520 |
| tgtatttaga aaataaaca aatagggggtt ccgcgcacat ttccccgaaa agtgccacct | 11580 |
| gacgtctaag aaaccattat tatcatgaca ttaacctata aaaataggcg tatcacgagg | 11640 |
| cccttcgtc ttcaagaatt cat | 11663 |

<210> SEQ ID NO 51
<211> LENGTH: 11399
<212> TYPE: DNA
<213> ORGANISM: Artificial Sequence
<220> FEATURE:
<223> OTHER INFORMATION: pAC3-T2A-yCD2

<400> SEQUENCE: 51

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |

```
ggactttcca aaatgtcgta acaactccgc cccattgacg caaatgggcg gtaggcgtgt   540
acggtgggag gtctatataa gcagagctgg tttagtgaac cggcgccagt cctccgattg   600
actgagtcgc ccgggtaccc gtgtatccaa taaaccctct tgcagttgca tccgacttgt   660
ggtctcgctg ttccttggga gggtctcctc tgagtgattg actacccgtc agcggggtc   720
tttcatttgg gggctcgtcc gggatcggga gaccctgcc cagggaccac cgacccacca   780
ccggaggta agctggccag caacttatct gtgtctgtcc gattgtctag tgtctatgac   840
tgatttatg cgcctgcgtc ggtactagtt agctaactag ctctgtatct ggcggacccg   900
tggtggaact gacgagttcg gaacacccgg ccgcaaccct gggagacgtc ccagggactt   960
cgggggccgt ttttgtggcc cgacctgagt ccaaaaatcc cgatcgtttt ggactctttg  1020
gtgcaccccc cttagaggag ggatatgtgg ttctggtagg agacgagaac ctaaaacagt  1080
tcccgcctcc gtctgaattt ttgctttcgg tttgggaccg aagccgcgcc gcgcgtcttg  1140
tctgctgcag catcgttctg tgttgtctct gtctgactgt gtttctgtat ttgtctgaga  1200
atatgggcca gactgttacc actcccttaa gtttgacctt aggtcactgg aaagatgtcg  1260
agcggatcgc tcacaaccag tcggtagatg tcaagaagag acgttgggtt accttctgct  1320
ctgcagaatg gccaaccttt aacgtcggat ggccgcgaga cggcaccttt aaccgagacc  1380
tcatcaccca ggttaagatc aaggtctttt cacctggccc gcatggacac ccagaccagg  1440
tccctacat cgtgacctgg gaagccttgg cttttgaccc ccctccctgg gtcaagccct  1500
ttgtacaccc taagcctccg cctcctcttc ctccatccgc cccgtctctc cccttgaac   1560
ctcctcgttc gaccccgcct cgatcctccc tttatccagc cctcactcct tctctaggcg  1620
ccaaacctaa acctcaagtt ctttctgaca gtgggggggcc gctcatcgac ctacttacag  1680
aagacccccc gccttatagg gacccaagac caccccttc cgacagggac ggaaatggtg  1740
gagaagcgac ccctgcggga gaggcaccgg accctcccc aatggcatct cgcctacgtg  1800
ggagacggga gccccctgtg gccgactcca ctacctcgca ggcattcccc ctccgcgcag  1860
gaggaaacgg acagcttcaa tactggccgt tctcctcttc tgacctttac aactggaaaa  1920
ataataaccc ttcttttttct gaagatccag gtaaactgac agctctgatc gagtctgttc  1980
tcatcaccca tcagcccacc tgggacgact gtcagcagct gttggggact ctgctgaccg  2040
gagaagaaaa acaacgggtg ctcttagagg ctagaaaggc ggtgcggggc gatgatgggc  2100
gccccactca actgcccaat gaagtcgatg ccgcttttcc cctcgagcgc ccagactggg  2160
attacaccac ccaggcaggt aggaaccacc tagtccacta tcgccagttg ctcctagcgg  2220
gtctccaaaa cgcgggcaga agccccacca atttggccaa ggtaaaagga ataacacaag  2280
ggcccaatga gtctccctcg gccttcctag agagacttaa ggaagcctat cgcaggtaca  2340
ctccttatga ccctgaggac ccagggcaag aaactaatgt gtctatgtct ttcatttggc  2400
agtctgcccc agacattggg agaaagttag agaggttaga agatttaaaa acaagacgc  2460
ttggagattt ggttagagag gcagaaaaga tctttaataa acgagaaacc ccggaagaaa  2520
gagaggaacg tatcaggaga gaaacagagg aaaaagaaga acgccgtagg acagaggatg  2580
agcagaaaga gaaagaaaga gatcgtagga gacatagaga gatgagcaag ctattggcca  2640
ctgtcgttag tggacagaaa caggatagac agggaggaga acgaaggagg tcccaactcg  2700
atcgcgacca gtgtgcctac tgcaaagaaa aggggcactg ggctaaagat tgtcccaaga  2760
aaccacgagg acctcgggga ccaagacccc agacctccct cctgacccta gatgactagg  2820
```

```
gaggtcaggg tcaggagccc cccctgaac ccaggataac cctcaaagtc gggggcaac    2880 ccgtcacctt cctggtagat actgggccc aacactccgt gctgacccaa aatcctggac    2940
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagcccac atacagagac    3420 tgttggacca gggaatactg gtaccctgcc agtccccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttctgc ctgagactcc    3660 acccccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg ggtatcgggc ctcggccaag aaagcccaaa    3960
tttgccagaa acaggtcaag tatctgggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacg ggactctgtt taattgggc ccagaccaac    4200 aaaaggccta tcaagaaatc aagcaagctc ttctaactgc cccagccctg gggttgccag    4260
atttgactaa gccctttgaa ctctttgtcg acgagaagca gggctacgcc aaaggtgtcc    4320
taacgcaaaa actgggaccct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aaccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca gcggccga aaggcagcca    5160 tcacagagac tccagacacc tctaccctcc tcatagaaaa ttcatcaccc tacacctcag    5220
```

| | |
|---|---|
| aacattttca ttacacagtg actgatataa aggacctaac caagttgggg gccatttatg | 5280 |
| ataaaacaaa gaagtattgg gtctaccaag gaaaacctgt gatgcctgac cagtttactt | 5340 |
| ttgaattatt agactttctt catcagctga ctcacctcag cttctcaaaa atgaaggctc | 5400 |
| tcctagagag aagccacagt ccctactaca tgctgaaccg ggatcgaaca ctcaaaaata | 5460 |
| tcactgagac ctgcaaagct tgtgcacaag tcaacgccag caagtctgcc gttaaacagg | 5520 |
| gaactagggt ccgcgggcat cggcccggca ctcattggga gatcgatttc accgagataa | 5580 |
| agcccggatt gtatggctat aaatatcttc tagtttttat agatacccttt tctggctgga | 5640 |
| tagaagcctt cccaaccaag aaagaaaccg ccaaggtcgt aaccaagaag ctactagagg | 5700 |
| agatcttccc caggttcggc atgcctcagg tattgggaac tgacaatggg cctgccttcg | 5760 |
| tctccaaggt gagtcagaca gtggccgatc tgttggggat tgattggaaa ttacattgtg | 5820 |
| catacagacc ccaaagctca ggccaggtag aaagaatgaa tagaaccatc aaggagactt | 5880 |
| taactaaatt aacgcttgca actggctcta gagactgggg gctcctactc cccttagccc | 5940 |
| tgtaccgagc ccgcaacacg ccgggccccc atggcctcac cccatatgag atcttatatg | 6000 |
| gggcaccccc gccccttgta aacttccctg accctgacat gacaagagtt actaacagcc | 6060 |
| cctctctcca agctcactta caggctctct acttagtcca gcacgaagtc tggagacctc | 6120 |
| tggcggcagc ctaccaagaa caactggacc gaccggtggt acctcaccct taccgagtcg | 6180 |
| gcgacacagt gtgggtccgc cgacaccaga ctaagaacct agaacctcgc tggaaaggac | 6240 |
| cttacacagt cctgctgacc acccccaccg ccctcaaagt agacggcatc gcagcttgga | 6300 |
| tacacgccgc ccacgtgaag gctgccgacc ccggggtgg accatcctct agactgacat | 6360 |
| ggcgcgttca acgctctcaa aaccccctca agataagatt aacccgtgga agcccttaat | 6420 |
| agtcatggga gtcctgttag gagtagggat ggcagagagc cccatcagg tctttaatgt | 6480 |
| aacctggaga gtcaccaacc tgatgactgg gcgtaccgcc aatgccacct ccctcctggg | 6540 |
| aactgtacaa gatgccttcc caaaattata ttttgatcta tgtgatctgg tcggagagga | 6600 |
| gtgggaccct tcagaccagg aaccgtatgt cgggtatggc tgcaagtacc ccgcagggag | 6660 |
| acagcggacc cggactttg acttttacgt gtgccctggg cataccgtaa agtcggggtg | 6720 |
| tgggggacca ggagagggct actgtggtaa atgggggtgt gaaaccaccg gacaggctta | 6780 |
| ctggaagccc acatcatcgt gggacctaat ctcccttaag cgcggtaaca ccccctggga | 6840 |
| cacgggatgc tctaaagttg cctgtggccc ctgctacgac ctctccaaag tatccaattc | 6900 |
| cttccaaggg gctactcgag ggggcagatg caaccctcta gtcctagaat tcactgatgc | 6960 |
| aggaaaaaag gctaactggg acgggcccaa atcgtgggga ctgagactgt accggacagg | 7020 |
| aacagatcct attaccatgt tctccctgac ccggcaggtc cttaatgtgg accccgagt | 7080 |
| ccccatagg cccaacccag tattacccga ccaaagactc ccttcctcac caatagagat | 7140 |
| tgtaccggct ccacagccac ctagcccccct caataccagt taccccccctt ccactaccag | 7200 |
| tacaccctca acctcccta caagtccaag tgtcccacag ccaccccag gaactggaga | 7260 |
| tagactacta gctctagtca aaggagccta tcaggcgctt aacctcacca atcccgacaa | 7320 |
| gacccaagaa tgttggctgt gcttagtgtc gggacctcct tattacgaag gagtagcggt | 7380 |
| cgtgggcact tataccaatc attccaccgc tccggccaac tgtacggcca cttcccaaca | 7440 |
| taagcttacc ctatctgaag tgacaggaca gggcctatgc atgggggcag tacctaaaac | 7500 |
| tcaccaggcc ttatgtaaca ccacccaaag cgccggctca ggatcctact accttgcagc | 7560 |

```
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgtttttat gcagaccaca cggggctagt    8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca gagggcagag gaagtcttct    8340
aacatgcggt gacgtggagg agaatcccgg ccctggcgcg cctatggtga ccggcggcat    8400
ggcctccaag tgggatcaaa agggcatgga tatcgcttac gaggaggccc tgctgggcta    8460
caaggagggc ggcgtgccta tcggcggctg tctgatcaac aacaaggacg gcagtgtgct    8520
gggcaggggc cacaacatga ggttccagaa gggctccgcc accctgcacg cgagatctc    8580 caccctggag aactgtggca ggctggaggg caaggtgtac aaggacacca ccctgtacac    8640
caccctgtcc ccttgtgaca tgtgtaccgg cgctatcatc atgtacgca tccctaggtg    8700 tgtgatcggc gagaacgtga acttcaagtc caagggcgag aagtacctgc aaaccagggg    8760
ccacgaggtg tgggttgttg acgatgagag gtgtaagaag ctgatgaagc agttcatcga    8820
cgagaggcct caggactggt tcgaggatat cggcgagtaa gcggccgcag ataaaataaa    8880
agattttatt tagtctccag aaaaagggg gaatgaaaga ccccacctgt aggtttggca    8940
agctagctta agtaacgcca ttttgcaagg catggaaaaa tacataactg agaatagaga    9000
agttcagatc aaggtcagga acagatggaa cagctgaata tgggccaaac aggatatctg    9060
tggtaagcag ttcctgcccc ggctcagggc caagaacaga tggaacagct gaatatgggc    9120
caaacaggat atctgtggta agcagttcct gccccggctc agggccaaga acagatggtc    9180
cccagatgcg gtccagccct cagcagtttc tagagaacca tcagatgttt ccagggtgcc    9240
ccaaggacct gaaatgaccc tgtgccttat ttgaactaac caatcagttc gcttctcgct    9300
tctgttcgcg cgcttctgct ccccgagctc aataaaagag cccacaaccc ctcactcggg    9360
gcgccagtcc tccgattgac tgagtcgccc gggtacccgt gtatccaata acccctcttg    9420
cagttgcatc cgacttgtgg tctcgctgtt ccttgggagg gtctcctctg agtgattgac    9480
tacccgtcag cggggtctt tcattacatg tgagcaaaag gccagcaaaa ggccaggaac    9540
cgtaaaaagg ccgcgttgct ggcgtttttc cataggctcc gcccccctga cgagcatcac    9600
aaaaatcgac gctcaagtca gaggtggcga aacccgacag gactataaag ataccaggcg    9660
tttccccctg gaagctccct cgtgcgctct cctgttccga cctgccgct taccggatac    9720 ctgtccgcct ttctcccttc gggaagcgtg gcgctttctc aatgctcacg ctgtaggtat    9780
ctcagttcgg tgtaggtcgt tcgctccaag ctgggctgtg tgcacgaacc cccgttcag    9840 cccgaccgct gcgccttatc cggtaactat cgtcttgagt ccaacccggt aagacacgac    9900
ttatcgccac tggcagcagc cactggtaac aggattagca gagcgaggta tgtaggcggt    9960
```

```
gctacagagt tcttgaagtg gtggcctaac tacggctaca ctagaaggac agtatttggt    10020
atctgcgctc tgctgaagcc agttaccttc ggaaaaagag ttggtagctc ttgatccggc    10080
aaacaaacca ccgctggtag cggtggtttt tttgtttgca agcagcagat tacgcgcaga    10140
aaaaaaggat ctcaagaaga tcctttgatc ttttctacgg ggtctgacgc tcagtggaac    10200
gaaaactcac gttaagggat tttggtcatg agattatcaa aaaggatctt cacctagatc    10260
cttttaaatt aaaaatgaag ttttaaatca atctaaagta tatatgagta aacttggtct    10320
gacagttacc aatgcttaat cagtgaggca cctatctcag cgatctgtct atttcgttca    10380
tccatagttg cctgactccc cgtcgtgtag ataactacga tacgggaggg cttaccatct    10440
ggccccagtg ctgcaatgat accgcgagac ccacgctcac cggctccaga tttatcagca    10500
ataaaccagc cagccggaag ggccgagcgc agaagtggtc ctgcaacttt atccgcctcc    10560
atccagtcta ttaattgttg ccgggaagct agagtaagta gttcgccagt taatagtttg    10620
cgcaacgttg ttgccattgc tgcaggcatc gtggtgtcac gctcgtcgtt tggtatggct    10680
tcattcagct ccggttccca acgatcaagg cgagttacat gatcccccat gttgtgcaaa    10740
aaagcggtta gctccttcgg tcctccgatc gttgtcagaa gtaagttggc cgcagtgtta    10800
tcactcatgg ttatggcagc actgcataat tctcttactg tcatgccatc cgtaagatgc    10860
ttttctgtga ctggtgagta ctcaaccaag tcattctgag aatagtgtat gcggcgaccg    10920
agttgctctt gcccggcgtc aacacgggat aataccgcgc cacatagcag aactttaaaa    10980
gtgctcatca ttggaaaacg ttcttcgggg cgaaaactct caaggatctt accgctgttg    11040
agatccagtt cgatgtaacc cactcgtgca cccaactgat cttcagcatc ttttactttc    11100
accagcgttt ctgggtgagc aaaaacagga aggcaaaatg ccgcaaaaaa gggaataagg    11160
gcgacacgga aatgttgaat actcatactc ttcctttttc aatattattg aagcatttat    11220
cagggttatt gtctcatgag cggatacata tttgaatgta tttagaaaaa taaacaaata    11280
ggggttccgc gcacatttcc ccgaaaagtg ccacctgacg tctaagaaac cattattatc    11340
atgacattaa cctataaaaa taggcgtatc acgaggccct ttcgtcttca agaattcat    11399
```

<210> SEQ ID NO 52
<211> LENGTH: 11408
<212> TYPE: DNA
<213> ORGANISM: Artificial Sequence
<220> FEATURE:
<223> OTHER INFORMATION: pAC3-GSG-T2A-yCD2

<400> SEQUENCE: 52

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctgg tttagtgaac cggcgccagt cctccgattg     600
```

```
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga daccccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacaccccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcacctttt aaccgagacc   1380 tcatcccca ggttaagatc aaggtctttt cacctggccc gcatggacac ccagaccagg   1440 tccctacat cgtgacctgg gaagccttgg cttttgaccc ccctccctgg gtcaagccct   1500
ttgtacaccc taagcctccg cctcctcttc ctccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtgggggggcc gctcatcgac ctacttacag   1680
aagacccccc gccttatagg gacccaagac caccccctttc cgacagggac ggaaatggtg   1740
gagaagcgac ccctgcggga gaggcaccgg accccctcccc aatggcatct cgcctacgtg   1800
ggagacggga gcccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgttc   1980
tcatcaccca tcagcccacc tgggacgact gtcagcagct gttggggact ctgctgaccg   2040
gagaagaaaa acaacggggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta cgccagttg ctcctagcgg   2220 gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacatttggg agaaagttag agaggttaga agattttaaaa aacaagacgc   2460 ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc gggggggcaac   2880 ccgtcacctt cctggtagat actggggcccc aacactccgt gctgacccaa aatcctggac   2940
ccctaagtga taagtctgcc tgggtccaag ggctactgg aggaaagcgg tatcgctgga   3000
```

```
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagccctg caagtgttga     3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagccccac atacagagac    3420
tgttggacca gggaatactg gtaccctgcc agtcccctg gaacacgccc ctgctacccg      3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttctgc ctgagactcc      3660
acccaccag tcagcctctc ttcgcctttg agtggagaga tccagagatg ggaatctcag     3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaaccta gggaacctcg ggtatcgggc ctcggccaag aaagcccaaa      3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gcccttttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa     4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcgacc ggtggtagcc ctgaacccgg      4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cggacatcc gctcagcggg     4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttcacagtg actgatataa aggacctaac caagtggggg gccatttatg     5280
ataaaacaaa gaagtattgg gtctaccaag gaaaacctgt gatgcctgac cagtttactt    5340
```

```
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agataccttt tctggctgga    5640
tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccaccg ccctcaaagt agacggcatc gcagcttgga    6300
tacacgccgc cacgtgaag gctgccgacc ccggggtgg accatcctct agactgacat    6360
ggcgcgttca acgctctcaa aacccctca agataagatt aacccgtgga gcccttaat    6420 agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttg actttacgt gtgccctggg cataccgtaa agtcggggtg    6720
tgggggacca ggagagggct actgtggtaa atgggggtgt gaaaccaccg gacaggctta    6780
ctggaagccc acatcatcgt gggacctaat ctcccttaag cgcggtaaca cccctggga    6840 cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atccgacaa    7320 gacccaagaa tgttggctgt gcttagtgtc gggacctcct tattacgaag gagtagcggt    7380
cgtgggcact tataccaatc attccaccgc tccgccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680 ctccccccgat tatatgtatg gtcagcttga acagcgtacc aaatataaaa gagagccagt    7740
```

```
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat tgctattcc taaaggaggg    7980 aggtctctgc gcagccctaa aagaagaatg ttgtttttat gcagaccaca cggggctagt    8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca ggaagcggag agggcagagg    8340
aagtcttcta acatgcggtg acgtggagga gaatcccggc cctggcgcgc ctatggtgac    8400
cggcggcatg gcctccaagt gggatcaaaa gggcatggat atcgcttacg aggaggccct    8460
gctgggctac aaggagggcg gcgtgcctat cggcggctgt ctgatcaaca caaggacgg    8520 cagtgtgctg ggcaggggcc acaacatgag gttccagaag ggctccgcca ccctgcacgg    8580
cgagatctcc accctggaga actgtggcag gctggagggc aaggtgtaca aggacaccac    8640
cctgtacacc accctgtccc cttgtgacat gtgtaccggc gctatcatca tgtacgcat    8700 ccctaggtgt gtgatcggcg agaacgtgaa cttcaagtcc aagggcgaga gtacctgca    8760 aaccaggggc cacgaggtgg tggttgttga cgatgagagg tgtaagaagc tgatgaagca    8820
gttcatcgac gagaggcctc aggactggtt cgaggatatc ggcgagtaag cggccgcaga    8880
taaaataaaa gattttattt agtctccaga aaaaggggg aatgaaagac cccacctgta    8940
ggtttggcaa gctagcttaa gtaacgccat tttgcaaggc atggaaaaat acataactga    9000
gaatagagaa gttcagatca aggtcaggaa cagatggaac agctgaatat gggccaaaca    9060
ggatatctgt ggtaagcagt tcctgccccg gctcagggcc aagaacagat ggaacagctg    9120
aatatgggcc aaacaggata tctgtggtaa gcagttcctg ccccggctca gggccaagaa    9180
cagatggtcc ccagatgcgg tccagccctc agcagtttct agagaaccat cagatgtttc    9240
cagggtgccc caaggacctg aaatgaccct gtgccttatt tgaactaacc aatcagttcg    9300
cttctcgctt ctgttcgcgc gcttctgctc cccgagctca ataaaagagc ccacaacccc    9360
tcactcgggg cgccagtcct ccgattgact gagtcgcccg ggtacccgtg tatccaataa    9420
accctcttgc agttgcatcc gacttgtggt ctcgctgttc cttgggaggg tctcctctga    9480
gtgattgact acccgtcagc gggggtcttt cattacatgt gagcaaaagg ccagcaaaag    9540
gccaggaacc gtaaaaaggc cgcgttgctg gcgtttttcc ataggctccg ccccctgac    9600 gagcatcaca aaaatcgacg ctcaagtcag aggtggcgaa acccgacagg actataaaga    9660
taccaggcgt ttccccctgg aagctccctc gtgcgctctc ctgttccgac cctgccgctt    9720
accggatacc tgtccgcctt tctcccttcg ggaagcgtgg cgctttctca atgctcacgc    9780
tgtaggtatc tcagttcggt gtaggtcgtt cgctccaagc tgggctgtgt gcacgaaccc    9840
cccgttcagc ccgaccgctg cgccttatcc ggtaactatc gtcttgagtc caacccggta    9900
agacacgact tatcgccact ggcagcagcc actggtaaca ggattagcag agcgaggtat    9960
gtaggcggtg ctacagagtt cttgaagtgg tggcctaact acggctacac tagaaggaca   10020
gtatttggta tctgcgctct gctgaagcca gttaccttcg gaaaaagagt tggtagctct   10080
```

```
tgatccggca aacaaaccac cgctggtagc ggtggttttt ttgtttgcaa gcagcagatt    10140
acgcgcagaa aaaaggatc tcaagaagat cctttgatct tttctacggg gtctgacgct     10200
cagtggaacg aaaactcacg ttaagggatt ttggtcatga gattatcaaa aaggatcttc    10260
acctagatcc ttttaaatta aaaatgaagt tttaaatcaa tctaaagtat atatgagtaa    10320
acttggtctg acagttacca atgcttaatc agtgaggcac ctatctcagc gatctgtcta    10380
tttcgttcat ccatagttgc ctgactcccc gtcgtgtaga taactacgat acgggagggc    10440
ttaccatctg gccccagtgc tgcaatgata ccgcgagacc cacgctcacc ggctccagat    10500
ttatcagcaa taaaccagcc agccggaagg gccgagcgca gaagtggtcc tgcaacttta    10560
tccgcctcca tccagtctat taattgttgc cgggaagcta gagtaagtag ttcgccagtt    10620
aatagtttgc gcaacgttgt tgccattgct gcaggcatcg tggtgtcacg ctcgtcgttt    10680
ggtatggctt cattcagctc cggttcccaa cgatcaaggc gagttacatg atcccccatg    10740
ttgtgcaaaa aagcggttag ctccttcggt cctccgatcg ttgtcagaag taagttggcc    10800
gcagtgttat cactcatggt tatggcagca ctgcataatt ctcttactgt catgccatcc    10860
gtaagatgct tttctgtgac tggtgagtac tcaaccaagt cattctgaga atagtgtatg    10920
cggcgaccga gttgctcttg cccggcgtca cacgggata ataccgcgcc acatagcaga     10980
actttaaaag tgctcatcat tggaaaacgt tcttcggggc gaaaactctc aaggatctta    11040
ccgctgttga tccagttc gatgtaaccc actcgtgcac ccaactgatc ttcagcatct      11100
tttactttca ccagcgtttc tgggtgagca aaaacaggaa ggcaaaatgc cgcaaaaaag    11160
ggaataaggg cgacacggaa atgttgaata ctcatactct ccttttttca atattattga    11220
agcatttatc agggttattg tctcatgagc ggatacatat ttgaatgtat ttagaaaaat    11280
aaacaaatag gggttccgcg cacatttccc cgaaaagtgc cacctgacgt ctaagaaacc    11340
attattatca tgacattaac ctataaaaat aggcgtatca cgaggccctt tcgtcttcaa    11400
gaattcat                                                            11408
```

<210> SEQ ID NO 53
<211> LENGTH: 11402
<212> TYPE: DNA
<213> ORGANISM: Artificial Sequence
<220> FEATURE:
<223> OTHER INFORMATION: pAC3-P2A-yCD2

<400> SEQUENCE: 53

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcggggtc     720
```

```
tttcatttgg gggctcgtcc gggatcggga gaccccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg ccaaccttt  aacgtcggat ggccgcgaga cggcaccttt aaccgagacc   1380
tcatcaccca ggttaagatc aaggtctttt cacctggccc gcatggacac ccagaccagg   1440 tccccctacat cgtgacctgg gaagccttgg cttttgaccc ccctccctgg gtcaagccct   1500
ttgtacaccc taagcctccg cctcctcttc ctccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtgggggggcc gctcatcgac ctacttacag   1680
aagacccccc gccttatagg gacccaagac caccccttc  cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttcttttttct gaagatccag gtaaactgac agctctgatc gagtctgttc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaagaagaa acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc cccctgaac  ccaggataac cctcaaagtc gggggcaac    2880 ccgtcacctt cctggtagat actggggccc aacactccgt gctgacccaa aatcctggac   2940
ccctaagtga taagtctgcc tgggtccaag gggctactgg aggaaagcgg tatcgctgga   3000
ccacggatcg caaagtacat ctagctaccg gtaaggtcac ccactctttc ctccatgtac   3060
```

```
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagcccac atacagagac     3420 tgttggacca gggaatactg gtaccctgcc agtcccctg gaacacgccc ctgctacccg      3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttttctgc ctgagactcc    3660 accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaaccta gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gccctttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggcccta agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340 tgaattatt agactttctt catcagctga ctcacctcag cttctcaaaa atgaaggctc    5400
tcctagagag aagccacagt ccctactaca tgctgaaccg ggatcgaaca ctcaaaaata    5460
```

```
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacccttt tctggctgga   5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggc acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt agacggcatc gcagcttgga    6300
tacacgccgc ccacgtgaag gctgccgacc ccgggggtgg accatcctct agactgacat    6360
ggcgcgttca acgctctcaa aaccccctca agataagatt aacccgtgga agcccttaat    6420
agtcatggga gtcctgttag gagtagggat ggcagagagc cccatcagg  tctttaatgt    6480 aacctgagaa gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggacttttg acttttacgt gtgccctggg cataccgtaa agtcggggtg    6720
tgggggacca ggagagggct actgtggtaa atggggggtgt gaaaccaccg gacaggctta    6780
ctggaagccc acatcatcgt gggacctaat ctcccttaag cgcggtaaca cccctggga    6840 cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg gaccccgagt    7080
ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtgtg gtcagcttga acagcgtacc aaatataaaa gagagccagt    7740
atcattgacc ctggcccttc tactaggagg attaaccatg ggagggattg cagctggaat    7800
```

```
agggacgggg accactgcct taattaaaac ccagcagttt gagcagcttc atgccgctat      7860
ccagacagac ctcaacgaag tcgaaaagtc aattaccaac ctagaaaagt cactgacctc      7920
gttgtctgaa gtagtcctac agaaccgcag aggcctagat ttgctattcc taaaggaggg      7980
aggtctctgc gcagccctaa aagaagaatg ttgtttttat gcagaccaca cggggctagt      8040
gagagacagc atggccaaat taagagaaag gcttaatcag agacaaaaac tatttgagac      8100
aggccaagga tggttcgaag ggctgtttaa tagatccccc tggtttacca ccttaatctc      8160
caccatcatg ggacctctaa tagtactctt actgatctta ctctttggac cttgcattct      8220
caatcgattg gtccaatttg ttaaagacag gatctcagtg gtccaggctc tggttttgac      8280
tcagcaatat caccagctaa aacccataga gtacgagcca gctactaact tcagcctgct      8340
gaagcaggct ggagacgtgg aggagaaccc tggacctggc gcgccatatgg tgaccggcgg      8400 catggcctcc aagtgggatc aaaagggcat ggatatcgct tacgaggagg ccctgctggg      8460
ctacaaggag ggcggcgtgc ctatcggcgg ctgtctgatc aacaacaagg acggcagtgt      8520
gctgggcagg ggccacaaca tgaggttcca gaagggctcc gccaccctgc acggcgagat      8580
ctccaccctg gagaactgtg gcaggctgga gggcaaggtg tacaaggaca ccaccctgta      8640
caccaccctg tccccttgtg acatgtgtac cggcgctatc atcatgtacg gcatccctag      8700
gtgtgtgatc ggcgagaacg tgaacttcaa gtccaagggc gagaagtacc tgcaaaccag      8760
gggccacgag gtggtggttg ttgacgatga gaggtgtaag aagctgatga gcagttcat       8820 cgacgagagg cctcaggact ggttcgagga tatcggcgag taagcggccg cagataaaat      8880
aaaagatttt atttagtctc cagaaaaagg ggggaatgaa agaccccacc tgtaggtttg      8940
gcaagctagc ttaagtaacg ccattttgca aggcatggaa aaatacataa ctgagaatag      9000
agaagttcag atcaaggtca ggaacagatg gaacagctga atatgggcca acaggatat       9060 ctgtggtaag cagttcctgc cccggctcag ggccaagaac agatggaaca gctgaatatg      9120
ggccaaacag gatatctgtg gtaagcagtt cctgccccgg ctcagggcca agaacagatg      9180
gtccccagat gcggtccagc cctcagcagt ttctagagaa ccatcagatg tttccagggt      9240
gccccaagga cctgaaatga ccctgtgcct tatttgaact aaccaatcag ttcgcttctc      9300
gcttctgttc gcgcgcttct gctccccgag ctcaataaaa gagcccacaa cccctcactc      9360
ggggcgccag tcctccgatt gactgagtcg cccgggtacc cgtgtatcca ataaaccctc      9420
ttgcagttgc atccgacttg tggtctcgct gttccttggg agggtctcct ctgagtgatt      9480
gactacccgt cagcggggt ctttcattac atgtgagcaa aaggccagca aaaggccagg      9540
aaccgtaaaa aggccgcgtt gctggcgttt ttccataggc tccgcccccc tgacgagcat      9600
cacaaaaatc gacgctcaag tcagaggtgg cgaaacccga caggactata agataccag       9660 gcgtttcccc ctggaagctc cctcgtgcgc tctcctgttc cgaccctgcc gcttaccgga      9720
tacctgtccg cctttctccc ttcgggaagc gtggcgcttt ctcaatgctc acgctgtagg      9780
tatctcagtt cggtgtaggt cgttcgctcc aagctgggct gtgtgcacga acccccgtt       9840 cagcccgacc gctgcgcctt atccggtaac tatcgtcttg agtccaaccc ggtaagacac      9900
gacttatcgc cactggcagc agccactggt aacaggatta gcagagcgag gtatgtaggc      9960
ggtgctacag agttcttgaa gtggtggcct aactacggct acactagaag gacagtattt     10020
ggtatctgcg ctctgctgaa gccagttacc ttcggaaaaa gagttggtag ctcttgatcc     10080
ggcaaacaaa ccaccgctgg tagcggtggt ttttttgttt gcaagcagca gattacgcgc     10140
agaaaaaaag gatctcaaga agatcctttg atcttttcta cggggtctga cgctcagtgg     10200
```

```
aacgaaaact cacgttaagg gattttggtc atgagattat caaaaaggat cttcacctag    10260
atccttttaa attaaaaatg aagttttaaa tcaatctaaa gtatatatga gtaaacttgg    10320
tctgacagtt accaatgctt aatcagtgag gcacctatct cagcgatctg tctatttcgt    10380
tcatccatag ttgcctgact ccccgtcgtg tagataacta cgatacggga gggcttacca    10440
tctggcccca gtgctgcaat gataccgcga gacccacgct caccggctcc agatttatca    10500
gcaataaacc agccagccgg aagggccgag cgcagaagtg gtcctgcaac tttatccgcc    10560
tccatccagt ctattaattg ttgccgggaa gctagagtaa gtagttcgcc agttaatagt    10620
ttgcgcaacg ttgttgccat tgctgcaggc atcgtggtgt cacgctcgtc gtttggtatg    10680
gcttcattca gctccggttc ccaacgatca aggcgagtta catgatcccc catgttgtgc    10740
aaaaaagcgg ttagctcctt cggtcctccg atcgttgtca gaagtaagtt ggccgcagtg    10800
ttatcactca tggttatggc agcactgcat aattctctta ctgtcatgcc atccgtaaga    10860
tgcttttctg tgactggtga gtactcaacc aagtcattct gagaatagtg tatgcggcga    10920
ccgagttgct cttgcccggc gtcaacacgg gataataccg cgccacatag cagaacttta    10980
aaagtgctca tcattggaaa acgttcttcg gggcgaaaac tctcaaggat cttaccgctg    11040
ttgagatcca gttcgatgta acccactcgt gcacccaact gatcttcagc atcttttact    11100
ttcaccagcg tttctgggtg agcaaaaaca ggaaggcaaa atgccgcaaa aaagggaata    11160
agggcgacac ggaaatgttg aatactcata ctcttccttt ttcaatatta ttgaagcatt    11220
tatcagggtt attgtctcat gagcggatac atatttgaat gtatttagaa aaataaacaa    11280 atagggggttc cgcgcacatt tccccgaaaa gtgccacctg acgtctaaga aaccattatt    11340
atcatgacat taacctataa aaataggcgt atcacgaggc cctttcgtct tcaagaattc    11400
at                                                                   11402
```

<210> SEQ ID NO 54
<211> LENGTH: 11411
<212> TYPE: DNA
<213> ORGANISM: Artificial Sequence
<220> FEATURE:
<223> OTHER INFORMATION: pAC3-GSG-P2A-yCD2

<400> SEQUENCE: 54

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540 acggtggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actacccgtc agcgggggtc     720
tttcatttgg gggctcgtcc gggatcggga gacccctgcc cagggaccac cgacccacca     780
```

| | |
|---|---|
| ccgggaggta agctggccag caacttatct gtgtctgtcc gattgtctag tgtctatgac | 840 |
| tgattttatg cgcctgcgtc ggtactagtt agctaactag ctctgtatct ggcggacccg | 900 |
| tggtggaact gacgagttcg gaacacccgg ccgcaaccct gggagacgtc ccagggactt | 960 |
| cgggggccgt ttttgtggcc cgacctgagt ccaaaaatcc cgatcgtttt ggactctttg | 1020 |
| gtgcaccccc cttagaggag ggatatgtgg ttctggtagg agacgagaac ctaaaacagt | 1080 |
| tcccgcctcc gtctgaattt ttgctttcgg tttgggaccg aagccgcgcc gcgcgtcttg | 1140 |
| tctgctgcag catcgttctg tgttgtctct gtctgactgt gtttctgtat ttgtctgaga | 1200 |
| atatgggcca gactgttacc actcccttaa gtttgacctt aggtcactgg aaagatgtcg | 1260 |
| agcggatcgc tcacaaccag tcggtagatg tcaagaagag acgttgggtt accttctgct | 1320 |
| ctgcagaatg ccaacctttt aacgtcggat ggccgcgaga cggcacctttt aaccgagacc | 1380 |
| tcatcaccca ggttaagatc aaggtctttt cacctggccc gcatggacac ccagaccagg | 1440 |
| tcccctacat cgtgacctgg gaagccttgg cttttgaccc ccctccctgg gtcaagccct | 1500 |
| ttgtacaccc taagcctccg cctcctcttc ctccatccgc cccgtctctc ccccttgaac | 1560 |
| ctcctcgttc gaccccgcct cgatcctccc tttatccagc cctcactcct tctctaggcg | 1620 |
| ccaaacctaa acctcaagtt cttctgaca gtggggggcc gctcatcgac ctacttacag | 1680 |
| aagaccccc gccttatagg gacccaagac caccccttc cgacagggac ggaaatggtg | 1740 |
| gagaagcgac ccctgcggga gaggcaccgg acccctcccc aatggcatct cgcctacgtg | 1800 |
| ggagacggga gccccctgtg gccgactcca ctacctcgca ggcattcccc ctccgcgcag | 1860 |
| gaggaaacgg acagcttcaa tactggccgt tctcctcttc tgacctttac aactggaaaa | 1920 |
| ataataaccc ttcttttttct gaagatccag gtaaactgac agctctgatc gagtctgttc | 1980 |
| tcatcaccca tcagcccacc tgggacgact gtcagcagct gttggggact ctgctgaccg | 2040 |
| gagaagaaaa acaacgggtg ctcttagagg ctagaaaggc ggtgcggggc gatgatgggc | 2100 |
| gccccactca actgcccaat gaagtcgatg ccgcttttcc cctcgagcgc ccagactggg | 2160 |
| attacaccac ccaggcaggt aggaaccacc tagtccacta tcgccagttg ctcctagcgg | 2220 |
| gtctccaaaa cgcgggcaga agccccacca atttggccaa ggtaaaagga ataacacaag | 2280 |
| ggcccaatga gtctccctcg gccttcctag agagacttaa ggaagcctat cgcaggtaca | 2340 |
| ctccttatga ccctgaggac ccagggcaag aaactaatgt gtctatgtct ttcatttggc | 2400 |
| agtctgcccc agacattggg agaaagttag agaggttaga agatttaaaa aacaagacgc | 2460 |
| ttggagattt ggttagagag gcagaaaaga tctttaataa acgagaaacc ccggaagaaa | 2520 |
| gagaggaacg tatcaggaga gaaacagagg aaaagaaga acgccgtagg acagaggatg | 2580 |
| agcagaaaga gaaagaaaga gatcgtagga gacatagaga gatgagcaag ctattggcca | 2640 |
| ctgtcgttag tggacagaaa caggatagac agggaggaga acgaaggagg tcccaactcg | 2700 |
| atcgcgacca gtgtgcctac tgcaaagaaa aggggcactg gctaaagat tgtcccaaga | 2760 |
| aaccacgagg acctcgggga ccaagacccc agacctccct cctgacccta gatgactagg | 2820 |
| gaggtcaggg tcaggagccc cccctgaac ccaggataac cctcaaagtc ggggggcaac | 2880 |
| ccgtcaccttt cctggtagat actgggggcc aacactccgt gctgacccaa aatcctggac | 2940 |
| ccctaagtga taagtctgcc tgggtccaag ggctactgg aggaaagcgg tatcgctgga | 3000 |
| ccacggatcg caaagtacat ctagctaccg gtaaggtcac ccactctttc ctccatgtac | 3060 |
| cagactgtcc ctatcctctg ttaggaagag atttgctgac taaactaaaa gcccaaatcc | 3120 |
| actttgaggg atcaggagcc caggttatgg gaccaatggg gcagcccctg caagtgttga | 3180 |

```
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagcccac atacagagac     3420 tgttggacca gggaatactg gtaccctgcc agtcccctg gaacacgccc ctgctacccg     3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttctgc ctgagactcc     3660 accccaccag tcagcctctc ttcgcctttg agtggagaga tccagagatg gaatctcag    3720 gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg gtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagaccct cgacaactaa     4080 gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gcccttgaa ctctttgtcg acgagaagca gggctacgcc aaaggtgtcc     4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc atgcagtag    4500 aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggcccta agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca gcggccgga aaggcagcca    5160 tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
```

```
gaactagggt ccgcgggcat cggcccggca ctcattggga gatcgatttc accgagataa      5580
agcccggatt gtatggctat aaatatcttc tagtttttat agatacctt tctggctgga       5640
tagaagcctt cccaaccaag aaagaaaccg ccaaggtcgt aaccaagaag ctactagagg      5700
agatcttccc caggttcggc atgcctcagg tattgggaac tgacaatggg cctgccttcg     5760
tctccaaggt gagtcagaca gtggccgatc tgttggggat tgattggaaa ttacattgtg     5820
catacagacc ccaaagctca ggccaggtag aaagaatgaa tagaaccatc aaggagactt      5880
taactaaatt aacgcttgca actggctcta gagactgggt gctcctactc cccttagccc     5940
tgtaccgagc ccgcaacacg ccgggccccc atggcctcac cccatatgag atcttatatg     6000
gggcaccccc gccccttgta aacttccctg accctgacat gacaagagtt actaacagcc     6060
cctctctcca agctcactta caggctctct acttagtcca gcacgaagtc tggagacctc     6120
tggcggcagc ctaccaagaa caactggacc gaccggtggt acctcaccct taccgagtcg     6180
gcgacacagt gtgggtccgc cgacaccaga ctaagaacct agaacctcgc tggaaaggac     6240
cttacacagt cctgctgacc acccccaccg ccctcaaagt agacggcatc gcagcttgga     6300
tacacgccgc ccacgtgaag gctgccgacc ccggggtgg accatcctct agactgacat      6360
ggcgcgttca acgctctcaa aaccccctca agataagatt aacccgtgga agcccttaat     6420
agtcatggga gtcctgttag gagtagggat ggcagagagc ccccatcagg tctttaatgt     6480
aacctggaga gtcaccaacc tgatgactgg gcgtaccgcc aatgccacct ccctcctggg     6540
aactgtacaa gatgccttcc caaaattata ttttgatcta tgtgatctgg tcggagagga     6600
gtgggacccct tcagaccagg aaccgtatgt cgggtatggc tgcaagtacc ccgcagggag    6660
acagcggacc cggactttg acttttacgt gtgccctggg cataccgtaa agtcggggtg      6720
tgggggacca ggagagggct actgtggtaa atggggggtgt gaaaccaccg gacaggctta    6780
ctggaagccc acatcatcgt gggacctaat ctcccttaag cgcggtaaca cccccctggga   6840
cacgggatgc tctaaagttg cctgtggccc ctgctacgac ctctccaaag tatccaattc    6900
cttccaaggg gctactcgag ggggcagatg caaccctcta gtcctagaat tcactgatgc   6960
aggaaaaaag gctaactggg acgggcccaa atcgtgggga ctgagactgt accggacagg    7020
aacagatcct attaccatgt tctccctgac ccggcaggtc cttaatgtgg gaccccgagt    7080
ccccataggg cccaacccag tattacccga ccaaagactc ccttcctcac caatagagat    7140
tgtaccggct ccacagccac ctagcccct caataccagt taccccccctt ccactaccag    7200
tacaccctca acctcccta caagtccaag tgtcccacag ccaccccag gaactggaga      7260
tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac   7500
tcaccaggcc ttatgtaaca ccacccaaag cgccggctca ggatcctact accttgcagc    7560
acccgccgga caatgtgggc ttgcagcac tggattgact ccctgcttgt ccaccacggt    7620
gctcaatcta accacagatt attgtgtatt agttgaactc tggcccagag taattaccacc  7680
ctcccccgat tatatgtatg gtcagcttga acagcgtacc aaatataaaa gagagccagt    7740
atcattgacc ctggcccttc tactaggagg attaaccatg ggaggggattg cagctggaat   7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
```

-continued

| | |
|---|---|
| gttgtctgaa gtagtcctac agaaccgcag aggcctagat ttgctattcc taaaggaggg | 7980 |
| aggtctctgc gcagccctaa aagaagaatg ttgtttttat gcagaccaca cggggctagt | 8040 |
| gagagacagc atggccaaat taagagaaag gcttaatcag agacaaaaac tatttgagac | 8100 |
| aggccaagga tggttcgaag ggctgtttaa tagatccccc tggtttacca ccttaatctc | 8160 |
| caccatcatg ggacctctaa tagtactctt actgatctta ctctttggac cttgcattct | 8220 |
| caatcgattg gtccaatttg ttaaagacag gatctcagtg gtccaggctc tggttttgac | 8280 |
| tcagcaatat caccagctaa aacccataga gtacgagcca ggaagcggag ctactaactt | 8340 |
| cagcctgctg aagcaggctg gagacgtgga ggagaaccct ggacctggcg cgcctatggt | 8400 |
| gaccggcggc atggcctcca gtgggatca aaagggcatg gatatcgctt acgaggaggc | 8460 |
| cctgctgggc tacaaggagg gcggcgtgcc tatcggcggc tgtctgatca acaacaagga | 8520 |
| cggcagtgtg ctgggcaggg gccacaacat gaggttccag aagggctccg ccaccctgca | 8580 |
| cggcgagatc tccaccctgg agaactgtgg caggctggag ggcaaggtgt acaaggacac | 8640 |
| caccctgtac accacctgt ccccttgtga catgtgtacc ggcgctatca tcatgtacgg | 8700 |
| catccctagg tgtgtgatcg gcgagaacgt gaacttcaag tccaagggcg agaagtacct | 8760 |
| gcaaaccagg ggccacgagg tggtggttgt tgacgatgag aggtgtaaga agctgatgaa | 8820 |
| gcagttcatc gacgagaggc ctcaggactg gttcgaggat atcggcgagt aagcggccgc | 8880 |
| agataaaata aagattttta tttagtctcc agaaaaaggg gggaatgaaa gaccccacct | 8940 |
| gtaggtttgg caagctagct taagtaacgc cattttgcaa ggcatggaaa atacataac | 9000 |
| tgagaataga gaagttcaga tcaaggtcag gaacagatgg aacagctgaa tatgggccaa | 9060 |
| acaggatatc tgtggtaagc agttcctgcc ccggctcagg gccaagaaca gatggaacag | 9120 |
| ctgaatatgg gccaaacagg atatctgtgg taagcagttc ctgccccggc tcagggccaa | 9180 |
| gaacagatgg tccccagatg cggtccagcc ctcagcagtt tctagagaac catcagatgt | 9240 |
| ttccagggtg ccccaaggac ctgaaatgac cctgtgcctt atttgaacta accaatcagt | 9300 |
| tcgcttctcg cttctgttcg cgcgcttctg ctccccgagc tcaataaaag agcccacaac | 9360 |
| ccctcactcg gggcgccagt cctccgattg actgagtcgc ccgggtaccc gtgtatccaa | 9420 |
| taaaccctct tgcagttgca tccgacttgt ggtctcgctg ttccttggga gggtctcctc | 9480 |
| tgagtgattg actacccgtc agcggggtc tttcattaca tgtgagcaaa aggccagcaa | 9540 |
| aaggccagga accgtaaaaa ggccgcgttg ctggcgtttt tccataggct ccgcccccct | 9600 |
| gacgagcatc acaaaaatcg acgctcaagt cagaggtggc gaaacccgac aggactataa | 9660 |
| agataccagg cgtttccccc tggaagctcc ctcgtgcgct ctcctgttcc gaccctgccg | 9720 |
| cttaccggat acctgtccgc ctttctccct tcgggaagcg tggcgctttc tcaatgctca | 9780 |
| cgctgtaggt atctcagttc ggtgtaggtc gttcgctcca agctgggctg tgtgcacgaa | 9840 |
| ccccccgttc agcccgaccg ctgcgcctta tccggtaact atcgtcttga gtccaacccg | 9900 |
| gtaagacacg acttatcgcc actggcagca gccactggta acaggattag cagagcgagg | 9960 |
| tatgtaggcg gtgctacaga gttcttgaag tggtggccta actacggcta cactagaagg | 10020 |
| acagtatttg gtatctgcgc tctgctgaag ccagttacct tcggaaaaag agttggtagc | 10080 |
| tcttgatccg gcaaacaaac caccgctggt agcggtggtt ttttgtttg caagcagcag | 10140 |
| attacgcgca gaaaaaaagg atctcaagaa gatcctttga tcttttctac ggggtctgac | 10200 |
| gctcagtgga acgaaaactc acgttaaggg attttggtca tgagattatc aaaaaggatc | 10260 |

-continued

```
ttcacctaga tccttttaaa ttaaaaatga agttttaaat caatctaaag tatatatgag    10320
taaacttggt ctgacagtta ccaatgctta atcagtgagg cacctatctc agcgatctgt    10380
ctatttcgtt catccatagt tgcctgactc cccgtcgtgt agataactac gatacgggag    10440
ggcttaccat ctggcccag tgctgcaatg ataccgcgag acccacgctc accggctcca    10500
gatttatcag caataaacca gccagccgga agggccgagc gcagaagtgg tcctgcaact    10560
ttatccgcct ccatccagtc tattaattgt tgccgggaag ctagagtaag tagttcgcca    10620
gttaatagtt tgcgcaacgt tgttgccatt gctgcaggca tcgtggtgtc acgctcgtcg    10680
tttggtatgg cttcattcag ctccggttcc aacgatcaa ggcgagttac atgatccccc    10740
atgttgtgca aaaagcggt tagctccttc ggtcctccga tcgttgtcag aagtaagttg    10800
gccgcagtgt tatcactcat ggttatggca gcactgcata attctcttac tgtcatgcca    10860
tccgtaagat gcttttctgt gactggtgag tactcaacca agtcattctg agaatagtgt    10920
atgcggcgac cgagttgctc ttgcccggcg tcaacacggg ataataccgc gccacatagc    10980
agaactttaa aagtgctcat cattggaaaa cgttcttcgg ggcgaaaact ctcaaggatc    11040
ttaccgctgt tgagatccag ttcgatgtaa cccactcgtg cacccaactg atcttcagca    11100
tcttttactt tcaccagcgt ttctgggtga gcaaaaacag gaaggcaaaa tgccgcaaaa    11160
aagggaataa gggcgacacg gaaatgttga atactcatac tcttcctttt tcaatattat    11220
tgaagcattt atcagggtta ttgtctcatg agccggataca tatttgaatg tatttagaaa    11280
aataaacaaa taggggttcc gcgcacattt ccccgaaaag tgccacctga cgtctaagaa    11340
accattatta tcatgacatt aacctataaa aataggcgta tcacgaggcc ctttcgtctt    11400
caagaattca t                                                          11411
```

<210> SEQ ID NO 55
<211> LENGTH: 20
<212> TYPE: PRT
<213> ORGANISM: Artificial Sequence
<220> FEATURE:
<223> OTHER INFORMATION: Equine rhinitis A virus 2A peptide

<400> SEQUENCE: 55

Gln Cys Thr Asn Tyr Ala Leu Leu Lys Leu Ala Gly Asp Val Glu Ser
1               5                   10                  15

Asn Pro Gly Pro
            20

<210> SEQ ID NO 56
<211> LENGTH: 23
<212> TYPE: PRT
<213> ORGANISM: Artificial Sequence
<220> FEATURE:
<223> OTHER INFORMATION: Foot-and-mouth disease 2A peptide

<400> SEQUENCE: 56

Pro Val Lys Gln Leu Leu Asn Phe Asp Leu Leu Lys Leu Ala Gly Asp
1               5                   10                  15

Val Glu Ser Asn Pro Gly Pro
            20

<210> SEQ ID NO 57
<211> LENGTH: 19
<212> TYPE: PRT
<213> ORGANISM: Artificial Sequence
<220> FEATURE:
<223> OTHER INFORMATION: Porcine teschovirus-1 2A peptide

<400> SEQUENCE: 57

Ala Thr Asn Phe Ser Leu Leu Lys Gln Ala Gly Asp Val Glu Glu Asn
1               5                   10                  15

Pro Gly Pro

<210> SEQ ID NO 58
<211> LENGTH: 18
<212> TYPE: PRT
<213> ORGANISM: Artificial Sequence
<220> FEATURE:
<223> OTHER INFORMATION: Thosea asigna virus 2A peptide

<400> SEQUENCE: 58

Glu Gly Arg Gly Ser Leu Leu Thr Cys Gly Asp Val Glu Glu Asn Pro
1               5                   10                  15

Gly Pro

<210> SEQ ID NO 59
<211> LENGTH: 25
<212> TYPE: PRT
<213> ORGANISM: Artificial Sequence
<220> FEATURE:
<223> OTHER INFORMATION: Encephalomyocarditis virus-B 2A peptide

<400> SEQUENCE: 59

Gly Ile Phe Asn Ala His Tyr Ala Gly Tyr Phe Ala Asp Leu Leu Ile
1               5                   10                  15

His Asp Ile Glu Thr Asn Pro Gly Pro
            20                  25

<210> SEQ ID NO 60
<211> LENGTH: 17
<212> TYPE: PRT
<213> ORGANISM: Artificial Sequence
<220> FEATURE:
<223> OTHER INFORMATION: Encephalomyocarditis virus-D 2A peptide

<400> SEQUENCE: 60

Gly Tyr Phe Ala Asp Leu Leu Ile His Asp Ile Glu Thr Asn Pro Gly
1               5                   10                  15

Pro

<210> SEQ ID NO 61
<211> LENGTH: 25
<212> TYPE: PRT
<213> ORGANISM: Artificial Sequence
<220> FEATURE:
<223> OTHER INFORMATION: Encephalomyocarditis virus-PV21 2A peptide

<400> SEQUENCE: 61

Arg Ile Phe Asn Ala His Tyr Ala Gly Tyr Phe Ala Asp Leu Leu Ile
1               5                   10                  15

His Asp Ile Glu Thr Asn Pro Gly Pro
            20                  25

<210> SEQ ID NO 62
<211> LENGTH: 25
<212> TYPE: PRT
<213> ORGANISM: Artificial Sequence
<220> FEATURE:
<223> OTHER INFORMATION: Mengovirus 2A peptide

<400> SEQUENCE: 62

-continued

```
His Val Phe Glu Thr His Tyr Ala Gly Tyr Phe Ser Lys Leu Leu Ile
1               5                   10                  15

His Asp Val Glu Thr Asn Pro Gly Pro
            20                  25

<210> SEQ ID NO 63
<211> LENGTH: 25
<212> TYPE: PRT
<213> ORGANISM: Artificial Sequence
<220> FEATURE:
<223> OTHER INFORMATION: Theiler's encephalomyelitis virus-GD7 2A
      peptide

<400> SEQUENCE: 63

Lys Ala Val Arg Gly Tyr His Ala Asp Tyr Tyr Lys Gln Arg Leu Ile
1               5                   10                  15

His Asp Val Glu Met Asn Pro Gly Pro
            20                  25

<210> SEQ ID NO 64
<211> LENGTH: 25
<212> TYPE: PRT
<213> ORGANISM: Artificial Sequence
<220> FEATURE:
<223> OTHER INFORMATION: Theiler's encephalomyelitis virus-DA 2A peptide

<400> SEQUENCE: 64

Arg Ala Val Arg Ala Tyr His Ala Asp Tyr Tyr Lys Gln Arg Leu Ile
1               5                   10                  15

His Asp Val Glu Met Asn Pro Gly Pro
            20                  25

<210> SEQ ID NO 65
<211> LENGTH: 25
<212> TYPE: PRT
<213> ORGANISM: Artificial Sequence
<220> FEATURE:
<223> OTHER INFORMATION: Theiler's encephalomyelitis virus-BEAN 2A
      peptide

<400> SEQUENCE: 65

Lys Ala Val Arg Gly Tyr His Ala Asp Tyr Tyr Arg Gln Arg Leu Ile
1               5                   10                  15

His Asp Val Glu Thr Asn Pro Gly Pro
            20                  25

<210> SEQ ID NO 66
<211> LENGTH: 25
<212> TYPE: PRT
<213> ORGANISM: Artificial Sequence
<220> FEATURE:
<223> OTHER INFORMATION: Theiler's-Like Virus 2A peptide

<400> SEQUENCE: 66

Lys His Val Arg Glu Tyr His Ala Ala Tyr Tyr Lys Gln Arg Leu Met
1               5                   10                  15

His Asp Val Glu Thr Asn Pro Gly Pro
            20                  25

<210> SEQ ID NO 67
<211> LENGTH: 26
<212> TYPE: PRT
<213> ORGANISM: Artificial Sequence
<220> FEATURE:
```

```
<223> OTHER INFORMATION: Ljungan virus-174F 2A peptide

<400> SEQUENCE: 67

Met His Ser Asp Glu Met Asp Phe Ala Gly Gly Lys Phe Leu Asn Gln
1               5                   10                  15

Cys Gly Asp Val Glu Thr Asn Pro Gly Pro
            20                  25

<210> SEQ ID NO 68
<211> LENGTH: 26
<212> TYPE: PRT
<213> ORGANISM: Artificial Sequence
<220> FEATURE:
<223> OTHER INFORMATION: Ljungan virus-145SL 2A peptide

<400> SEQUENCE: 68

Met His Asn Asp Glu Met Asp Tyr Ser Gly Gly Lys Phe Leu Asn Gln
1               5                   10                  15

Cys Gly Asp Val Glu Ser Asn Pro Gly Pro
            20                  25

<210> SEQ ID NO 69
<211> LENGTH: 26
<212> TYPE: PRT
<213> ORGANISM: Artificial Sequence
<220> FEATURE:
<223> OTHER INFORMATION: Ljungan virus-(87-012) 2A peptide

<400> SEQUENCE: 69

Met His Ser Asp Glu Met Asp Phe Ala Gly Gly Lys Phe Leu Asn Gln
1               5                   10                  15

Cys Gly Asp Val Glu Thr Asn Pro Gly Pro
            20                  25

<210> SEQ ID NO 70
<211> LENGTH: 26
<212> TYPE: PRT
<213> ORGANISM: Artificial Sequence
<220> FEATURE:
<223> OTHER INFORMATION: Ljungan Virus - (M1146) 2A peptide

<400> SEQUENCE: 70

Tyr His Asp Lys Asp Met Asp Tyr Ala Gly Gly Lys Phe Leu Asn Gln
1               5                   10                  15

Cys Gly Asp Val Glu Thr Asn Pro Gly Pro
            20                  25

<210> SEQ ID NO 71
<211> LENGTH: 24
<212> TYPE: PRT
<213> ORGANISM: Artificial Sequence
<220> FEATURE:
<223> OTHER INFORMATION: Foot and Mouth Disease Virus 2A Peptide

<400> SEQUENCE: 71

Ala Pro Ala Lys Gln Leu Leu Asn Phe Asp Leu Leu Lys Leu Ala Gly
1               5                   10                  15

Asp Val Glu Ser Asn Pro Gly Pro
            20

<210> SEQ ID NO 72
<211> LENGTH: 24
<212> TYPE: PRT
<213> ORGANISM: Artificial Sequence
```

-continued

```
<220> FEATURE:
<223> OTHER INFORMATION: Foot and Mouth Disease Virus-A12 2A Peptide

<400> SEQUENCE: 72

Ala Pro Gly Lys Gln Leu Leu Asn Phe Asp Leu Leu Lys Leu Ala Gly
1               5                   10                  15

Asp Val Glu Ser Asn Pro Gly Pro
            20

<210> SEQ ID NO 73
<211> LENGTH: 24
<212> TYPE: PRT
<213> ORGANISM: Artificial Sequence
<220> FEATURE:
<223> OTHER INFORMATION: Foot and Mouth Disease Virus-C1 2A Peptide

<400> SEQUENCE: 73

Ala Pro Ala Lys Gln Leu Leu Asn Phe Asp Leu Leu Lys Leu Ala Gly
1               5                   10                  15

Asp Val Glu Ser Asn Pro Gly Pro
            20

<210> SEQ ID NO 74
<211> LENGTH: 24
<212> TYPE: PRT
<213> ORGANISM: Artificial Sequence
<220> FEATURE:
<223> OTHER INFORMATION: Foot and Mouth Disease Virus-O1G 2A Peptide

<400> SEQUENCE: 74

Ala Pro Val Lys Gln Leu Leu Asn Phe Asp Leu Leu Lys Leu Ala Gly
1               5                   10                  15

Asp Met Glu Ser Asn Pro Gly Pro
            20

<210> SEQ ID NO 75
<211> LENGTH: 24
<212> TYPE: PRT
<213> ORGANISM: Artificial Sequence
<220> FEATURE:
<223> OTHER INFORMATION: Foot and Mouth Disease Virus O1K 2A Peptide

<400> SEQUENCE: 75

Ala Pro Val Lys Gln Leu Thr Asn Phe Asp Leu Leu Lys Leu Ala Gly
1               5                   10                  15

Asp Val Glu Ser Asn Pro Gly Pro
            20

<210> SEQ ID NO 76
<211> LENGTH: 24
<212> TYPE: PRT
<213> ORGANISM: Artificial Sequence
<220> FEATURE:
<223> OTHER INFORMATION: Foot and Mouth Disease Virus - O (Taiwan) 2A
      Peptide

<400> SEQUENCE: 76

Ala Pro Ala Lys Gln Leu Leu Asn Phe Asp Leu Leu Lys Leu Ala Gly
1               5                   10                  15

Asp Val Glu Ser Asn Pro Gly Pro
            20

<210> SEQ ID NO 77
<211> LENGTH: 24
```

```
<212> TYPE: PRT
<213> ORGANISM: Artificial Sequence
<220> FEATURE:
<223> OTHER INFORMATION: Foot and Mouth Disease Virus - O/SK 2A Peptide

<400> SEQUENCE: 77

Ala Pro Val Lys Gln Leu Leu Ser Phe Asp Leu Leu Lys Leu Ala Gly
1               5                   10                  15

Asp Val Glu Ser Asn Pro Gly Pro
            20

<210> SEQ ID NO 78
<211> LENGTH: 24
<212> TYPE: PRT
<213> ORGANISM: Artificial Sequence
<220> FEATURE:
<223> OTHER INFORMATION: Foot and Mouth Disease Virus - SAT3 2A Peptide

<400> SEQUENCE: 78

Lys Pro Asp Lys Gln Met Cys Asn Phe Asp Leu Leu Lys Leu Ala Gly
1               5                   10                  15

Asp Val Glu Ser Asn Pro Gly Pro
            20

<210> SEQ ID NO 79
<211> LENGTH: 24
<212> TYPE: PRT
<213> ORGANISM: Artificial Sequence
<220> FEATURE:
<223> OTHER INFORMATION: Foot and Mouth Disease Virus - SAT2 2A Peptide

<400> SEQUENCE: 79

Gly Val Ala Lys Gln Leu Leu Asn Phe Asp Leu Leu Lys Leu Ala Gly
1               5                   10                  15

Asp Val Glu Ser Asn Pro Gly Pro
            20

<210> SEQ ID NO 80
<211> LENGTH: 24
<212> TYPE: PRT
<213> ORGANISM: Artificial Sequence
<220> FEATURE:
<223> OTHER INFORMATION: Equine Rhinits A Virus 2A Peptide

<400> SEQUENCE: 80

Asn Ile Asn Lys Gln Cys Thr Asn Tyr Ser Leu Leu Lys Leu Ala Gly
1               5                   10                  15

Asp Val Glu Ser Asn Pro Gly Pro
            20

<210> SEQ ID NO 81
<211> LENGTH: 25
<212> TYPE: PRT
<213> ORGANISM: Artificial Sequence
<220> FEATURE:
<223> OTHER INFORMATION: Equine Rhinitis B Virus 2A Peptide

<400> SEQUENCE: 81

Thr Ile Leu Ser Glu Gly Ala Thr Asn Phe Ser Leu Leu Lys Leu Ala
1               5                   10                  15

Gly Asp Val Glu Leu Asn Pro Gly Pro
            20                  25

<210> SEQ ID NO 82
```

<211> LENGTH: 25
<212> TYPE: PRT
<213> ORGANISM: Artificial Sequence
<220> FEATURE:
<223> OTHER INFORMATION: Endogenous Retrovirus-3 2A Peptide

<400> SEQUENCE: 82

```
Asn Leu Leu Ser Gln Gly Ala Thr Asn Phe Asp Leu Leu Lys Leu Ala
1               5                   10                  15

Gly Asp Val Glu Ser Asn Pro Gly Pro
            20                  25
```

<210> SEQ ID NO 83
<211> LENGTH: 27
<212> TYPE: PRT
<213> ORGANISM: Artificial Sequence
<220> FEATURE:
<223> OTHER INFORMATION: Punta Toro Virus-1 2A Peptide

<400> SEQUENCE: 83

```
Val Met Ala Phe Gln Gly Pro Gly Ala Thr Asn Phe Ser Leu Leu Lys
1               5                   10                  15

Gln Ala Gly Asp Val Glu Glu Asn Pro Gly Pro
            20                  25
```

<210> SEQ ID NO 84
<211> LENGTH: 27
<212> TYPE: PRT
<213> ORGANISM: Artificial Sequence
<220> FEATURE:
<223> OTHER INFORMATION: Punta Toro Virus-2 2A Peptide

<400> SEQUENCE: 84

```
Thr Met Met Leu Gln Gly Pro Gly Ala Thr Asn Phe Ser Leu Leu Lys
1               5                   10                  15

Gln Ala Gly Asp Val Glu Glu Asn Pro Gly Pro
            20                  25
```

<210> SEQ ID NO 85
<211> LENGTH: 27
<212> TYPE: PRT
<213> ORGANISM: Artificial Sequence
<220> FEATURE:
<223> OTHER INFORMATION: Punta Toro Virus-3 2A Peptide

<400> SEQUENCE: 85

```
Thr Met Ser Phe Gln Gly Pro Gly Ala Ser Ser Phe Ser Leu Leu Lys
1               5                   10                  15

Gln Ala Gly Asp Val Glu Glu Asn Pro Gly Pro
            20                  25
```

<210> SEQ ID NO 86
<211> LENGTH: 27
<212> TYPE: PRT
<213> ORGANISM: Artificial Sequence
<220> FEATURE:
<223> OTHER INFORMATION: Punta Toro Virus-4 2A Peptide

<400> SEQUENCE: 86

```
Thr Met Met Leu Gln Gly Pro Gly Ala Ser Asn Phe Ser Leu Leu Lys
1               5                   10                  15

Gln Ala Gly Asp Val Glu Glu Asn Pro Gly Pro
            20                  25
```

```
<210> SEQ ID NO 87
<211> LENGTH: 27
<212> TYPE: PRT
<213> ORGANISM: Artificial Sequence
<220> FEATURE:
<223> OTHER INFORMATION: Punta Toro Virus-5 2A Peptide

<400> SEQUENCE: 87

Thr Met Leu Phe Gln Gly Pro Gly Ala Ala Asn Phe Ser Leu Leu Arg
1               5                   10                  15

Gln Ala Gly Asp Val Glu Glu Asn Pro Gly Pro
            20                  25

<210> SEQ ID NO 88
<211> LENGTH: 27
<212> TYPE: PRT
<213> ORGANISM: Artificial Sequence
<220> FEATURE:
<223> OTHER INFORMATION: Punta Toro Virus-6 2A Peptide

<400> SEQUENCE: 88

Thr Met Ser Phe Gln Gly Pro Gly Ala Thr Asn Phe Ser Leu Leu Lys
1               5                   10                  15

Gln Ala Gly Asp Val Glu Glu Asn Pro Gly Pro
            20                  25

<210> SEQ ID NO 89
<211> LENGTH: 27
<212> TYPE: PRT
<213> ORGANISM: Artificial Sequence
<220> FEATURE:
<223> OTHER INFORMATION: Punta Toro Virus-7 2A Peptide

<400> SEQUENCE: 89

Val Val Ser Phe Gln Gly Pro Gly Ala Thr Asn Phe Ser Leu Leu Lys
1               5                   10                  15

Gln Ala Gly Asp Val Glu Glu Asn Pro Gly Pro
            20                  25

<210> SEQ ID NO 90
<211> LENGTH: 27
<212> TYPE: PRT
<213> ORGANISM: Artificial Sequence
<220> FEATURE:
<223> OTHER INFORMATION: Punta Toro Virus-8 2A Peptide

<400> SEQUENCE: 90

Thr Met Ser Leu Gln Gly Pro Gly Ala Thr Asn Phe Ser Leu Leu Lys
1               5                   10                  15

Gln Ala Gly Asp Ile Glu Glu Asn Pro Gly Pro
            20                  25

<210> SEQ ID NO 91
<211> LENGTH: 27
<212> TYPE: PRT
<213> ORGANISM: Artificial Sequence
<220> FEATURE:
<223> OTHER INFORMATION: Punta Toro Virus-9 2A Peptide

<400> SEQUENCE: 91

Thr Met Ala Phe Gln Gly Pro Gly Ala Thr Asn Phe Ser Leu Leu Lys
1               5                   10                  15

Gln Ala Gly Asp Val Glu Glu Asn Pro Gly Pro
            20                  25
```

<210> SEQ ID NO 92
<211> LENGTH: 27
<212> TYPE: PRT
<213> ORGANISM: Artificial Sequence
<220> FEATURE:
<223> OTHER INFORMATION: Punta Toro Virus-10 2A Peptide

<400> SEQUENCE: 92

Thr Leu Ser Phe Gln Gly Pro Gly Ala Thr Asn Phe Ser Leu Leu Lys
1               5                   10                  15

Gln Ala Gly Asp Val Glu Glu Asn Pro Gly Pro
            20                  25

<210> SEQ ID NO 93
<211> LENGTH: 27
<212> TYPE: PRT
<213> ORGANISM: Artificial Sequence
<220> FEATURE:
<223> OTHER INFORMATION: Punta Toro Virus-11 2A Peptide

<400> SEQUENCE: 93

Arg Met Ser Phe Gln Gly Pro Gly Ala Thr Asn Phe Ser Leu Leu Lys
1               5                   10                  15

Arg Ala Gly Asp Val Glu Glu Asn Pro Gly Pro
            20                  25

<210> SEQ ID NO 94
<211> LENGTH: 20
<212> TYPE: PRT
<213> ORGANISM: Artificial Sequence
<220> FEATURE:
<223> OTHER INFORMATION: Ciricket Paralysis Virus 2A Peptide

<400> SEQUENCE: 94

Phe Leu Arg Lys Arg Thr Gln Leu Leu Met Ser Gly Asp Val Glu Ser
1               5                   10                  15

Asn Pro Gly Pro
            20

<210> SEQ ID NO 95
<211> LENGTH: 20
<212> TYPE: PRT
<213> ORGANISM: Artificial Sequence
<220> FEATURE:
<223> OTHER INFORMATION: Drosophila C Virus 2A Peptide

<400> SEQUENCE: 95

Glu Ala Ala Arg Gln Met Leu Leu Leu Leu Ser Gly Asp Val Glu Thr
1               5                   10                  15

Asn Pro Gly Pro
            20

<210> SEQ ID NO 96
<211> LENGTH: 20
<212> TYPE: PRT
<213> ORGANISM: Artificial Sequence
<220> FEATURE:
<223> OTHER INFORMATION: Acute Bee Paralysis Virus 2A Peptide

<400> SEQUENCE: 96

Gly Ser Trp Thr Asp Ile Leu Leu Leu Leu Ser Gly Asp Val Glu Thr
1               5                   10                  15

Asn Pro Gly Pro
            20

<210> SEQ ID NO 97
<211> LENGTH: 20
<212> TYPE: PRT
<213> ORGANISM: Artificial Sequence
<220> FEATURE:
<223> OTHER INFORMATION: Acute Bee Paralysis Virus Poland 1 isolate 2A
      Peptide

<400> SEQUENCE: 97

Gly Ser Trp Thr Asp Ile Leu Leu Leu Ser Gly Asp Val Glu Thr
1               5                   10                  15

Asn Pro Gly Pro
            20

<210> SEQ ID NO 98
<211> LENGTH: 20
<212> TYPE: PRT
<213> ORGANISM: Artificial Sequence
<220> FEATURE:
<223> OTHER INFORMATION: Acute Bee Paralysis Virus Hungary 1 isolate 2A
      Peptide

<400> SEQUENCE: 98

Gly Ser Trp Thr Asp Ile Leu Leu Leu Trp Ser Gly Asp Val Glu Thr
1               5                   10                  15

Asn Pro Gly Pro
            20

<210> SEQ ID NO 99
<211> LENGTH: 20
<212> TYPE: PRT
<213> ORGANISM: Artificial Sequence
<220> FEATURE:
<223> OTHER INFORMATION: Infectious Flacherie Virus 2A Peptide

<400> SEQUENCE: 99

Thr Arg Ala Glu Ile Glu Asp Glu Leu Ile Arg Ala Gly Ile Glu Ser
1               5                   10                  15

Asn Pro Gly Pro
            20

<210> SEQ ID NO 100
<211> LENGTH: 20
<212> TYPE: PRT
<213> ORGANISM: Artificial Sequence
<220> FEATURE:
<223> OTHER INFORMATION: Tomato Aspermy Virus 2A Peptide

<400> SEQUENCE: 100

Arg Ala Glu Gly Arg Gly Ser Leu Leu Thr Cys Gly Asp Val Glu Glu
1               5                   10                  15

Asn Pro Gly Pro
            20

<210> SEQ ID NO 101
<211> LENGTH: 20
<212> TYPE: PRT
<213> ORGANISM: Artificial Sequence
<220> FEATURE:
<223> OTHER INFORMATION: Equine Encephalosis Virus 2A Peptide

<400> SEQUENCE: 101

Gln Gly Ala Gly Arg Gly Ser Leu Val Thr Cys Gly Asp Val Glu Glu
1               5                   10                  15

Asn Pro Gly Pro
            20

<210> SEQ ID NO 102
<211> LENGTH: 20
<212> TYPE: PRT
<213> ORGANISM: Artificial Sequence
<220> FEATURE:
<223> OTHER INFORMATION: Avian Polyoma Virus 2A Peptide

<400> SEQUENCE: 102

Asn Tyr Pro Met Pro Glu Ala Leu Gln Lys Ile Ile Asp Leu Glu Ser
1               5                   10                  15

Asn Pro Pro Pro
            20

<210> SEQ ID NO 103
<211> LENGTH: 20
<212> TYPE: PRT
<213> ORGANISM: Artificial Sequence
<220> FEATURE:
<223> OTHER INFORMATION: Kashmir bee virus 2A Peptide

<400> SEQUENCE: 103

Gly Thr Trp Glu Ser Val Leu Asn Leu Leu Ala Gly Asp Ile Glu Leu
1               5                   10                  15

Asn Pro Gly Pro
            20

<210> SEQ ID NO 104
<211> LENGTH: 20
<212> TYPE: PRT
<213> ORGANISM: Artificial Sequence
<220> FEATURE:
<223> OTHER INFORMATION: Perina Nuda Picorna-like Virus (a) 2A Peptide

<400> SEQUENCE: 104

Ala Gln Gly Trp Val Pro Asp Leu Thr Val Asp Gly Asp Val Glu Ser
1               5                   10                  15

Asn Pro Gly Pro
            20

<210> SEQ ID NO 105
<211> LENGTH: 20
<212> TYPE: PRT
<213> ORGANISM: Artificial Sequence
<220> FEATURE:
<223> OTHER INFORMATION: Perina Nuda Picorna-like Virus (b) 2A Peptide

<400> SEQUENCE: 105

Ile Gly Gly Gly Gln Lys Asp Leu Thr Gln Asp Gly Asp Ile Glu Ser
1               5                   10                  15

Asn Pro Gly Pro
            20

<210> SEQ ID NO 106
<211> LENGTH: 20
<212> TYPE: PRT
<213> ORGANISM: Artificial Sequence
<220> FEATURE:
<223> OTHER INFORMATION: Ectropis Obliqua Picorna-like Virus (a) 2A
      Peptide

<400> SEQUENCE: 106

```
Ala Gln Gly Trp Ala Pro Asp Leu Thr Gln Asp Gly Asp Val Glu Ser
1               5                   10                  15

Asn Pro Gly Pro
            20
```

<210> SEQ ID NO 107
<211> LENGTH: 20
<212> TYPE: PRT
<213> ORGANISM: Artificial Sequence
<220> FEATURE:
<223> OTHER INFORMATION: Ectropis Obliqua Picorna-like Virus (b) 2A
      Peptide

<400> SEQUENCE: 107

```
Ile Gly Gly Gly Gln Arg Asp Leu Thr Gln Asp Gly Asp Ile Glu Ser
1               5                   10                  15

Asn Pro Gly Pro
            20
```

<210> SEQ ID NO 108
<211> LENGTH: 19
<212> TYPE: PRT
<213> ORGANISM: Artificial Sequence
<220> FEATURE:
<223> OTHER INFORMATION: Providence Virus (a) 2A Peptide

<400> SEQUENCE: 108

```
Val Gly Asp Arg Gly Ser Leu Leu Thr Cys Gly Asp Val Glu Ser Asn
1               5                   10                  15

Pro Gly Pro
```

<210> SEQ ID NO 109
<211> LENGTH: 19
<212> TYPE: PRT
<213> ORGANISM: Artificial Sequence
<220> FEATURE:
<223> OTHER INFORMATION: Providence Virus (b) 2A Peptide

<400> SEQUENCE: 109

```
Gly Asp Pro Ile Glu Asp Leu Thr Asp Asp Gly Asp Ile Glu Lys Asn
1               5                   10                  15

Pro Gly Pro
```

<210> SEQ ID NO 110
<211> LENGTH: 19
<212> TYPE: PRT
<213> ORGANISM: Artificial Sequence
<220> FEATURE:
<223> OTHER INFORMATION: Providence Virus (c) 2A Peptide

<400> SEQUENCE: 110

```
Ser Gly Gly Arg Gly Ser Leu Leu Thr Ala Gly Asp Val Glu Lys Asn
1               5                   10                  15

Pro Gly Pro
```

<210> SEQ ID NO 111
<211> LENGTH: 20
<212> TYPE: PRT
<213> ORGANISM: Artificial Sequence
<220> FEATURE:
<223> OTHER INFORMATION: Bovine Rotavirus 2A Peptide

<400> SEQUENCE: 111

```
Ser Lys Phe Gln Ile Asp Arg Ile Leu Ile Ser Gly Asp Ile Glu Leu
```

Asn Pro Gly Pro
        20

<210> SEQ ID NO 112
<211> LENGTH: 20
<212> TYPE: PRT
<213> ORGANISM: Artificial Sequence
<220> FEATURE:
<223> OTHER INFORMATION: Porcine Rotavirus 2A Peptide

<400> SEQUENCE: 112

Ala Lys Phe Gln Ile Asp Lys Ile Leu Ile Ser Gly Asp Val Glu Leu
1               5                   10                  15

Asn Pro Gly Pro
        20

<210> SEQ ID NO 113
<211> LENGTH: 20
<212> TYPE: PRT
<213> ORGANISM: Artificial Sequence
<220> FEATURE:
<223> OTHER INFORMATION: Human Rotavirus 2A Peptide

<400> SEQUENCE: 113

Ser Lys Phe Gln Ile Asp Lys Ile Leu Ile Ser Gly Asp Ile Glu Leu
1               5                   10                  15

Asn Pro Gly Pro
        20

<210> SEQ ID NO 114
<211> LENGTH: 20
<212> TYPE: PRT
<213> ORGANISM: Artificial Sequence
<220> FEATURE:
<223> OTHER INFORMATION: Bombyx Mori Reovirus 2A Peptide

<400> SEQUENCE: 114

Phe Arg Ser Asn Tyr Asp Leu Leu Lys Leu Cys Gly Asp Ile Glu Ser
1               5                   10                  15

Asn Pro Gly Pro
        20

<210> SEQ ID NO 115
<211> LENGTH: 20
<212> TYPE: PRT
<213> ORGANISM: Artificial Sequence
<220> FEATURE:
<223> OTHER INFORMATION: Lymantria Dispar Reovirus 2A Peptide

<400> SEQUENCE: 115

Phe Arg Ser Asn Tyr Asp Leu Leu Lys Leu Cys Gly Asp Val Glu Ser
1               5                   10                  15

Asn Pro Gly Pro
        20

<210> SEQ ID NO 116
<211> LENGTH: 20
<212> TYPE: PRT
<213> ORGANISM: Artificial Sequence
<220> FEATURE:
<223> OTHER INFORMATION: Dendrolimus Punctatus Reovirus 2A Peptide

<400> SEQUENCE: 116

```
Phe Arg Ser Asn Tyr Asp Leu Leu Lys Leu Cys Gly Asp Val Glu Ser
1               5                   10                  15

Asn Pro Gly Pro
            20
```

<210> SEQ ID NO 117
<211> LENGTH: 20
<212> TYPE: PRT
<213> ORGANISM: Artificial Sequence
<220> FEATURE:
<223> OTHER INFORMATION: Trypansoma Brucei TSR1 2A Peptide

<400> SEQUENCE: 117

```
Ser Ser Ile Ile Arg Thr Lys Met Leu Val Ser Gly Asp Val Glu Glu
1               5                   10                  15

Asn Pro Gly Pro
            20
```

<210> SEQ ID NO 118
<211> LENGTH: 20
<212> TYPE: PRT
<213> ORGANISM: Artificial Sequence
<220> FEATURE:
<223> OTHER INFORMATION: Trypansoma Spp. CAB95325.1 2A Peptide

<400> SEQUENCE: 118

```
Ser Ser Ile Ile Arg Thr Lys Met Leu Leu Ser Gly Asp Val Glu Glu
1               5                   10                  15

Asn Pro Gly Pro
            20
```

<210> SEQ ID NO 119
<211> LENGTH: 20
<212> TYPE: PRT
<213> ORGANISM: Artificial Sequence
<220> FEATURE:
<223> OTHER INFORMATION: Trypansoma Spp. CAB95559.1 2A Peptide

<400> SEQUENCE: 119

```
Ser Ser Ile Ile Arg Thr Lys Ile Leu Leu Ser Gly Asp Val Glu Glu
1               5                   10                  15

Asn Pro Gly Pro
            20
```

<210> SEQ ID NO 120
<211> LENGTH: 20
<212> TYPE: PRT
<213> ORGANISM: Artificial Sequence
<220> FEATURE:
<223> OTHER INFORMATION: Trypansoma Cruzi 2A Peptide

<400> SEQUENCE: 120

```
Cys Asp Ala Gln Arg Gln Lys Leu Leu Leu Ser Gly Asp Ile Glu Gln
1               5                   10                  15

Asn Pro Gly Pro
            20
```

<210> SEQ ID NO 121
<211> LENGTH: 20
<212> TYPE: PRT
<213> ORGANISM: Artificial Sequence
<220> FEATURE:
<223> OTHER INFORMATION: T. maritima aguA 2A Peptide

<400> SEQUENCE: 121

```
Tyr Ile Pro Asp Phe Gly Gly Phe Leu Val Lys Ala Asp Ser Glu Phe
1               5                   10                  15

Asn Pro Gly Pro
            20

<210> SEQ ID NO 122
<211> LENGTH: 21
<212> TYPE: PRT
<213> ORGANISM: Artificial Sequence
<220> FEATURE:
<223> OTHER INFORMATION: B. bronchiseptica 2A Peptide

<400> SEQUENCE: 122

Val His Cys Ala Gly Arg Gly Gly Pro Val Arg Leu Leu Asp Lys Glu
1               5                   10                  15

Gly Asn Pro Gly Pro
            20

<210> SEQ ID NO 123
<211> LENGTH: 20
<212> TYPE: PRT
<213> ORGANISM: Artificial Sequence
<220> FEATURE:
<223> OTHER INFORMATION: Murine mor-1F 2A Peptide

<400> SEQUENCE: 123

Asp Leu Glu Leu Glu Thr Val Gly Ser His Gln Ala Asp Ala Glu Thr
1               5                   10                  15

Asn Pro Gly Pro
            20

<210> SEQ ID NO 124
<211> LENGTH: 20
<212> TYPE: PRT
<213> ORGANISM: Artificial Sequence
<220> FEATURE:
<223> OTHER INFORMATION: D. melanogaster mod(mdg4) 2A Peptide

<400> SEQUENCE: 124

Thr Ala Ala Asp Lys Ile Gln Gly Ser Trp Lys Met Asp Thr Glu Gly
1               5                   10                  15

Asn Pro Gly Pro
            20

<210> SEQ ID NO 125
<211> LENGTH: 20
<212> TYPE: PRT
<213> ORGANISM: Artificial Sequence
<220> FEATURE:
<223> OTHER INFORMATION: A. nidulans Ca Channel MID1 2A Peptide

<400> SEQUENCE: 125

Pro Ile Thr Asn Arg Pro Arg Asn Ser Gly Leu Ile Asp Thr Glu Ile
1               5                   10                  15

Asn Pro Gly Pro
            20
```